US007102009B2

(12) United States Patent
Patel et al.

(10) Patent No.: US 7,102,009 B2
(45) Date of Patent: *Sep. 5, 2006

(54) SUBSTITUTED AMINE DERIVATIVES AND METHODS OF USE

(75) Inventors: Vinod F. Patel, Acton, MA (US); Benny Askew, Newbury Park, CA (US); Shon Booker, Newbury Park, CA (US); Guoqing Chen, Thousand Oaks, CA (US); Lucian V. DiPietro, Gloucester, MA (US); Julie Germain, Somerville, MA (US); Gregory J. Habgood, Merrimac, MA (US); Qi Huang, Moorpark, CA (US); Tae-Seong Kim, Thousand Oaks, CA (US); Aiwen Li, Westlake Village, CA (US); Nobuko Nishimura, West Hills, CA (US); Rana Nomak, Westlake Village, CA (US); Babak Riahi, Woodland Hills, CA (US); Chester Chenguang Yuan, Newbury Park, CA (US); Daniel Elbaum, Newton, MA (US)

(73) Assignee: Amgen Inc., Thousand Oaks, CA (US)

( * ) Notice: Subject to any disclaimer, the term of this patent is extended or adjusted under 35 U.S.C. 154(b) by 142 days.

This patent is subject to a terminal disclaimer.

(21) Appl. No.: 10/197,918

(22) Filed: Jul. 17, 2002

(65) Prior Publication Data

US 2003/0203922 A1 Oct. 30, 2003

Related U.S. Application Data

(63) Continuation-in-part of application No. 10/046,622, filed on Jan. 10, 2002.

(60) Provisional application No. 60/261,882, filed on Jan. 12, 2001, and provisional application No. 60/323,808, filed on Sep. 19, 2001.

(51) Int. Cl.
   *C07D 401/02* (2006.01)
   *A61K 31/44* (2006.01)

(52) U.S. Cl. ............................... 546/277.1; 546/273.7; 546/275.7; 544/253; 514/255; 514/338; 514/339

(58) Field of Classification Search .............. 546/277.1, 546/273.7, 275.7, 256; 544/253, 116, 360; 514/338, 339, 255, 233
See application file for complete search history.

(56) References Cited

U.S. PATENT DOCUMENTS 3,226,394 A    12/1965  Schipper et al.
3,406,168 A    10/1968  Schmidt (Continued)

FOREIGN PATENT DOCUMENTS

DE   100 23 492 A1   11/2001
EP   0 393 529 A1    10/1990
EP   0 410 148 A1    1/1991
EP   0 429 987 A2    6/1991
EP   0 393 529 B1    6/1993

(Continued)

OTHER PUBLICATIONS

Konshin et al., "Synthesis and antimicrobial activity of arylamides of N–(4–pyridyl)anthrailc acid", Chem Abstr. 97:109837 (1981).
Breier et al., "The role of vascular endothelial growth factor in blood vessel formation", Trends in Cell Biology 6:454–456 (1996).
Connell et al., "Patent focus on cancer chemotherapeutics. II Angiogenesis agents: Apr. 2000–Sep. 2000", Exp. Opin. Ther. Patents 11:77–114 (2001).
Singh, et al., "Substituted Imidazolines and Their CNS Activity" Ind.J.Het.Chem. 2: 129–132 (1992).
Seto, et al., "Molecular Self–Assembly through Hydrogen Bonding: Supramolecular Aggregates Based on the Cyanuric Acid•Melamine Lattice" J.Am.Chem. 115: 905–916 (1993).
Pawel, Nantka–Namirski; "Nicotinic Acid Derivatives. II. Synthesis of Some Derivatives of 2–Amino–3–Cyanopyridine and 2–Aminonicotinic Acid", Acta Poloniae Pharmaceutica, 24(2):113–121 (1967).
Proudfoot et al., "Novel Non–nucleoside Inhibitors or HIV–1 Reverse Transcriptase. 3. Dipyrido[2,3–b:2',3'–e]diazepinones", J. Med. Chem., 38:1406–1410 (1995).
Smrckova–Voltrova et al., "Structure and Properties of Quaternized 2–and 4–aminonicotinamides", Collect. Czech. Chem. Commun., 50:1009–1015 (1995).
Samvelyan et al., "Discussion of Some New Amino Acid Derivatives of Nicotinic Acid and Their Antisoporific Properties", Farmakologiia I Toksikologiia, 49(3):35–37 (1986).
Hargrave et al., "Novel Non–Nucleoside Inhibitors of HIV–1 Reverse Transcriptase. 1. Tricyclic Pyridobenzo–and Dipyridodiazepinones", J. Med. Chem., 34:2231–2241 (1991).
Adams et al. "Discovery and Development of a Non–nucleoside Reverse Transcriptase Inhibitor", Royal Society of Chemistry, Recent Advances in the Chemistry of Anti–infective Agents, 19:282–296 (1993).

*Primary Examiner*—Shailendra Kumar
(74) *Attorney, Agent, or Firm*—Joseph W. Bulock

(57) ABSTRACT

Selected amines are effective for prophylaxis and treatment of diseases, such as angiogenesis mediated diseases. The invention encompasses novel compounds, analogs, prodrugs and pharmaceutically acceptable salts thereof, pharmaceutical compositions and methods for prophylaxis and treatment of diseases and other maladies or conditions involving, cancer and the like. The subject invention also relates to processes for making such compounds as well as to intermediates useful in such processes.

20 Claims, No Drawings

U.S. PATENT DOCUMENTS

| | | | |
|---|---|---|---|
| 3,822,277 | A | 7/1974 | Dufour |
| 4,321,371 | A | 3/1982 | Parg et al. |
| 4,816,485 | A | 3/1989 | Satzinger et al. |
| 4,857,662 | A | 8/1989 | Satzinger et al. |
| 5,532,358 | A | 7/1996 | Kelly |
| 5,559,135 | A | 9/1996 | Ashton et al. |
| 5,571,912 | A | 11/1996 | Grozinger et al. |
| 5,770,613 | A | 6/1998 | Gaeta et al. |
| 6,008,234 | A | 12/1999 | Kochanny et al. |
| 6,051,713 | A | 4/2000 | Teng et al. |
| 6,140,351 | A | 10/2000 | Arnaiz et al. |
| 6,156,766 | A | 12/2000 | Arita et al. |
| 6,271,237 | B1 | 8/2001 | Galemmo, Jr. et al. |
| 6,313,122 | B1 | 11/2001 | Beight et al. |
| 6,313,151 | B1 | 11/2001 | Beight et al. |
| 6,372,759 | B1 | 4/2002 | Beight et al. |
| 6,417,200 | B1 | 7/2002 | Beight et al. |
| 6,448,290 | B1 | 9/2002 | Ohuchida et al. |
| 6,593,352 | B1 | 7/2003 | Weichert et al. |
| 6,605,626 | B1 | 8/2003 | Beight et al. |
| 6,608,058 | B1 * | 8/2003 | Yoon et al. .............. 514/234.5 |
| 6,610,704 | B1 | 8/2003 | Beight et al. |
| 6,635,657 | B1 | 10/2003 | Beight et al. |
| 6,660,755 | B1 | 12/2003 | Song et al. |
| 6,794,397 | B1 | 9/2004 | Cai et al. |
| 2003/0069250 | A1 | 4/2003 | Zhu et al. |
| 2003/0125339 | A1 | 7/2003 | Chen et al. |
| 2003/0195192 | A1 | 10/2003 | Haviv et al. |
| 2003/0195195 | A1 | 10/2003 | Haviv et al. |
| 2003/0195230 | A1 | 10/2003 | Chen et al. |
| 2003/0225106 | A1 | 12/2003 | Askew et al. |
| 2004/0063775 | A1 | 4/2004 | Momose et al. |
| 2004/0102441 | A1 | 5/2004 | Krueger et al. |
| 2004/0254185 | A1 | 12/2004 | Ernst et al. |
| 2005/0032816 | A1 | 2/2005 | Ernst et al. |
| 2005/0054654 | A1 | 3/2005 | Huth et al. |

FOREIGN PATENT DOCUMENTS

| | | |
|---|---|---|
| EP | 0 947 500 A1 | 10/1999 |
| FR | 2 168 227 | 8/1973 |
| JP | 2000 256358 | 9/2000 |
| WO | WO 96/15118 | 5/1996 |
| WO | WO 96/41795 | 12/1996 |
| WO | WO 98/24771 | 6/1998 |
| WO | WO 98/45268 | 10/1998 |
| WO | WO 99/32477 | 7/1999 |
| WO | WO 99/62885 | 12/1999 |
| WO | WO 00/02851 | 1/2000 |
| WO | WO 00/27819 | 5/2000 |
| WO | WO 00/27820 | 5/2000 |
| WO | WO 00/39111 | 7/2000 |
| WO | WO 00/39117 | 7/2000 |
| WO | WO 00/47212 | 8/2000 |
| WO | WO 00/62778 | 10/2000 |
| WO | WO 00/71532 | 11/2000 |
| WO | WO 01/29009 A1 | 4/2001 |
| WO | WO 01/30745 A1 | 5/2001 |
| WO | WO 01/55114 A1 | 8/2001 |
| WO | WO 01/55115 A1 | 8/2001 |
| WO | WO 01/78648 A2 * | 10/2001 |
| WO | WO 01/81311 A1 | 11/2001 |
| WO | WO 01/85671 A2 | 11/2001 |
| WO | WO 01/85691 A1 | 11/2001 |
| WO | WO 01/85715 A2 | 11/2001 |
| WO | WO 02/055501 | 7/2002 |
| WO | WO 02/068406 | 9/2002 |
| WO | WO 03/068232 A1 | 8/2003 |
| WO | WO 03/068235 A1 | 8/2003 |

* cited by examiner

SUBSTITUTED AMINE DERIVATIVES AND METHODS OF USE

This application is a continuation-in-part of U.S. patent application Ser. No. 10/046,622 filed Jan. 10, 2002 claiming the benefit of U.S. Provisional Application Nos. 60/261,882, filed Jan. 12, 2001, and 60/323,808 filed Sep. 19, 2001, which are hereby incorporated by reference.

FIELD OF THE INVENTION

This invention is in the field of pharmaceutical agents and specifically relates to compounds, compositions, uses and methods for treating cancer and angiogenesis-related disorders.

BACKGROUND OF THE INVENTION

Protein kinases represent a large family of proteins which play a central role in the regulation of a wide variety of cellular processes, maintaining control over cellular function. A partial list of such kinases includes ab1, Akt, bcr-ab1, Blk, Brk, Btk, c-kit, c-met, c-src, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

Certain diseases are known to be associated with deregulated angiogenesis, for example ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

At the center of the network regulating the growth and differentiation of the vascular system and its components, both during embryonic development and normal growth, and in a wide number of pathological anomalies and diseases, lies the angiogenic factor known as Vascular Endothelial Growth Factor" (VEGF; originally termed 'Vascular Permeability Factor", VPF), along with its cellular receptors (see G. Breier et al., Trends in Cell Biology, 6, 454–6 (1996)).

VEGF is a dimeric, disulfide-linked 46-kDa glycoprotein related to "Platelet-Derived Growth Factor" (PDGF); it is produced by normal cell lines and tumor cell lines; is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PlGF) and VEGF-C.

VEGF receptors (VEGFR) are transmembranous receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerate tumor growth. Increased VEGF expression could explain the occurrence of cerebral edema in patients with glioma. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with antisense-VEGF RNA techniques. All approaches led to a reduction in the growth of glioma cell lines or other tumor cell lines in vivo as a result of inhibited tumor angiogenesis.

Angiogenesis is regarded as an absolute prerequisite for tumors which grow beyond a diameter of about 1–2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into avascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels. See R. Connell and J. Beebe, Exp. Opin. Ther. Patents, 11, 77–114 (2001).

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production.

Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, regulators of angiogenesis have become an important therapeutic target.

Schipper U.S. Pat. No. 3,226,394, issued Dec. 28, 1965, describes anthranilamides as CNS depressants. Japanese patent JP2000256358 describes pyrazole derivatives that block the calcium release-activated calcium channel. EP application 9475000, published Oct. 6, 1999, describes compounds as PGE$_2$ antagonists. PCT publication WO96/41795, published Dec. 27, 1996, describes benzamides as vasopressin antagonists. WO01/29009 describes aminopyridines as KDR inhibitors. WO01/30745 describes anthranilic acids as cGMP phosphodiesterase inhibitors. WO00/

02851, published Jan. 20, 2000 describes arylsulfonylamnoaryl amides as guanylate cyclase activators. WO98/45268 describes nicotinamide derivatives as PDE4 inhibitors. WO98/24771 describes benzamides as vasopressin antagonists.

U.S. Pat. No. 5,532,358, issued Jul. 2, 1996, describes the preparation of 2-(cyclopropylamino)-N-(2-methoxy-4-methyl-3-pyridinyl)-3-pyridinecarboxamide as an intermediate for HIV inhibitors. Triazine-substituted amines are described for their aggregating ability (J. Amer. Chem. Soc., 115, 905–16 (1993). Substituted imidazolines were tested for their antidepressant activity in Ind. J. Het. Chem., 2, 129–32 (1992). N-(4-Pyridyl) anthranilic amides were described in Chem Abstr. 97:109837 (1981). PCT publication WO99/32477, published Jul. 1, 1999, describes anthranilamides as anti-coagulants. U.S. Pat. No. 6,140,351 describes anthranilamides as anti-coagulants. PCT publication WO99/62885, published Dec. 9, 1999, describes 1-(4-aminophenyl)pyrazoles as antiinflammatories. PCT publication WO00/39111, published Jul. 6, 2000, describes amides as factor Xa inhibitors. PCT publication WO00/39117, published Jul. 6, 2000, describes heteroaromatic amides as factor Xa inhibitors. PCT publication WO00/27819, published May 18, 2000, describes anthranilic acid amides as VEGF inhibitors. PCT publication WO00/27820 published May 18, 2000, describes N-aryl anthranilic acid amides as VEGF inhibitors. 7-Chloroquinolinylamines are described in FR2168227 as antiinflammatories. WO01/55114, published Aug. 2, 2001, describes nicotinamides for the treatment of cancer. WO01/55115, published Aug. 2, 2001, describes nicotinamides for the treatment of apoptosis. WO01/85715, published Nov. 15, 2001, describes substituted pyridines and pyrimidines as anti-angiogenesis agents. PCT publication WO01/85691 published Nov. 15, 2001, describes anthranilic amides as VEGF inhibitors. PCT publication WO01/85671 published Nov. 15, 2001, describes anthranyl amides as VEGF inhibitors. PCT publication WO01/81311 published Nov. 1, 2001, describes anthranilic amides as VEGF inhibitors. However, compounds of the current invention have not been described as inhibitors of angiogenesis such as for the treatment of cancer.

DESCRIPTION OF THE INVENTION

A class of compounds useful in treating cancer and angiogenesis is defined by Formula I

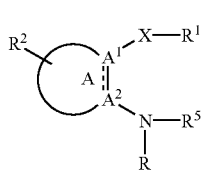

I wherein each of $A^1$ and $A^2$ is independently C, CH or N;
wherein ring A is selected from
   a) 5- or 6-membered partially saturated heterocyclyl, preferably dihydropyran, dihydrothienyl, dihydrofuryl, oxo-dihydrofuryl, pyrrolinyl, dihydrothiazolyl, dihydro-oxazolyl, dihydro-isothiazolyl, dihydro-isoxazolyl, imidazolinyl and pyrazolinyl,
   b) 5- or 6-membered heteroaryl,
      preferably
      I) 5-membered heteroaryl selected from thienyl, furanyl, pyrrolyl, thiazolyl, oxazolyl, imidazolyl, pyrazolyl, isoxazolyl, triazolyl and isothiazolyl, even more preferably 5-membered heteroaryl selected from

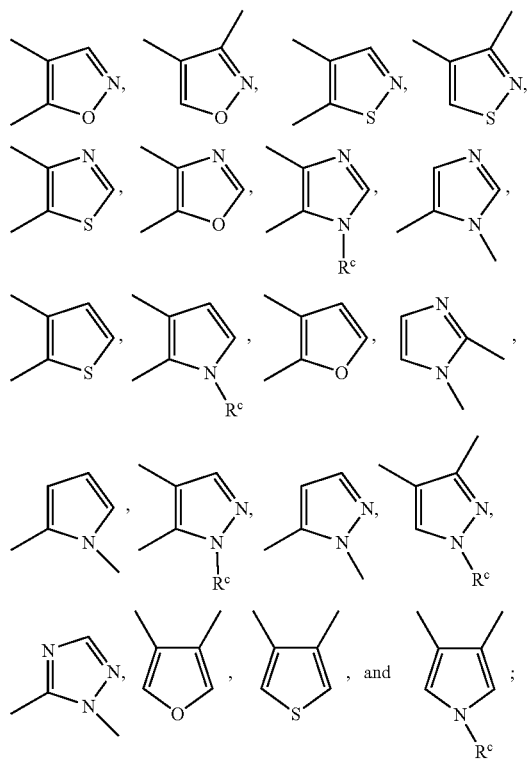

specifically

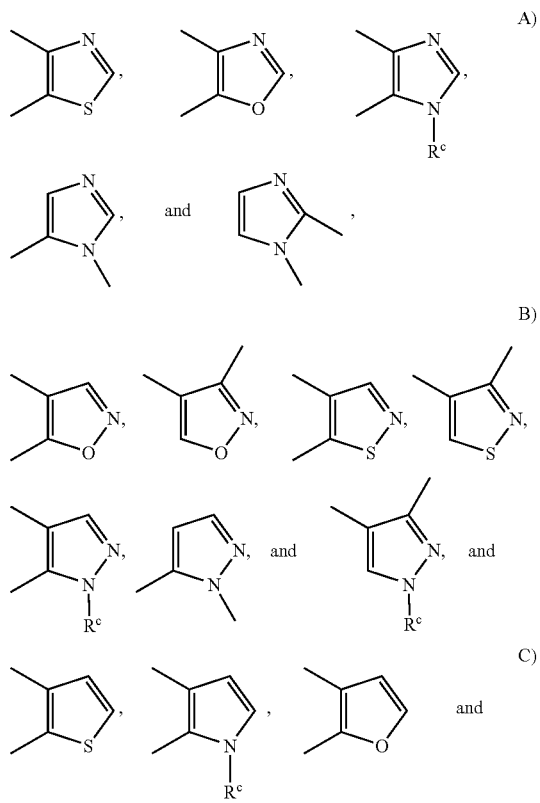

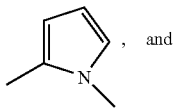

II) preferably 6-membered heteroaryl selected from pyridyl, pyrazinyl, pyrimidinyl, pyridazinyl, and triazinyl, even more preferably 6-membered heteroaryl selected from

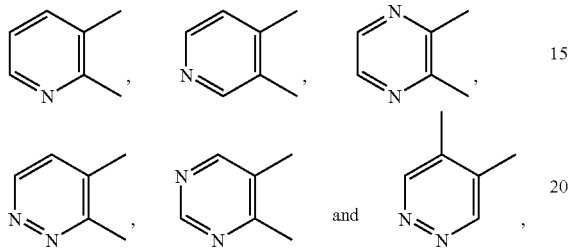

more specifically

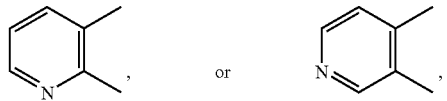

c) 9-, 10- or 11-membered fused partially saturated heterocyclyl,
    preferably tetrahydroquinolinyl,
d) 9- or 10-membered fused heteroaryl,
    preferably
        i) fused 9-membered fused heteroaryl selected from benzothienyl, benzothiazolyl, indolyl, benzimidazolyl, benzoxazolyl, benzofuryl, indazolyl and isoindolyl, and
        ii) fused 10-membered heteroaryl selected from quinolyl, isoquinolyl, naphthpyridinyl, quinoxalinyl and quinazolinyl,
e) aryl, and
f) 4-, 5- or 6-membered cycloalkenyl,
    preferably 5-membered cycloalkenyl,
        more preferably cyclopentadienyl or cyclopentenyl;
wherein X is

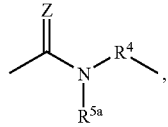

preferably X is selected from

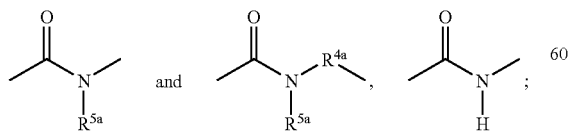

more preferably X is
wherein Z is oxygen or sulfur;
wherein R is selected from a) substituted or unsubstituted 4–6 membered heterocyclyl,
    preferably substituted or unsubstituted 5–6 membered heteroaryl comprising one or more nitrogen atoms,
        more preferably pyrazolyl, triazolyl, pyridyl, pyrimidinyl, and pyridazinyl,
            even more preferably 4-pyridyl, 3-pyridyl, 2-pyridyl, triazolyl, 4-pyrimidinyl and 4-pyridazinyl,
                most preferably 4-pyridyl,
b) substituted aryl,
    preferably substituted phenyl,
        more preferably optionally substituted (heterocyclyl-substituted phenyl), and
c) substituted or unsubstituted 9–14-membered bicyclic or tricyclic heterocyclyl,
    preferably substituted or unsubstituted 9–10 membered bicyclic or 13–14 membered tricyclic heterocyclyl,
        more preferably substituted or unsubstituted 9–10 membered fused heterocyclyl,
            even more preferably indazolyl, indolyl, isoindolyl, quinolinyl, isoquinolinyl, benzotriazolyl, 2,3-dihydrobenzofuryl, 1,2-dihydroquinolyl, naphthyridinyl and quinazolinyl,
            even more preferably 5-indazolyl, 6-indazolyl, 4-quinolyl, 5-quinolyl, 6-quinolyl, indolyl, isoindolyl, benzotriazolyl, 2,3-dihydrobenzofuryl, 1,2-dihydroquinolyl, quinozalinyl, 4-isoquinolyl, 5-isoquinolyl, naphthyridinyl and 6-isoquinolyl,
            especially preferred is 6-indazolyl;
wherein substituted R is substituted with one or more substituents independently selected from halo, —$OR^3$, —$SR^3$, —$SO_2R^3$, —$CO_2R^3$, —$CONR^3R^3$, —$COR^3$, —$NR^3R^3$, —$SO_2NR^3R^3$, —$NR^3C(O)OR^3$, —$NR^3C(O)R^3$, —$NR^3C(O)NR^3R^3$, cycloalkyl, optionally substituted 4–6 membered heterocyclyl, optionally substituted phenyl, nitro, oxo, alkylaminoalkoxyalkoxy, cyano, alkylaminoalkoxy, lower alkyl substituted with $R^2$, lower alkenyl substituted with $R^2$, and lower alkynyl substituted with $R^2$;
    preferably halo, —$OR^3$, —$SR^3$, —$SO_2R^3$, —$CO_2R^3$, —$CONR^3R^3$, —$COR^3$, —$NR^3R^3$, —$SO_2NR^3R^3$, —$NR^3C(O)OR^3$, —$NR^3C(O)R^3$, $C_{3-6}$-cycloalkyl, optionally substituted 4–6 membered heterocyclyl, optionally substituted phenyl, nitro, $C_{1-4}$-alkylamino-$C_{1-4}$-alkoxy-$C_{1-4}$-alkoxy, cyano, $C_{1-4}$-alkylamino-$C_{1-4}$-alkoxy, $C_{1-2}$-alkyl substituted with $R^2$, $C_{2-3}$-alkenyl substituted with $R^2$, and $C_{2-3}$-alkynyl substituted with $R^2$,
        more preferably halo, hydroxy, $C_{1-4}$-alkyl, $C_{1-2}$-alkoxy, optionally substituted 4–6 membered heterocyclyl-$C_{1-2}$-alkoxy, amino, $C_{1-2}$-alkylamino, aminosulfonyl, —$NR^3C(O)R^3$, —$NR^3C(O)R^3$, $C_{3-6}$-cycloalkyl, optionally substituted 4–6 membered heterocyclyl, optionally substituted phenyl, nitro, $C_{1-2}$-alkylamino-$C_{1-2}$-alkoxy-$C_{1-2}$-alkoxy, cyano, $C_{1-2}$-alkylamino-$C_{1-2}$-alkoxy, $C_{1-2}$-alkylamino-$C_{1-2}$-alkyl, $C_{1-2}$-alkylamino-$C_{2-3}$-alkynyl, $C_{1-2}$-hydroxyalkyl, $C_{1-2}$-aminoalkyl, $C_{1-2}$-haloalkyl, optionally substituted 4–6 membered heterocyclyl-$C_{2-3}$-alkenyl, and optionally substituted 4–6 membered heterocyclyl-$C_{2-3}$-alkynyl,
            even more preferably chloro, fluoro, bromo, hydroxy, methoxy, ethoxy, amino, dimethylamino, diethylamino, 1-methylpiperidinylmethoxy, aminosulfonyl, cyclohexyl, dimethylaminopropynyl, dimethylaminoethoxy, 3-(4-morpholinyl)propyn-1-yl, dimethylaminoethoxyethoxy, optionally substituted piperidinyl, morpholinyl, optionally substituted piperazinyl, optionally substituted phenyl, methyl, ethyl, propyl, cyano, hydroxymethyl, aminomethyl, nitro and trifluoromethyl;

wherein $R^1$ is selected from
  a) substituted or unsubstituted 6–10 membered aryl,
     preferably phenyl, naphthyl, indanyl, indenyl and tetrahydronaphthyl,
       more preferably phenyl, tetrahydronaphthyl, and naphthyl,
  b) substituted or unsubstituted 4–6 membered heterocyclyl,
     preferably 5–6 membered heteroaryl,
       more preferably isoxazolyl, pyrazolyl, thiazolyl, thiadiazolyl, thienyl, pyridyl, pyrimidinyl, pyridazinyl, imidazolyl, oxazolyl, furyl and pyrrolyl,
  c) substituted or unsubstituted 9–14 membered bicyclic or tricyclic heterocyclyl,
     preferably 9–10 membered bicyclic or 13–14 membered tricyclic heterocyclyl,
       more preferably indazolyl, indolyl, isoindolyl, 2,3-dihydro-1H-indolyl, naphthyridinyl, 2,1,3-benzothiadiazolyl, isoquinolyl, quinolyl, 1,2-dihydroquinolyl, 1,2,3,4-tetrahydro-isoquinolyl, 2,3,4,4a,9,9a-hexahydro-1H-3-aza-fluorenyl, 5,6,7-trihydro-1,2,4-triazolo[3,4-a]isoquinolyl, benzo[d]isothiazolyl, benzothienyl, tetrahydroquinolyl, benzofuryl, dihydrobenimidazolyl, benzimidazolyl, benzoxazolyl, benzthiazolyl, benzodioxanyl and quinazolinyl,
  d) cycloalkyl,
     preferably $C_{3-6}$-cycloalkyl,
       more preferably cyclohexyl, and
  e) cycloalkenyl,
     wherein substituted $R^1$ is substituted with one or more substituents independently selected from halo, oxo, —$OR^3$, —$SR^3$, —$CO_2R^3$, —$CONR^3R^3$, —$COR^3$, —$NR^3R^3$, —$NH(C_1$–$C_4$ alkylenyl$R^{14}$), —$SO_2R^3$, —$SO_2NR^3R^3$, —$NR^3C(O)OR^3$, —$NR^3C(O)R^3$, —$NR^3C(O)NR^3R^3$, optionally substituted cycloalkyl, optionally substituted 4–6 membered heterocyclyl, optionally substituted phenyl, halosulfonyl, cyano, alkylaminoalkoxy, alkylaminoalkoxyalkoxy, nitro, lower alkyl substituted with $R^2$, lower alkenyl substituted with $R^2$, and lower alkynyl substituted with $R^2$,
       preferably halo, —$OR^3$, oxo, —$SR^3$, —$SO_2R^3$, —$CO_2R^3$, —$CONR^3R^3$, —$COR^3$, —$NR^3R^3$, —$NH(C_1$–$C_4$ alkylenyl$R^3$), —$(C_1$–$C_4$ alkylenyl)$NR^3R^3$, —$SO_2NR^3R^3$, —$NR^3C(O)OR^3$, —$NR^3C(O)R^3$, $C_{1-6}$-alkylamino-$C_{1-6}$-alkoxy, $C_{1-6}$-alkylamino-$C_{1-6}$-alkoxy-$C_{1-6}$-alkoxy, halosulfonyl, optionally substituted 4–6 membered heterocyclylcarbonylalkyl, $C_{1-4}$-alkoxycarbonylamino-$C_{1-6}$-alkyl,

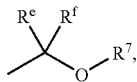

optionally substituted $C_{3-6}$-cycloalkyl, optionally substituted 4–6 membered heterocyclyl, optionally substituted phenyl, optionally substituted phenyl-$C_{1-6}$-alkylenyl, optionally substituted 4–6 membered heterocyclyl-$C_{1-}C_6$-alkylenyl, 4–6 membered heterocyclyl-$C_{2-}C_6$-alkenylenyl, $C_{1-4}$-alkyl, cyano, $C_{1-4}$-hydroxyalkyl, nitro and $C_{1-4}$-haloalkyl,
  more preferably halo, $C_{1-4}$-alkyl, optionally substituted $C_{3-6}$-cycloalkyl, optionally substituted phenyl, optionally substituted phenyl-$C_{1-}C_4$-alkylenyl, $C_{1-2}$-haloalkoxy, optionally substituted phenyloxy, optionally substituted 4–6 membered heterocyclyl-$C_1$-$C_4$-alkylenyl, optionally substituted 4–6 membered heterocyclyl-$C_2$-$C_4$-alkenylenyl, optionally substituted 4–6 membered heterocyclyl, optionally substituted 4–6 membered heterocyclyloxy, optionally substituted 4–6 membered heterocyclylsulfonyl, optionally substituted 4–6 membered heterocyclylamino, optionally substituted 4–6 membered heterocyclylcarbonyl, optionally substituted 4–6 membered heterocyclyl-$C_{1-4}$-alkylcarbonyl, $C_{1-2}$-haloalkyl, $C_{1-4}$-aminoalkyl, nitro, amino, hydroxy, oxo, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-4}$-hydroxyalkyl,

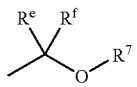

and $C_{1-4}$-alkoxy, and
  even more preferably bromo, chloro, fluoro, iodo, nitro, amino, cyano, aminoethyl, Boc-aminoethyl, hydroxy, oxo, aminosulfonyl, 4-methylpiperazinylsulfonyl, cyclohexyl, phenyl, phenylmethyl, morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, fluorosulfonyl, methylsulfonyl, methylcarbonyl, Boc, piperidin-1-ylmethylcarbonyl, 4-methylpiperazin-1-ylcarbonylethyl, methoxycarbonyl, aminomethylcarbonyl, dimethylaminomethylcarbonyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperdin-4-ylmethoxy, piperdin-4-ylmethoxy, 1-methylpiperdin-4-yloxy, isopropoxy, methoxy and ethoxy;

wherein $R^2$ is one or more substituents independently selected from H, halo, —$OR^3$, oxo, —$SR^3$, —$CO_2R^3$, —$COR^3$, —$CONR^3R^3$, —$NR^3R^3$, —$SO_2NR^3R^3$, —$NR^3C(O)OR^3$, —$NR^3C(O)R^3$, cycloalkyl, optionally substituted phenylalkyl, optionally substituted 4–6 membered heterocyclyl, optionally substituted heteroarylalkyl, optionally substituted phenyl, lower alkyl, cyano, lower hydroxyalkyl, lower carboxyalkyl, nitro, lower alkenyl, lower alkynyl, $C_{1-4}$-alkoxy-$C_{1-4}$-alkoxy and $C_{1-4}$-alkoxy-$C_{1-4}$-alkoxy-$C_{1-4}$-alkoxy, lower aminoalkyl, lower alkylaminoalkyl and lower haloalkyl, preferably H, halo, —$OR^3$, —$SR^3$, —$CO_2R^3$, —$CONR^3R^3$, —$COR^3$, —$NR^3R^3$, —$SO_2NR^3R^3$, —$NR^3C(O)OR^3$, —$NR^3C(O)R^3$, $C_{3-6}$-cycloalkyl, optionally substituted 4–6 membered heterocyclyl, optionally substituted phenyl, $C_{1-6}$-alkyl, cyano, $C_{1-4}$-hydroxyalkyl, $C_{1-4}$-carboxyalkyl, nitro, $C_{1-3}$-alkoxy-$C_{1-2}$-alkoxy, $C_{1-3}$-alkoxy-$C_{1-3}$-alkoxy-$C_{1-3}$-alkoxy, $C_{2-3}$-alkenyl, $C_{2-3}$-alkynyl and $C_{1-4}$-haloalkyl, more preferably H, halo, hydroxy, $C_{1-2}$-alkoxy, $C_{1-2}$-haloalkoxy, amino, $C_{1-2}$-alkylamino, optionally substituted 4–6 membered heterocyclyl-$C_{1-2}$-alkylamino, aminosulfonyl, $C_{3-6}$-cycloalkyl, optionally substituted 4–6 membered heterocyclyl, optionally substituted phenyl, $C_{1-4}$-alkyl, cyano, $C_{1-2}$-hydroxyalkyl, $C_{1-3}$-carboxyalkyl, nitro, $C_{2-3}$-alkenyl, $C_{2-3}$-alkynyl and $C_{1-2}$-haloalkyl, and even more preferably H, chloro, fluoro, bromo, hydroxy, methoxy, ethoxy, trifluoromethoxy, amino, dimethylamino, aminosulfonyl, carboxymethyl, cyclopropyl, optionally substituted phenyl, methyl, ethyl, propyl, cyano, hydroxymethyl, nitro, propenyl, propynyl and trifluoromethyl and unsubstituted or substituted heteroaryl selected from thienyl, furanyl, pyridyl, imidazolyl, and pyrazolyl;

wherein $R^3$ is selected from H, lower alkyl, optionally substituted phenyl, optionally substituted 3–6 membered heterocyclyl, optionally substituted $C_3$–$C_6$-cycloalkyl, optionally substituted phenylalkyl, optionally substituted 3–6 membered heterocyclylalkyl, optionally substituted $C_3$–$C_6$ cycloalkylalkyl, and lower haloalkyl, preferably H, $C_{1-4}$-alkyl, optionally substituted phenyl, optionally substituted phenyl-$C_{1-4}$-alkyl, optionally substituted 4–6 membered heterocyclyl, optionally substituted 4–6 membered heterocyclyl-$C_{1-4}$-alkyl, optionally substituted $C_3$–$C_6$ cycloalkyl and $C_{1-2}$-haloalkyl, more preferably H, methyl, phenyl, cyclopropyl, cyclohexyl, benzyl, morpholinylmethyl, 4-methylpiperazinylmethyl, azetidinyl, azetidinylmethyl, 4-methylpiperdinylmethyl, 4-morpholinylmethyl, 4-morpholinylethyl, 1-(4-morpholinyl)-2,2-dimethylpropyl, 1-piperdinylethyl, 1-piperdinylpropyl, 1-pyrrolidinylpropyl and trifluoromethyl;

wherein $R^4$ is independently selected from a direct bond, $C_{2-4}$-alkylenyl, $C_{2-4}$-alkenylenyl and $C_{2-4}$-alkynylenyl, where one of the $CH_2$ groups may be replaced with an oxygen atom or an —NH—, wherein $R^4$ is optionally substituted with hydroxy, preferably a direct bond or $R^{4a}$;

wherein $R^{4a}$ is selected from $C_{2-4}$-alkylenyl where one of the $CH_2$ groups may be replaced with an oxygen atom or an —NH—, wherein $R^{4a}$ is optionally substituted with hydroxy;

preferably ethyl, butyl, and

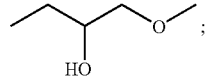

wherein $R^5$ is selected from H, lower alkyl, optionally substituted phenyl and optionally substituted lower aralkyl, preferably H, methyl or ethyl, more preferably H;

wherein $R^{5a}$ is selected from H, lower alkyl, optionally substituted phenyl and lower aralkyl, preferably H, methyl or ethyl, more preferably H;

wherein $R^7$ is selected from H, $C_{1-6}$-alkyl, optionally substituted phenyl, optionally substituted phenyl-$C_{1-6}$-alkyl, optionally substituted cycloalkyl, optionally substituted cycloalkyl-alkyl, optionally substituted 4–6 membered heterocyclyl, optionally substituted 4–6 membered heterocyclyl-$C_{1-}C_6$-alkyl, $C_{1-4}$-alkoxy-$C_{1-4}$-alkyl and $C_{1-4}$-alkoxy-$C_{1-4}$-alkoxy-$C_{1-4}$-alkyl, preferably H, $C_{1-3}$-alkyl, optionally substituted phenyl, optionally substituted phenyl-$C_{1-3}$-alkyl, optionally substituted 4–6 membered heterocyclyl, optionally substituted 4–6 membered heterocyclyl-$C_{1-}C_3$-alkyl, $C_{1-3}$-alkoxy-$C_{1-2}$-alkyl and $C_{1-3}$-alkoxy-$C_{1-3}$-alkoxy-$C_{1-3}$-alkyl;

wherein $R^c$ is selected from H, methyl and optionally substituted phenyl; and wherein $R^e$ and $R^f$ are independently selected from H and $C_{1-2}$-haloalkyl, preferably —$CF_3$;

wherein $R^{14}$ is selected from H, optionally substituted phenyl, optionally substituted 4–6 membered heterocyclyl and optionally substituted $C_3$–$C_6$ cycloalkyl;

provided A is not pyridyl when X is —C(O)NH— and when $R^1$ is 4-[3,5-bis(trifluoromethyl)-1H-pyrazol-1-yl]phenyl when $R^5$ is methyl and when R is 4-methylpiperidyl;

further provided A is not pyridyl when X is —C(O)NH—, when $R^5$ is H, when $R^2$ is 6-methyl and when R is indazolyl;

further provided A is not phenyl when X is —C(O)NH—, when $R^1$ is phenyl, 4-bromophenyl, 2-methylphenyl, 4-methoxyphenyl, when $R^5$ is H and when R is 4-pyridyl;

further provided A is not phenyl when X is —C(O)NH—, when $R^1$ is phenyl, when $R^5$ is H and when R is 2-oxobenzopyan-4-yl;

further provided A is not phenyl when X is —C(O)NH—, when $R^1$ is phenyl, 4-chlorophenyl, 3-nitrophenyl, 4-methoxyphenyl, when $R^5$ is H and when R is 4-imidazolinyl;

further provided A is not phenyl when X is —C(O)NH—, when $R^5$ is H, when $R^5$ is substituted benzyl and when R is substituted triazinyl;

further provided A is not phenyl when X is —C(O)NH—, when $R^1$ is phenyl or 2-chlorophenyl, when $R^5$ is H and when R is 4-quinazolinyl;

further provided A is not phenyl when X is —C(O)NH—, when $R^1$ is phenyl, when $R^5$ is H and when R is isoquinolin-1-yl;

further provided A is not phenyl when X is —C(O)NH—, when $R^1$ is 2-chlorophenyl or 4-chlorophenyl, when $R^5$ is H and when R is 3-chloroisoquinolin-1-yl;

further provided A is not phenyl when X is —C(O)NH—, when $R^1$ is 1-ethylpiperid-3-yl or 1-ethylpiperid-4-yl, when $R^5$ is H and when R is 8-trifluoromethylquinolin-4-yl;

further provided A is not phenyl when X is —C(O)NH—, when $R^1$ is 1-ethylpiperid-3-yl, when $R^5$ is H and when R is 8-chloroquinolin-4-yl;

further provided A is not phenyl when X is —C(O)NH—, when $R^1$ is halo substituted phenyl, 1-butylpiperid-4-yl, 1-ethylpiperid-3-yl or 1-ethylpiperid-4-yl, when $R^5$ is H and when R is 7-chloroquinolin-4-yl; and further provided R is not unsubstituted 2-thienyl, unsubstituted 2-pyridyl or unsubstituted 3-pyridyl.

The invention also relates to compounds of Formula II

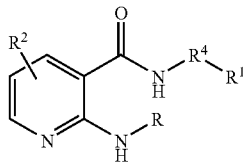

II wherein R is selected from unsubstituted or substituted 9-or 10-membered fused nitrogen-containing heteroaryl,
  preferably indolyl, isoindolyl, indazolyl, quinolyl, isoquinolyl, naphthyridinyl and quinozalinyl,
  more preferably 6-indazolyl,
  where R is substituted with one or more substituents selected from halo, amino, hydroxy, $C_{1-6}$-alkyl, $C_{1-6}$-haloalkyl, $C_{1-6}$-alkoxy, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, optionally substituted heterocyclyl-$C_{2-4}$-alkynyl, and optionally substituted heterocyclylalkoxy,
    preferably chloro, fluoro, amino, hydroxy, methyl, ethyl, propyl, trifluoromethyl, dimethylaminopropynyl, 1-methylpiperdinylmethoxy, dimethylaminoethoxyethoxy, methoxy and ethoxy;

wherein $R^1$ is selected from unsubstituted or substituted aryl,
  preferably phenyl, tetrahydronaphthyl, indanyl, indenyl and naphthyl,
cycloalkyl,
  preferably cyclohexyl,
4–6 membered heterocyclyl,
  preferably isoxazolyl, pyrazolyl, thiazolyl, thiadiazolyl, thienyl, pyridyl, pyrimidinyl and pyridazinyl, and
9–10 membered bicyclic and 13–14 membered tricyclic heterocyclyl,
  preferably 1,2-dihydroquinolyl, 1,2,3,4-tetrahydro-isoquinolyl, isoquinolyl, quinolyl, indolyl, isoindolyl, 2,3-dihydro-1H-indolyl, naphthyridinyl, quinozalinyl, benzo[d]isothiazolyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, 2,1,3-benzothiadiazolyl, benzodioxanyl, benzothienyl, benzofuryl, benzimidazolyl, benzoxazolyl and benzthiazolyl;

wherein substituted $R^1$ is substituted with one or more substituents selected from halo, $C_{1-4}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4–6 membered heterocyclyl-$C_1$-$C_4$-alkylenyl, optionally substituted 4–6 membered heterocyclyl-$C_2$-$C_4$-alkenylenyl, optionally substituted 4–6 membered heterocyclyl, optionally substituted 4–6 membered heterocyclyloxy, optionally substituted 4–6 membered heterocyclyl-$C_{1-4}$-alkoxy, optionally substituted 4–6 membered heterocyclylsulfonyl, optionally substituted 4–6 membered heterocyclylamino, optionally substituted 4–6 membered heterocyclylcarbonyl, optionally substituted 4–6 membered heterocyclyl-$C_{1-4}$-alkylcarbonyl, $C_{1-2}$-haloalkyl, $C_{1-4}$-aminoalkyl, nitro, amino, hydroxy, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-4}$-hydroxyalkyl,

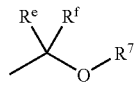

and $C_{1-4}$-alkoxy,
preferably bromo, chloro, fluoro, iodo, nitro, amino, cyano, aminoethyl, Boc-aminoethyl, hydroxy, oxo, aminosulfonyl, 4-methylpiperazinylsulfonyl, cyclohexyl, phenyl, phenylmethyl, morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, fluorosulfonyl, methylsulfonyl, methylcarbonyl, Boc, piperidin-1-ylmethylcarbonyl, 4-methylpiperazin-1-ylcarbonylethyl, methoxycarbonyl, aminomethylcarbonyl, dimethylaminomethylcarbonyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperdin-4-ylmethoxy, piperdin-4-ylmethoxy, 1-methylpiperdin-4-yloxy, isopropoxy, methoxy and ethoxy;

wherein $R^2$ is one or more substituents independently selected from

H, halo, hydroxy, amino, $C_{1-6}$-alkyl, $C_{1-6}$-haloalkyl, $C_{1-6}$-alkoxy, $C_{1-2}$-alkylamino, aminosulfonyl, $C_{3-6}$-cycloalkyl, cyano, $C_{1-2}$-hydroxyalkyl, nitro, $C_{2-3}$-alkenyl, $C_{2-3}$-alkynyl, $C_{1-6}$-haloalkoxy, $C_{1-6}$-carboxyalkyl, 5–6-membered heterocyclyl-$C_{1-6}$-alkylamino, unsubstituted or substituted phenyl and unsubstituted or substituted 4–6 membered heterocyclyl;

preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from thienyl, furanyl, pyridyl, imidazolyl, and pyrazolyl;

wherein $R^4$ is selected from a direct bond, $C_{1-4}$-alkyl, and

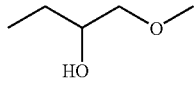

preferably direct bond, ethyl, butyl, and

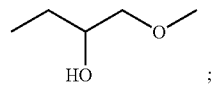

wherein $R^e$ and $R^f$ are independently selected from H and $C_{1-2}$-haloalkyl, preferably —$CF_3$; and wherein $R^7$ is selected from H, $C_{1-3}$-alkyl, optionally substituted phenyl, optionally substituted phenyl-$C_{1-3}$-alkyl, optionally substituted 4–6 membered heterocyclyl, optionally substituted 4–6 membered heterocyclyl-$C_1C_3$-alkyl, $C_{1-3}$-alkoxy-$C_{1-2}$-alkyl and $C_{1-3}$-alkoxy-$C_{1-3}$-alkoxy-$C_{1-3}$-alkyl.

The invention also relates to compounds of Formula III

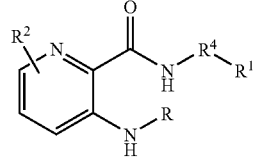

III wherein R is selected from unsubstituted or substituted 9- or 10-membered fused nitrogen-containing heteroaryl, preferably indolyl, isoindolyl, indazolyl, quinolyl, isoquinolyl, naphthyridinyl and quinozalinyl, more preferably 5-indazolyl and 6-indazolyl, even more preferably 6-indazolyl, where R is substituted with one or more substituents selected from halo, amino, hydroxy, $C_{1-6}$-alkyl, $C_{1-6}$-haloalkyl, $C_{1-6}$-alkoxy, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, optionally substituted heterocyclyl-$C_{2-4}$-alkynyl, and optionally substituted heterocyclylalkoxy, preferably chloro, fluoro, amino, hydroxy, methyl, ethyl, propyl, trifluoromethyl, dimethylaminopropynyl, 1-methylpiperdinylmethoxy, dimethylaminoethoxyethoxy, methoxy and ethoxy;

wherein $R^1$ is selected from unsubstituted or substituted aryl, preferably phenyl, tetrahydronaphthyl, indanyl, indenyl and naphthyl, cycloalkyl, preferably cyclohexyl, 4–6 membered heterocyclyl, preferably isoxazolyl, pyrazolyl, thiazolyl, thiadiazolyl, thienyl, pyridyl, pyrimidinyl and pyridazinyl, and 9–10 membered bicyclic and 13–14 membered tricyclic heterocyclyl, preferably 1,2-dihydroquinolyl, 1,2,3,4-tetrahydroisoquinolyl, isoquinolyl, quinolyl, indolyl, isoindolyl, 2,3-dihydro-1H-indolyl, naphthyridinyl, quinozalinyl, benzo[d]isothiazolyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, 2,1,3-benzothiadiazolyl, benzodioxanyl, benzothienyl, benzofuryl, benzimidazolyl, benzoxazolyl and benzthiazolyl;

wherein R¹ is substituted with one or more substituents selected from halo, $C_{1-4}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4–6 membered heterocyclyl-$C_1$-$C_4$-alkyl, optionally substituted 4–6 membered heterocyclyl-$C_2$-$C_4$-alkenylenyl, optionally substituted 4–6 membered heterocyclyl, optionally substituted 4–6 membered heterocylyloxy, optionally substituted 4–6 membered heterocyclyl-$C_{1-4}$-alkoxy, optionally substituted 4–6 membered heterocyclylsulfonyl, optionally substituted 4–6 membered heterocyclylamino, optionally substituted 4–6 membered heterocyclylcarbonyl, optionally substituted 4–6 membered heterocyclyl-$C_{1-4}$-alkylcarbonyl, $C_{1-2}$-haloalkyl, $C_{1-4}$-aminoalkyl, nitro, amino, hydroxy, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-4}$-hydroxyalkyl,

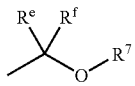

and $C_{1-4}$-alkoxy, preferably bromo, chloro, fluoro, iodo, nitro, amino, cyano, aminoethyl, Boc-aminoethyl, hydroxy, aminosulfonyl, 4-methylpiperazinylsulfonyl, cyclohexyl, phenyl, phenylmethyl, morpholinylmethyl, methylpiperazinylmethyl, methylpiperazinylpropyl, morpholinylpropyl, methylpiperidinylmethyl, morpholinylethyl, 1-(4-morpholinyl)-2,2-dimethylpropyl, piperidinylethyl, piperidinylmethyl, piperidinylpropyl, pyrrolidinylpropyl, pyrrolidinylpropenyl, pyrrolidinylbutenyl, fluorosulfonyl, methylsulfonyl, methylcarbonyl, piperidinylmethylcarbonyl, methylpiperazinylcarbonylethyl, methoxycarbonyl, 3-ethoxycarbonyl-2-methyl-fur-5-yl, methylpiperazinyl, methylpiperidyl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, 1-methylpiperdin-4-yloxy, isopropoxy, methoxy and ethoxy;

wherein R² is one or more substituents independently selected from
H,
halo,
hydroxy,
amino,
$C_{1-6}$-alkyl,
$C_{1-6}$-haloalkyl,
$C_{1-6}$-alkoxy,
$C_{1-2}$-alkylamino,
aminosulfonyl,
$C_{3-6}$-cycloalkyl,
cyano,
$C_{1-2}$-hydroxyalkyl,
nitro,
$C_{2-3}$-alkenyl,
$C_{2-3}$-alkynyl,
$C_{1-6}$-haloalkoxy,
$C_{1-6}$-carboxyalkyl,
5–6-membered heterocyclyl-$C_{1-6}$-alkylamino,
unsubstituted or substituted phenyl and
unsubstituted or substituted 4–6 membered heterocyclyl;

preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from
thienyl, furanyl, pyridyl, imidazolyl, and pyrazolyl;

wherein R⁴ is selected from a direct bond, $C_{1-4}$-alkyl, and

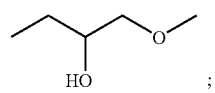

preferably direct bond, ethyl, butyl, and

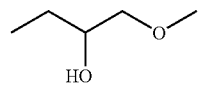

wherein $R^e$ and $R^f$ are independently selected from H and $C_{1-2}$-haloalkyl,
preferably —CF₃; and
wherein R⁷ is selected from H, $C_{1-3}$-alkyl, optionally substituted phenyl-$C_{1-3}$-alkyl, 4–6 membered heterocyclyl, optionally substituted 4–6 membered heterocyclyl-$C_1$-$C_3$-alkyl, $C_{1-3}$-alkoxy-$C_{1-2}$-alkyl and $C_{1-3}$-alkoxy-$C_{1-3}$-alkoxy-$C_{1-3}$-alkyl.

The invention also relates to compounds of Formula IV

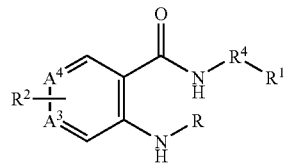

wherein A³ is selected from CR² and N;
wherein A⁴ is selected from CR² and N; provided one of A³ and A⁴ is not CR²;
wherein R is selected from
unsubstituted or substituted 9- or 10-membered fused nitrogen-containing heteroaryl,
preferably indolyl, isoindolyl, indazolyl, quinolyl, isoquinolyl, naphthyridinyl and quinozalinyl,
more preferably 5-indazolyl and 6-indazolyl,
even more preferably 6-indazolyl,
where R is substituted with one or more substituents selected from halo, amino, hydroxy, $C_{1-6}$-alkyl, $C_{1-6}$- haloalkyl, C$_{1-6}$-alkoxy, C$_{1-6}$-alkylamino-C$_{2-4}$-alkynyl, C$_{1-6}$-alkylamino-C$_{1-6}$-alkoxy, C$_{1-6}$-alkylamino-C$_{1-6}$-alkoxy-C$_{1-6}$-alkoxy, optionally substituted heterocyclyl-C$_{2-4}$-alkynyl, and optionally substituted heterocyclylalkoxy, preferably chloro, fluoro, amino, hydroxy, methyl, ethyl, propyl, trifluoromethyl, dimethylaminopropynyl, 1-methylpiperdinylmethoxy, dimethylaminoethoxyethoxy, methoxy and ethoxy;

wherein R$^1$ is selected from unsubstituted or substituted aryl, preferably phenyl, tetrahydronaphthyl, indanyl, indenyl and naphthyl, cycloalkyl, preferably cyclohexyl, 4–6 membered heterocyclyl, preferably isoxazolyl, pyrazolyl, thiazolyl, thiadiazolyl, thienyl, pyridyl, pyrimidinyl and pyridazinyl, and 9–10 membered bicyclic and 13–14 membered tricyclic heterocyclyl, preferably 1,2-dihydroquinolyl, 1,2,3,4-tetrahydro-isoquinolyl, isoquinolyl, quinolyl, indolyl, isoindolyl, 2,3-dihydro-1H-indolyl, naphthyridinyl, quinozalinyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, benzo[d]isothiazolyl, 2,1,3-benzothiadiazolyl, benzodioxanyl, benzothienyl, benzofuryl, benzimidazolyl, benzoxazolyl and benzthiazolyl;

wherein R$^1$ is substituted with one or more substituents selected from halo, C$_{1-4}$-alkyl, optionally substituted C$_{3-6}$-cycloalkyl, optionally substituted phenyl, optionally substituted phenyl-C$_1$-C$_4$-alkylenyl, C$_{1-2}$-haloalkoxy, optionally substituted phenyloxy, optionally substituted 4–6 membered heterocyclyl-C$_1$-C$_4$-alkylenyl, optionally substituted 4–6 membered heterocyclyl-C$_{2}$-C$_4$-alkenylenyl, optionally substituted 4–6 membered heterocyclyl, optionally substituted 4–6 membered heterocyclyloxy, optionally substituted 4–6 membered heterocyclyl-C$_{1-4}$-alkoxy, optionally substituted 4–6 membered heterocyclylsulfonyl, optionally substituted 4–6 membered heterocyclylamino, optionally substituted 4–6 membered heterocyclylcarbonyl, optionally substituted 4–6 membered heterocyclyl-C$_{1-4}$-alkylcarbonyl, C$_{1-2}$-haloalkyl, C$_{1-4}$-aminoalkyl, nitro, amino, hydroxy, cyano, aminosulfonyl, C$_{1-2}$-alkylsulfonyl, halosulfonyl, C$_{1-4}$-alkylcarbonyl, C$_{1-3}$-alkylamino-C$_{1-3}$-alkyl, C$_{1-3}$-alkylamino-C$_{1-3}$-alkoxy, C$_{1-3}$-alkylamino-C$_{1-3}$-alkoxy-C$_{1-3}$-alkoxy, C$_{1-4}$-alkoxycarbonyl, C$_{1-4}$-alkoxycarbonylamino-C$_{1-4}$-alkyl, C$_{1-4}$-hydroxyalkyl,

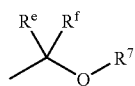

and C$_{1-4}$-alkoxy, preferably bromo, chloro, fluoro, iodo, nitro, amino, cyano, aminoethyl, Boc-aminoethyl, hydroxy, aminosulfonyl, 4-methylpiperazinylsulfonyl, cyclohexyl, phenyl, phenylmethyl, morpholinylmethyl, methylpiperazinylmethyl, methylpiperazinylpropyl, morpholinylpropyl, methylpiperidinylmethyl, morpholinylethyl, 1-(4-morpholinyl)-2,2-dimethylpropyl, piperidinylethyl, piperidinylmethyl, piperidinylpropyl, pyrrolidinylpropyl, pyrrolidinylpropenyl, pyrrolidinylbutenyl, fluorosulfonyl, methylsulfonyl, methylcarbonyl, piperidinylmethylcarbonyl, methylpiperazinylcarbonylethyl, methoxycarbonyl, 3-ethoxycarbonyl-2-methyl-fur-5-yl, methylpiperazinyl, methylpiperidyl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, 1-methylpiperdin-4-yloxy, isopropoxy, methoxy and ethoxy;

wherein R$^2$ is one or more substituents independently selected from

H, halo, hydroxy, amino,

C$_{1-6}$-alkyl,

C$_{1-6}$-haloalkyl,

C$_{1-6}$-alkoxy,

C$_{1-2}$-alkylamino, aminosulfonyl,

C$_{3-6}$-cycloalkyl, cyano,

C$_{1-2}$-hydroxyalkyl, nitro,

C$_{2-3}$-alkenyl,

C$_{2-3}$-alkynyl,

C$_{1-6}$-haloalkoxy,

C$_{1-6}$-carboxyalkyl,

5–6-membered heterocyclyl-C$_{1-6}$-alkylamino, unsubstituted or substituted phenyl and unsubstituted or substituted 4–6 membered heterocyclyl;

preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from thienyl, furanyl, pyridyl, imidazolyl, and pyrazolyl;

wherein R$^4$ is selected from a direct bond, C$_{1-4}$-alkyl, and

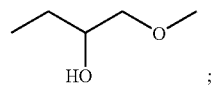

preferably direct bond, ethyl, butyl, and

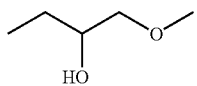

;

wherein $R^e$ and $R^f$ are independently selected from H and $C_{1-2}$-haloalkyl,
preferably —$CF_3$; and
wherein $R^7$ is selected from H, $C_{1-3}$-alkyl, optionally substituted phenyl-$C_{1-3}$-alkyl, 4–6 membered heterocyclyl, optionally substituted 4–6 membered heterocyclyl-$C_{1-3}$-alkyl, $C_{1-3}$-alkoxy-$C_{1-2}$-alkyl and $C_{1-3}$-alkoxy-$C_{1-3}$-alkoxy-$C_{1-3}$-alkyl.

The invention also relates to compounds of Formula V

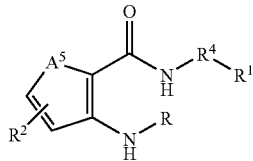

V wherein $A^5$ is selected from S, O and $NR^6$;
wherein R is selected from
  unsubstituted or substituted 9- or 10-membered fused nitrogen-containing heteroaryl,
    preferably indolyl, isoindolyl, indazolyl, quinolyl, isoquinolyl, naphthyridinyl and quinozalinyl,
    more preferably 5-indazolyl and 6-indazolyl, even more preferably 6-indazolyl,
  where R is substituted with one or more substituents selected from halo, amino, hydroxy, $C_{1-6}$-alkyl, $C_{1-6}$-haloalkyl, $C_{1-6}$-alkoxy, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, optionally substituted heterocyclyl-$C_{2-4}$-alkynyl, and optionally substituted heterocyclylalkoxy,
    preferably chloro, fluoro, amino, hydroxy, methyl, ethyl, propyl, trifluoromethyl, dimethylaminopropynyl, 1-methylpiperdinylmethoxy, dimethylaminoethoxyethoxy, methoxy and ethoxy;
wherein $R^1$ is selected from unsubstituted or substituted aryl,
  preferably phenyl, tetrahydronaphthyl, indanyl, indenyl and naphthyl,
cycloalkyl,
  preferably cyclohexyl,
4–6 membered heterocyclyl,
  preferably isoxazolyl, pyrazolyl, thiazolyl, thiadiazolyl, thienyl, pyridyl, pyrimidinyl and pyridazinyl, and
9–10 membered bicyclic and 13–14 membered tricyclic heterocyclyl,
  preferably 1,2-dihydroquinolyl, 1,2,3,4-tetrahydroisoquinolyl, isoquinolyl, quinolyl, indolyl, isoindolyl, 2,3-dihydro-1H-indolyl, naphthyridinyl, quinozalinyl, 2,3,4,4a,9,9a-hexahydro-1H-3-aza-fluorenyl, 5,6,7-trihydro-1,2,4-triazolo[3,4-a]isoquinolyl, benzo[d]isothiazolyl, tetrahydroquinolinyl, indazolyl, 2,1,3-benzothiadiazolyl, benzodioxanyl, benzothienyl, benzofuryl, benzimidazolyl, benzoxazolyl and benzthiazolyl;

wherein $R^1$ is substituted with one or more substituents selected from halo, $C_{1-4}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4–6 membered heterocyclyl-$C_1$-$C_4$-alkylenyl, optionally substituted 4–6 membered heterocyclyl-$C_2$-$C_4$-alkenylenyl, optionally substituted 4–6 membered heterocyclyl, optionally substituted 4–6 membered heterocyclyloxy, optionally substituted 4–6 membered heterocyclyl-$C_{1-4}$-alkoxy, optionally substituted 4–6 membered heterocyclylsulfonyl, optionally substituted 4–6 membered heterocyclylamino, optionally substituted 4–6 membered heterocyclylcarbonyl, optionally substituted 4–6 membered heterocyclyl-$C_{1-4}$-alkylcarbonyl, $C_{1-2}$-haloalkyl, $C_{1-4}$-aminoalkyl, nitro, amino, hydroxy, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-4}$-hydroxyalkyl,

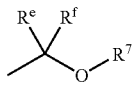

and $C_{1-4}$-alkoxy,
preferably bromo, chloro, fluoro, iodo, nitro, amino, cyano, aminoethyl, Boc-aminoethyl, hydroxy, aminosulfonyl, 4-methylpiperazinylsulfonyl, cyclohexyl, phenyl, phenylmethyl, morpholinylmethyl, methylpiperazinylmethyl, methylpiperazinylpropyl, morpholinylpropyl, methylpiperidinylmethyl, morpholinylethyl, 1-(4-morpholinyl)-2,2-dimethylpropyl, piperidinylethyl, piperidinylmethyl, piperidinylpropyl, pyrrolidinylpropyl, pyrrolidinylpropenyl, pyrrolidinylbutenyl, fluorosulfonyl, methylsulfonyl, methylcarbonyl, piperidinylmethylcarbonyl, methylpiperazinylcarbonylethyl, methoxycarbonyl, 3-ethoxycarbonyl-2-methyl-fur-5-yl, methylpiperazinyl, methylpiperidyl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, 1-methylpiperdin-4-yloxy, isopropoxy, methoxy and ethoxy;
wherein $R^2$ is one or more substituents independently selected from
H,
halo,
hydroxy,
amino,
$C_{1-6}$-alkyl,
$C_{1-6}$-haloalkyl,
$C_{1-6}$-alkoxy, $C_{1-2}$-alkylamino,
aminosulfonyl,
$C_{3-6}$-cycloalkyl,
cyano,
$C_{1-2}$-hydroxyalkyl,
nitro,
$C_{2-3}$-alkenyl,
$C_{2-3}$-alkynyl,
$C_{1-6}$-haloalkoxy,
$C_{1-6}$-carboxyalkyl,
5–6-membered heterocyclyl-$C_{1-6}$-alkylamino,
unsubstituted or substituted phenyl and
unsubstituted or substituted 4–6 membered heterocyclyl;
preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from
thienyl, furanyl, pyridyl, imidazolyl, and pyrazolyl;
wherein $R^4$ is selected from a direct bond, $C_{1-4}$-alkyl, and

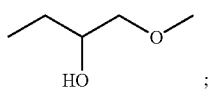

preferably direct bond, ethyl, butyl, and

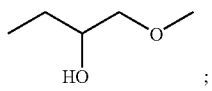

wherein $R^e$ and $R^f$ are independently selected from H and $C_{1-2}$-haloalkyl,
preferably —$CF_3$;
wherein $R^6$ is H or $C_{1-2}$-alkyl, preferably H or methyl; and
wherein $R^7$ is selected from H, $C_{1-3}$-alkyl, optionally substituted phenyl-$C_{1-3}$-alkyl, 4–6 membered heterocyclyl, optionally substituted 4–6 membered heterocyclyl-$C_{1-3}$-alkyl, $C_{1-3}$-alkoxy-$C_{1-2}$-alkyl and $C_{1-3}$-alkoxy-$C_{1-3}$-alkoxy-$C_{1-3}$-alkyl.

The invention also relates to compounds of Formula VI

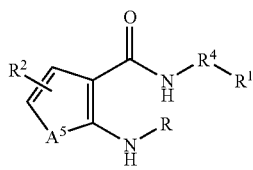

VI wherein $A^5$ is selected from S, O and $NR^6$;
wherein R is selected from
unsubstituted or substituted 9- or 10-membered fused nitrogen-containing heteroaryl,
preferably indolyl, isoindolyl, indazolyl, quinolyl, isoquinolyl, naphthyridinyl and quinozalinyl,
more preferably 5-indazolyl and 6-indazolyl,
even more preferably 6-indazolyl,
where R is substituted with one or more substituents selected from halo, amino, hydroxy, $C_{1-6}$-alkyl, $C_{1-6}$-haloalkyl, $C_{1-6}$-alkoxy, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, optionally substituted heterocyclyl-$C_{2-4}$-alkynyl, and optionally substituted heterocyclylalkoxy,
preferably chloro, fluoro, amino, hydroxy, methyl, ethyl, propyl, trifluoromethyl, dimethylaminopropynyl, 1-methylpiperdinylmethoxy, dimethylaminoethoxyethoxy, methoxy and ethoxy;
wherein $R^1$ is selected from unsubstituted or substituted aryl,
preferably phenyl, tetrahydronaphthyl, indanyl, indenyl and naphthyl,
cycloalkyl,
preferably cyclohexyl,
4–6 membered heterocyclyl,
preferably isoxazolyl, pyrazolyl, thiazolyl, thiadiazolyl, thienyl, pyridyl, pyrimidinyl and pyridazinyl, and
9–10 membered bicyclic and 13–14 membered tricyclic heterocyclyl,
preferably 1,2-dihydroquinolyl, 1,2,3,4-tetrahydroisoquinolyl, isoquinolyl, quinolyl, indolyl, isoindolyl, 2,3-dihydro-1H-indolyl, naphthyridinyl, quinozalinyl, 2,3,4,4a,9,9a-hexahydro-1H-3-aza-fluorenyl, 5,6,7-trihydro-1,2,4-triazolo[3,4-a]isoquinolyl, benzo[d]isothiazolyl, tetrahydroquinolinyl, indazolyl, 2,1,3-benzothiadiazolyl, benzodioxanyl, benzothienyl, benzofuryl, benzimidazolyl, benzoxazolyl and benzthiazolyl;
wherein $R^1$ is substituted with one or more substituents selected from halo, $C_{1-4}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4–6 membered heterocyclyl-$C_1$-$C_4$-alkylenyl, optionally substituted 4–6 membered heterocyclyl-$C_2$-$C_4$-alkenylenyl, optionally substituted 4–6 membered heterocyclyl, optionally substituted 4–6 membered heterocyclyloxy, optionally substituted 4–6 membered heterocyclyl-$C_{1-4}$-alkoxy, optionally substituted 4–6 membered heterocyclylsulfonyl, optionally substituted 4–6 membered heterocyclylamino, optionally substituted 4–6 membered heterocyclylcarbonyl, optionally substituted 4–6 membered heterocyclyl-$C_{1-4}$-alkylcarbonyl, $C_{1-2}$-haloalkyl, $C_{1-4}$-aminoalkyl, nitro, amino, hydroxy, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-4}$-hydroxyalkyl,

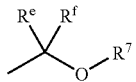

and $C_{1-4}$-alkoxy,
preferably bromo, chloro, fluoro, iodo, nitro, amino, cyano, aminoethyl, Boc-aminoethyl, hydroxy, aminosulfonyl, 4-methylpiperazinylsulfonyl, cyclohexyl, phenyl, phenylmethyl, morpholinylmethyl, methylpiperazinylmethyl, methylpiperazinylpropyl, morpholinylpropyl, methylpiperidinylmethyl, morpholinylethyl, 1-(4-morpholinyl)-2,2-dimethylpropyl, piperidinylethyl, piperidinylmethyl, piperidinylpropyl, pyrrolidinylpropyl, pyrrolidinylpropenyl, pyrrolidinylbutenyl, fluorosulfonyl, methylsulfonyl, methylcarbonyl, piperidinylmethylcarbonyl, methylpiperazinylcarbonylethyl, methoxycarbonyl, 3-ethoxycarbonyl-2-methyl-fur-5-yl, methylpiperazinyl, methylpiperidyl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, 1-methylpiperdin-4-yloxy, isopropoxy, methoxy and ethoxy;

wherein $R^2$ is one or more substituents independently selected from

H,
halo,
hydroxy,
amino,
$C_{1-6}$-alkyl,
$C_{1-6}$-haloalkyl,
$C_{1-6}$-alkoxy,
$C_{1-2}$-alkylamino,
aminosulfonyl,
$C_{3-6}$-cycloalkyl,
cyano,
$C_{1-2}$-hydroxyalkyl,
nitro,
$C_{2-3}$-alkenyl,
$C_{2-3}$-alkynyl,
$C_{1-6}$-haloalkoxy,
$C_{1-6}$-carboxyalkyl,
5–6-membered heterocyclyl-$C_{1-6}$-alkylamino,
unsubstituted or substituted phenyl and
unsubstituted or substituted 4–6 membered heterocyclyl;
preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from thienyl, furanyl, pyridyl, imidazolyl, and pyrazolyl;
wherein $R^4$ is selected from a direct bond, $C_{1-4}$-alkyl, and

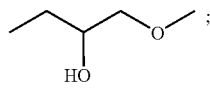

preferably direct bond, ethyl, butyl, and

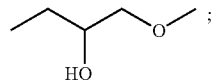

wherein $R^e$ and $R^f$ are independently selected from H and $C_{1-2}$-haloalkyl,
preferably —$CF_3$;
wherein $R^6$ is H or $C_{1-2}$-alkyl, preferably H or methyl; and
wherein $R^7$ is selected from H, $C_{1-3}$-alkyl, optionally substituted phenyl-$C_{1-3}$-alkyl, 4–6 membered heterocyclyl, optionally substituted 4–6 membered heterocyclyl-$C_{1-3}$-alkyl, $C_{1-3}$-alkoxy-$C_{1-2}$-alkyl and $C_{1-3}$-alkoxy-$C_{1-3}$-alkoxy-$C_{1-3}$-alkyl.

The invention also relates to compounds of Formulas VIIa and VIIb

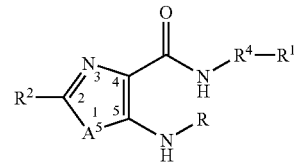

VIIa and

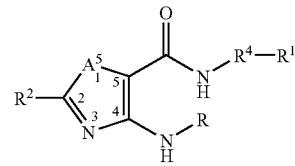

VIIb wherein $A^5$ is selected from S, O and $NR^6$;
wherein R is selected from
unsubstituted or substituted 9- or 10-membered fused nitrogen-containing heteroaryl,
preferably indolyl, isoindolyl, indazolyl, quinolyl, isoquinolyl, naphthyridinyl and quinozalinyl,
more preferably 5-indazolyl and 6-indazolyl,
even more preferably 6-indazolyl,
where R is substituted with one or more substituents selected from halo, amino, hydroxy, $C_{1-6}$-alkyl, $C_{1-6}$-haloalkyl, $C_{1-6}$-alkoxy, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, optionally substituted heterocyclyl-$C_{2-4}$-alkynyl, and optionally substituted heterocyclylalkoxy,
preferably chloro, fluoro, amino, hydroxy, methyl, ethyl, propyl, trifluoromethyl, dimethylaminopropynyl, 1-methylpiperdinylmethoxy, dimethylaminoethoxyethoxy, methoxy and ethoxy;
wherein $R^1$ is selected from unsubstituted or substituted aryl,
preferably phenyl, tetrahydronaphthyl, indanyl, indenyl and naphthyl,
cycloalkyl,
preferably cyclohexyl,
4–6 membered heterocyclyl,
preferably isoxazolyl, pyrazolyl, thiazolyl, thiadiazolyl, thienyl, pyridyl, pyrimidinyl and pyridazinyl, and
9–10 membered bicyclic and 13–14 membered tricyclic heterocyclyl, preferably 1,2-dihydroquinolyl, -1,2,3,4-tetrahydro-isoquinolyl, isoquinolyl, quinolyl, indolyl, isoindolyl, 2,3-dihydro-1H-indolyl, naphthyridinyl, quinozalinyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, 2,1,3-benzothiadiazolyl, benzo[d]isothiazolyl, benzodioxanyl, benzothienyl, benzofuryl, benzimidazolyl, benzoxazolyl and benzthiazolyl;

wherein $R^1$ is substituted with one or more substituents selected from halo, $C_{1-4}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4–6 membered heterocyclyl-$C_1$-$C_4$-alkyl, optionally substituted 4–6 membered heterocyclyl-$C_2$-$C_4$-alkenyl, optionally substituted 4–6 membered heterocyclyl, optionally substituted 4–6 membered heterocyclyloxy, optionally substituted 4–6 membered heterocyclyl-$C_{1-4}$-alkoxy, optionally substituted 4–6 membered heterocyclylsulfonyl, optionally substituted 4–6 membered heterocyclylamino, optionally substituted 4–6 membered heterocyclylcarbonyl, optionally substituted 4–6 membered heterocyclyl-$C_{1-4}$-alkylcarbonyl, $C_{1-2}$-haloalkyl, $C_{1-4}$-aminoalkyl, nitro, amino, hydroxy, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-4}$-hydroxyalkyl,

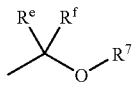

and $C_{1-4}$-alkoxy, preferably bromo, chloro, fluoro, iodo, nitro, amino, cyano, aminoethyl, Boc-aminoethyl, hydroxy, aminosulfonyl, 4-methylpiperazinylsulfonyl, cyclohexyl, phenyl, phenylmethyl, morpholinylmethyl, methylpiperazinylmethyl, methylpiperazinylpropyl, morpholinylpropyl, methylpiperidinylmethyl, morpholinylethyl, 1-(4-morpholinyl)-2,2-dimethylpropyl, piperidinylethyl, piperidinylmethyl, piperidinylpropyl, pyrrolidinylpropyl, pyrrolidinylpropenyl, pyrrolidinylbutenyl, fluorosulfonyl, methylsulfonyl, methylcarbonyl, piperidinylmethylcarbonyl, methylpiperazinylcarbonylethyl, methoxycarbonyl, 3-ethoxycarbonyl-2-methyl-fur-5-yl, methylpiperazinyl, methylpiperidyl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, 1-methylpiperdin-4-yloxy, isopropoxy, methoxy and ethoxy;

wherein $R^2$ is one or more substituents independently selected from

H,
halo,
hydroxy,
amino,
$C_{1-6}$-alkyl,
$C_{1-6}$-haloalkyl,
$C_{1-6}$-alkoxy,
$C_{1-2}$-alkylamino,
aminosulfonyl,
$C_{3-6}$-cycloalkyl,
cyano,
$C_{1-2}$-hydroxyalkyl,
nitro,
$C_{2-3}$-alkenyl,
$C_{2-3}$-alkynyl,
$C_{1-6}$-haloalkoxy,
$C_{1-6}$-carboxyalkyl,
5–6-membered heterocyclyl-$C_{1-6}$-alkylamino,
unsubstituted or substituted phenyl and
unsubstituted or substituted 4–6 membered heterocyclyl;

preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from thienyl, furanyl, pyridyl, imidazolyl, and pyrazolyl;

wherein $R^4$ is selected from a direct bond, $C_{1-4}$-alkyl, and

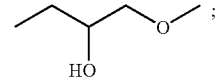

preferably direct bond, ethyl, butyl, and

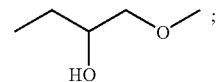

wherein $R^e$ and $R^f$ are independently selected from H and $C_{1-2}$-haloalkyl,
preferably —CF$_3$;
wherein $R^6$ is H or $C_{1-2}$-alkyl, preferably H or methyl; and
wherein $R^7$ is selected from H, $C_{1-3}$-alkyl, optionally substituted phenyl-$C_{1-3}$-alkyl, 4–6 membered heterocyclyl, optionally substituted 4–6 membered heterocyclyl-$C_{1-3}$-alkyl, $C_{1-3}$-alkoxy-$C_{1-2}$-alkyl and $C_{1-3}$-alkoxy-$C_{1-3}$-alkoxy-$C_{1-3}$-alkyl.

The invention also relates to compounds of Formulas VIIIa and VIIIb

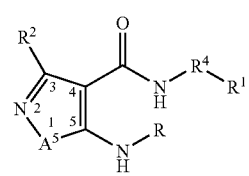

VIIIa

-continued

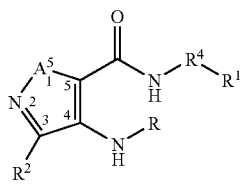
VIIIb wherein $A^5$ is selected from S, O and $NR^6$;
wherein R is selected from
  unsubstituted or substituted 9- or 10-membered fused nitrogen-containing heteroaryl,
    preferably indolyl, isoindolyl, indazolyl, quinolyl, isoquinolyl, naphthyridinyl and quinozalinyl,
    more preferably 5-indazolyl and 6-indazolyl, even more preferably 6-indazolyl,
  where R is substituted with one or more substituents selected from halo, amino, hydroxy, $C_{1-6}$-alkyl, $C_{1-6}$-haloalkyl, $C_{1-6}$-alkoxy, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, optionally substituted heterocyclyl-$C_{2-4}$-alkynyl, and optionally substituted heterocyclylalkoxy,
    preferably chloro, fluoro, amino, hydroxy, methyl, ethyl, propyl, trifluoromethyl, dimethylaminopropynyl, 1-methylpiperdinylmethoxy, dimethylaminoethoxyethoxy, methoxy and ethoxy;
wherein $R^1$ is selected from unsubstituted or substituted aryl,
  preferably phenyl, tetrahydronaphthyl, indanyl, indenyl and naphthyl,
  cycloalkyl,
  preferably cyclohexyl,
  4–6 membered heterocyclyl,
  preferably isoxazolyl, pyrazolyl, thiazolyl, thiadiazolyl, thienyl, pyridyl, pyrimidinyl and pyridazinyl, and
  9–10 membered bicyclic and 13–14 membered tricyclic heterocyclyl,
  preferably 1,2-dihydroquinolyl, 1,2,3,4-tetrahydroisoquinolyl, isoquinolyl, quinolyl, indolyl, isoindolyl, 2,3-dihydro-1H-indolyl, naphthyridinyl, quinozalinyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, benzo[d]isothiazolyl, 2,1,3-benzothiadiazolyl, benzodioxanyl, benzothienyl, benzofuryl, benzimidazolyl, benzoxazolyl and benzthiazolyl;
  wherein $R^1$ is substituted with one or more substituents selected from halo, $C_{1-4}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4–6 membered heterocyclyl-$C_1$-$C_4$-alkyl, optionally substituted 4–6 membered heterocyclyl-$C_2$-$C_4$-alkenylenyl, optionally substituted 4–6 membered heterocyclyl, optionally substituted 4–6 membered heterocyclyloxy, optionally substituted 4–6 membered heterocyclyl-$C_{1-4}$-alkoxy, optionally substituted 4–6 membered heterocyclylsulfonyl, optionally substituted 4–6 membered heterocyclylamino, optionally substituted 4–6 membered heterocyclylcarbonyl, optionally substituted 4–6 membered heterocyclyl-$C_{1-4}$-alkylcarbonyl, $C_{1-2}$-haloalkyl, $C_{1-4}$-aminoalkyl, nitro, amino, hydroxy, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-4}$-hydroxyalkyl,

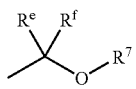

and $C_{1-4}$-alkoxy,
  preferably bromo, chloro, fluoro, iodo, nitro, amino, cyano, aminoethyl, Boc-aminoethyl, hydroxy, aminosulfonyl, 4-methylpiperazinylsulfonyl, cyclohexyl, phenyl, phenylmethyl, morpholinylmethyl, methylpiperazinylmethyl, methylpiperazinylpropyl, morpholinylpropyl, methylpiperidinylmethyl, morpholinylethyl, 1-(4-morpholinyl)-2,2-dimethylpropyl, piperidinylethyl, piperidinylmethyl, piperidinylpropyl, pyrrolidinylpropyl, pyrrolidinylpropenyl, pyrrolidinylbutenyl, fluorosulfonyl, methylsulfonyl, methylcarbonyl, piperidinylmethylcarbonyl, methylpiperazinylcarbonylethyl, methoxycarbonyl, 3-ethoxycarbonyl-2-methyl-fur-5-yl, methylpiperazinyl, methylpiperidyl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, 1-methylpiperdin-4-yloxy, isopropoxy, methoxy and ethoxy;
wherein $R^2$ is one or more substituents independently selected from
  H,
  halo,
  hydroxy,
  amino,
  $C_{1-6}$-alkyl,
  $C_{1-6}$-haloalkyl,
  $C_{1-6}$-alkoxy,
  $C_{1-2}$-alkylamino,
  aminosulfonyl,
  $C_{3-6}$-cycloalkyl,
  cyano,
  $C_{1-2}$-hydroxyalkyl,
  nitro,
  $C_{2-3}$-alkenyl,
  $C_{2-3}$-alkynyl,
  $C_{1-6}$-haloalkoxy,
  $C_{1-6}$-carboxyalkyl,
  5–6-membered heterocyclyl-$C_{1-6}$-alkylamino,
  unsubstituted or substituted phenyl and unsubstituted or substituted 4–6 membered heterocyclyl;
preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from
thienyl, furanyl, pyridyl, imidazolyl, and pyrazolyl;
wherein $R^4$ is selected from a direct bond, $C_{1-4}$-alkyl, and

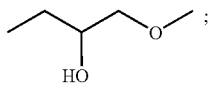

preferably direct bond, ethyl, butyl, and

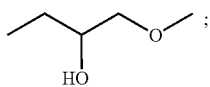

wherein $R^e$ and $R^f$ are independently selected from H and $C_{1-2}$-haloalkyl,
preferably —$CF_3$;
wherein $R^6$ is H or $C_{1-2}$-alkyl, preferably H or methyl; and
wherein $R^7$ is selected from H, $C_{1-3}$-alkyl, optionally substituted phenyl-$C_{1-3}$-alkyl, 4–6 membered heterocyclyl, optionally substituted 4–6 membered heterocyclyl-$C_{1-3}$-alkyl, $C_{1-3}$-alkoxy-$C_{1-2}$-alkyl and $C_{1-3}$-alkoxy-$C_{1-3}$-alkoxy-$C_{1-3}$-alkyl.

The invention also relates to compounds of Formula IX

IX

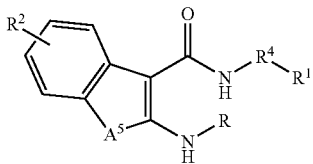

wherein $A^5$ is selected from S, O and $NR^6$;
wherein R is selected from
unsubstituted or substituted 9- or 10-membered fused nitrogen-containing heteroaryl,
preferably indolyl, isoindolyl, indazolyl, quinolyl, isoquinolyl, naphthyridinyl and quinozalinyl,
more preferably 5-indazolyl and 6-indazolyl, even more preferably 6-indazolyl,
where R is substituted with one or more substituents selected from halo, amino, hydroxy, $C_{1-6}$-alkyl, $C_{1-6}$-haloalkyl, $C_{1-6}$-alkoxy, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, optionally substituted heterocyclyl-$C_{2-4}$-alkynyl, and optionally substituted heterocyclylalkoxy,
preferably chloro, fluoro, amino, hydroxy, methyl, ethyl, propyl, trifluoromethyl, dimethylaminopropynyl, 1-methylpiperdinylmethoxy, dimethylaminoethoxyethoxy, methoxy and ethoxy;
wherein $R^1$ is selected from unsubstituted or substituted aryl,
preferably phenyl, tetrahydronaphthyl, indanyl, indenyl and naphthyl,
cycloalkyl,
preferably cyclohexyl,
4–6 membered heterocyclyl,
preferably isoxazolyl, pyrazolyl, thiazolyl, thiadiazolyl, thienyl, pyridyl, pyrimidinyl and pyridazinyl, and
9–10 membered bicyclic and 13–14 membered tricyclic heterocyclyl,
preferably 1,2-dihydroquinolyl, 1,2,3,4-tetrahydroisoquinolyl, isoquinolyl, quinolyl, indolyl, isoindolyl, 2,3-dihydro-1H-indolyl, naphthyridinyl, quinozalinyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, 2,1,3-benzothiadiazolyl, benzo[d]isothiazolyl, benzodioxanyl, benzothienyl, benzofuryl, benzimidazolyl, benzoxazolyl and benzthiazolyl;
wherein $R^1$ is substituted with one or more substituents selected from halo, $C_{1-4}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4–6 membered heterocyclyl-$C_1$-$C_4$-alkyl, optionally substituted 4–6 membered heterocyclyl-$C_2$-$C_4$-alkenylenyl, optionally substituted 4–6 membered heterocyclyl, optionally substituted 4–6 membered heterocyclyloxy, optionally substituted 4–6 membered heterocyclyl-$C_{1-4}$-alkoxy, optionally substituted 4–6 membered heterocyclylsulfonyl, optionally substituted 4–6 membered heterocyclylamino, optionally substituted 4–6 membered heterocyclylcarbonyl, optionally substituted 4–6 membered heterocyclyl-$C_{1-4}$-alkylcarbonyl, $C_{1-2}$-haloalkyl, $C_{1-4}$-aminoalkyl, nitro, amino, hydroxy, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-4}$-hydroxyalkyl,

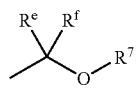

and $C_{1-4}$-alkoxy,
preferably bromo, chloro, fluoro, iodo, nitro, amino, cyano, aminoethyl, Boc-aminoethyl, hydroxy, aminosulfonyl, 4-methylpiperazinylsulfonyl, cyclohexyl, phenyl, phenylmethyl, morpholinylmethyl, methylpiperazinylmethyl, methylpiperazinylpropyl, morpholinylpropyl, methylpiperidinylmethyl, morpholinylethyl, 1-(4-morpholinyl)-2,2-dimethylpropyl, piperidinylethyl, piperidinylmethyl, piperidinylpropyl, pyrrolidinylpropyl, pyrrolidinylpropenyl, pyrrolidinylbutenyl, fluorosulfonyl, methylsulfonyl, methylcarbonyl, piperidinylmethylcarbonyl, methylpiperazinylcarbonylethyl, methoxycarbonyl, 3-ethoxycarbonyl-2-methyl-fur-5-yl, methylpiperazinyl, methylpiperidyl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-

(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, 1-methylpiperdin-4-yloxy, isopropoxy, methoxy and ethoxy;

wherein $R^2$ is one or more substituents independently selected from

H,
halo,
hydroxy,
amino,
$C_{1-6}$-alkyl,
$C_{1-6}$-haloalkyl,
$C_{1-6}$-alkoxy,
$C_{1-2}$-alkylamino,
aminosulfonyl,
$C_{3-6}$-cycloalkyl,
cyano,
$C_{1-2}$-hydroxyalkyl,
nitro,
$C_{2-3}$-alkenyl,
$C_{2-3}$-alkynyl,
$C_{1-6}$-haloalkoxy,
$C_{1-6}$-carboxyalkyl,
5–6-membered heterocyclyl-$C_{1-6}$-alkylamino,
unsubstituted or substituted phenyl and
unsubstituted or substituted 4–6 membered heterocyclyl;
preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from
thienyl, furanyl, pyridyl, imidazolyl, and pyrazolyl;

wherein $R^4$ is selected from a direct bond, $C_{1-4}$-alkyl, and

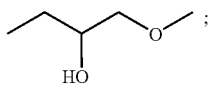

preferably direct bond, ethyl, butyl, and

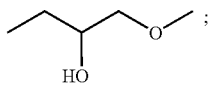

wherein $R^e$ and $R^f$ are independently selected from H and $C_{1-2}$-haloalkyl,
preferably —$CF_3$;

wherein $R^6$ is H or $C_{1-2}$-alkyl, preferably H or methyl; and wherein $R^7$ is selected from H, $C_{1-3}$-alkyl, optionally substituted phenyl-$C_{1-3}$-alkyl, 4–6 membered heterocyclyl, optionally substituted 4–6 membered heterocyclyl-$C_{1-3}$-alkyl, $C_{1-3}$-alkoxy-$C_{1-2}$-alkyl and $C_{1-3}$-alkoxy-$C_{1-3}$-alkoxy-$C_{1-3}$-alkyl.

The invention also relates to compounds of Formula X

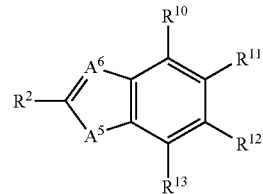

wherein $A^5$ is selected from S, O and $NR^6$;
wherein $A^6$ is selected from N and $CR^2$;
wherein R is selected from
unsubstituted or substituted 9- or 10-membered fused nitrogen-containing heteroaryl,
preferably indolyl, isoindolyl, indazolyl, quinolyl, isoquinolyl, naphthyridinyl and quinozalinyl,
more preferably 5-indazolyl and 6-indazolyl, even more preferably 6-indazolyl,
where R is substituted with one or more substituents selected from halo, amino, hydroxy, $C_{1-6}$-alkyl, $C_{1-6}$-haloalkyl, $C_{1-6}$-alkoxy, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, optionally substituted heterocyclyl-$C_{2-4}$-alkynyl, and optionally substituted heterocyclylalkoxy,
preferably chloro, fluoro, amino, hydroxy, methyl, ethyl, propyl, trifluoromethyl, dimethylaminopropynyl, 1-methylpiperdinylmethoxy, dimethylaminoethoxyethoxy, methoxy and ethoxy;

wherein $R^1$ is selected from unsubstituted or substituted aryl,
preferably phenyl, tetrahydronaphthyl, indanyl, indenyl and naphthyl,
cycloalkyl,
preferably cyclohexyl,
4–6 membered heterocyclyl,
preferably isoxazolyl, pyrazolyl, thiazolyl, thiadiazolyl, thienyl, pyridyl, pyrimidinyl and pyridazinyl, and
9–10 membered bicyclic and 13–14 membered tricyclic heterocyclyl,
preferably 1,2-dihydroquinolyl, 1,2,3,4-tetrahydroisoquinolyl, isoquinolyl, quinolyl, indolyl, isoindolyl, 2,3-dihydro-1H-indolyl, naphthyridinyl, quinozalinyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, 2,1,3-benzothiadiazolyl, benzo[d]isothiazolyl, benzodioxanyl, benzothienyl, benzofuryl, benzimidazolyl, benzoxazolyl and benzthiazolyl;

wherein $R^1$ is substituted with one or more substituents selected from halo, $C_{1-4}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4–6 membered heterocyclyl-$C_1$-$C_4$-alkylenyl, optionally substituted 4–6 membered heterocyclyl-$C_2$-$C_4$-alkenylenyl, optionally substituted 4–6 membered heterocyclyl, optionally substituted 4–6 membered heterocyclyloxy, optionally substituted 4–6 membered heterocyclyl-$C_{1-4}$-alkoxy, optionally substituted 4–6 membered heterocyclylsulfonyl, optionally substituted 4–6 membered heterocyclylamino, optionally substituted 4–6 membered heterocyclylcarbonyl, optionally substituted 4–6 membered heterocyclyl-$C_{1-4}$-alkylcarbonyl, $C_{1-2}$-haloalkyl, $C_{1-4}$-aminoalkyl, nitro, amino, hydroxy, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-4}$-hydroxyalkyl,

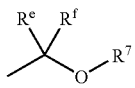

and $C_{1-4}$-alkoxy, preferably bromo, chloro, fluoro, iodo, nitro, amino, cyano, aminoethyl, Boc-aminoethyl, hydroxy, aminosulfonyl, 4-methylpiperazinylsulfonyl, cyclohexyl, phenyl, phenylmethyl, morpholinylmethyl, methylpiperazinylmethyl, methylpiperazinylpropyl, morpholinylpropyl, methylpiperidinylmethyl, morpholinylethyl, 1-(4-morpholinyl)-2,2-dimethylpropyl, piperidinylethyl, piperidinylmethyl, piperidinylpropyl, pyrrolidinylpropyl, pyrrolidinylpropenyl, pyrrolidinylbutenyl, fluorosulfonyl, methylsulfonyl, methylcarbonyl, piperidinylmethylcarbonyl, methylpiperazinylcarbonylethyl, methoxycarbonyl, 3-ethoxycarbonyl-2-methyl-fur-5-yl, methylpiperazinyl, methylpiperidyl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, 1-methylpiperdin-4-yloxy, isopropoxy, methoxy and ethoxy;

wherein $R^2$ is one or more substituents independently selected from

H,
halo,
hydroxy,
amino,
$C_{1-6}$-alkyl,
$C_{1-6}$-haloalkyl,
$C_{1-6}$-alkoxy,
$C_{1-2}$-alkylamino,
aminosulfonyl,
$C_{3-6}$-cycloalkyl,
cyano,
$C_{1-2}$-hydroxyalkyl,
nitro,
$C_{2-3}$-alkenyl,
$C_{2-3}$-alkynyl,
$C_{1-6}$-haloalkoxy,
$C_{1-6}$-carboxyalkyl,
5–6-membered heterocyclyl-$C_{1-6}$-alkylamino, unsubstituted or substituted phenyl and unsubstituted or substituted 4–6 membered heterocyclyl;

preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from thienyl, furanyl, pyridyl, imidazolyl, and pyrazolyl;

wherein $R^4$ is selected from a direct bond, $C_{1-4}$-alkyl, and

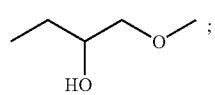

preferably direct bond, ethyl, butyl, and

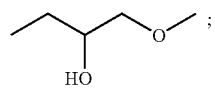

wherein $R^e$ and $R^f$ are independently selected from H and $C_{1-2}$-haloalkyl, preferably —$CF_3$;

wherein $R^6$ is H or $C_{1-2}$-alkyl, preferably H or methyl;

wherein $R^7$ is selected from H, $C_{1-3}$-alkyl, optionally substituted phenyl-$C_{1-3}$-alkyl, 4–6 membered heterocyclyl, optionally substituted 4–6 membered heterocyclyl-$C_1$-$C_3$-alkyl, $C_{1-3}$-alkoxy-$C_{1-2}$-alkyl and $C_{1-3}$-alkoxy-$C_{1-3}$-alkoxy-$C_{1-3}$-alkyl; and wherein a) $R^{10}$ is

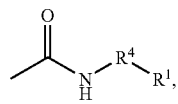

$R^{11}$ is —NHR, $R^{12}$ is H, and $R^{13}$ is H; or b) $R^{10}$ is —NHR, $R^{11}$ is

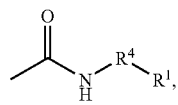

$R^{12}$ is H, and $R^{13}$ is H; or c) $R^{10}$ is H, $R^{11}$ is —NHR, $R^{12}$ is

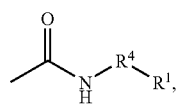

and $R^{13}$ is H; or d) $R^{10}$ is H, $R^{11}$ is

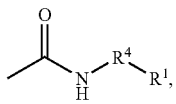

$R^{12}$ is —NHR, and $R^{13}$ is H; or e) $R^{10}$ is H, $R^{11}$ is H, $R^{12}$ is

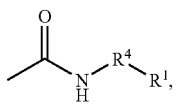

and $R^{13}$ is —NHR; or f) $R^{10}$ is H, $R^{11}$ is H, $R^{12}$ is —NHR, and $R^{13}$ is

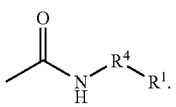

The invention also relates to compounds of Formula XI

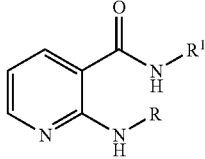

wherein R is selected from unsubstituted or substituted 9-or 10-membered fused nitrogen-containing heteroaryl selected from 6-indazolyl, 1-oxo-2,3-dihydro-1H-isoindol-4-yl, 2-oxo-2,3-dihydro-1H-benzoimidazol-5-yl, and 4-oxo-3,4-dihydro-quinazolin-6-yl;

wherein $R^1$ is selected from unsubstituted or substituted
  aryl,
  cycloalkyl,
  5–6 membered heteroaryl and
  9–10 membered bicyclic and 11–14 membered tricyclic heterocyclyl,
    preferably phenyl, tetrahydronaphthyl, indanyl, indenyl, naphthyl, cyclohexyl, isoxazolyl, pyrazolyl, thiazolyl, thiadiazolyl, thienyl, pyridyl, pyrimidinyl, pyridazinyl, 1,2-dihydroquinolyl, 1,2,3,4-tetrahydro-isoquinolyl, 1',2'-dihydro-spiro[cyclopropane-1,3'-[3H]indol]-6'-yl, isoquinolyl, quinolyl, indolyl, isoindolyl, 2,3-dihydro-1H-indolyl, naphthyridinyl, 3,4-dihydro-[1,8]naphthyridinyl, 1,2,3,4-tetrahydro-[1,8]naphthyridinyl, quinozalinyl, benzo[d]isothiazolyl, 3,4-dihydroquinazolinyl, 2,3,4,4a,9,9a-hexahydro-1H-3-azafluorenyl, 5,6,7-trihydro-1,2,4-triazolo[3,4-a]isoquinolyl, tetrahydroquinolinyl, indazolyl, 2,1,3-benzothiadiazolyl, benzodioxanyl, benzothienyl, benzofuryl, benzimidazolyl, dihydro-benzimidazolyl, benzoxazolyl and benzthiazolyl,
    more preferably phenyl, 1,2,3,4-tetrahydroisoquinolyl, 2,3-dihydro-1H-indolyl, 1,2,3,4-tetrahydro-[1,8]naphthyridinyl, 1',2'-dihydro-spiro[cyclopropane-1,3'-[3H]indol]-6'-yl, and tetrahydroquinolinyl,
    even more preferably
      phenyl substituted with one or more substituents selected from chloro, 2-methyl-2-(1-methylpiperidin-4-yl)ethyl, methylsulfonylamino, dimethylaminomethylcarbonylamino, 1-pyrrolidinyl-CH$_2$—C(=O)—NH—, 4-morpholinyl-CH$_2$—C(=O)—NH—, 3-tetrahydrofuryl-O—C(=O)—NH—, tert-butyl, trifluoromethyl, pentafluoroethyl, 1,1-di(trifluoromethyl)-1-hydroxymethyl, 1,1-di(trifluoromethyl)-1-(pyrrolidin-2-ylmethoxy)methyl, 3-tetrahydrofuryloxy, 1-methylcarbonyl-pyrrolidin-2-ylmethoxy, 1-methyl-pyrrolindin-2-ylmethoxy, and methylsulfonylaminoethoxy;
      4,4-dimethyl-3,4-dihydro-2-oxo-1H-quinolinyl;
      4,4-dimethyl-1,2,3,4-tetrahydro-1H-quinolinyl;
      4,4-dimethyl-3,4-dihydro-2-oxo-1H-[1,8]naphthyridinyl
      3,3-dimethyl-2,3-dihydro-1H-indolyl optionally substituted with a substituent selected from pyrrolidin-1-yl-carbonyl, methylcarbonyl, and methylsulfonyl; and
      4,4-dimethyl-1,2,3,4-tetrahydro-1H-isoquinolinyl;
  wherein substituted $R^1$ is substituted with one or more substituents selected from halo, $C_{1-6}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4–6 membered heterocyclyl-$C_1$-$C_6$-alkyl, optionally substituted 4–6 membered heterocyclyl-$C_2$-$C_4$-alkenyl, optionally substituted 4–6 membered heterocyclyl, optionally substituted 4–6 membered heterocyclyloxy, optionally substituted 4–6 membered heterocyclyl-$C_{1-4}$-alkoxy, optionally substituted 4–6 membered heterocyclylsulfonyl, optionally substituted 4–6 membered heterocyclylamino, optionally substituted 4–6 membered heterocyclylcarbonyl, optionally substituted 4–6 membered heterocyclyl-$C_{1-4}$-alkylcarbonyl, optionally substituted 4–6 membered heterocyclylcarbonyl-$C_{1-4}$-alkyl, optionally substituted 4–6 membered heterocyclyl-$C_{1-4}$-alkylcarbonylamino, optionally substituted 4–6 membered heterocyclyloxycarbonylamino, $C_{1-2}$-haloalkyl, $C_{1-4}$-aminoalkyl, nitro, amino, $C_{1-3}$-alkylsulfonylamino, hydroxy, cyano, aminosulfonyl, $C_{1-2}$-alkylsulfonyl, halosulfonyl, $C_{1-4}$-alkylcarbonyl, amino-$C_{1-4}$-alkylcarbonyl, $C_{1-3}$-alkylamino-$C_{1-4}$-alkylcarbonyl, $C_{1-3}$-alkylamino-$C_{1-4}$-alkylcarbonylamino, $C_{1-4}$-alkoxycarbonyl-$C_{1-4}$-alkyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-3}$-alkylsulfonylamino-$C_{1-3}$-alkoxy, $C_{1-4}$-hydroxyalkyl,

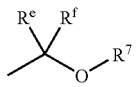

and $C_{1-4}$-alkoxy;
  preferably bromo, chloro, fluoro, iodo, nitro, amino, cyano, Boc-aminoethyl, hydroxy, oxo, fluorosulfonyl, methylsulfonyl, aminosulfonyl, 4-methylpiperazinylsulfonyl, cyclohexyl, phenyl, phenylmethyl, 4-pyridylmethyl, 4-morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, 2-methyl-2-(4-pyrimidinyl)ethyl, 2-methyl-2-(5-methyloxadiazol-2-yl)ethyl, 2-methyl-2-(pyrazol-5-yl)ethyl, 2-methyl-2-(1-ethoxycarbonyl-1,2,3,6-tetrahydropyridin-4-yl)ethyl, morpholinylethyl, 1-(4-morpholinyl)-2,2-dimethylpropyl, 1-(4-morpholinyl)-2,2-dimethylethyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, 1-(pyrrolidin-1-yl)-2-methylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, methylcarbonyl, Boc, piperidin-1-ylmethylcarbonyl, pyrrolidin-1-yl-carbonyl, 4-pyridylcarbonyl, 4-methylpiperazin-1-ylcarbonylethyl, CH$_3$O—C(=O)—CH$_2$—, methoxycarbonyl, aminomethylcarbonyl, dimethylaminomethylcarbonyl, methylsulfonylamino, dimethylaminomethylcarbonylamino, 1-pyrrolidinyl-CH$_2$—C(=O)—NH—, 4-morpholinyl-CH$_2$—C(=O)—NH—, 3-tetrahydrofuryl-O—C(=O)—NH—, cyclohexyl-N(CH$_3$)—, (4-pyrimidinyl)amino, (2-methylthio-4-pyrimidinyl)amino, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(pyrrolidin-2-ylmethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, 3-tetrahydrofuryloxy, dimethylaminoethoxy, 4-chlorophenoxy, phenyloxy, azetidin-3-ylmethoxy, 1-Boc-azetidin-3-ylmethoxy, 3-tetrahydrofurylmethoxy, pyrrolidin-2-ylmethoxy, 1-methylcarbonyl-pyrrolidin-2-ylmethoxy, 1-Boc-pyrrolidin-2-ylmethoxy, pyrrolidin-1-ylmethoxy, 1-methyl-pyrrolidin-2-ylmethoxy, 1-isopropyl-pyrrolidin-2-ylmethoxy, 1-Boc-piperdin-4-ylmethoxy, (1-pyrrolidinyl)ethoxy, piperdin-4-ylmethoxy, piperdin-3-ylmethoxy, 1-methylpiperdin-4-yloxy, methylsulfonylaminoethoxy, isopropoxy, methoxy and ethoxy;

even more preferably chloro, oxo, methylsulfonyl, 2-methyl-2-(1-methylpiperidin-4-yl)ethyl, pyrrolidin-1-yl-carbonyl, methylsulfonylamino, dimethylaminomethylcarbonylamino, 1-pyrrolidinyl-CH$_2$—C(=O)—NH—, 4-morpholinyl-CH$_2$—C(=O)—NH—, 3-tetrahydrofuryl-O—C(=O)—NH—, methyl, tert-butyl, trifluoromethyl, pentafluoroethyl, 1,1-di(trifluoromethyl)-1-hydroxymethyl, 1,1-di(trifluoromethyl)-1-(pyrrolidin-2-ylmethoxy)methyl, 3-tetrahydrofuryloxy, 1-methylcarbonyl-pyrrolidin-2-ylmethoxy, 1-methyl-pyrrolidin-2-ylmethoxy, and methylsulfonylaminoethoxy;

particularly 2-methyl-2-(1-ethoxycarbonyl-1,2,3,6-tetrahydropyridin-4-yl)ethyl, 1-(4-morpholinyl)-2,2-dimethylethyl, pyrrolidin-1-yl-carbonyl, CH$_3$O—C(=O)—CH$_2$—, methylsulfonylamino, dimethylaminomethylcarbonylamino, 1-pyrrolidinyl-CH$_2$—C(=O)—NH—, 4-morpholinyl-CH$_2$—C(=O)—NH—, 3-tetrahydrofuryl-O—C(=O)—NH—, 1,1-di(trifluoromethyl)-1-(pyrrolidin-2-ylmethoxy)methyl, 3-tetrahydrofuryloxy, 1-methylcarbonyl-pyrrolidin-2-ylmethoxy, and methylsulfonylaminoethoxy;

wherein $R^e$ and $R^f$ are independently selected from H and $C_{1-2}$-haloalkyl; preferably —CF$_3$; and wherein $R^7$ is selected from H, $C_{1-3}$-alkyl, optionally substituted phenyl, optionally substituted phenyl-$C_{1-3}$-alkyl, 4–6 membered heterocyclyl, optionally substituted 4–6 membered heterocyclyl-$C_1$-$C_3$-alkyl, $C_{1-3}$-alkoxy-$C_{1-2}$-alkyl and $C_{1-3}$-alkoxy-$C_{1-3}$-alkoxy-$C_{1-3}$-alkyl;

and pharmaceutically acceptable derivatives thereof.

A family of specific compounds of particular interest within Formula I consists of compounds and pharmaceutically-acceptable derivatives thereof as follows:

N-(4-Chlorophenyl)[2-(6-quinolylamino)(3-pyridyl)]carboxamide;

N-(4-Chlorophenyl)[2-(5-isoquinolylamino)(3-pyridyl)]carboxamide;

N-(4-Chlorophenyl)[2-(1H-indazol-5-ylamino)(3-pyridyl)]carboxamide;

N-(4-Chlorophenyl)[2-(1H-indazol-6-ylamino)(3-pyridyl)]carboxamide;

2-(1H-Indazol-6-ylamino)-N-(4-isopropyl-phenyl)nicotinamide;

[2-(1H-Indazol-6-ylamino)(3-pyridyl)]-N-[3-(methylethyl)phenyl]carboxamide;

[2-(1H-Indazol-6-ylamino)(3-pyridyl)]-N-[4-(methylpropyl)phenyl]carboxamide;

N-[4-(tert-Butyl)phenyl][2-(1H-indazol-6-ylamino)(3-pyridyl)]carboxamide;

[2-(1H-Indazol-6-ylamino)(3-pyridyl)]-N-[3-(trifluoromethyl)phenyl]carboxamide;

N-[3-(tert-Butyl)phenyl][2-(1H-indazol-6-ylamino)(3-pyridyl)]carboxamide;

2-(1H-Indazol-6-ylamino)-N-(4-{2,2,2-trifluoro-1-[2-(2-methoxy-ethoxy)-ethoxy]-1-trifluoromethyl-ethyl}-phenyl)-nicotinamide trifluoroacetate;

[2-(Benzotriazol-6-ylamino)(3-pyridyl)]-N-[4-(tert-butyl)phenyl]carboxamide;

[2-(1H-Indazol-6-ylamino)(3-pyridyl)]-N-(3-phenylpyrazol-5-yl)carboxamide;

N-(4-Chloro-3-sulfamoylphenyl)[2-(1H-indazol-6-ylamino)(3-pyridyl)]carboxamide;

[2-(1H-Indazol-6-ylamino)(3-pyridyl)]-N-(4-methyl-2-oxo-1,2-dihydroquinol-7-yl)carboxamide;

N-[4-(Methylethyl)phenyl]{2-[(4-methyl-2-oxo(7-hydroquinolyl))amino](3-pyridyl)}carboxamide;

N-[5-(tert-Butyl)isoxazol-3-yl][2-(1H-indazol-6-ylamino)(3-pyridyl)]carboxamide;

N-[5-(tert-Butyl)-1-methylpyrazol-3-yl][2-(1H-indazol-6-ylamino)(3-pyridyl)]carboxamide;

N-[4-(tert-Butyl)(1,3-thiazol-2-yl)][2-(1H-indazol-6-ylamino)(3-pyridyl)]carboxamide;

N-(4-Chlorophenyl)[2-(1H-indazol-6-ylamino)(3-pyridyl)]carboxamide hydrochloride;

N-[5-(tert-Butyl)(1,3,4-thiadiazol-2-yl)][2-(1H-indazol-6-ylamino)(3-pyridyl)]carboxamide;

[2-(1H-Indazol-6-ylamino)(3-pyridyl)]-N-[4-(1,1,2,2,3,3,4,4,4-nonafluorobutyl)phenyl]carboxamide;

{2-[(1-Methyl(1H-indazol-6-yl))amino](3-pyridyl)}-N-[4-(methylethyl)phenyl]carboxamide;

N-[4-(tert-Butyl)phenyl]{2-[(7-bromo(1H-indazol-6-yl))amino](3-pyridyl)}carboxamide;

2-(1H-Indazol-6-ylamino)-N-[4-tert-butyl-3-(1,2,3,6-tetrahydropyridin-4-yl)phenyl]nicotinamide;

[2-(1H-Indazol-6-ylamino)(3-pyridyl)]-N-{4-[2,2,2-trifluoro-1-hydroxy-1-(trifluoromethyl)ethyl]phenyl}carboxamide;
N-[5-(tert-Butyl)-2-methoxyphenyl][2-(1H-indazol-6-ylamino)(3-pyridyl)]carboxamide;
N-[4-(tert-Butyl)phenyl][2-(1H-indazol-6-ylamino)(3-pyridyl)]carboxamide hydrochloride;
[2-(1H-Indazol-6-ylamino)(3-pyridyl)]-N-{6-[4-(trifluoromethyl)piperidyl](3-pyridyl)}carboxamide;
[2-(1H-Indazol-6-ylamino)(3-pyridyl)]-N-(1-oxo(7-2, 3,4-trihydroisoquinolyl))carboxamide;
[2-(1H-Indazol-6-ylamino)(3-pyridyl)]-N-[4-(methylethoxy)phenyl]carboxamide;
[2-(1H-Indazol-6-ylamino)(3-pyridyl)]-N-{4-[2,2,2-trifluoro-1-hydroxy-1-(trifluoromethyl)ethyl]phenyl}carboxamide;
N-(4-{(1S)-1-[(Methylethyl)amino]ethyl}phenyl)[2-(1H-indazol-6-ylamino)(3-pyridyl)]carboxamide;
N-[4-(tert-Butyl)-3-(4-methylpiperazinyl)phenyl][2-(1H-indazol-6-ylamino)(3-pyridyl)]carboxamide;
[2-(1H-Indazol-6-ylamino)(3-pyridyl)]-N-[3-(4-methylpiperazinyl)phenyl]carboxamide;
N-[4-(tert-Butyl)-2-(4-methylpiperazinyl)phenyl][2-(1H-indazol-6-ylamino)(3-pyridyl)]carboxamide;
N-{2-[2-(Dimethylamino)ethoxy]-5-(tert-butyl)phenyl}[2-(1H-indazol-6-ylamino)(3-pyridyl)]carboxamide;
N-{3-[2-(Dimethylamino)ethoxy]phenyl}[2-(1H-indazol-6-ylamino)(3-pyridyl)]carboxamide;
2-(1H-Indazol-6-ylamino)-N-[3-(2-pyrrolidin-1-yl-ethoxy)-4-trifluoromethyl-phenyl]-nicotinamide hydrochloride;
N-(3-Hydroxy-4-methoxyphenyl)[2-(1H-indazol-6-ylamino)(3-pyridyl)]carboxamide;
N-{3-[2-(Dimethylamino)ethoxy]-4-methoxyphenyl}[2-(1H-indazol-6-ylamino)(3-pyridyl)]carboxamide;
[2-(1H-Indazol-6-ylamino)(3-pyridyl)]-N-[4-methoxy-3-(1-methyl(4-piperidyl)oxy)phenyl]carboxamide;
[2-(1H-Indazol-6-ylamino)(3-pyridyl)]-N-(5,6,7-trihydro-1,2,4-triazolo[3,4-a]isoquinolin-2-yl)carboxamide;
[2-({3-[2-(Dimethylamino)ethoxy](1H-indazol-6-yl)}amino)(3-pyridyl)]-N-[4-(tert-butyl)phenyl]carboxamide;
N-[3,3-Dimethyl-1-(4-piperidylmethyl)indolin-6-yl][2-(1H-indazol-6-ylamino)(3-pyridyl)]carboxamide;
2-(1H-Indazol-6-ylamino)-N-(3-morpholin-4-ylmethyl-4-pentafluoroethyl-phenyl)-nicotinamide hydrochloride;
N-[3,3-Dimethyl-1-(1-methyl-piperidin-4-ylmethyl)-2,3-dihydro-1H-indol-6-yl]-2-(1H-indazol-6-ylamino)-nicotinamide;
2-(1H-Indazol-6-ylamino)-N-(4-phenoxy-phenyl)-nicotinamide;
[2-(1H-Indazol-5-ylamino)(3-pyridyl)]-N-(4-phenoxyphenyl)carboxamide;
[2-(1H-Indazol-6-ylamino)(3-pyridyl)]-N-(4-phenylphenyl)carboxamide;
[2-(1H-indazol-6-ylamino)(3-pyridyl)]-N-[4-(methylsulfonyl)phenyl]carboxamide;
[2-(1H-Indazol-6-ylamino)(3-pyridyl)]-N-[1-(1-methyl(4-piperidyl))indolin-6-yl]carboxamide;
N-[3,3-Dimethyl-1-(1-methyl(4-piperidyl))indolin-6-yl][2-(1H-indazol-6-ylamino)(3-pyridyl)]carboxamide;
[2-(1H-Indazol-6-ylamino)(3-pyridyl)]-N-[3-(1-methyl(4-piperidyl))indol-5-yl]carboxamide;
[2-(1H-Indazol-6-ylamino)(3-pyridyl)]-N-[4-(trifluoromethyl)phenyl]carboxamide;
N-{3-[3-(Dimethylamino)propyl]-5-(trifluoromethyl)phenyl}[2-(1H-indazol-6-ylamino)(3-pyridyl)]carboxamide;
2-(1H-Indazol-6-ylamino)-N-(2-oxo-4-trifluoromethyl-2H-chromen-7-yl)-nicotinamide hydrochloride;
[2-(1H-Indazol-6-ylamino)(3-pyridyl)]-N-[5-(1-methyl(4-1,2,5,6-tetrahydropyridyl))-3-(trifluoromethyl)phenyl]carboxamide;
[2-(1H-Indazol-6-ylamino)(3-pyridyl)]-N-[4-(1-methyl(4-piperidyl))phenyl]carboxamide;
N-[4-(tert-Butyl)-3-(3-piperidylpropyl)phenyl][2-(1H-indazol-6-ylamino)(3-pyridyl)]carboxamide;
N-[3-((1E)-4-Pyrrolidinylbut-1-enyl)-4-(tert-butyl)phenyl][2-(1H-indazol-6-ylamino)(3-pyridyl)]carboxamide;
N-[4-(tert-Butyl)-3-(3-pyrrolidinylpropyl)phenyl][2-(1H-indazol-6-ylamino)(3-pyridyl)]carboxamide;
N-[4-(tert-Butyl)-3-(3-morpholin-4-ylpropyl)phenyl][2-(1H-indazol-6-ylamino)(3-pyridyl)]carboxamide;
[2-(1H-Indazol-6-ylamino)(3-pyridyl)]-N-{3-[3-(4-methylpiperazinyl)-3-oxopropyl]phenyl}carboxamide;
[2-(1H-Indazol-6-ylamino)(3-pyridyl)]-N-{4-[3-(4-methylpiperazinyl)-3-oxopropyl]phenyl}carboxamide;
[2-(1H-Indazol-6-ylamino)(3-pyridyl)]-N-{3-[3-(4-methylpiperazinyl)propyl]phenyl}carboxamide;
[2-(1H-Indazol-6-ylamino)(3-pyridyl)]-N-{4-[3-(4-methylpiperazinyl)propyl]phenyl}carboxamide;
[2-(1H-Indazol-6-ylamino)(3-pyridyl)]-N-[1-(2-morpholin-4-ylethyl)indol-6-yl]carboxamide;
N-[4-(1,1-Dimethyl-3-morpholin-4-ylpropyl)phenyl][2-(1H-indazol-6-ylamino)(3-pyridyl)]carboxamide;
2-(1H-Indazol-6-ylamino)-N-(4-{2,2,2-trifluoro-1-[2-(2-methoxy-ethoxy)-ethoxy]-1-trifluoromethyl-ethyl}-phenyl)-nicotinamide;
[2-(1H-Indazol-6-ylamino)(3-pyridyl)]-N-{4-[2,2,2-trifluoro-1-(2-piperidylethoxy)-1-(trifluoromethyl)ethyl]phenyl}carboxamide;
N-[4-(tert-Butyl)phenyl][6-fluoro-2-(1H-indazol-6-ylamino)(3-pyridyl)]carboxamide;
[6-Fluoro-2-(1H-indazol-6-ylamino)(3-pyridyl)]-N-[4-(methylethyl)phenyl]carboxamide;
[6-Fluoro-2-(1H-indazol-6-ylamino)(3-pyridyl)]-N-[3-(trifluoromethyl)phenyl]carboxamide; and
{2-[(1-(2-Pyridyl)pyrrolidin-3-yl)amino](3-pyridyl)}-N-[3-(trifluoromethyl)phenyl]carboxamide.

Another family of specific compounds of particular interest within Formula I consists of compounds and pharmaceutically-acceptable derivatives thereof as follows:
2-(1H-Indazol-6-ylamino)-N-(3-((((2R)-1-methyl-2-pyrrolidinyl)methyl)oxy)-5-(trifluoromethyl)phenyl)-3-pyridinecarboxamide;
2-(1H-Indazol-6-ylamino)-N-(3-(((2S)-tetrahydro-2-furanylmethyl)oxy)-5-(trifluoromethyl)phenyl)-3-pyridinecsarboxamide;
2-(1H-Indazol-6-ylamino)-N-(3-(((2R)-tetrahydro-2-furanylmethyl)oxy)-5-(trifluoromethyl)phenyl)-3-pyridinecsarboxamide;
2-(1H-Indazol-6-ylamino)-N-(3-((3R)-tetrahydro-3-furanyloxy)-5-(trifluoromethyl)phenyl)-3-pyridinecarboxamide;
N-(3-((((2R)-1-Acetyl-2-pyrrolidinyl)methyl)oxy)-5-(trifluoromethyl)phenyl)-2-(1H-indazol-6-ylamino)-3-pyridinecarboxamide;
(3S)-Tetrahydro-3-furanyl 3-(((2-(1H-indazol-6-ylamino)-3-pyridinyl)carbonyl)amino)-5-(trifluoromethyl)phenylcarbamate;
2-(1H-Indazol-6-ylamino)-N-(3-((2-((methylsulfonyl)amino)ethyl)oxy)-5-(trifluoromethyl)phenyl)-3-pyridinecarboxamide;
2-(1H-Indazol-6-ylamino)-N-(3-((((2S)-1-(1-methylethyl)-2-pyrrolidinyl)methyl)oxy)-5-(trifluoromethyl)phenyl)-3-pyridinecarboxamide;

N-(2-Oxo-3,3-bis(trifluoromethyl)-2,3-dihydro-1H-indol-6-yl)-2-((1-oxo-2,3-dihydro-1H-isoindol-4-yl)amino)-3-pyridinecarboxamide;

N-(3-((((2R)-1-Methyl-2-pyrrolidinyl)methyl)oxy)-4-(trifluoromethyl)phenyl)-2-((1-oxo-2,3-dihydro-1H-isoindol-4-yl)amino)-3-pyridinecarboxamide;

2-(1H-Indazol-6-ylamino)-N-(3-((methylsulfonyl)amino)-5-(trifluoromethyl)phenyl)-3-pyridinecarboxamide;

N-(4-(1,1-Dimethylethyl)-3-((1-pyrrolidinylacetyl)amino)phenyl)-2-(1H-indazol-6-ylamino)-3-pyridinecarboxamide;

N-(4-(1,1-Dimethylethyl)-3-((4-morpholinylacetyl)amino)phenyl)-2-(1H-indazol-6-ylamino)-3-pyridinecarboxamide;

4-((3-((3-(2-(1-Acetyl-2-pyrrolidinyl)ethyl)-5-(trifluoromethyl)phenyl)acetyl)-2-pyridinyl)amino)-2,3-dihydro-1H-isoindol-1-one;

N-[3-Chloro-5-(2-dimethylamino-acetylamino)-phenyl]-2-(1H-indazol-6-ylamino)-nicotinamide;

N-{4-[1-Methyl-1-(1-methyl-piperidin-4-yl)-ethyl]-phenyl}-2-(4-oxo-3,4-dihydro-quinazolin-6-ylamino)-nicotinamide;

N-{4-[1-Methyl-1-(1-methyl-piperidin-4-yl)-ethyl]-phenyl}-2-(2-oxo-2,3-dihydro-1H-indol-6-ylamino)-nicotinamide;

N-(5,5-Dimethyl-7-oxo-5,6,7,8-tetrahydro-[1,8]naphthyridin-2-yl)-2-(1H-indazol-6-ylamino)-nicotinamide;

N-(4,4-Dimethyl-1,2,3,4-tetrahydro-isoquinolin-7-yl)-2-(2-oxo-2,3-dihydro-1H-benzoimidazol-5-ylamino)-nicotinamide;

N-(1-Acetyl-3,3-dimethyl-2,3-dihydro-1H-indol-6-yl)-2-(2-oxo-2,3-dihydro-1H-benzoimidazol-5-ylamino)-nicotinamide;

N-(3,3-Dimethyl-2,3-dihydro-1H-indol-6-yl)-2-(2-oxo-2,3-dihydro-1H-benzoimidazol-5-ylamino)-nicotinamide;

N-{4-[1-Methyl-1-(1-methyl-piperidin-4-yl)-ethyl]-phenyl}-2-(2-oxo-2,3-dihydro-1H-benzoimidazol-5-ylamino)-nicotinamide;

2-(2-Oxo-2,3-dihydro-1H-benzoimidazol-5-ylamino)-N-(3-trifluoromethyl-phenyl)-nicotinamide;

N-[3-(1-Methyl-pyrrolidin-2-ylmethoxy)-5-trifluoromethyl-phenyl]-2-(2-oxo-2,3-dihydro-1H-benzoimidazol-5-ylamino)-nicotinamide;

N-(4-tert-Butyl-phenyl)-2-(1-oxo-2,3-dihydro-1H-isoindol-4-ylamino)-nicotinamide;

2-(1-Oxo-2,3-dihydro-1H-isoindol-4-ylamino)-N-(4-trifluoromethyl-phenyl)-nicotinamide;

2-(1-Oxo-2,3-dihydro-1H-isoindol-4-ylamino)-N-(4-pentafluoroethyl-phenyl)-nicotinamide;

N-{4-[1-Methyl-1-(1-methyl-piperidin-4-yl)-ethyl]-phenyl}-2-(1-oxo-2,3-dihydro-1H-isoindol-4-ylamino)-nicotinamide;

2-(1-Oxo-2,3-dihydro-1H-isoindol-4-ylamino)-N-(3-trifluoromethyl-phenyl)-nicotinamide;

2-(1H-Indazol-6-ylamino)-N-{3-[2,2,2-trifluoro-1-(pyrrolidin-2-ylmethoxy)-1-trifluoromethyl-ethyl]-phenyl-}-nicotinamide;

2-[2,2,2-Trifluoro-1-(4-{[2-(1H-indazol-6-ylamino)-pyridine-3-carbonyl]-amino}-phenyl)-1-trifluoromethyl-ethoxymethyl]-pyrrolidine-1-carboxylic acid tert-butyl ester;

2-(1H-Indazol-6-ylamino)-N-{4-[2,2,2-trifluoro-1-(pyrrolidin-2-ylmethoxy)-1-trifluoromethyl-ethyl]-phenyl}-nicotinamide;

2-(1-Oxo-2,3-dihydro-1H-isoindol-4-ylamino)-N-[4-(2,2,2-trifluoro-1-hydroxy-1-trifluoromethyl-ethyl)-phenyl]-nicotinamide;

2-(1-Oxo-2,3-dihydro-1H-isoindol-4-ylamino)-N-[3-(2,2,2-trifluoro-1-hydroxy-1-trifluoromethyl-ethyl)-phenyl]-nicotinamide;

N-(1-Acetyl-3,3-dimethyl-2,3-dihydro-1H-indol-6-yl)-2-(1-oxo-2,3-dihydro-1H-isoindol-4-ylamino)-nicotinamide;

N-(3,3-Dimethyl-2,3-dihydro-1H-indol-6-yl)-2-(1-oxo-2,3-dihydro-1H-isoindol-4-ylamino)-nicotinamide;

2-(1-Oxo-2,3-dihydro-1H-isoindol-4-ylamino)-N-[3-(tetrahydro-furan-3-yloxy)-5-trifluoromethyl-phenyl]-nicotinamide;

N-(4-(1,1-Dimethylethyl)-3-((N,N-dimethylglycyl)amino)phenyl)-2-(1H-indazol-6-ylamino)-3-pyridinecarboxamide;

N-(2-Oxo-3,3-bis(trifluoromethyl)-2,3-dihydro-1H-indol-6-yl)-2-((1-oxo-2,3-dihydro-1H-isoindol-4-yl)amino)-3-pyridinecarboxamide;

N-(3-((((2R)-1-Methyl-2-pyrrolidinyl)methyl)oxy)-4-(trifluoromethyl)phenyt)-2-((1-oxo-2,3-dihydro-1H-isoindol-4-yl)amino)-3-pyridinecarboxamide;

2-(1H-indazol-6-ylamino)-N-(3-((((2S)-1-methyl-2-pyrrolidinyl)methyl)oxy)-4-(trifluoromethyl)phenyl)-3-pyridinecarboxamide;

N-[3-(1-Methyl-pyrrolidin-2-ylmethoxy)-4-pentafluoroethyl-phenyl]-2-(1-oxo-2,3-dihydro-1H-isoindol-4-ylamino)-nicotinamide;

N-[3-(1-Methyl-pyrrolidin-2-ylmethoxy)-4-trifluoromethyl-phenyl]-2-(1-oxo-2,3-dihydro-1H-isoindol-4-ylamino)-nicotinamide;

N-[3-(2-Dimethylamino-ethoxy)-4-trifluoromethyl-phenyl]-2-(1-oxo-2,3-dihydro-1H-isoindol-4-ylamino)-nicotinamide;

N-[3-(1-Methyl-pyrrolidin-2-ylmethoxy)-4-pentafluoroethyl-phenyl]-2-(1-oxo-2,3-dihydro-1H-isoindol-4-ylamino)-nicotinamide;

N-(3,3-Bis-trifluoromethyl-2,3-dihydro-1H-indol-6-yl)-2-(1-oxo-2,3-dihydro-1H-isoindol-4-ylamino)-nicotinamide;

N-[1-(2-Dimethylamino-acetyl)-3,3-bis-trifluoromethyl-2,3-dihydro-1H-indol-6-yl]-2-(1-oxo-2,3-dihydro-1H-isoindol-4-ylamino)-nicotinamide;

N-(4,4-Bis-trifluoromethyl-1,2,3,4-tetrahydro-isoquinolin-7-yl)-2-(1-oxo-2,3-dihydro-1H-isoindol-4-ylamino)-nicotinamide;

N-(2-Methyl-4,4-bis-trifluoromethyl-1,2,3,4-tetrahydro-isoquinolin-7-yl)-2-(1-oxo-2,3-dihydro-1H-isoindol-4-ylamino)-nicotinamide;

N-(3,3-dimethyl-1-(methylsulfonyl)-2,3-dihydro-1H-indol-6-yl)-2-(1H-indazol-6-ylamino)-3-pyridinecarboxamide;

1,1-Dimethylethyl 3-(((2-(1,1-dimethylethyl))-5-(((2-(1H-indazol-6-ylamino)-3-pyridinyl)carbonyl)amino)phenyl)oxy)methyl)-1-azetidinecarboxylate;

N-[4-tert-Butyl-3-(2-dimethylamino-acetylamino)-phenyl]-2-(1-oxo-2,3-dihydro-1H-isoindol-4-ylamino)-nicotinamide;

N-[4-tert-Butyl-3-(2-methylamino-acetylamino)-phenyl]-2-(3H-indazol-5-ylamino)-nicotinamide;

N-(4,4-Dimethyl-1,2,3,4-tetrahydro-isoquinolin-7-yl)-2-(1-oxo-2,3-dihydro-1H-isoindol-4-ylamino)-nicotinamide;

N-(4,4-Dimethyl-1,2,3,4-tetrahydro-isoquinolin-7-yl)-2-(1-oxo-2,3-dihydro-1H-isoindol-4-ylamino)-nicotinamide; and N-[3,3-Dimethyl-1-(pyrrolidine-2-carbonyl)-2,3-dihydro-1H-indol-6-yl]-2-(1H-indazol-6-ylamino)-nicotinamide.

Indications

Compounds of the present invention would be useful for, but not limited to, the prevention or treatment of angiogenesis related diseases. The compounds of the invention have kinase inhibitory activity, such as VEGFR/KDR inhibitory activity. The compounds of the invention are useful in therapy as antineoplasia agents or to minimize deleterious effects of VEGF.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, be consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anaemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of sub-cutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

The compounds of this invention may also act as inhibitors of other protein kinases, e.g. p38, EGFR, CDK-2, CDK-5, IKK, JNK3, bFGFR, PDGFR and RAF and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Definitions

The term "treatment" includes therapeutic treatment as well as prophylactic treatment (either preventing the onset of disorders altogether or delaying the onset of a preclinically evident stage of disorders in individuals).

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —$SO_2$—.

The terms "sulfamyl," "aminosulfonyl" and "sulfonamidyl," denotes a sulfonyl radical substituted with an amine radical, forming a sulfonamide (—$SO_2NH_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—.

The term "aminocarbonyl" denotes an amide group of the formula —C(=O)$NH_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The term "heterocyclylalkylenyl" embraces heterocyclic-substituted alkyl radicals. More preferred heterocyclylalkylenyl radicals are "5- or 6-membered heteroarylalkylenyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S$—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The arylamino radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-$C_1$–$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$–$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$–$C_6$ rings. More preferred compounds include, cyclopentyl, cyclopropyl, and cyclohexyl.

The term "cycloalkenyl" includes carbocyclic groups having one or more carbon-carbon double bonds including "cycloalkyldienyl" compounds. Preferred cycloalkenyl groups include $C_3$–$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The term "Formulas I–XI" includes any sub formulas.

The compounds of the invention are endowed with kinase inhibitory activity, such as KDR inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of KDR.

The present invention comprises a pharmaceutical composition comprising a therapeutically-effective amount of a compound of Formulas I–XI in association with a least one pharmaceutically-acceptable carrier, adjuvant or diluent.

The present invention also comprises a method of treating angiogenesis related disorders in a subject having or susceptible to such disorder, the method comprising treating the subject with a therapeutically-effective amount of a compound of Formula I

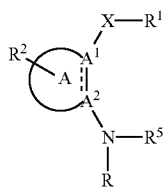

wherein each of $A^1$ and $A^2$ is independently C, CH or N;
wherein ring A is selected from
a) 5- or 6-membered partially saturated heterocyclyl,
b) 5- or 6-membered heteroaryl,
c) 9-, 10- or 11-membered fused partially saturated heterocyclyl,
d) 9- or 10-membered fused heteroaryl,
e) aryl, and
f) 4-, 5- or 6-membered cycloalkenyl;
wherein X is

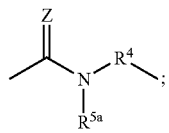

wherein Z is oxygen or sulfur;
wherein R is selected from
a) substituted or unsubstituted 4–6 membered heterocyclyl,
b) substituted aryl, and
c) substituted or unsubstituted fused 9–14-membered bicyclic or tricyclic heterocyclyl;
  wherein substituted R is substituted with one or more substituents independently selected from halo, —$OR^3$, —$SR^3$, —$SO_2R^3$, —$CO_2R^3$, —$CONR^3R^3$, —$COR^3$, —$NR^3R^3$—, $SO_2NR^3R^3$, —$NR^3C(O)OR^3$, —$NR^3C(O)R^3$, cycloalkyl, optionally substituted 4–6 membered heterocyclyl, optionally substituted phenyl, nitro, alkylaminoalkoxyalkoxy, cyano, alkylaminoalkoxy, lower alkyl substituted with $R^2$, lower alkenyl substituted with $R^2$, and lower alkynyl substituted with $R^2$;
wherein $R^1$ is selected from
a) substituted or unsubstituted 6–10 membered aryl,
b) substituted or unsubstituted 4–6 membered heterocyclyl,
c) substituted or unsubstituted 9–14 membered bicyclic or tricyclic heterocyclyl,
d) cycloalkyl, and
e) cycloalkenyl,
  wherein substituted $R^1$ is substituted with one or more substituents independently selected from halo, —$OR^3$ —$SR^3$, —$CO_2R^3$, —$CONR^3R^3$, —$COR^3$, —$NR^3R^3$, —NH ($C_1$–$C_4$ alkylenyl$R^{14}$), —$SO_2R^3$, —$SO_2NR^3R^3$, —$NR^3C(O)OR^3$, —$NR^3C(O)R^3$, optionally substituted cycloalkyl, optionally substituted 4–6 membered heterocyclyl, optionally substituted phenyl, halosulfonyl, cyano, alkylaminoalkoxy, alkylaminoalkoxyalkoxy, nitro, lower alkyl substituted with $R^2$, lower alkenyl substituted with $R^2$, and lower alkynyl substituted with $R^2$;

wherein $R^2$ is one or more substituents independently selected from H, halo, —$OR^3$, oxo, —$SR^3$, —$CO_2R^3$, —$COR^3$, —$CONR^3R^3$, —$NR^3R^3$, —$SO_2NR^3R^3$, —$NR^3C(O)OR^3$, —$NR^3C(O)R^3$, cycloalkyl, optionally substituted phenylalkylenyl, optionally substituted 4–6 membered heterocyclyl, optionally substituted heteroarylalkylenyl, optionally substituted phenyl, lower alkyl, cyano, lower hydroxyalkyl, lower carboxyalkyl, nitro, lower alkenyl, lower alkynyl, lower aminoalkyl, lower alkylaminoalkyl and lower haloalkyl;
wherein $R^3$ is selected from H, lower alkyl, optionally substituted phenyl, optionally substituted 4–6 membered heterocyclyl, optionally substituted $C_3$–$C_6$-cycloalkyl, optionally substituted phenylalkyl, optionally substituted 4–6 membered heterocyclylalkyl, optionally substituted $C_3$–$C_6$ cycloalkylalkyl, and lower haloalkyl;
wherein $R^4$ is selected from a direct bond, $C_{2-4}$-alkylenyl, $C_{2-4}$-alkenylenyl and $C_{2-4}$-alkynylenyl, where one of the $CH_2$ groups may be substituted with an oxygen atom or an —NH—, wherein $R^4$ is optionally substituted with hydroxy;
wherein $R^5$ is selected from H, lower alkyl, optionally substituted phenyl and lower aralkyl;
wherein $R^{14}$ is selected from H, phenyl, 4–6 membered heterocyclyl and $C_3$–$C_6$ cycloalkyl;
and pharmaceutically acceptable derivatives thereof;
provided R is not unsubstituted 2-thienyl, 2-pyridyl or 3-pyridyl.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCT NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19–384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-Al, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-Al, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181–2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit anti-thymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other anti-neoplastic agents, such as other kinase inhibitors including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The present invention comprises processes for the preparation of a compound of Formula I–XI.

Also included in the family of compounds of Formula I–X are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I–X may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I–X include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I–X.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases. Preferred salts include hydrochloride, phosphate and edisylate.

Additional examples of such salts can be found in Berge et al., J. Pharm. Sci., 66, 1 (1977).

General Synthetic Procedures

The compounds of the invention can be synthesized according to the following procedures of Schemes 1–31, wherein the substituents are as defined for Formulas I–XI, above, except where further noted.

Scheme 1

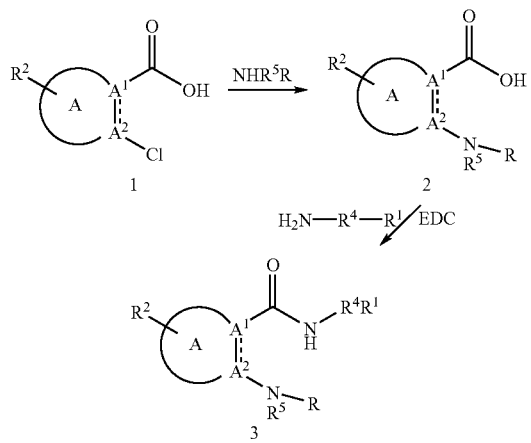

Substituted carboxamides 3 can be prepared from the corresponding halo analogs 1 by the process outlined in Scheme 1. Substituted amino acids 2 are prepared from the corresponding chloro compounds 1 such as by reacting with an amine at a suitable temperature, such as about 80° C. The acid 2 is coupled with an amine, preferably in the presence of a coupling agent such as EDC, to form the corresponding amide 3.

The amination process can be carried out as an Ullmann type reaction using a copper catalyst, such as copper[0] or a copper[I] compound such as copper[I]oxide, copper[I] bromide or copper[I]iodide in the presence of a suitable base (such as a metal carbonate, for example $K_2CO_3$ to neutralize the acid generated in the reaction.

This reaction is reviewed in Houben-Weyl "Methoden der Organischen Chemie", Band 11/1, page 32–33, 1958, in Organic Reactions, 14, page 19–24, 1965 and by J. Lindley (1984) in Tetrahedron, 40, page 1433–1456. The amount of catalyst is typically in the range of 1 to 20 mole percent. The reaction is carried out in an inert, aprotic solvent such as an ether (for example dimethoxyethane or dioxane) or an amide (for example dimethylformamide or N-methylpyrrolidone), under an inert atmosphere in the temperature range of 60–180° C.

An alternative amination process involves using a Group VIII element, where the metal core of the catalyst should be a zero-valent transition metal, such as palladium or nickel, which has the ability to undergo oxidative addition to the aryl-halogen bond. The zero valent state of the metal may be generated in situ from the M[II] state. The catalyst complexes may include chelating ligands, such as alkyl, aryl or heteroaryl derivatives of phoshines or biphosphines, imines or arsines. Preferred catalysts contain palladium or nickel. Examples of such catalysts include palladium[II]chloride, palladium[II]acetate, tetrakis(triphenylphosphine)palladium [0] and nickel[II]acetylacetonate. The metal catalyst is typically in the range of 0.1 to 10 mole percent. The chelating ligands may be either monodentate, as in the case for example of trialkyphosphines, such as tributylphosphine, triarylphosphines, such as tri-(ortho-tolyl)phosphine, and triheteroaryl phosphines, such as tri-2-furylphosphine; or they may be bidentate such as in the case of 2,2'-bis (diphenylphosphino)-1,1'binaphthyl, 1,2-bis (diphenylphosphino)ethane, 1,1'-bis(diphenylphosphino) ferrocene and 1-(N,N-dimethyl-amino)-1'-(dicyclohexylphosphino)biphenyl. The supporting ligand may be complexed to the metal center in the form of a metal complex prior to being added to the reaction mixture or may be added to the reaction mixture as a separate compound. The supporting ligand is typically present in the range 0.01 to 20 mole percent. It is often necessary to add a suitable base to the reaction mixture, such as a trialkylamine (for example, DIEA or 1,5-diazabicyclo[5,4,O]undec-5-ene), a Group I alkali metal alkoxide (for example potassium tert-butoxide) or carbonate (for example cesium carbonate) or potassium phosphate. The reaction is typically carried out in an inert aprotic solvent such as an ether (for example dimethoxyethane or dioxane) or an amide (for example, DMF or N-methylpyrrolidone), under an inert atmosphere in the temperature range of 60–180° C.

The amination is preferably carried out in an inert, aprotic, preferably anhydrous, solvent or solvent mixture, for example in a carboxylic acid amide, for example DMF or dimethylacetamide, a cyclic ether, for example THF or dioxane, or a nitrile, for example $CH_3CN$, or in a mixture thereof, at an appropriate temperature, for example in a temperature range of from about 40° C. to about 180° C., and if necessary under an inert gas atmosphere, for example a nitrogen or argon atmosphere.

Scheme 2

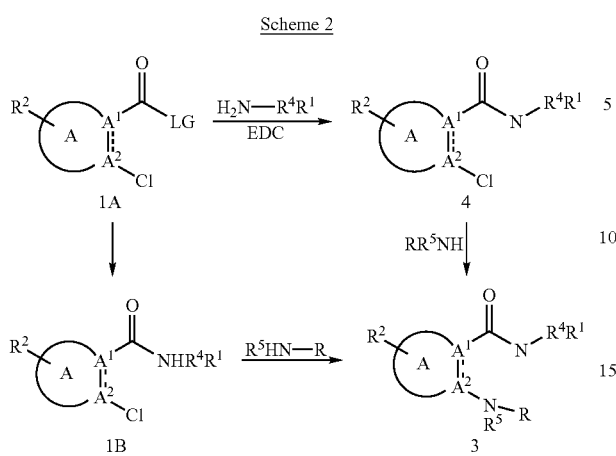

Substituted carboxamides 3 can be prepared from the corresponding halo analogs 1A by the process outlined in Scheme 2. The chloro acid 1 (LG is OH) is coupled with an amine, preferably in the presence of a coupling agent such as EDC, to form the corresponding chloro amide 4. Substituted amino-amides 3 are prepared from the corresponding chloro compounds 4 such as by reacting with an amine at a suitable temperature, such as about 80° C. The amination reaction can be run in the presence of an appropriate catalyst such as a palladium catalyst, in the presence of an aprotic base such as sodium t-butoxide or cesium carbonate, or a nickel catalyst, or a copper catalyst.

Alternatively, carboxamides 3 can be prepared from 2-chloro-heterocyclyl acid chloride 1A (LG is Cl) by coupling first with $R^1$—$NH_2$ such as in the presence of base, e.g., NaHCO_3, in a suitable solvent, such as $CH_2Cl_2$, to form the amide 1B, then coupling with a primary or secondary amine to yield the substituted carboxamide 3.

Additionally, where A is a pi-electron rich heterocycle, the addition of KF, such as 40% KF on alumina in IpOH, at a temperature over about 100° C., preferably about 160° C., can be used in the formation of 3 from 1B.

Scheme 3

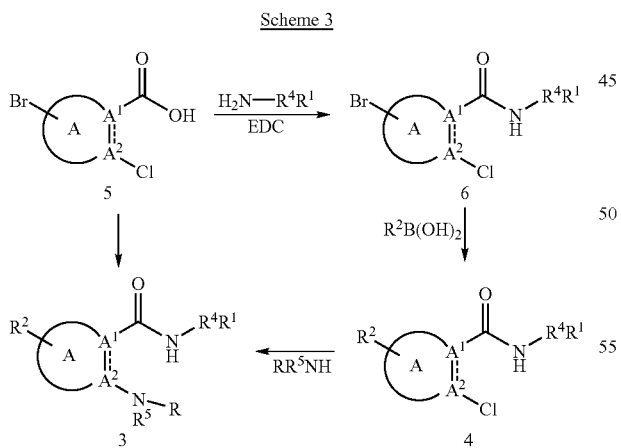

Substituted carboxamides 3 can be prepared from the corresponding bromo/chloro analogs 5 by the process outlined in Scheme 3. The bromo/chloro acid 5 is coupled with an amine, preferably in the presence of a coupling agent such as EDC, to form the corresponding bromo substituted amide 6. Suzuki coupling with the bromo amide 6 and suitable boronic acids provides the substituted amide 4.

Substituted amino-amides 3 are prepared from the corresponding chloro compounds 4 as described in Scheme 2.

Scheme 4

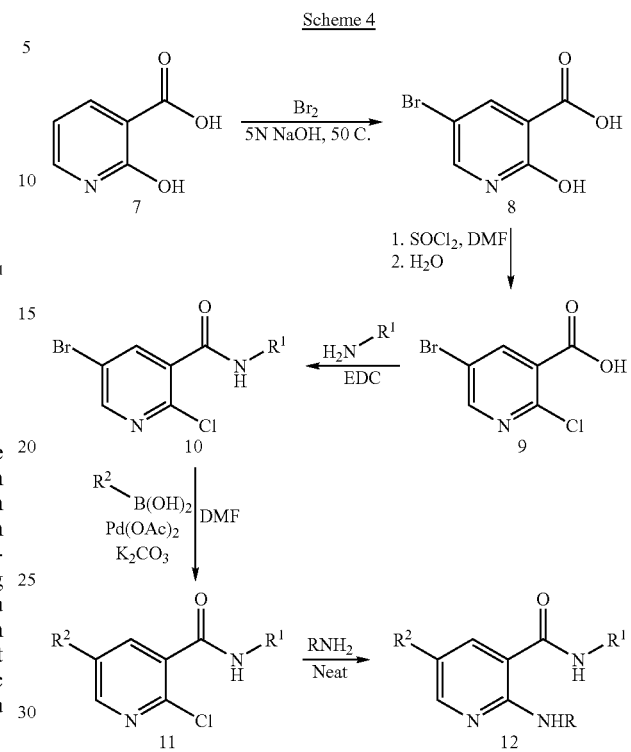

Substituted pyridines can be prepared by the process outlined in Scheme 4. A solution of sodium hypobromite is freshly prepared and added to a 2-hydroxynicotinic acid 7 and heated, preferably at a temperature at about 50° C. Additional sodium hypobromide may be needed to form the bromo compound 8. The 5-bromo-2-hydroxynicotinic acid 8 is reacted with thionyl chloride, preferably at a temperature >RT, more preferably at about 80° C. to form the 2-chloronicotinic acid analog 9. The acid is coupled with an amine, preferably in the presence of EDC, HOBT, and DIEA to form the corresponding substituted amide 10. Suzuki coupling with the bromo amide and suitable boronic acids, provides the substituted nicotinamide 11. 2-Aminonicotinamides 12 are prepared from the corresponding chloro compounds 11 such as by reacting with substituted amines at a suitable temperature, such as about 80° C.

Scheme 5

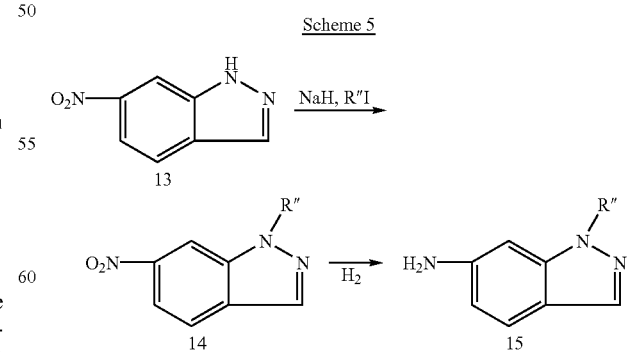

Alkylated indazoles can be prepared by the process outlined in Scheme 5. To a solution of 6-nitroindazole 13 in a solvent such as THF is added strong base, such as NaH at a temperature below RT, preferably at about 0° C. Alkylhalides, such as where R" is methyl, are added and reacted at a temperature about RT to give 1-alkyl-6-nitro-1H-indazole 14. The nitro indazole 14 is hydrogenated, such as with an H₂ atmosphere in the presence of a catalyst, such as Pd/C to give the 1-substituted-6-amino-1H-indazole 15.

perature at about 130° C. to give the 1-[5-(substituted)-2-nitrophenyl]-4-methylpiperazine 19. The nitro compound 19 is hydrogenated, such as with an H₂ atmosphere in the presence of a catalyst, such as Pd/C to furnish 4-(substituted)-2-(4-methylpiperazinyl)phenylamine 20.

Scheme 6

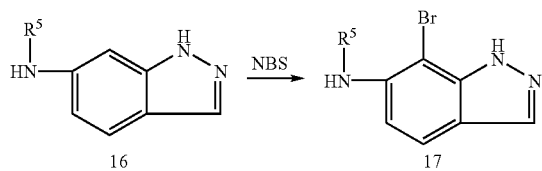

Brominated indazoles can be prepared by the process outlined in Scheme 6. NBS is slowly added to an acidic solution, such as a mixture of TFA:H₂SO₄ (5:1) and tert-butyl-4-nitrobenzene 16 at a temperature of about RT to yield the brominated compound 17.

Scheme 7

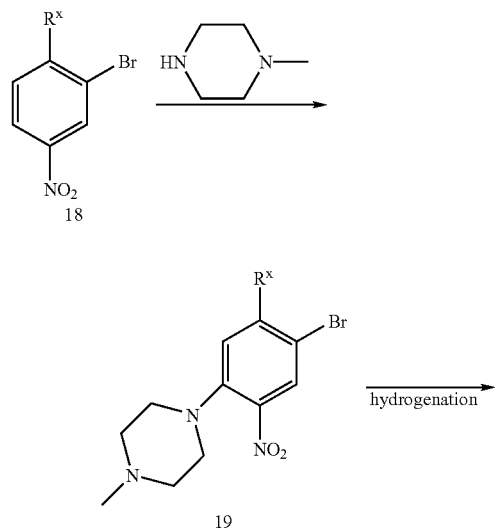

Substituted anilines can be prepared by the process outlined in Scheme 7. A mixture of 1-(substituted)-2-bromo-4-nitrobenzene 18 (where R^x is a substituent selected from those available for substituted R²) and N-methylpiperazine is heated, such as with or without solvent, preferably without solvent, at a temperature above RT, preferably at a temperature above about 100° C., and more preferably at a tem- Scheme 8

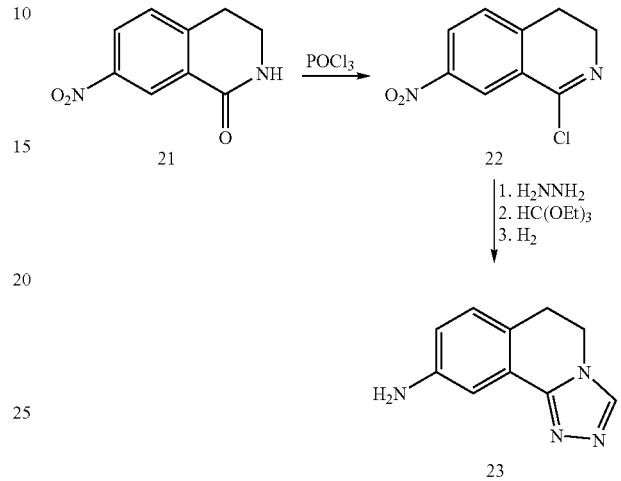

Tricyclic heterocycles can be prepared by the process outlined in Scheme 8. 7-Nitro-2,3,4-trihydroisoquinolin-1-one 21 is heated in POCl₃ at a temperature above RT, preferably at a temperature sufficient for reflux, to form the 1-chloro-7-nitro-3,4-dihydroisoquinoline 22. The 1-chloro-7-nitro-3,4-dihydroisoquinoline 22 is dissolved in a solvent, such as THF, and H₂NNH₂ is added. The reaction is heated with HC(OEt)₃ at a temperature above RT, preferably at a temperature above about 75° C., and more preferably at a temperature at about 115° C. to give the nitro-substituted tricyclic. Hydrogenation, such as with an H₂ atmosphere in the presence of a catalyst, such as Pd/C, gives 2-amino-5,6,7-trihydro-1,2,4-triazolo[3,4-a]isoquinoline 23.

Scheme 9

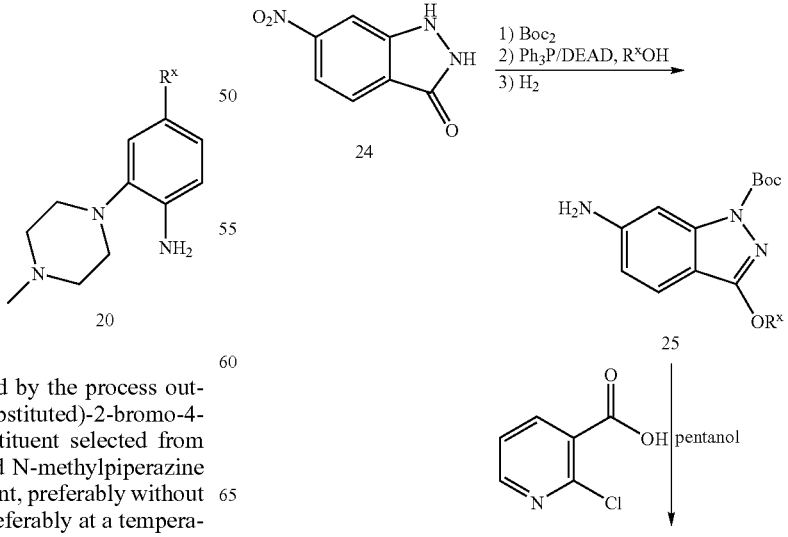

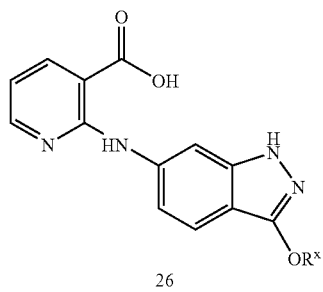

Indazolyl ethers can be prepared by the process outlined in Scheme 9. 6-Nitro-1H-2-hydroindazol-3-one 24 is protected such as with Boc₂O and DMAP in CH₂Cl₂ at a temperature of about RT, to give the protected 6-nitro-2-hydroindazol-3-one. The protected 6-nitro-2-hydroindazol-3-one is reacted with an alcohol (where $R^x$ is an appropriate substituent selected from the possible substituents on $R^1$) and Ph₃P in a solvent, such as THF, and DEAD, at a temperature of about RT, to give the protected 6-nitro(indazol-3-yl) ether. The nitro intermediate is hydrogenated, such as with an H₂ atmosphere in the presence of a catalyst, such as Pd/C, to give the protected 6-amino(indazol-3-yl) ether 25. The amine 25 is coupled with 2-chloronicotinic acid in a solvent, such as an alcohol, preferably pentanol, at a temperature above RT, preferably at a temperature above about 75° C., and more preferably at a temperature at about 130° C. to give the coupled and deprotected compound 26.

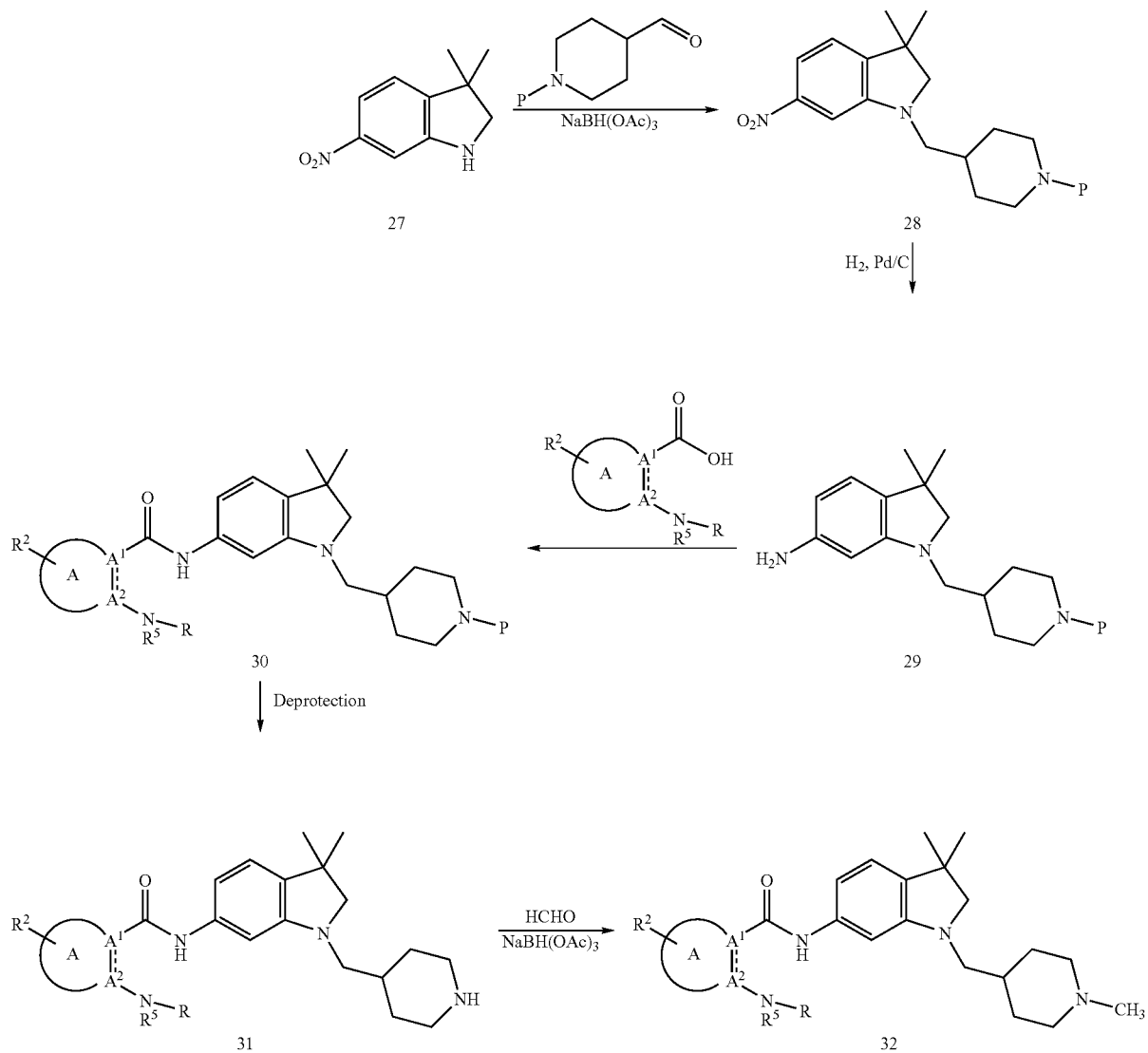

Indolinyl substituted carboxamides can be prepared from the corresponding nitro indoline 27 by the process outlined in Scheme 10. For example, 3,3-dimethyl-6-nitroindoline 27 is alkylated, such as with N-protected-4-formylpiperidine in the presence of NaHB(OAc)$_3$ and acid, such as glacial AcOH, and solvent, such as dichloromethane, at a temperature of about RT, to afford the alkylated indane 28. Hydrogenation of the alkylated indane 28, such as with an H$_2$ atmosphere in the presence of a catalyst, such as Pd/C, in the presence of a solvent, such as an alcohol, preferably MeOH, to give the amino intermediate 29. Alternatively, other hydrogenation methods can be used, such as Fe powder with NH$_4$Cl. Coupling of the amine 29, such as with 2-chloronicotinic acid and DIEA, HOBt and EDC, in a solvent such as CH$_2$Cl$_2$ at a temperature of about RT provides the protected carboxamide 30, which upon deprotection and alkylation yields other compounds of the invention, 31 and 32, respectively. Alternatively, amine 29 is reacted with 2-fluoronicotinoyl chloride to form a 2-fluoronicotinamide, which can be alkylated, such as in Scheme 10.

Scheme 11

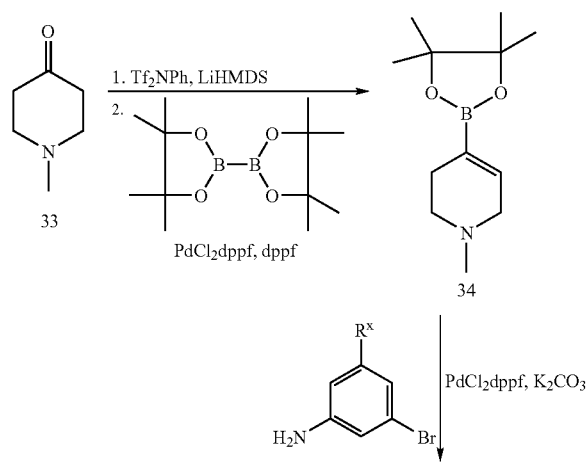

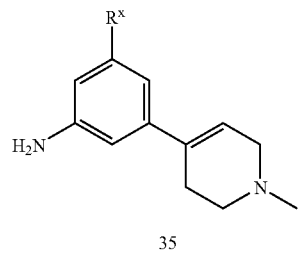

Substituted anilines can be prepared by the process outlined in Scheme 11 (where $R^x$ is a substituent selected those available for substituted $R^1$, preferably haloalkyl and alkyl). 1-Methyl-4-piperidinone is added to a solution of strong base such as LiHMDS, in a solvent such as THF, at a temperature below RT, preferably lower than about −50° C., more preferably at about −78° C. Tf$_2$NPh is reacted with the enolate at a temperature of about RT, to give 1-methyl-4-(1,2,5,6-tetrahydro)pyridyl-(trifluoromethyl)sulfonate. A mixture of the triflate intermediate, bis(pinacolato)diboron, potassium acetate, PdCl$_2$(dppf), and dppf in a solvent such as dioxane and heated at a temperature above RT, preferably at a temperature above about 50° C., and more preferably at a temperature at about 80° C. to give 4,4,5,5-tetramethyl-2-(1-methyl(4-1,2,5,6-tetrahydropyridyl))-1,3,2-dioxaborolane 34. The substituted aniline 35 is formed from the 1,3,2-dioxaborolane 34 such as with treatment with an amine in the presence of PdCl$_2$(dppf) and base, such as K$_2$CO$_3$, in a solvent such as DMF at a temperature above RT, preferably at a temperature above about 50° C., and more preferably at a temperature at about 80° C.

Scheme 12

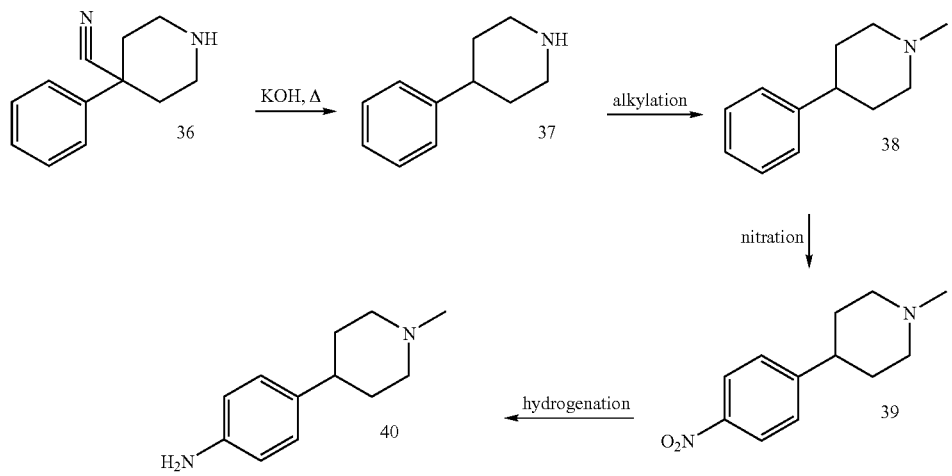

Substituted anilines can be prepared by the process outlined in Scheme 12. 4-Cyano-4-phenylpiperidine hydrochloride 36 is treated with base, such as KOH, at a temperature above RT, preferably at a temperature above about 100° C., and more preferably at a temperature at about 160° C., to provide the phenyl piperidine 37. Alkylation of the phenyl piperidine 37, such as with formaldehyde and NaCNBH₃ in a solvent such as CH₃CN, with sufficient acid to maintain the reaction pH near 7, to provide the alkylated piperidine 38. Nitration of the phenylpiperidine 38, such as with H₂SO₄ and fuming HNO₃ at a temperature below RT, and preferably at about 0° C., gives the nitro intermediate 39. Hydrogenation of the nitro intermediate 39, such as with an H₂ atmosphere in the presence of a catalyst, such as Pd/C, in the presence of a solvent, such as an alcohol, preferably MeOH, to give the amino intermediate 40.

1,2,3,6-Tetrahydro-pyridyl substituted anilines are prepared such as by the procedure described in Scheme 14. Nitrobenzenes 43 are brominated, such as with bromine in the presence of acid, H₂SO₄ for example, or with NBS to yield the 3-bromo derivative 44. Suzuki coupling of the bromo-derivative 44 and a substituted pyridylboronic acid, such as at a temperature above RT, preferably above about 50° C., and more preferably at about 80° C., yields the pyridyl derivative 45. Alkylation of the nitrophenyl-pyridine 45, such as by treatment with iodomethane, preferably above about 50° C., and more preferably at about 80° C., yields the pyridinium compound 46, which upon reduction, such as by NaBH₄, yields the tetrahydropyridine 47.

Scheme 13

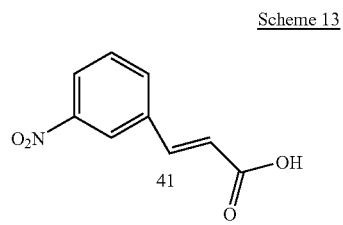

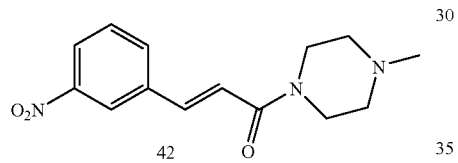

Substituted amides can be prepared by the process outlined in Scheme 13. 3-Nitrocinnamic acid 41 is coupled with 1-methylpiperazine in the presence of EDC and a solvent such as CH₂Cl₂, at a temperature of about RT gives the carboxamide 42.

Scheme 15

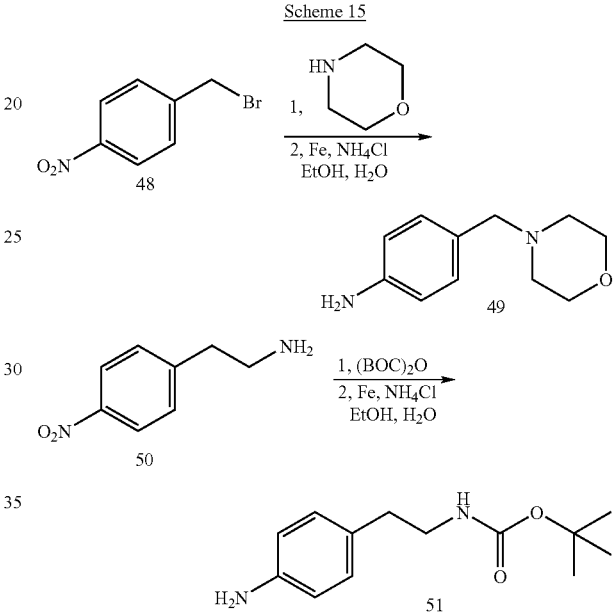

Scheme 14

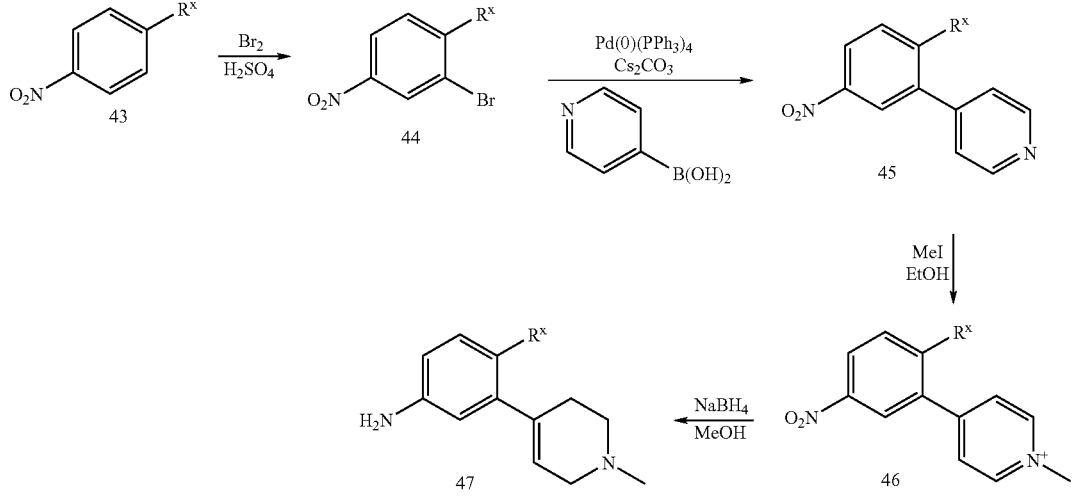

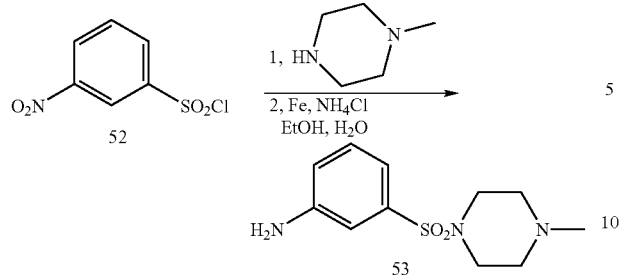

A series of substituted anilines are prepared such as by the procedure described in Scheme 15. A nitrobenzyl bromide 48 is coupled with morpholine, such as at a temperature at about RT, to yield the heterocyclylmethyl nitrobenzene derivative. Reduction of the nitro compound, such as with iron powder, preferably above about 50° C., and more preferably at about 80° C., yields the heterocyclylmethyl substituted aniline 49.

Protected alkylamine substituted anilines can be prepared from the nitro free amines 50, such as with standard protecting agents and chemistry known in the art, such as BOC chemistry. Reduction of the protected nitro compound, such as with iron powder, preferably above about 50° C., and more preferably at about 80° C., yields the aniline 51.

Sulfonamide substituted anilines can be prepared from nitrobezenesulfonyl chlorides 52. Coupling of nitrobezenesulfonyl chlorides 52 with reactive heterocyclic compounds, such as substituted piperazines, piperidines, and the like, in a protic solvent such as EtOH, such as at a temperature about RT, yields the nitrobezenesulfonamides 52. Reduction of the nitro benzenesulfonamide, such as with iron powder, preferably above about 50° C., and more preferably at about 80° C., yields the aniline 53.

Scheme 16

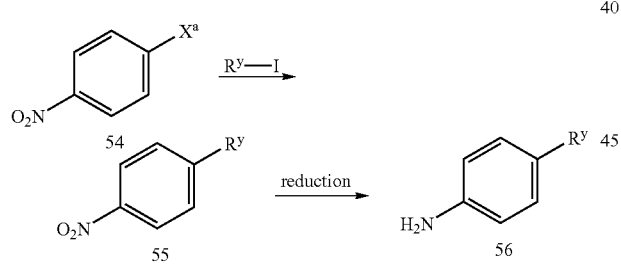

A series of perhaloalkyl-substituted anilines 56, where $R^y$ represents perhaloalkyl radicals, are prepared such as by the procedure described in Scheme 16. 1-Nitro-4-(perfluoroethyl)benzene can be synthesized by the method described in the reference [John N. Freskos, Synthetic Communications, 18(9), 965–972 (1988)]. Alternatively, 1-Nitro-4-(perfluoroalkyl)benzene can be synthesized from the nitro compound, where $X^a$ is a leaving group, such as bromo or iodo, by the method described by W. A. Gregory, et al. [J. Med. Chem., 1990, 33, 2569–2578].

Reduction of the nitrobenzenes 55, such as with iron powder, at a temperature above about 50° C., and preferably at about 80° C., yields the aniline 56. Hydrogenation, such as with $H_2$ atmosphere in the presence of a catalyst, such as 10% Pd/C, is also possible.

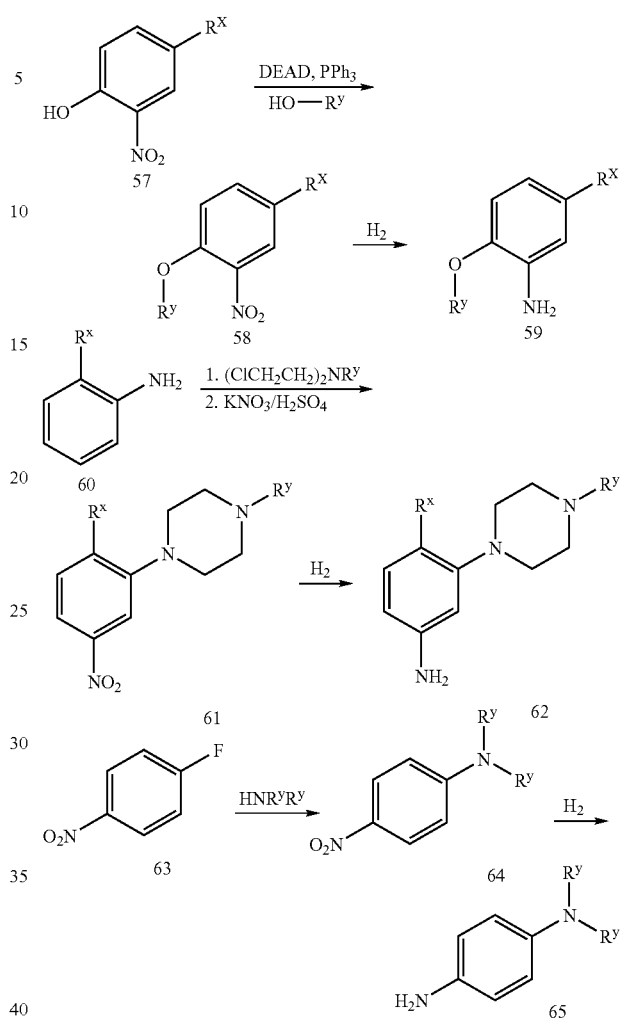

Additional series of substituted anilines are prepared such as by the procedures described in Scheme 17 (where $R^x$ is a substituent selected those available for substituted $R^1$, preferably haloalkyl and alkyl). 2-Alkoxy substituted anilines 59 are prepared from the corresponding phenol compounds 57 such as by the Mitsunobu reaction, including treatment with a N,N-dialkylethanolamine and PPh$_3$ and DEAD to give the corresponding nitro compound 58, followed by hydrogenation, such as with $H_2$ to give the aniline 59.

Alternatively, piperazinyl substituted anilines 62 can be prepared by the treatment of an aniline 60 with an N-substituted-bis(2-chloroethyl)amine, base, such as $K_2CO_3$ and NaI, at a temperature above about 50° C., preferably above about 100° C., and more preferably at about 170° C., to give the piperazinylbenzene compound 61. Nitration, such as with $H_2SO_4$ and $HNO_3$, at a temperature above 0° C., and preferably at about RT, followed by hydrogenation, such as with $H_2$ atmosphere gives the substituted aniline 62.

Alternatively, piperazinyl substituted anilines 65 can be prepared by the treatment of a fluoro-nitro-substituted aryl compounds 63. The fluoro-nitro-substituted aryl compounds 63 and 1-substituted piperazines are heated, preferably neat, at a temperature above about 50° C., and preferably at about 90° C., to yield the piperazinyl-nitroaryl compounds 64. Hydrogenation, such as with $H_2$ atmosphere in the presence of a catalyst, such as 10% Pd/C, gives the substituted aniline 65.

Scheme 18

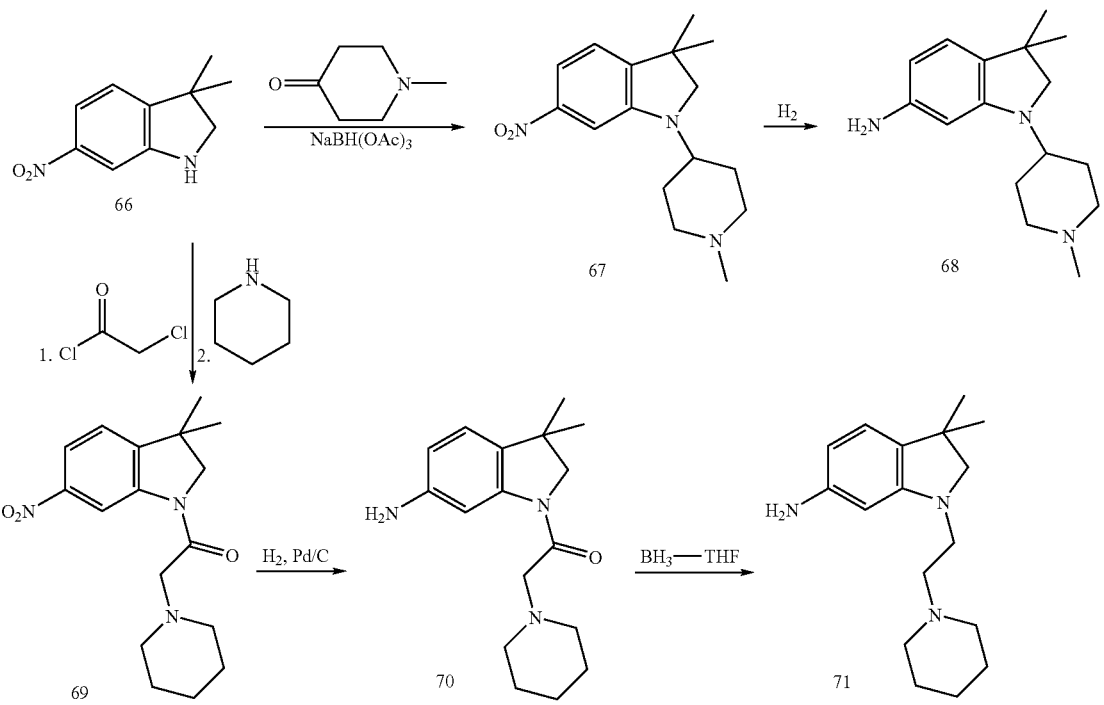

Substituted indolines are prepared such as by the procedures described in Scheme 18. Substituted amino-indolines 68 are prepared from the nitroindoline 66 and a ketone in the presence of NaHB(OAc)$_3$ to form the 1-substituted indoline 67. The nitroindoline 67 is hydrogenated, such as with H$_2$ in the presence of a catalyst, such as Pd/C, to yield the amino-indoline 68.

Alternatively, substituted amino-indolines 71 are prepared from the nitroindoline 66. Nitroindoline 66, is reacted with an acid chloride to form an amide. Further treatment with a primary or secondary amine, preferably a secondary amine, such as in the presence of NaI, at a temperature above about 50° C., and preferably at about 70° C. yields the nitroindoline 69. The nitro compound 69 is hydrogenated, such as with H$_2$ in the presence of a catalyst, such as Pd/C, to yield the amino-indoline) 70. The carbonyl is reduced, such as with BH$_3$-THF yields 1-aminoalkyl-indolines 71.

Scheme 19

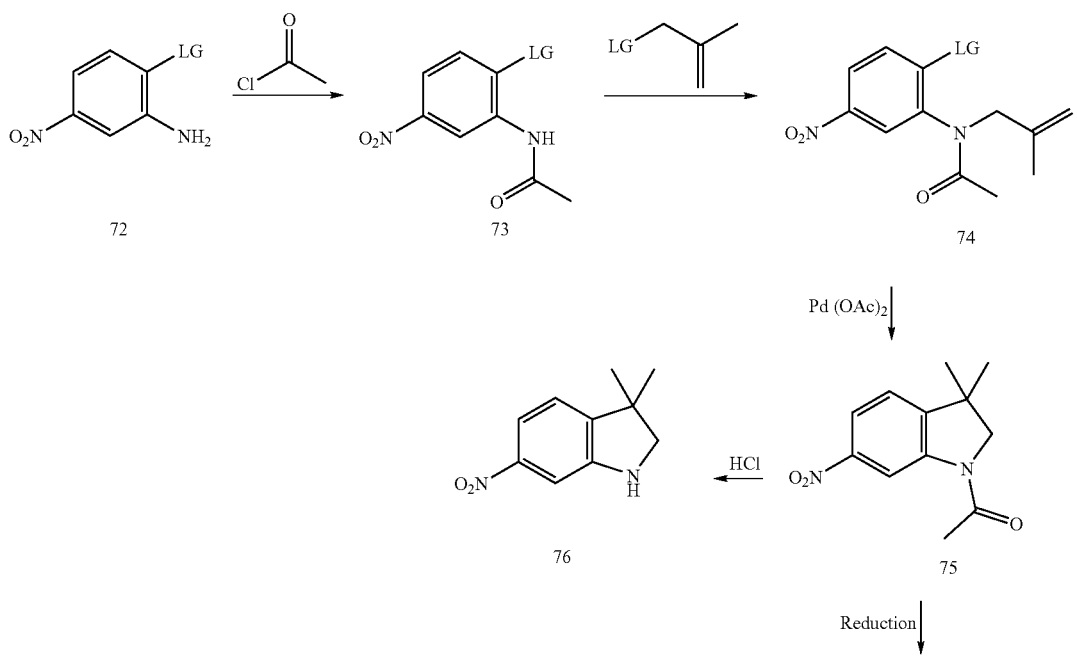

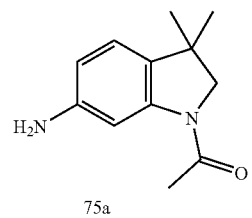

75a

Substituted indolines are prepared such as by the procedures described in Scheme 19. Substituted acetamides 73 are prepared from the coupling of halo-5-nitroanilines 72 (where LG is bromo or chloro, preferably chloro) and an acylating agent, such as acetyl chloride or acetic anhydride, under standard coupling chemistry, such as with DIEA, and DMAP, at a temperature of about RT, in a suitable solvent, such as CH$_2$Cl$_2$, DMF and/or DMAC. The N-(2-methylprop-2-enyl)acetamide 74 is prepared from the acetamide 73, such as by the treatment of base, such as NaH in a suitable solvent such as NMP or anhydrous DMF and a 3-halo-2-methylpropene such as 3-bromo-2-methylpropene or 3-chloro-2-methylpropene, at a temperature between about 0° C. and RT, and preferably at about RT; or with CSCO$_3$ at a temperature above RT, preferably above about 50° C. and more preferably above about 60° C. Cyclization of the N-(2-methylprop-2-enyl)acetamide 74, such as by the Heck-type reaction (treatment with Pd(OAc)$_2$ in the presence of base, for example tetraethyl-ammonium chloride, sodium formate, and NaOAc) at a temperature above about 50° C., and preferably at about 80° C., yields the protected (3,3-dimethyl-6-nitro-2,3-dihydro-indol-1-yl)ethanone 75. Deprotection, such as with strong acid such as HCl or AcOH at a temperature above about 50° C., and preferably at about 70–80° C., yields the 3,3-dimethyl-6-nitro-2,3-dihydro-indol-1-yl 76. Alternatively, the protected dihydro-6-nitro indoline 75 can be reduced, such as with Fe, or with 10% Pd/C in the presence of an excess of NH$_4$CO$_2$H, or with H$_2$ in the presence of a catalyst to form the protected dihydro-6-amino indoline 75a.

Scheme 20

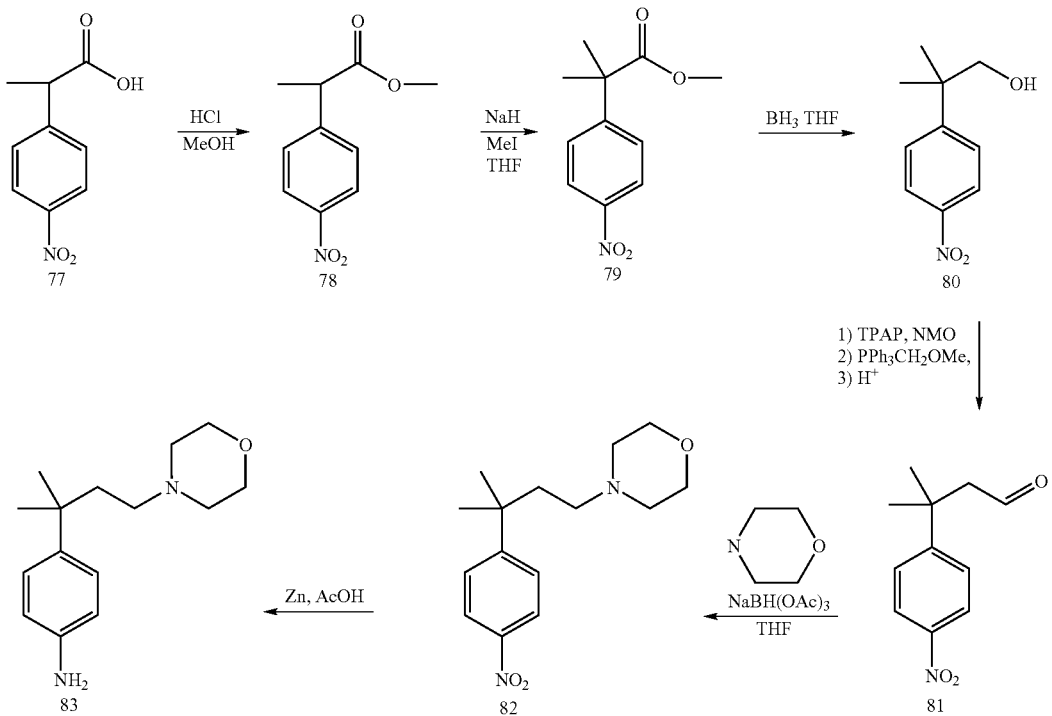

Substituted anilines are prepared such as by the procedures described in Scheme 20. Nitrophenyl esters 78 are formed from the acid 77, such as by treatment with MeOH and acid. Alkylation of the ester 78, such as by treatment with base, followed by alkyl halide, yields the branched alklyl compounds 79. Reduction of the ester 79, such as with BH$_3$, yields the alcohol 80. The aldehyde 81 is prepared from the alcohol 80, such as by treatment with TPAP in the presence of N-methylmorpholine-N-oxide. Subsequent treatment with methoxymethyltriphenylphosphonium chloride and KHMDS yields 81. Coupling of the aldehyde 81 and morpholine, such as with NaBH(OAc)$_3$ yields the tertiary amine 82. Reduction of the nitro compound, such as with acid, for example AcOH, and zinc yields the aniline 83.

Scheme 21

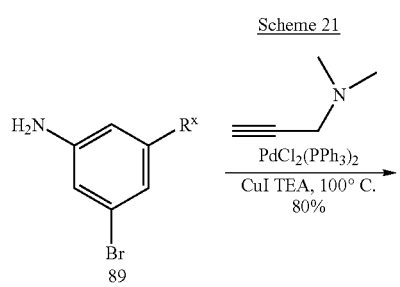

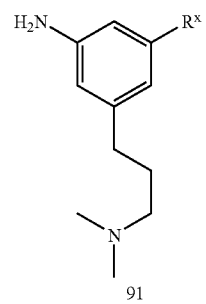

Substituted aniline compounds are prepared such as by the procedure described in Scheme 21 (where $R^x$ is a substituent selected those available for substituted $R^1$, preferably haloalkyl and alkyl). Alkynyl-aniline 90, prepared similar to that described in Scheme 22, is hydrogenated such as with $H_2$ in the presence of a catalyst, such as $Pd(OH)_2$, to yield the substituted alkyl 91.

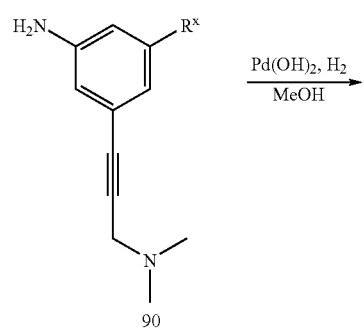

Scheme 22

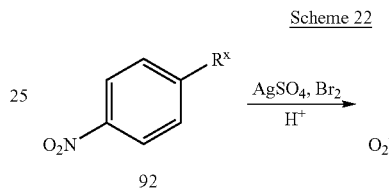

Substituted bromophenyl compounds are prepared such as by the procedure described in Scheme 22. Bromine is added to a optionally substituted nitrobenzene 92, silver(II) sulfate and acid, such as $H_2SO_4$, to provide the bromo derivative 93.

Scheme 23

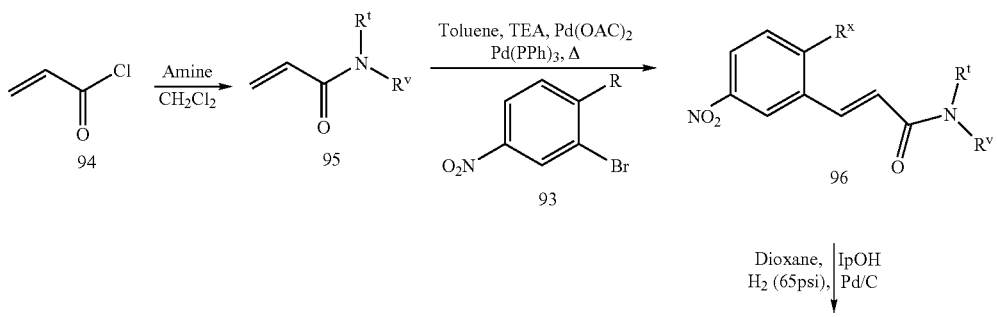

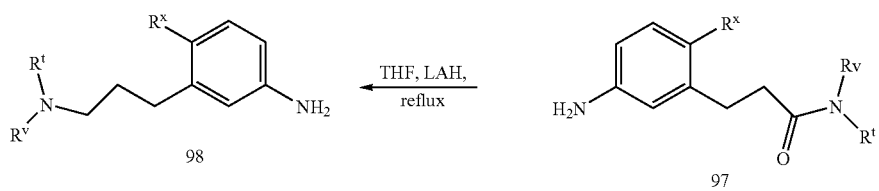

Substituted anilines are prepared such as by the procedure described in Scheme 23 (where $R^t$ and $R^v$ are alkyl, or together with the nitrogen atom form a 4–6 membered heterocyclic ring). Acryloyl chloride 94 is reacted with an amine, preferably a secondary amine, such as at a temperature between about 0° C. and about RT, to form the amide 95. A bromo-nitrobenzene 93 is reacted with the amide 95, such as in the presence of base, for example TEA, together with $Pd(OAc)_2$ and $Pd(PPh_3)_4$, at a temperature above about 50° C., and preferably at about 120° C., such as in a sealed container, to form the substituted alkene 96. Hydrogenation of the alkene 96, such as with $H_2$-in the presence of a catalyst, for example Pd/C catalyst yields the substituted aniline 97. Reduction of the amide 97, such as with $LiALH_4$, at a temperature above about 50° C., and preferably at about 80° C. yields the aniline 98.

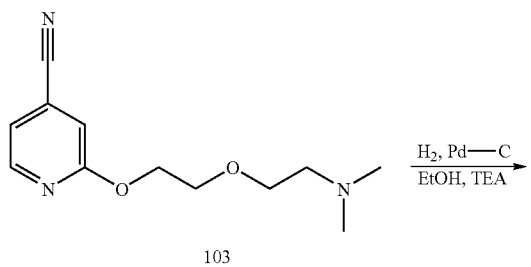

103

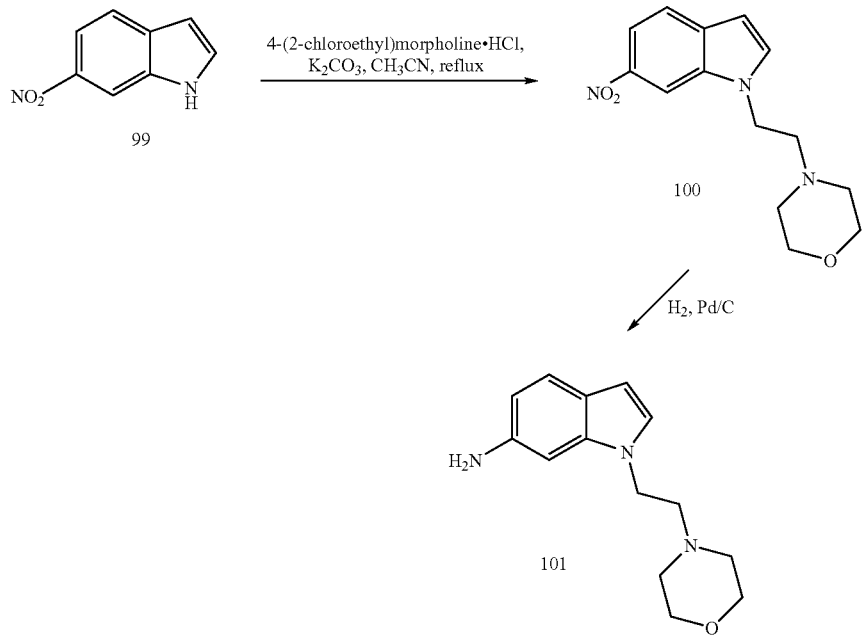

Substituted indoles are prepared such as by the procedure described in Scheme 24. A nitroindole 99 is coupled with a halo compound, in the presence of base, for example $K_2CO_3$. Heating at a temperature above about 50° C., and preferably at about reflux yields the substituted-nitro-1H-indole 100. Hydrogenation similar to conditions described above yield the amino derivative 101.

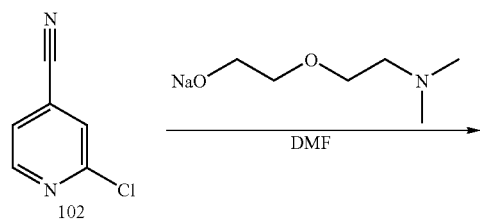

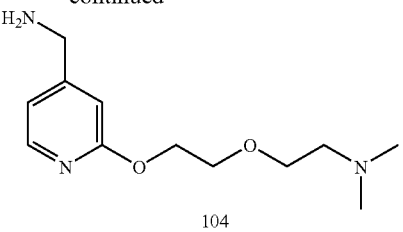

104

Substituted aminomethyl compounds are prepared such as by the procedure described in Scheme 25. NaH is added to an alcohol and heated at a temperature above about RT, and preferably at about 50° C., to form the sodium alkoxide, which is added to a halo compound 102, such as a 2-chloro-4-cyanopyridine and heated at a temperature above about 50° C., and preferably at about 70° C. to form the ether 103. Hydrogenation yields the aminomethyl derivative 104.

Scheme 26

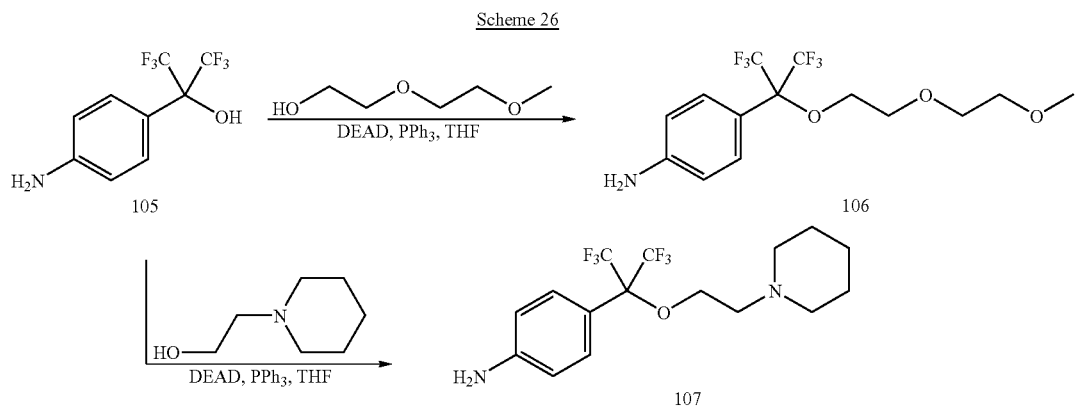

Substituted anilines are prepared such as by the procedure described in Scheme 26. Treatment with the haloalkyl alcohol 105 with an alcohol, such as in the presence of DEAD and $PPh_3$ yields the ether 107 or 106.

Scheme 27

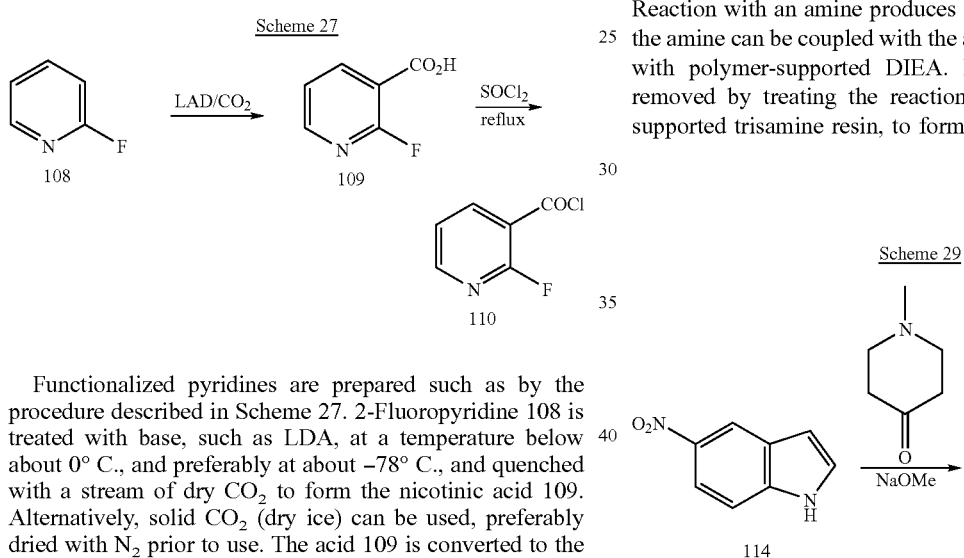

Functionalized pyridines are prepared such as by the procedure described in Scheme 27. 2-Fluoropyridine 108 is treated with base, such as LDA, at a temperature below about 0° C., and preferably at about −78° C., and quenched with a stream of dry $CO_2$ to form the nicotinic acid 109. Alternatively, solid $CO_2$ (dry ice) can be used, preferably dried with $N_2$ prior to use. The acid 109 is converted to the acid halide 110, such as by treatment with thionyl chloride and heating at a temperature above about 50° C., and preferably at about reflux.

Chloro-substituted pyridines 113 are prepared such as by the procedure described in Scheme 28. 2-Chloronicotinic acid 112 is activated with ethyl chloroformate, in the presence of base, such as TEA, at a temperature of about RT. Reaction with an amine produces amide 113. Alternatively, the amine can be coupled with the acid chloride 111, such as with polymer-supported DIEA. Excess acid chloride is removed by treating the reaction mixture with polymer-supported trisamine resin, to form amide 113.

Scheme 29

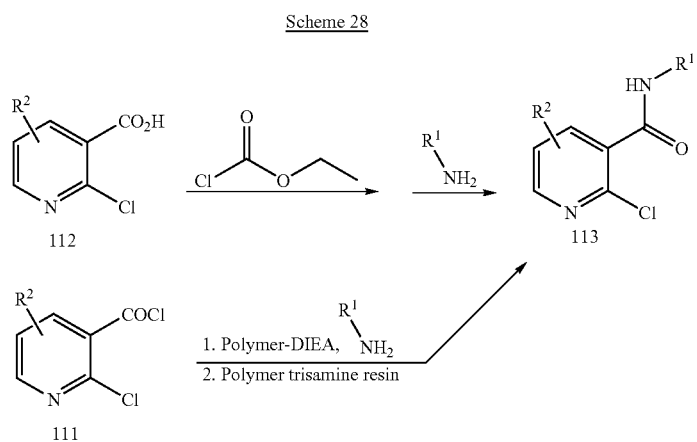

Scheme 28

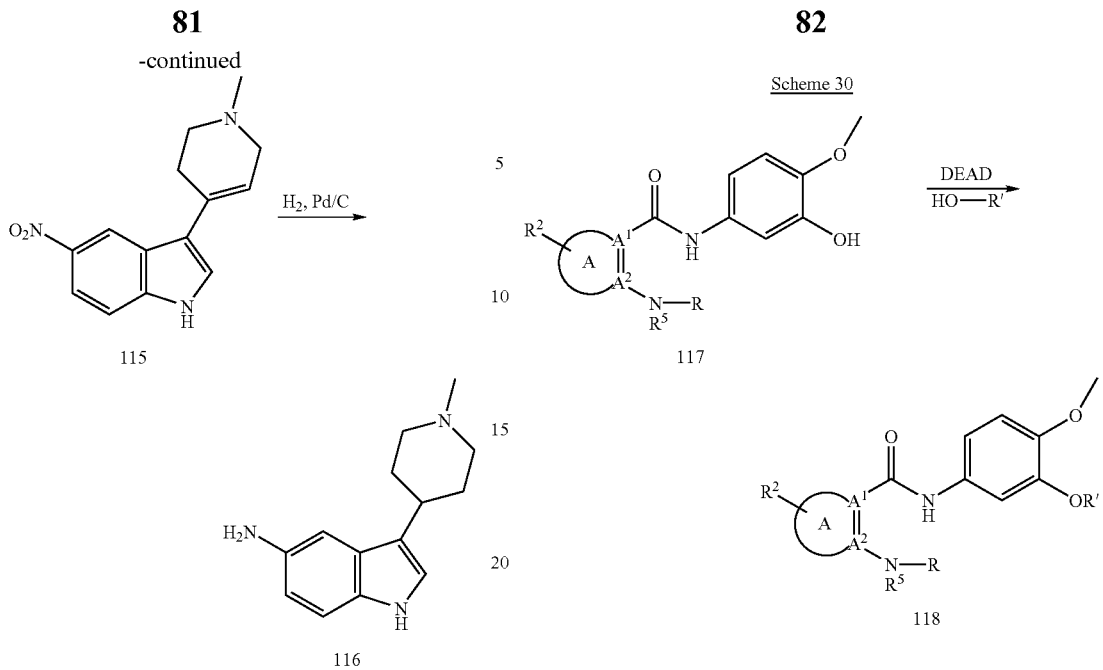

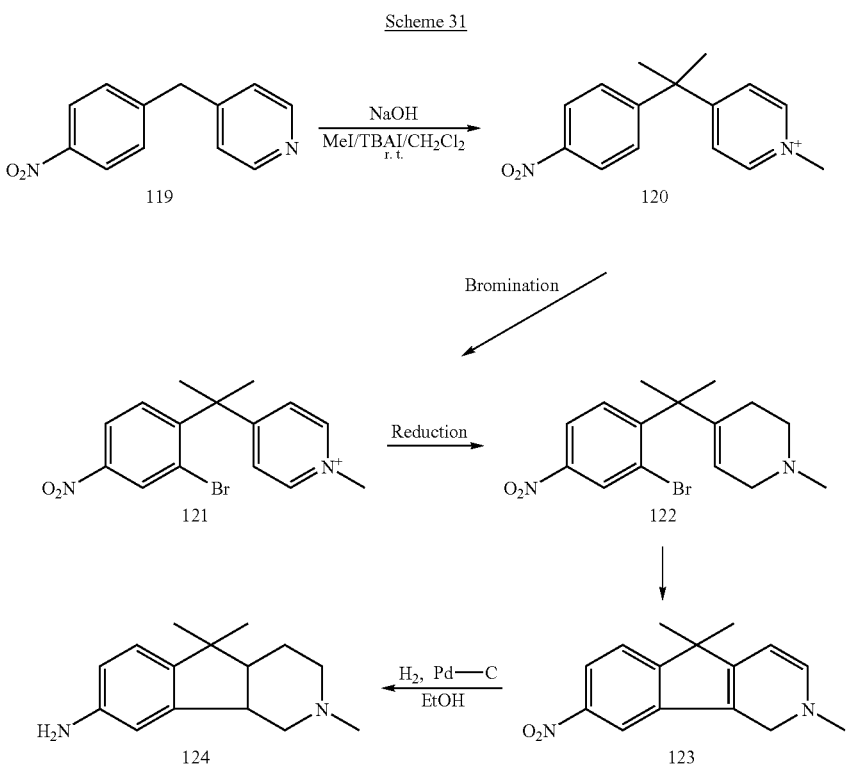

Amino-substituted indoles 116 are prepared such as by the procedure described in Scheme 291. Nitroindoline 114 is reacted with N-methyl-4-piperidone in the presence of NaOMe at a temperature above about 50° C., and preferably at about reflux, to form the 3-substituted indole 115. Hydrogenation as previously discussed yields the amino indole 116.

Substituted carboxamides 118 can be prepared from the corresponding phenols 117 of the invention, by the process outlined in Scheme 30. A carboxamide 117 is coupled with an alcohol, such as 4-hydroxy-N-methylpiperidine, in the presence of DEAD and triphenylphosphine, in a solvent such as THF, at a temperature of about RT, provides the ether 118.

2,3,4,4a,9,9a-hexahydro-1H-3-aza-fluoren-6-ylamine may be prepared by the method found in Scheme 31. Nitrobenzylpyridines 119 are alkylated, such as with MeI, in the presence of TBAI and base to form the pyridinium compound 120. The pyridinium compounds 120 are halogenated, such as brominated with NBS, to form the brominated pyridinium compounds 121 which are reduced such as with NaBH$_4$, dehalogenated and reduced to form the hexahydro-fluorenes 124.

The starting compounds defined in Schemes 1–31 may also be present with functional groups in protected form if necessary and/or in the form of salts, provided a salt-forming group is present and the reaction in salt form is possible. If so desired, one compound of Formulas I–XI can be converted into another compound of Formulas I–XI or a N-oxide thereof; a compound of Formulas I–XI can be converted into a salt; a salt of a compound of Formulas I–XI can be converted into the free compound or another salt; and/or a mixture of isomeric compounds of Formulas I–XI can be separated into the individual isomers.

N-Oxides can be obtained in a known matter by reacting a compound of Formulas I–XI with hydrogen peroxide or a peracid, e.g. 3-chloroperoxy-benzoic acid, in an inert solvent, e.g. dichloromethane, at a temperature between about −10–35° C., such as about 0° C.–RT.

If one or more other functional groups, for example carboxy, hydroxy, amino, or mercapto, are or need to be protected in a compound of Formulas I–XI or in the preparation of compounds of Formulas I–XI, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of Formulas I–XI with a salt-forming group may be prepared in a manner known per se. Acid addition salts of compounds of Formulas I–XI may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of Formulas I–XI.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

A compound of Formulas I–XI, wherein Z is oxygen, can be converted into the respective compound wherein Z is sulfur, for example, by using an appropriate sulfur compound, e. g. using reaction with Lawesson's reagent (2,4-bis-(4-methoxyphenyl)2,4-dithioxo-1,2,3,4-dithiaphosphetan) in a halogenated hydrocarbon, such as $CH_2Cl_2$, or an aprotic solvent, such as toluene or xylene, at temperatures from about 30° C. to reflux.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H+ form, depending on the type of reaction and/or reactants at reduced, normal, or elevated temperature, for example in the range from about −100° C. to about 190° C., preferably from about −80° C. to about 150° C., for example at about −80 to about 60° C., at room temperature, at about −20 to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g., ethyl acetate, ethers, typically aliphatic ethers, e.g., diethylether, or cyclic ethers, e.g., THF, liquid aromatic hydrocarbons, typically benzene or toluene, alcohols, typically MeOH, EtOH or 1-propanol, IPOH, nitrites, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g., AcOH, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of Formulas I–XI, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

For example, amine 1 can be prepared by reduction of the corresponding nitro. The reduction preferably takes place in the presence of a suitable reducing agent, such as tin(II) chloride or hydrogen in the presence of an appropriate catalyst, such as Raney nickel (then preferably the hydrogen is used under pressure, e.g. between 2 and 20 bar) or $PtO_2$, in an appropriate solvent, e.g. an alcohol, such as MeOH. The reaction temperature is preferably between about 0° C. and about 80° C., especially about 15° C. to about 30° C.

It would also be possible to reduce the nitro compound after forming the amide compound under reaction conditions analogous to those for the reduction of nitro compounds described above. This would eliminate the need to protect the free amino group as described in Scheme 1.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

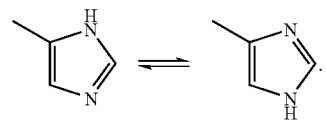

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necesssary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, simulated moving bed ("SMB")), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); A. Katritzky and A. Pozharski, Handbook of Heterocyclic Chemistry, 2$^{nd}$ Ed. (2001); M. Bodanszky, A. Bodanszky: *The practice of Peptide Synthesis* Springer-Verlag, Berlin Heidelberg 1984; J. Seyden-Penne: *Reductions by the Alumino-and Borohydrides in Organic Synthesis*, 2$^{nd}$ Ed., Wiley-VCH, 1997; and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The following examples contain detailed descriptions of the methods of preparation of compounds of Formulas I–XI. These detailed descriptions fall within the scope, and serve to exemplify, the above described General Synthetic Procedures which form part of the invention. These detailed descriptions are presented for illustrative purposes only and are not intended as a restriction on the scope of the invention.

Unless otherwise noted, all materials were obtained from commercial suppliers and used without further purification. Anhydrous solvents such as DMF, THF, $CH_2Cl_2$ and toluene were obtained from the Aldrich Chemical Company. All reactions involving air- or moisture-sensitive compounds were performed under a nitrogen atmosphere. Flash chromatography was performed using Aldrich Chemical Company silica gel (200–400 mesh, 60A) or Biotage pre-packed column. Thin-layer chromatography (TLC) was performed with Analtech gel TLC plates (250μ). Preparative TLC was performed with Analtech silica gel plates (1000–2000μ). Preparative HPLC was conducted on a Beckman or Waters HPLC system with 0.1% TFA/$H_2O$ and 0.1% TFA/$CH_3CN$ as mobile phase. The flow rate was at 20 ml/min. and gradient method was used. $^1H$ NMR spectra were determined with super conducting FT NMR spectrometers operating at 400 MHz or a Varian 300 MHz instrument. Chemical shifts are expressed in ppm downfield from internal standard tetramethylsilane. All compounds showed NMR spectra consistent with their assigned structures. Mass spectra (MS) were determined on a Perkin Elmer—SCIEX API 165 electrospray mass spectrometer (positive and, or negative) or an HP 1100 MSD LC-MS with eletrospray ionization and quadrupole detection. All parts are by weight and temperatures are in Degrees centigrade unless otherwise indicated.

The following abbreviations are used:

| | |
|---|---|
| AcOH | acetic acid |
| $Ac_2O$ | acetic anhydride |
| AIBN | 2,2'-azobisisobutyronitrile |
| Ar | argon |
| $AgSO_4$ | silver sulfate |
| $AlCl_3$ | aluminum trichloride |
| ATP | adenosine triphosphate |
| $BH_3$ | borane |
| Boc | tert-butyloxycarbonyl |
| $Boc_2O$ | Boc anhydride |
| BOP-Cl | bis(2-oxo-3-oxazolidinyl)phosphinic chloride |
| $Br_2$ | bromine |
| BSA | bovine serum albumin |
| t-BuOH | tert-butanol |
| CAN | ammonium cerium(IV) nitrate |
| $CH_3CN$, AcCN | acetonitrile |
| $CH_2Cl_2$ | dichloromethane |
| $CH_3I$, MeI | iodomethane, methyl iodide |
| $CCl_4$ | carbon tetrachloride |
| $CCl_3$ | chloroform |
| $CO_2$ | carbon dioxide |
| $Cs_2CO_3$ | cesium carbonate |
| DIEA | diisopropylethylamine |
| CuI | copper iodide |
| CuCN | copper cyanide |
| DCE | 1,2-dichloroethane |
| DEAD | diethyl azodicarboxylate |
| DIEA | diisopropylethylamine |
| dppf | 1,1-diphenylphosphinoferrocene |
| DMAP | 4-(dimethylamino) pyridine |
| DMAC | N,N-dimethylacetamide |
| DMF | dimethylformamide |
| DMSO | dimethylsulfoxide |
| DTT | dithiothreitol |
| EDC, EDAC | 1-(3-dimethylaminopropyl)-3-ethylcarbodiimide hydrochloride |
| EGTA | ethylene glycol-bis(β-aminoethyl ether)-N,N,N',N'-tetraacetic acid |
| EtOAc | ethyl acetate |
| EtOH | ethanol |
| $Et_2O$ | diethyl ether |
| Fe | iron |
| g | gram |
| h | hour |
| HATU | O-(7-azabenzotriazol-1-yl)-N,N,N',N'-tetramethyluronium hexafluorophosphate |
| $H_2$ | hydrogen |
| $H_2$ | water |
| HCl | hydrochloric acid |
| $H_2SO_4$ | sulfuric acid |
| $H_2NNH_2$ | hydrazine |
| $HC(OEt)_3$ | triethylorthoformate |
| HCHO, $H_2CO$ | formaldehyde |
| $HCO_2Na$ | sodium formate |
| HOAc, AcOH | acetic acid |
| HOAt | 1-hydroxy-7-azabenzotriazole |
| HOBt | hydroxybenzotriazole |
| IpOH | isopropanol |
| KF | potassium fluoride |
| $K_2CO_3$ | potassium carbonate |
| KHMDS | potassium hexamethylsilazane |
| $KNO_3$ | potassium nitrate |
| KOAc | potassium acetate |
| KOH | potassium hydroxide |
| LAH, $LiAlH_4$ | lithium aluminum hydride |
| LDA | lithium diisopropylamide |
| LiCl | lithium chloride |
| LiHMDS | lithium hexamethyldisilazide |
| MeOH | methanol |
| $MgCl_2$ | magnesium chloride |
| $MgSO_4$ | magnesium sulfate |
| mg | milligram |
| ml | milliliter |
| $MnCl_2$ | manganese chloride |
| NBS | N-bromosuccinimide |
| NMO | 4-methylmorpholine, N-oxide |
| NMP | N-methylpyrrolidone |
| $Na_2SO_4$ | sodium sulfate |
| $Na_2S_2O_5$ | sodium metabisulfite |
| $NaHSO_3$ | sodium bisulfite |

| | |
|---|---|
| NaHCO₃ | sodium bicarbonate |
| Na₂CO₃ | sodium carbonate |
| NaCl | sodium chloride |
| NaH | sodium hydride |
| NaI | sodium iodide |
| NaOH | sodium hydroxide |
| NaOMe | sodium methoxide |
| NaOEt | sodium ethoxide |
| NaCNBH₃ | sodium cyanoborohydride |
| NaBH₄ | sodium borohydride |
| NaNO₂ | sodium nitrate |
| NaBH(OAc)₃ | sodium triacetoxyborohydride |
| NH₄Cl | ammonium chloride |
| N₂ | nitrogen |
| Pd/C | palladium on carbon |
| PdCl₂(PPh₃)₂ | palladium chloride bis(triphenylphosphine) |
| PdCl₂(dppf) | 1,1-bis(diphenylphosphino) ferrocene palladium chloride |
| Pd(PPh₃)₄ | palladium tetrakis triphenylphosphine |
| Pd(OH)₂ | palladium hydroxide |
| Pd(OAc)₂ | palladium acetate |
| PMB | para methoxybenzyl |
| POCl₃ | phosphorus oxychloride |
| PPh₃ | triphenylphosphine |
| PtO₂ | platinum oxide |
| RT | room temperature |
| SiO₂ | silica |
| SOCl₂ | thionyl chloride |
| TBAI | tetrabutylammonium iodide |
| TBTU | O-(1H-benzotriazol-1-yl)-N,N,N',N'-tetramethyluronium tetrafluoroborate |
| TEA | triethylamine |
| Tf₂NPh | N-phenyltrifluoromethanesulfonimide |
| TFA | trifluoroacetic acid |
| THF | tetrahydrofuran |
| TPAP | tetrapropylammoniumperruthenate |
| Tris-HCl | Tris(hydroxymethyl) aminomethane hydrochloride salt |
| Zn | zinc |

Preparation I—3-nitro-5-trifluoromethyl-phenol:

1-Methoxy-3-nitro-5-trifluoromethyl-benzene (10 g, Aldrich) and pyridine-HCl (41.8 g, Aldrich) were mixed together and heated neat at 210° C. in an open flask. After 2.5 h the mixture was cooled to RT and partitioned between 1N HCl and EtOAc. The EtOAc fraction was washed with 1N HCl (4×), brine (1×), dried with Na₂SO₄, filtered and concentrated in vacuo to form 3-nitro-5-trifluoromethyl-phenol as an off-white solid.

Preparation II—1-Boc-4-(3-nitro-5-trifluoromethyl-phenoxy)-piperidine:

3-Nitro-5-trifluoromethyl-phenol (8.81 g) was dissolved in THF (76 ml). 1-Boc-4-hydroxy-piperidine (8.81 g, Aldrich) and Ph₃P (11.15 g) were added and the solution was cooled to −20° C. A solution of DEAD (6.8 ml, Aldrich) in THF (36 ml) was added dropwise, maintaining the temperature between −20 and −10° C. The reaction was warmed to RT and stirred overnight. The reaction was concentrated in vacuo and triturated with hexane. The yellow solid was removed by filtration and washed with Et₂O (25 ml), and hexane. The white filtrate was washed with 1N NaOH (2×), brine (1×) and the hexane layer was dried over Na₂SO₄, filtered and concentrated in vacuo. The crude material was purified with flash chromatography (SiO₂, 5–10% EtOAc/hexane) to obtain 1-Boc-4-(3-nitro-5-trifluoromethyl-phenoxy)-piperidine.

The following compounds were prepared similarly to the procedure outlined above:
a) (S)-1-Boc-[2-(5-nitro-2-trifluoromethylphenoxymethyl]-pyrrolidine
b) (R)-1-Boc-[2-(5-nitro-2-trifluoromethylphenoxymethyl]-pyrrolidine.
c) (R) 1-Boc-2-(3-Nitro-5-trifluoromethyl-phenoxymethyl)-pyrrolidine
d) 4-(2-tert-Butyl-5-nitro-phenoxymethyl)-1-methyl-piperidine.
e) (S) 1-Boc-2-(3-Nitro-5-trifluoromethyl-phenoxymethyl)-pyrrolidine
f) 1-Boc-3-(5-nitro-2-pentafluoroethyl-phenoxymethyl)-azetidine.
g) N-Boc-[2-(5-nitro-2-pentafluoroethyl-phenoxy)-ethyl] amine.
h) (R) 3-(2-tert-Butyl-5-nitro-phenoxymethyl)-1-Boc-pyrrolidine.
i) 3-(2-tert-Butyl-5-nitro-phenoxymethyl)-1-Boc-azetidine.
j) (S)-1-Boc-[2-(5-nitro-2-tert-butylphenoxymethyl]-pyrrolidine
k) (S) 3-(2-tert-Butyl-5-nitro-phenoxymethyl)-1-Boc-pyrrolidine.
l) (R)-1-Boc-[2-(5-nitro-2-tert-butylphenoxymethyl]-pyrrolidine Preparation III—1-Boc-4-(3-amino-5-trifluoromethyl-phenoxy)-piperidine:

1-Boc-4-(3-nitro-5-trifluoromethyl-phenoxy)-piperidine (470 mg) was dissolved in MeOH (12 ml) and Pd/C (10 mg) was added. After sparging briefly with H₂, the mixture was stirred under H₂ for 6 H. The catalyst was removed by filtration and the MeOH solution was concentrated in vacuo to yield 1-Boc-4-(3-amino-5-trifluoromethyl-phenoxy)-piperidine as an off-white foam.

The following compounds were prepared similarly to the procedure outlined above:
a) 1-Boc-2-(3-Amino-5-trifluoromethyl-phenoxymethyl)-pyrrolidine.
b) 2-(3-Amino-5-trifluoromethyl-phenoxymethyl)-1-methyl-pyrrolidine.
c) [2-(1-Methylpiperidin-4-yloxy)-pyridin-4-yl]methylamine. ESI (M+H)=222.
d) [2-(2-Morpholin-4-yl-ethoxy)-pyridin-4-yl]methylamine.
e) [2-(2-Morpholin-4-yl-propoxy)-pyridin-4-yl]methylamine.
f) [2-(1-Methyl-pyrrolidin-2-ylmethoxy)-pyridin-4-yl]methylamine. ESI MS: (M+H)=222.
g) (4-Aminomethyl-pyridin-2-yl)-(3-morpholin-4-yl-propyl)-amine. ESI MS: (M+H)=251.
h) 4-tert-Butyl-3-(1-methyl-piperidin-4-ylmethoxy)-phenylamine.
i) 4-tert-Butyl-3-(2-piperidin-1-yl-ethoxy)-phenylamine.
j) 3-(1-Methyl-piperidin-4-ylmethoxy)-4-pentafluoroethyl-phenylamine.
k) 3-(1-Isopropyl-piperidin-4-ylmethoxy)-4-pentafluoroethyl-phenylamine.
l) (S) 3-Oxiranylmethoxy-4-pentafluoroethyl-phenylamine.
m) 3-(2-Pyrrolidin-1-yl-ethoxy)-4-trifluoromethyl-phenylamine.
n) 3-(2-Piperidin-1-yl-ethoxy)-4-trifluoromethyl-phenylamine.
o) (S) 3-(1-Boc-pyrrolidin-2-ylmethoxy)-4-pentafluoroethyl-phenylamine.
p) (R) 3-(1-Boc-pyrrolidin-2-ylmethoxy)-4-pentafluoroethyl-phenylamine.
q) (R) 3-(1-Methyl-pyrrolidin-2-ylmethoxy)-5-trifluoromethyl-phenylamine.
r) (S) 3-(1-Methyl-pyrrolidin-2-ylmethoxy)-5-trifluoromethyl-phenylamine.
s) (R) 3-Oxiranylmethoxy-4-pentafluoroethyl-phenylamine.
t) (R) 2-(5-Amino-2-pentafluoroethyl-phenoxy)-1-pyrrolidin-1-yl-ethanol.

u) 3-(1-Boc-azetidin-3-ylmethoxy)-4-pentafluoroethyl-phenylamine.
v) 3-(2-(Boc-amino)ethoxy)-4-pentafluoroethyl-phenylamine.
w) 6-Amino-2,2-dimethyl-4H-benzo[1,4]oxazin-3-one. M+H 193.2. Calc'd 192.1.
x) 2,2,4-Trimethyl-3,4-dihydro-2H-benzo[1,4]oxazin-6-ylamine.
y) 1-(6-Amino-2,2-dimethyl-2,3-dihydro-benzo[1,4]oxazin-4-yl)-ethanone. M+H 221.4. Calc'd 220.3.
z) [2-(1-Benzhydryl-azetidin-3-yloxy)-pyridin-4-yl]-methylamine.
aa) [2-(1-Methyl-piperidin-4-ylmethoxy)-pyridin-4-yl]-methylamine. M+H 236.3. Calc'd 235.2.
ab) 3-(4-Boc-piperazin-1-ylmethyl)-5-trifluoromethyl-phenylamine. M+H 360.3.
ac) 2-Boc-4,4-dimethyl-1,2,3,4-tetrahydro-isoquinolin-7-ylamine.
ad) 3-Morpholin-4-ylmethyl-4-pentafluoroethyl-phenylamine.
ae) 3-(4-Methyl-piperazin-1-ylmethyl)-4-pentafluoroethyl-phenylamine. M+H 410.3. Calc'd 409.4.
af) 7-Amino-2-(4-methoxy-benzyl)-4,4-dimethyl-3,4-dihydro-2H-isoquinolin-1-one. M+H 311.1.
ag) 7-Amino-4,4-dimethyl-3,4-dihydro-2H-isoquinolin-1-one.
ah) (3-Amino-5-trifluoromethyl-phenyl)-(4-Boc-piperazin-1-yl)-methanone. M+H 374.3; Calc'd 373.
ai) 3-(4-Boc-Piperazin-1-ylmethyl)-5-trifluoromethyl-phenylamine.
aj) 1-(7-Amino-4,4-dimethyl-3,4-dihydro-1H-isoquinolin-2-yl)-ethanone. M+H 219.2.
ak) {2-[2-(1-Methylpiperidin-4-yl)ethoxy]-pyridin-4-yl}-methylamine.
al) 12-[2-(1-Pyrrolidinyl)ethoxy]-pyridin-4-yl)-methylamine.
am) {2-[2-(1-Methylpyrrolin-2-yl)ethoxy]-pyridin-4-yl}-methylamine.
an) (2-Chloro-pyrimidin-4-yl)-methylamine.
ao) 3-(1-Boc-azetidin-3-ylmethoxy)-5-trifluoromethyl-phenylamine.
ap) 4-tert-Butyl-3-(1-Boc-pyrrolidin-3-ylmethoxy)-phenylamine. M+H 385.
aq) 4-tert-Butyl-3-(1-Boc-azetidin-3-ylmethoxy)-phenylamine. M+Na 357.
ar) (S) 4-tert-Butyl-3-(1-Boc-pyrrolidin-2-ylmethoxy)-phenylamine. M+Na 371.
as) 3-tert-Butyl-4-(4-Boc-piperazin-1-yl)-phenylamine
at) 3-(1-Methyl-piperidin-4-yl)-5-trifluoromethyl-phenylamine.
au) 3,3-Dimethyl-2,3-dihydro-benzofuran-6-ylamine.
av) 3,9,9-Trimethyl-2,3,4,4a,9,9a-hexahydro-1H-3-aza-fluoren-6-ylamine.
aw) 4-[1-Methyl-1-(1-methyl-piperidin-4-yl)-ethyl]-phenylamine was prepared using EtOH as the solvent.
ax) 4-tert-Butyl-3-(4-pyrrolidin-1-yl-but-1-enyl)-phenylamine.
ay) (R) 3-(1-Boc-pyrrolidin-2-ylmethoxy)-5-trifluoromethyl-phenylamine.
az) (S) 3-(1-Boc-pyrrolidin-2-ylmethoxy)-5-trifluoromethyl-phenylamine.

Preparation IV—1-Boc-4-{3-[(2-fluoro-pyridine-3-carbonyl)-amino]-5-trifluoromethyl-phenoxy}-piperidine:
1-Boc-4-(3-amino-5-trifluoromethyl-phenoxy)-piperidine (4.37 g) was dissolved in CH$_2$Cl$_2$ (100 ml) and NaHCO$_3$ (2.4 g, Baker) was added. 2-Fluoropyridine-3-carbonyl chloride (2.12 g) was added an the reaction was stirred at RT for 2.5 h. The reaction was filtered and concentrated in vacuo to yield a yellow foam. (30%) EtOAc/Hexane was added and 1-Boc-4-{3-[(2-fluoro-pyridine-3-carbonyl)-amino]-5-trifluoromethyl-phenoxy}-piperidine precipitated as an off white solid.

The following compounds were prepared similarly to the procedure outlined above:

a) 2-Fluoro-N-[3-(3-piperidin-1-yl-propyl)-5-trifluoromethyl-phenyl]-nicotinamide.
b) N-[4-tert-Butyl-3-(2-piperidin-1-yl-ethoxy)-phenyl]-2-fluoro-nicotinamide.
c) N-[3,3-Dimethyl-1-(1-methyl-piperidin-4-ylmethyl)-2,3-dihydro-1H-indol-6-yl]-2-fluoro-nicotinamide.
d) N-[1-(2-Dimethylamino-acetyl)-3,3-dimethyl-2,3-dihydro-1H-indol-6-yl]-2-fluoro-nicotinamide
e) N-[3,3-Dimethyl-1-(2-(Boc-amino)acetyl)-2,3-dihydro-1H-indol-6-yl]-2-fluoro-nicotinamide.
f) N-(4-Acetyl-2,2-dimethyl-3,4-dihydro-2H-benzo[1,4]oxazin-6-yl)-2-fluoro-nicotinamide. M+H 344.5. Calc'd 343.4.
g) 2-Fluoro-N-(2,2,4-trimethyl-3,4-dihydro-2H-benzo[1,4]oxazin-6-yl)-nicotinamide. M+H 316.2. Calc'd 315.1.
h) N-(2,2-Dimethyl-3-oxo-3,4-dihydro-2H-benzo[1,4]oxazin-6-yl)-2-fluoro-nicotinamide. M+H 316.1. Calc'd 315.10.
i) 2-Fluoro-N-[3-(4-methyl-piperazin-1-ylmethyl)-5-trifluoromethyl-phenyl]-nicotinamide. M+H 481. Calc'd 480.
j) 2-Fluoro-N-(2-Boc-4,4-dimethyl-1,2,3,4-tetrahydro-isoquinolin-7-yl)-nicotinamide. M+H 400.
k) 2-Fluoro-N-[3-(4-methyl-piperazin-1-ylmethyl)-4-pentafluoroethyl-phenyl]-nicotinamide. M+H 447.0. Calc'd 446.
l) 2-Fluoro-N-(3-morpholin-4-ylmethyl-4-pentafluoroethyl-phenyl)-nicotinamide.
m) 2-Fluoro-N-[4-iodophenyl]-nicotinamide.
n) 2-Fluoro-N-(4,4-dimethyl-1-oxo-1,2,3,4-tetrahydro-isoquinolin-7-yl)-nicotinamide. M+H 314.0, Calc'd 311.
o) 2-Fluoro-N-[3-(4-Boc-piperazine-1-carbonyl)-5-trifluoromethyl-phenyl]-nicotinamide. M+H 495.
p) 2-Fluoro-N-[3-(4-Boc-piperazin-1-ylmethyl)-5-trifluoromethyl-phenyl]-nicotinamide. M+H 483.3; Calc'd 482.
q) N-(2-Acetyl-4,4-dimethyl-1,2,3,4-tetrahydro-isoquinolin-7-yl)-2-fluoro-nicotinamide. M+H 430.0.
r) N-[3,3-Dimethyl-1-(1-methyl-piperidin-4-yl)-2,3-dihydro-1H-indol-6-yl]-2-fluoro-nicotinamide. M+H 383.2; Calc'd 382.5.
s) N-(4-tert-Butylphenyl)-2-fluoronicotinamide.
t) N-(4-Trifluoromethylphenyl)-2-fluoronicotinamide.
u) 2-Fluoro-N-[3-(1-Boc-azetidin-3-ylmethoxy)-5-trifluoromethyl-phenyl]-nicotinamide. M−H 468.2; Calc'd 469.16.
v) 2-Fluoro-N-[3-(1-Boc-azetidin-3-ylmethoxy)-4-tert-butyl-phenyl]-nicotinamide.
w) (S) N-[4-tert-Butyl-3-(1-Boc-pyrrolidin-2-ylmethoxy)-phenyl]-2-fluoro-nicotinamide. M+Na 494.
x) N-[3-(1-Methyl-piperidin-4-yl)-5-trifluoromethyl-phenyl]-2-fluoro-nicotinamide was prepared with K$_2$CO$_3$. instead of NaHCO$_3$.
y) N-(3-Bromo-5-trifluoromethyl-phenyl)-2-fluoro-nicotinamide.
z) 2-Fluoro-N-(3,9,9-trimethyl-2,3,4,4a,9,9a-hexahydro-1H-3-aza-fluoren-6-yl)-nicotinamide.
aa) 2-Fluoro-N-{4-[1-methyl-1-(1-methyl-piperidin-4-yl)-ethyl]-phenyl}-nicotinamide ab) N-[3,3-Dimethyl-1-(1-Boc-piperidin-4-ylmethyl)-2,3-dihydro-1H-indol-6-yl]-2-fluoro-nicotinamide.

Preparation V—1-Boc-4-{3-[(2-chloro-pyridine-3-carbonyl)-amino]-5-trifluoromethyl-phenoxy}-piperidine:

1-Boc-4-{3-[(2-chloro-pyridine-3-carbonyl)-amino]-5-trifluoromethyl-phenoxy}-piperidine was prepared from 1-Boc-4-(3-amino-5-trifluoromethyl-phenoxy)-piperidine and 2-chloropyridine-3-carbonyl chloride by a procedure similar to that described in the preparation of 1-Boc-4-{3-[(2-fluoro-pyridine-3-carbonyl)-amino]-5-trifluoromethyl-phenoxy}-piperidine.

The following compounds were prepared similarly to the procedure outlined above:

a) N-(4-tert-Butyl-3-nitro-phenyl)-2-chloro-nicotinamide.
b) 2-Chloro-N-[3-(3-piperidin-1-yl-propyl)-5-trifluoromethyl-phenyl]-nicotinamide.
c) 2-Chloro-N-[3-(3-morpholin-4-yl-propyl)-5-trifluoromethyl-phenyl]-nicotinamide.
d) 2-Chloro-N-[3-(1-methylpiperidin-4-yl)-5-trifluoromethyl-phenyl]-nicotinamide.
e) 2-Chloro-N-[3-(1-methyl-piperidin-4-ylmethoxy)-4-pentafluoroethyl-phenyl]-nicotinamide.
f) 2-Chloro-N-[3-(1-isopropyl-piperidin-4-ylmethoxy)-4-pentafluoroethyl-phenyl]-nicotinamide.
g) (S) 2-Chloro-N-[4-(oxiranylmethoxy)-3-pentafluoroethyl-phenyl]-nicotinamide.
h) 2-Chloro-N-[3-(2-pyrrolidin-1-yl-ethoxy)-4-trifluoromethyl-phenyl]-nicotinamide.
i) 2-Chloro-N-[3-(2-piperidin-1-yl-ethoxy)-4-pentafluoroethyl-phenyl]-nicotinamide.
j) (R) 2-Chloro-N-[3-(1-Boc-pyrrolidin-2-ylmethoxy)-4-pentafluoroethyl-phenyl]-nicotinamide.
k) (S) 2-Chloro-N-[3-(1-Boc-pyrrolidin-2-ylmethoxy)-4-pentafluoroethyl-phenyl]-nicotinamide.
l) (R) 2-Chloro-N-[3-(1-methyl-pyrrolidin-2-ylmethoxy)-5-trifluoromethyl-phenyl]-nicotinamide.
m) (S) 2-Chloro-N-[3-(1-methyl-pyrrolidin-2-ylmethoxy)-5-trifluoromethyl-phenyl]-nicotinamide.
n) (R) 2-Chloro-N-[4-(oxiranylmethoxy)-3-pentafluoroethyl-phenyl]-nicotinamide.
o) (R) Acetic acid 2-{5-[(2-chloro-pyridine-3-carbonyl)-amino]-2-pentafluoroethyl-phenoxy}-1-pyrrolidin-1-yl-ethyl ester.
p) 2-Chloro-N-[3-(4-methyl-piperazin-1-ylmethyl)-5-trifluoromethyl-phenyl]-nicotinamide.
q) 2-Chloro-N-[2-(4-methoxy-benzyl)-4,4-dimethyl-1-oxo-1,2,3,4-tetrahydro-isoquinolin-7-yl]-nicotinamide. M+H 450.2. Calc'd 449.
r) 2-Chloro-N-(4,4-dimethyl-1-oxo-1,2,3,4-tetrahydro-isoquinolin-7-yl)-nicotinamide. M+H 330.1, Calc'd 329.
s) 2-Chloro-N-[3-(4-Boc-piperazin-1-ylmethyl)-5-trifluoromethyl-phenyl]-nicotinamide.
t) 2-{3-[(2-Chloro-pyridine-3-carbonyl)-amino]-phenyl}-2-methyl-propionic acid methyl ester. M+H 405
u) N-{4-tert-Butyl-3-[2-(1-Boc-piperidin-4-yl)-ethyl]-phenyl}-2-chloro-nicotinamide. M+Na 524. Calc'd 501.1.
v) N-[3,3-Dimethyl-1,1-dioxo-2,3-dihydro-1H-benzo[d]isothiazol-6-yl]-2-chloro-nicotinamide.
w) N-[1,1,4,4-Tetramethyl-1,2,3,4-tetrahydro-naphth-6-yl]-2-chloro-nicotinamide.
x) 2-Chloro-N-[3,3-dimethyl-2,3-dihydro-benzofuran-6-yl]-2-chloro-nicotinamide.
y) 2-Chloro-N-[3-(1-Boc-piperidin-4-yloxy)-5-trifluoromethyl-phenyl]-nicotinamide.
z) 2-Chloro-N-[3-(1-methyl-piperidin-4-ylmethyl)-5-trifluoromethyl-phenyl]-nicotinamide.
aa) 2-Chloro-N-[3-(3-piperidin-1-yl-propyl)-5-trifluoromethyl-phenyl]-nicotinamide.
ab) N-[4-tert-Butyl-3-(4-pyrrolidin-1-yl-but-1-enyl)-phenyl]-2-chloro-nicotinamide.
ac) (R) 2-Chloro-N-[3-(1-Boc-pyrrolidin-2-ylmethoxy)-5-trifluoromethyl-phenyl]-nicotinamide.
ad) (S) 2-Chloro-N-[3-(1-Boc-pyrrolidin-2-ylmethoxy)-5-trifluoromethyl-phenyl]-nicotinamide.

Preparation VI—1-Boc-2-{3-[(2-fluoro-pyridine-3-carbonyl)-amino]-5-trifluoromethyl-phenoxymethyl}-pyrrolidine:

1-Boc-2-{3-[(2-Fluoro-pyridine-3-carbonyl)-amino]-5-trifluoromethyl-phenoxymethyl}-pyrrolidine was prepared from 1-Boc-2-(3-amino-5-trifluoromethyl-phenoxymethyl)-pyrrolidine by a procedure similar to that described in the preparation of 1-Boc-4-{3-[(2-fluoro-pyridine-3-carbonyl)-amino]-5-trifluoromethyl-phenoxy}-piperidine.

Preparation VII—2-(3-nitro-5-trifluoromethyl-phenoxymethyl)-pyrrolidine:

1-Boc-2-(3-nitro-5-trifluoromethyl-phenoxymethyl)-pyrrolidine (2.35 g) was dissolved in CH$_2$Cl$_2$ (60 ml) and TFA (20 ml) was added. After stirring for 1 h at RT, the mixture was concentrated in vacuo to yield 2-(3-nitro-5-trifluoromethyl-phenoxymethyl)-pyrrolidine as an oil that solidified upon standing. The material was used as is without further purification.

The following compounds were prepared similarly to the procedure outlined above:

a) (4-Aminomethyl-pyrimidin-2-yl)-(3-morpholin-4-yl-propyl)-amine.
b) (4-Aminomethyl-pyrimidin-2-yl)-[2-(1-methyl-pyrrolidin-2-yl)-ethyl]-amine.

Preparation VIII—1-methyl-2-(3-nitro-5-trifluoromethyl-phenoxymethyl)-pyrrolidine:

2-(3-Nitro-5-trifluoromethyl-phenoxymethyl)-pyrrolidine (6 mmol) was dissolved in CH$_3$CN (20 ml) and formaldehyde (2.4 ml, 37% aqueous) was added. NaBH$_3$CN (607 mg) was added, an exotherm was observed. The pH is monitored every 15 min and adjusted to ~7 with AcOH. After 45 min, the mixture was concentrated in vacuo and the residue is dissolved in EtOAc, washed with 6N NaOH, 1N NaOH, and 2N HCl (3×). The acid washings were combined, adjusted to ~pH 10 with solid Na$_2$CO$_3$ and extracted with EtOAc (2×). The EtOAc fractions were combined, dried with Na$_2$SO$_4$, and purified with flash chromatography (SiO$_2$, 95:5:0.5 CH$_2$Cl$_2$:MeOH:NH$_4$OH) to afford 1-methyl-2-(3-nitro-5-trifluoromethyl-phenoxymethyl)-pyrrolidine.

The following compounds were prepared similarly to the procedure outlined above:

a) 2-(1-Methylpiperidin-4-yl)-ethanol.
b) 2-{3-[(2-Fluoro-pyridine-3-carbonyl)-amino]-5-trifluoromethyl-phenoxymethyl}-1-methylpyrrolidine.

Preparation IX—4-tert-butyl-3-nitro-phenylamine:

A mixture of 1,3-dinitro-4-tert-butylbenzene (10.0 g) in H$_2$O (56 ml) was heated to reflux. A mixture of Na$_2$S (21.42 g) and sulfur (2.85 g) in H$_2$O (34 ml) was added over 1 h via an addition funnel. The reaction maintained at reflux for 1.5 h then cooled to RT and extracted with EtOAc. The organic extracts were combined and washed with H$_2$O, brine, dried over MgSO$_4$ and concentrated in vacuo to afford 4-tert-butyl-3-nitro-phenylamine which was used as is without further purification.

Preparation X—N-(3-bromo-5-trifluoromethyl-phenyl)-acetamide:

3-Bromo-5-(trifluoromethyl)phenylamine (5 g, Alfa-Aesar) was dissolved in AcOH (140 ml) and Ac$_2$O (5.9 ml, Aldrich) was added. The reaction was stirred at RT overnight. The mixture was added slowly to H$_2$O (~700 ml) forming a white precipitate. The solid was isolated by filtration, washed with H$_2$O and dried under vacuum to yield N-(3-bromo-5-trifluoromethyl-phenyl)-acetamide.

Preparation XI—N-[3-(3-piperidin-1-yl-propyl)-5-trifluoromethyl-phenyl]-acetamide:

Allylpiperidine (1.96 g, Lancaster) was degassed under vacuum, dissolved in 0.5 M 9 BBN in THF (31.2 ml, Aldrich), and heated to reflux for 1 h, then cooled to RT. PD(dppf)Cl$_2$/CH$_2$Cl$_2$ was added to a degassed mixture of N-(3-bromo-5-trifluoromethyl-phenyl)-acetamide, K$_2$CO$_3$ (9.8 g) DMF (32.1 ml and H$_2$O (3 ml). The allyl piperidine solution was added heated to 60° C. for 3 h. After cooling to RT and reheating at 60° C. for 6 h, the mixture was cooled to RT and poured into H$_2$O. The mixture was extracted with EtOAc (2x), and the EtOAc portion was washed with 2 N HCl (2x) and brine. The aqueous phases were combined and the pH was adjusted to ~11 with NaOH (15%) forming a cloudy suspension. The cloudy suspension was extracted with EtOAc (2x) and the EtOAc portion was dried with Na$_2$SO$_4$, filtered and concentrated in vacuo. The crude material was purified by flash chromatography (SiO$_2$, 95:5:0.5 CH$_2$Cl$_2$:MeOH:NH$_4$OH) to afford N-[3-(3-piperidin-1-yl-propyl)-5-trifluoromethyl-phenyl]-acetamide as a brown oil that solidified under vacuum.

The following compounds were prepared similarly to the procedure outlined above:
a) N-(3-Morpholin-4-ylpropyl-5-trifluoromethyl-phenyl)-acetamide from 4-allyl-morpholine.
b) N-(3-(1-methylpiperdin-4-ylmethyl-5-trifluoromethyl-phenyl)-acetamide from 1-Methyl-4-methylene-piperidine.

Preparation XII—3-(3-piperidin-1-yl-propyl)-5-trifluoromethyl-phenylamine:

N-[3-(3-Piperidin-1-yl-propyl)-5-trifluoromethyl-phenyl]-acetamide (1.33 g) was dissolved in EtOH (40 ml) and 12 N HCl (40 ml) was added. After stirring overnight at 70° C. and RT, the mixture was concentrated in vacuo, affording 3-(3-piperidin-1-yl-propyl)-5-trifluoromethyl-phenylamine as a brown oil.

The following compounds were prepared similarly to the procedure outlined above:
a) 3,3-Dimethyl-6-nitro-2,3-dihydro-1H-indole. M+H 193.1; Calc'd 192.2.
b) 3-(1-Methyl-piperidin-4-ylmethyl)-5-trifluoromethyl-phenylamine.
c) 3-Morpholin-4-ylmethyl-5-trifluoromethyl-phenylamine.

Preparation XIII—3,3-Dimethyl-6-nitro-1-piperidin-4-ylmethyl-2,3-dihydro-1H-indole:

3,3-Dimethyl-1-(1-Boc-piperidin-4-ylmethyl)-6-nitro-2,3-dihydro-1H-indole was dissolved in HCl/EtOAc and stirred for 2 h. The mixture was concentrated in vacuo and partitioned between 1,2-dichloroethane and 1N NaOH. The organic layer was removed, washed with brine, dried (Na$_2$SO$_4$) and filtered. The material was used without further purification.

Preparation XIV—N-[3-(3-morpholin-4-yl-propyl)-5-trifluoromethyl-phenyl]-acetamide:

N-[3-(3-Morpholin-4-yl-propyl)-5-trifluoromethyl-phenyl]-acetamide was prepared from allyl morpholine and N-(3-bromo-5-trifluoromethyl-phenyl)-acetamide similar to that described in the preparation of N-[3-(3-piperidin-1-yl-propyl)-5-trifluoromethyl-phenyl]-acetamide.

Preparation XV—3-(3-morpholin-4-yl-propyl)-5-trifluoromethyl-phenylamine:

3-(3-Morpholin-4-yl-propyl)-5-trifluoromethyl-phenylamine was prepared from N-[3-(3-morpholin-4-yl-propyl)-5-trifluoromethyl-phenyl]-acetamide similar to that described in the preparation of 3-(3-piperidin-1-yl-propyl)-5-trifluoromethyl-phenylamine.

Preparation XVI—1-methyl-4-methylene-piperidine:

Ph$_3$PCH$_3$I (50 g, Aldrich) was suspended in Et$_2$O (20 ml) and butyllithium (77.3 ml, 1.6 M in hexanes, Aldrich) was added dropwise. The reaction was stirred for 2 h at RT then 1-methylpiperidone (12.3 ml, Aldrich) was added slowly. The mixture was stirred at RT overnight. The solid was removed by filtration, the volume was reduced to ~400 ml and additional solid was removed by filtration. The Et$_2$O was washed with H$_2$O (2x) and 2N HCl (4x). The pH of the acid washings was adjusted to ~11 with 6 N NaOH, then they were extracted with CH$_2$Cl$_2$ (4x). The CH$_2$Cl$_2$ washings were dried over Na$_2$SO$_4$ and concentrated cold in vacuo to provide 1-methyl-4-methylene-piperidine which was used as is.

Preparation XVII—N-[3-(1-methylpiperidin-4-yl)-5-trifluoromethyl-phenyl]-acetamide:

N-[3-(1-Methylpiperidin-4-yl)-5-trifluoromethyl-phenyl]-acetamide was prepared from 1-methyl-4-methylene-piperidine and N-(3-bromo-5-trifluoromethyl-phenyl)-acetamide similar to that described in the preparation of N-[3-(3-piperidin-1-yl-propyl)-5-trifluoromethyl-phenyl]-acetamide.

Preparation XVIII—3-(1-methylpiperidin-4-yl)-5-trifluoromethyl-phenylamine:

3-(1-Methylpiperidin-4-yl)-5-trifluoromethyl-phenylamine was prepared from N-[3-(1-methylpiperidin-4-yl)-5-trifluoromethyl-phenyl]-acetamide similar to the procedure described in the preparation of 3-(3-piperidin-1-yl-propyl)-5-trifluoromethyl-phenylamine.

Preparation XIX—2-(1-methylpiperidin-4-yloxy)-4-pyridylcarbonitrile:

4-Hydroxy-1-methylpiperidine (25.4 g) was dissolved in THF (50 ml) in a 100 mL r.b. flask. NaH/mineral oil mixture (9.58 g) was slowly added to the flask and stirred for 20 min. 2-Chloro-4-cyanopyridine was added to the mixture and stirred at RT until completion. Diluted mixture with EtOAc and added H$_2$O to quench mixture, then transferred contents to a sep. funnel. The organic phase was collected while the aqueous phase was washed two times with EtOAc. The combined organics were dried over Na$_2$SO$_4$, filtered, then concentrated in vacuo. Then redissolved mixture in CH$_2$Cl$_2$, 10% HCl (300 ml) was added and the mixture was transferred to sep. funnel. The org. was extracted, while EtOAc along with 300 mL 5N NaOH was added to the sep. funnel. The organic phases were collected, dried over Na$_2$SO$_4$, filtered and concentrated in vacuo affording 2-(1-methylpiperidin-4-yloxy)-4-pyridylcarbonitrile as a brown solid. ESI (M+H)=218.

The following compounds were prepared similarly to the procedure outlined above:
a) 2-(1-methylpiperidin-4-ylmethoxy)-4-pyridylcarbonitrile. M+H 232.1. Calc'd 231.1.
b) 2-(1-Benzhydryl-azetidin-3-yloxy)-4-pyridylcarbonitrile. M+H 342.2. Calc'd 341.2.
c) 2-(1-methylpiperidin-4-ylethoxy)-4-pyridylcarbonitrile.
d) 2-(1-pyrrolidinylethoxy)-4-pyridylcarbonitrile.
e) 2-(1-methylpyrrolin-2-ylethoxy)-4-pyridylcarbonitrile.
f) 2-[2-(1-Boc-azetidin-3-yl)-ethoxy]-4-pyridylcarbonitrile.

Preparation XX—[2-(1-methylpiperidin-4-yloxy)-pyridin-4-yl]methylamine bis hydrochloride:

[2-(1-Methylpiperidin-4-yloxy)-pyridin-4-yl]methylamine was diluted with Et$_2$O (50 ml) and 1M HCl/Et$_2$O (47 ml) was added. The vessel was swirled until precipitate formed.

Preparation XXI—2-(2-morpholin-4-yl-ethoxy)-4-pyridylcarbonitrile:

2-(2-Morpholin-4-yl-ethoxy)-4-pyridylcarbonitrile was prepared from 2-chloro-4-cyanopyridine and 2-morpholin-4-yl-ethanol by a procedure similar to that described in the preparation of 2-(1-methylpiperidin-4-yloxy)-4-pyridylcarbonitrile. The HCl salt was prepared similar to that described for [2-(1-methylpiperidin-4-yloxy)-pyridin-4-yl]methylamine bis hydrochloride.

Preparation XXII—2-morpholin-4-yl-propanol:

LAH powder (1.6 g) was added to a flask while under N$_2$ atmosphere, immediately followed by THF (50 ml). The mixture was chilled to 0° C., methyl 2-morpholin-4-yl-propionate (5 g) was added dropwise to the reaction mixture and stirred at 0° C. After 1 h, the mixture was worked up by adding H$_2$O (44 mL), 2N NaOH (44 mL), then H$_2$O (44 mL, 3×). After 30 min of stirring, the mixture was filtered through Celite® and the organic portion was concentrated in vacuo providing 2-morpholin-4-yl-propanol as a colorless oil.

The following compounds were prepared similarly to the procedure outlined above:
a) (1-Methyl-piperidin-4-yl)-methanol. M+H 130.2. Calc'd 129.1.

Preparation XXIII—2-(2-morpholin-4-yl-propoxy)-4-pyridylcarbonitrile:

2-(2-Morpholin-4-yl-propoxy)-4-pyridylcarbonitrile was prepared from 2-chloro-4-cyanopyridine and 2-morpholin-4-yl-propanol by a procedure similar to that described in the preparation of 2-(1-methylpiperidin-4-yloxy)-4-pyridylcarbonitrile.

Preparation XXIV—2-(1-Methyl-pyrrolidin-2-ylmethoxy)-4-pyridylcarbonitrile:

2-(1-Methyl-pyrrolidin-2-ylmethoxy)-4-pyridylcarbonitrile was prepared from 2-chloro-4-cyanopyridine and 1-methyl-pyrrolidin-2-ylmethanol by a procedure similar to that described in the preparation of 2-(1-methylpiperidin-4-yloxy)-4-pyridylcarbonitrile. ESI MS: (M+H)=218.

Preparation XXV—2-(3-morpholin-4-yl-propylamino)-4-pyridylcarbonitrile:

To a flask charged with 2-chloro-4-cyanopyridine (2.0 g), was added the aminopropyl morpholine (2.11 ml). The mixture was heated to 79° C. for 5 h and stirred. After 5 h the reaction was incomplete. The mixture was then heated at 60° C. overnight. The crude compound was purified on silica gel (1–5% MeOH/CH$_2$Cl$_2$ gradient). ESI MS: (M+H)=247, (M–H)=245.

Preparation XXVI—5-Nitro-2-pentafluoroethylphenol:

Combined 2-methoxy-4-nitro-1-pentafluoroethylbenzene (9.35 g) and pyridine HCl in a round bottom flask and heated at 210° C. for 1 h then cooled to RT. The mixture was diluted with EtOAc and 2N HCl (>500 ml) until all residue dissolved. The organic layer was removed, washed with 2N HCl (2×) and concentrated in vacuo. The residue was dissolved in hexanes and Et$_2$O, washed with 2N HCl, then brine. Dried organic layer over Na$_2$SO$_4$, filtered, concentrated in vacuo and dried under high vacuum to provide 5-nitro-2-pentafluoroethylphenol.

Preparation XXVII—2-tert-Butyl-5-nitro-aniline:

To H$_2$SO$_4$ (98%, 389 mL) in a 500 mL 3-neck flask was added 2-tert-butyl aniline (40.6 mL). The reaction was cooled to −10° C. and KNO$_3$ in 3.89 g aliquots was added every 6 min for a total of 10 aliquots. Tried to maintain temperature at −5° C. to −10° C. After final addition of KNO$_3$, stirred the reaction for five min then it was poured onto ice (50 g). The black mix was diluted with H$_2$O and extracted with EtOAc. The aqueous layer was basified with solid NaOH slowly then extracted with EtOAc (2×). The combined organic layers were washed with 6N NaOH and then with a mix of 6N NaOH and brine, dried over Na$_2$SO$_4$, filtered and concentrated in vacuo to obtain crude 2-tert-butyl-5-nitro-aniline as a dark red-black oil which solidified when standing at RT. The crude material was triturated with about 130 mL hexanes. After decanting the hexanes, the material was dried to obtain a dark-red black solid.

Preparation XXVIII—2-tert-Butyl-5-nitrophenol:

In a 250 ml round bottom flask, 20 mL concentrated H$_2$SO4 was added to 2-tert-butyl-5-nitro-aniline (7.15 g) by adding 5 mL aliquots of acid and sonicating with occasional heating until all of the starting aniline went into solution. H$_2$O (84 ml) was added with stirring, then the reaction was cooled to 0° C. forming a yellow-orange suspension. A solution of NaNO$_2$ (2.792 g) in H$_2$O (11.2 mL) was added dropwise to the suspension and stirred for 5 min. Excess NaNO$_2$ was neutralized with urea, then the cloudy solution was transferred to 500 ml 3-necked round bottom flask then added 17 mL of 1:2 H$_2$SO$_4$:H$_2$O solution, and heated at reflux. Two additional 5 mL aliquots of 1:2 H$_2$SO$_4$:H$_2$O solution, a 7 mL aliquot of 1:2 H$_2$SO$_4$:H$_2$O solution and another 10 mL of 1:2 H$_2$SO$_4$:H$_2$O were added while heating at reflux. The mixture was cooled to RT forming a black layer floating on top of the aqueous layer. The black layer was diluted with EtOAc (300 mL) and separated. The organic layer was washed with H$_2$O then brine, dried over Na$_2$SO$_4$ and concentrated in vacuo. Crude oil was purified on silica gel column with 8% EtOAc/Hexanes. Upon drying under vacuum, the 2-tert-butyl-5-nitrophenol was isolated as a brown solid.

Preparation XXIX—1-methylpiperidine-4-carboxylic acid ethyl ester:

Piperidine-4-carboxylic acid ethyl ester (78 g) was dissolved in MeOH (1.2 L) at RT then formaldehyde (37%, 90 ml) and acetic acid (42 ml) were added and stirred for 2 h. The mixture was cooled to 0° C., NaCNBH$_3$ (70 g) was added, and the mix was stirred for 20 min at 0° C., then overnight at RT. The mixture was cooled to 0° C. then quenched with 6N NaOH. The mixture was concentrated in vacuo to an aqueous layer, which was extracted with EtOAc (4×), brine-washed, dried over Na$_2$SO$_4$, and concentrated in vacuo to provide 1-methylpiperidine-4-carboxylic acid ethyl ester.

The following compounds were prepared similarly to the procedure outlined above:
a) (1-Methyl-piperidin-4-yl)-methanol. M+H 130.2. Calc'd 129.1.

Preparation XXX—N-[4-tert-Butyl-3-(1-methyl-piperidin-4-ylmethoxy)-phenyl]-2-chloro-nicotinamide:

N-[4-tert-Butyl-3-(1-methyl-piperidin-4-ylmethoxy)-phenyl]-2-chloro-nicotinamide was prepared from 4-tert-butyl-3-(1-methyl-piperidin-4-ylmethoxy)-phenylamine by a procedure similar to that described in the preparation of 1-Boc-4-{3-[(2-chloro-pyridine-3-carbonyl)-amino]-5-trifluoromethyl-phenoxy}-piperidine.

Preparation XXXI—1-[2-(2-tert-Butyl-5-nitro-phenoxy)-ethyl]-piperidine:

To 2-tert-butyl-5-nitrophenol (1.01 g) and K$_2$CO$_3$ (1.72 g) was added acetone (35 ml) and H$_2$O (10.5 mL), then 1-(2-chloroethyl)piperidine HCl (1.909 g) and TBAI (153 mg). The mixture was stirred at reflux overnight. Additional K$_2$CO$_3$ (850 mg) and 1-(2-chloroethyl)-piperidine HCl (950 mg) were added and the mixture was heated at reflux for 6 h. The mixture was concentrated in vacuo to an aqueous layer which was acidified with 2N HCl and extracted with EtOAc. The aqueous layer was basified with 6N NaOH and washed with CH$_2$Cl$_2$ (3×). The combined organic layers were washed with brine/1N NaOH and dried over Na$_2$SO$_4$. Washed the EtOAc layer with 2N NaOH/brine and dried over Na$_2$SO$_4$. The crude material was purified by silica gel column chromatography with 15% EtOAc/Hexanes to yield 1-[2-(2-tert-butyl-5-nitro-phenoxy)-ethyl]-piperidine as a light tan solid. (M+1)=307.3.

Preparation XXXII—1-Boc-Piperidine-4-carboxylic acid ethyl ester:

To a stirred solution of piperidine-4-carboxylic acid ethyl ester (23.5 g) in EtOAc (118 ml) at 0° C. was added dropwise Boc$_2$O in EtOAc (60 ml). The reaction was warmed to RT and stirred overnight. Washed reaction with H$_2$O, 0.1N HCl, H$_2$O, NaHCO$_3$ and brine. The organic layer was dried over Na$_2$SO$_4$, filtered and concentrated in vacuo. The liquid was dried under vacuum to provide 1-Boc-piperidine-4-carboxylic acid ethyl ester.

The following compounds were prepared similarly to the procedure outlined above:
a) N-Boc-(2-chloropyrimidin-4-yl)-methylamine.
b) 1-(2-tert-Butyl-4-nitrophenyl)-4-Boc-piperazine.
c) 1-Boc-azetidine-3-carboxylic acid
d) 1-Boc-4-Hydroxymethyl-piperidine using TEA.

Preparation XXXIII—1-Boc-4-hydroxymethyl-piperidine:

1-Boc-4-Hydroxymethyl-piperidine was prepared from 1-Boc-piperidine-4-carboxylic acid ethyl ester by a procedure similar to that described in the preparation of 2-morpholin-4-yl-propanol.

Preparation XXXIV—1-Boc-4-Methylsulfonyloxymethyl-piperidine:

Dissolved 1-Boc-4-hydroxymethyl-piperidine in anhydrous CH$_2$Cl$_2$ (50 ml) and TEA (4.5 ml) and cooled to 0° C. Mesyl chloride (840 μl) was added and the mixture was stirred for 15 min then at RT for 45 min. The mixture was washed with brine/1N HCl and then brine, dried over Na$_2$SO$_4$, concentrated in vacuo and dried under high vacuum to provide 1-Boc-4-methylsulfonyloxymethyl-piperidine as a yellow orange thick oil.

The following compounds were prepared similarly to the procedure outlined above:
a) 1-Boc-3-methylsulfonyloxymethyl-azetidine.

Preparation XXXV—1-Boc-4-(3-nitro-6-pentafluoroethyl-phenoxymethyl)-piperidine:

To a slurry of 60% NaH suspension in DMF (30 mL) at RT added a solution of 5-nitro-2-pentafluoroethyl-phenol (3.6 g) in 5 mL DMF. The dark red mixture was stirred at RT for 10 min then added a solution of 1-Boc-4-methylsulfonyloxymethyl-piperidine (3.1 g) in 5 mL DMF. The reaction was stirred at 60° C. and 95° C. After 1 h, added 2.94 g K$_2$CO$_3$ and stirred overnight at 105° C. After cooling to RT, the reaction was diluted with hexanes and 1N NaOH. Separated layers, and washed organic layer with 1N NaOH and with brine, dried over Na$_2$SO$_4$, filtered and concentrated in vacuo. Purification with silica gel column chromatography with 8% EtOAc/Hexanes yielded 1-Boc-4-(3-nitro-6-pentafluoroethyl-phenoxymethyl)-piperidine as a light yellow thick oil.

Preparation XXXVI—4-(3-nitro-6-pentafluoroethyl-phenoxymethyl)-piperidine:

4-(3-Nitro-6-pentafluoroethyl-phenoxymethyl)-piperidine was prepared from 1-Boc-4-(3-nitro-6-pentafluoroethyl-phenoxymethyl)-piperidine by a procedure similar to that described in the preparation of 2-(3-nitro-5-trifluoromethyl-phenoxymethyl)-pyrrolidine.

Preparation XXXVII—1-methyl-4-(3-nitro-6-pentafluoroethyl-phenoxymethyl)-piperidine:

4-(3-Nitro-6-pentafluoroethyl-phenoxymethyl)-piperidine (316.5 mg) was dissolved in 2.7 mL CH$_3$CN, then added 37% formaldehyde/H$_2$O (360 ul) and then NaBH$_3$CN (90 mg). Upon addition of NaCNBH$_3$ the reaction exothermed slightly. The reaction was stirred at RT and pH was maintained at ~7 by addition of drops of glacial AcOH. After about 1 h, the mixture was concentrated in vacua, treated with 8 mL 2N KOH and extracted two times with 10 mL Et$_2$O. The organic layers were washed with 0.5N KOH and then the combined organic layers were extracted two times with 1N HCl. The aqueous layer was basified with solid KOH and extracted two times with Et$_2$O. This organic layer was then washed with brine/1N NaOH, dried over Na$_2$SO$_4$, filtered, concentrated in vacuo and dried under high vacuum to give pure compound.

Preparation XXXVIII—1-Isopropyl-4-(5-nitro-2-pentafluoroethyl-phenoxymethyl)-piperidine:

Dissolved 4-(5-nitro-2-pentafluoroethyl-phenoxymethyl)-piperidine (646 mg) in 1,2-dichloroethane (6.4 ml), then added acetone (136 ul), NaBH(OAc)$_3$ (541 mg) and finally AcOH (105 ul). Stirred the cloudy yellow solution under N$_2$ at RT overnight. Added another 130 uL acetone and stirred at RT over weekend. Quenched the reaction with 30 mL N NaOH/H$_2$O and stirred 10 min. Extracted with Et$_2$O and the organic layer was brine-washed, dried over Na$_2$SO$_4$, filtered and concentrated in vacuo. Dried under high vacuum for several h to obtain 1-isopropyl-4-(5-nitro-2-pentafluoroethyl-phenoxymethyl)-piperidine as a yellow orange solid.

The following compounds were prepared similarly to the procedure outlined above:
a) 3,3-Dimethyl-1-(1-methyl-piperidin-4-yl)-6-nitro-2,3-dihydro-1H-indole was prepared using 1-methyl-piperidin-4-one. M+H 290; Calc'd 289.4.
b) 3,3-Dimethyl-1-(1-Boc-piperidin-4-ylmethyl)-6-nitro-2,3-dihydro-1H-indole using 1-Boc-4-formyl-piperidine.

Preparation XXXIX—3,3-Dimethyl-1-(1-methyl-piperidin-4-ylmethyl)-6-nitro-2,3-dihydro-1H-indole:

3,3-Dimethyl-1-piperidin-4-ylmethyl-6-nitro-2,3-dihydro-1H-indole was treated with an excess of formaldehyde and NaBH(OAc)$_3$ and stirred overnight at RT. The reaction was quenched with MeOH and concentrated in vacuo. The residue was partitioned between EtOAc and 1N NaOH. The organic layer was removed, washed with brine, dried (Na$_2$SO$_4$), filtered and concentrated to provide the compound.

Preparation XL—(S) 2-(5-Nitro-2-pentafluoroethyl-phenoxymethyl)-oxirane:

Combined 5-nitro-2-pentafluoromethylphenol (2.69 g), DMF (25 ml) K$_2$CO$_3$ (3.03 g) and (S) toluene-4-sulfonic acid oxiranyl-methyl ester (2.27 g) and stirred the mixture at 90° C. After about 4 h, the mix was cooled, diluted with EtOAc, washed with H$_2$O, 1N NaOH (2×), 1N HCl and then with brine. Dried over Na$_2$SO$_4$, filtered and concentrated in vacuo. Purified the crude on silica gel column with 5% EtOAc/hexane and drying under high vacuum provided the (S)-2-(5-nitro-2-pentafluoroethyl-phenoxymethyl)-oxirane.

The following compounds were prepared similarly to the procedure outlined above:
a) (R)-2-(5-Nitro-2-pentafluoroethyl-phenoxymethyl)-oxirane.

Preparation XLI—(S) 2-Chloro-N-[3-(2-hydroxy-3-pyrrolidin-1-yl-propoxy)-4-pentafluoroethyl-phenyl]-nicotinamide:

(S) 2-Chloro-N-[4-(2-oxiranylmethoxy-)-3-pentafluoroethyl-phenyl]-nicotinamide (1.11 g) in a sealed tube and added pyrrolidine (285 µl). Stirred after sealing tube at 60° C. After 12 h, the mix was concentrated in vacuo and purified on a silica gel column (5:95:0.5 MeOH:$CH_2Cl_2$:$NH_4$OH-8:92:1, MeOH:$CH_2Cl_2$:$NH_4$OH). Concentrated in vacuo and dried under high vacuum to obtain pure compound.

The following compounds were prepared similarly to the procedure outlined above:
a) (R) 1-(5-Nitro-2-pentafluoroethyl-phenoxy)-3-pyrrolidin-1-yl-propan-2-ol.

Preparation XLII—5-nitro-2-trifluoromethylanisole:

Cooled 140 mL pyridine in a large sealable vessel to −40° C. Bubbled in trifluoromethyl iodide from a gas cylinder which had been kept in freezer overnight. After adding $ICF_3$ for 20 min, added 2-iodo-5-nitroanisole (24.63 g) and copper powder (67.25 g). Sealed vessel and stirred vigorously for 22 h at 140° C. After cooling to −50° C., carefully unsealed reaction vessel and poured onto ice and $Et_2O$. Repeatedly washed with $Et_2O$ and $H_2O$. Allowed the ice—$Et_2O$ mixture to warm to RT. Separated layers, washed organic layer with 1N HCl (3×), then brine, dried over $Na_2SO_4$, filtered and concentrated in vacuo. Eluted material through silica gel plug (4.5:1 Hex:$CH_2Cl_2$) to provide 5-nitro-2-trifluoromethylanisole.

Preparation XLIII—1-[2-(5-nitro-2-trifluoromethylphenoxy)ethyl]pyrrolidine:

1-[2-(5-Nitro-2-trifluoromethylphenoxy)ethyl]-pyrrolidine was prepared from 5-nitro-2-trifluoromethyl-phenol and 1-(2-chloroethyl)pyrrolidine by a procedure similar to that described for 1-[2-(2-tert-butyl-5-nitro-phenoxy)-ethyl]-piperidine.

Preparation XLIV—1-[2-(5-Nitro-2-pentafluoroethyl-phenoxy)-ethyl]-piperidine:

1-[2-(5-Nitro-2-pentafluoroethyl-phenoxy)-ethyl]-piperidine was prepared from 5-nitro-2-pentafluoroethylphenol and 1-(2-chloroethyl)piperidine by a procedure similar to that described in the preparation of 1-[2-(2-tert-butyl-5-nitro-phenoxy)-ethyl]-piperidine.

Preparation XLV—3-(1-Boc-pyrrolidin-2-ylmethoxy)-4-pentafluoroethyl-phenylamine:

3-(2-Pyrrolidin-1-yl-methoxy)-4-trifluoromethyl-phenylamine was prepared from 1-[2-(5-nitro-2-trifluoromethylphenoxy)methyl]-pyrrolidine by a procedure similar to that described in the preparation of 1-Boc-4-(3-amino-5-trifluoromethyl-phenoxy)-piperidine.

Preparation XLVI—2-Chloro-N-[3-(2-pyrrolidin-1-yl-ethoxy)-4-trifluoromethyl-phenyl]-nicotinamide:

2-Chloro-N-[3-(2-pyrrolidin-1-yl-ethoxy)-4-trifluoromethyl-phenyl]-nicotinamide was prepared from 3-(2-pyrrolidin-1-yl-ethoxy)-4-trifluoromethyl-phenylamine and 2-chloropyridine-3-carbonyl chloride by a procedure similar to that described in the preparation of 1-Boc-4-{3-[(2-chloro-pyridine-3-carbonyl)-amino]-5-trifluoromethyl-phenoxy}-piperidine.

Preparation XLVII—(R) Acetic acid 2-(5-nitro-2-pentafluoroethyl-phenoxy)-1-pyrrolidin-1-ylmethyl-ethyl ester:

Dissolved 1-(5-nitro-2-pentafluoroethyl-phenoxy)-3-pyrrolidin-1-yl-propan-2-ol (3.5 g) in $CH_2Cl_2$ (15 ml) added TEA (2.55 ml) and cooled to 0° C. Acetyl chloride (781.3 µl) was added dropwise, forming a suspension. The mixture was warmed to RT and stirred for 1.5 h. Additional acetyl chloride (200 µl) was added and the mix was stirred for another h. The mixture was diluted with $CH_2Cl_2$ and washed with sat. $NaHCO_3$. The organic layer was removed, washed with brine and back extracted with $CH_2Cl_2$. Dried the combined organic layers over $Na_2SO_4$, filtered and concentrated in vacuo. The residue was purified over silica gel column (5:94.5:0.5 MeOH:$CH_2Cl_2$:$NH_4$OH) to provide acetic acid 2-(5-nitro-2-pentafluoroethyl-phenoxy)-1-pyrrolidin-1-ylmethyl-ethyl ester as a yellow brown oil.

The following compounds were prepared similarly to the procedure outlined above:
a) (R) Acetic acid 2-(5-amino-2-pentafluoroethyl-phenoxy)-1-pyrrolidin-1-yl-methyl-ethyl ester.
b) 1-(2,2-Dimethyl-6-nitro-2,3-dihydro-benzo[1,4]oxazin-4-yl)-ethanone. M−$NO_2$ 206.4; Calc'd 250.1.

Preparation XLVIII—(R) 2-Chloro-N-[3-(2-hydroxy-2-pyrrolidin-1-yl-propoxy)-4-pentafluoroethyl-phenyl]-nicotinamide:

(R) Acetic acid 2-{5-[(2-chloro-pyridine-3-carbonyl)-amino]-2-pentafluoroethyl-phenoxy}-1-pyrrolidin-1-yl-ethyl ester (408 mg) was dissolved in MeOH (15 ml) and $NH_4$OH (6 ml) was added and the mixture was stirred at RT for 6 h. The reaction was concentrated in vacuo and dried under high vacuum. The residue was purified over silica gel column (8:92:0.6 MeOH:$CH_2Cl_2$:$NH_4$OH). The purified fractions were concentrated in vacuo and dried again to provide (R)-2-chloro-N-[3-(2-hydroxy-2-pyrrolidin-1-yl-ethoxy)-4-pentafluoroethyl-phenyl]-nicotinamide as a white foam.

Preparation XLIX—2-Dimethylamino-1-(3,3-dimethyl-6-nitro-2,3-dihydro-indol-1-yl)-ethanone 3,3-Dimethyl-6-nitro-2,3-dihydro-1H-indole (5 g) was dissolved in DMF (100 ml) and HOAt (3.89 g) dimethylamino-acetic acid (5.83 g) and EDC (3.89 g) were added. The reaction was stirred overnight. The mixture was diluted with $CH_2Cl_2$ (1L) and washed with sat'd $NaHCO_3$ (3×200 ml). The organic layer was washed with brine, dried over $Na_2SO_4$, filtered and concentrated in vacuo. The residue was purified by flash chromatography ($SiO_2$, EtOAc to 5% MeOH/EtOAc) to afford the title compound.

The following compounds were prepared similarly to the procedure outlined above:
a) 1-(3,3-Dimethyl-6-nitro-2,3-dihydro-indol-1-yl)-2-(N-Boc-amino)-ethanone.

Preparation L—1-(6-Amino-3,3-dimethyl-2,3-dihydro-indol-1-yl)-2-(N-Boc-amino)-ethanone:

1-(3,3-Dimethyl-6-nitro-2,3-dihydro-indol-1-yl)-2-(N-Boc-amino)-ethanone (3.9 g) was dissolved in EtOH (30 ml) and Fe powder (3.1 g) $NH_4Cl$ (299 mg) and $H_2O$ (5 ml) were added. The reaction was stirred at 80° C. overnight. The reaction was filtered through Celite® and evaporated off the MeOH. The residue was partitioned between $CH_2Cl_2$ and sat'd $NaHCO_3$. The organic layer was removed, washed with brine, dried over $Na_2SO_4$, filtered and concentrated in vacuo. The residue was purified by flash chromatography ($SiO_2$, 25% EtOAc/hexane). The purified fractions were concentrated in vacuo to afford the compound as a white powder.

The following compounds were prepared similarly to the procedure outlined above:
a) 1-(6-Amino-3,3-dimethyl-2,3-dihydro-indol-1-yl)-2-dimethylamino-ethanone.
b) 3,3-Dimethyl-1-(1-methyl-piperidin-4-ylmethyl)-2,3-dihydro-1H-indol-6-ylamine.
c) 3-(4-Methyl-piperazin-1-ylmethyl)-4-pentafluoroethyl-phenylamine. M+H 324.2. Calc'd 323.
d) 3,3-Dimethyl-1-(1-methyl-piperidin-4-yl)-2,3-dihydro-1H-indol-6-ylamine. M+H 259.6; Calc'd 259.3.

e) 3,3-Dimethyl-1,1-dioxo-2,3-dihydro-1H-116-benzo[d]isothiazol-6-ylamine
f) 1,1,4,4-Tetramethyl-1,2,3,4-tetrahydro-naphth-6-ylamine.
g) 3,3-Dimethyl-1-(1-Boc-piperidin-4-ylmethyl)-2,3-dihydro-1H-indol-6-ylamine.

Preparation LI—2-Boc-4,4-dimethyl-7-nitro-1,2,3,4-tetrahydro-isoquinoline:

4,4-Dimethyl-7-nitro-1,2,3,4-tetrahydro-isoquinoline (150 mg) was dissolved with $CH_2Cl_2$ (3 ml) DIEA (100 ul) DMAP (208 mg and $Boc_2O$ (204 mg) and the mixture was stirred for 6 h at RT. The reaction was diluted with $CH_2Cl_2$, washed with sat'd $NaHCO_3$ and dried over $MgSO_4$, filtered and concentrated to provide the compound which was used without further purification.

The following compounds were prepared similarly to the procedure outlined above substituting $Ac_2O$:
a) 1-(4,4-Dimethyl-7-nitro-3,4-dihydro-1H-isoquinolin-2-yl)-ethanone. M+H 249.3.

Preparation LII—2-Bromo-N-(4-methoxy-benzyl)-5-nitro-benzamide:

PMB-amine (5.35 ml) in $CH_2Cl_2$ (130 ml) was slowly added to 2-bromo-5-nitro-benzoyl chloride (10.55 g) and $NaHCO_3$ (9.6 g) and the mixture was stirred at RT for 1 h. The mixture was diluted with $CH_2Cl_2$ (1 L), filtered, washed with diluted HCl, dried, filtered again, concentrated and dried under vacuum to provide the compound as a white solid. M+H 367. Calc'd 366.

Preparation LIII—2-Bromo-N-(4-methoxy-benzyl)-N-(2-methyl-allyl)-5-nitro-benzamide:

To a suspension of NaH (1.22 g) in DMF (130 ml) was added 2-bromo-N-(4-methoxy-benzyl)-5-nitro-benzamide (6.2 g) in DMF (60 ml) at −78C. The mixture was warmed to 0° C., 3-bromo-2-methyl-propene (4.57 g) was added and the mixture was stirred for 2 h at 0° C. The reaction was poured into ice $H_2O$, extracted with EtOAc (2×400 ml), dried over $MgSO_4$, filtered and concentrated to a DMF solution which was used without further purification.

Preparation LIV—of 2-(4-Methoxy-benzyl)-4,4-dimethyl-7-nitro-3,4-dihydro-2H-isoquinolin-1-one:

2-Bromo-N-(4-methoxy-benzyl)-N-(2-methyl-allyl)-5-nitro-benzamide (23.4 mmol) was dissolved in DMF (150 ml) and $Et_4NCl$ (4.25 g), $HCO_2Na$ (1.75 g) and NaOAc (4.99 g) were added. $N_2$ was bubbled through the solution for 10 min, then $Pd(OAc)_2$ (490 mg) was added and the mixture was stirred overnight at 70° C. The mixture was extracted with EtOAc, washed with sat'd $NH_4Cl$, dried over $MgSO_4$, filtered and concentrated until the compound precipitated as a white solid.

The following compounds were prepared similarly to the procedure outlined above:
a) 3,3-Dimethyl-6-nitro-2,3-dihydro-benzofuran was prepared from 1-bromo-2-(2-methyl-allyloxy)-4-nitro-benzene.
b) 3,9,9-Trimethyl-6-nitro-4,9-dihydro-3H-3-aza-fluorene was prepared from 4-[1-(2-bromo-4-nitro-phenyl)-1-methyl-ethyl]-1-methyl-1,2,3,6-tetrahydro-pyridine.

Preparation LV—4,4-Dimethyl-7-nitro-3,4-dihydro-2H-isoquinolin-1-one:

2-(4-Methoxy-benzyl)-4,4-dimethyl-7-nitro-3,4-dihydro-2H-isoquinolin-1-one (2.0 g) was dissolved in $CH_3CN$ (100 ml) and $H_2O$ (50 ml) and cooled to 0° C. CAN (9.64 g) was added and the reaction was stirred at 0° C. for 30 min, then warmed to RT and stirred for 6 h. The mixture was extracted with $CH_2Cl_2$ (2×300 ml) washed with sat'd $NH_4Cl$, dried over $MgSO_4$, filtered and concentrated. The crude material was recrystallized in $CH_2Cl_2$/EtOAc (1:1) to give 4,4-dimethyl-7-nitro-3,4-dihydro-2H-isoquinolin-1-one as a white solid.

Preparation LVI—4,4-Dimethyl-7-nitro-1,2,3,4-tetrahydro-isoquinoline:

4,4-Dimethyl-7-nitro-3,4-dihydro-2H-isoquinolin-1-one (230 mg) was dissolved in THF (10 ml) and $BH_3Me_2S$ (400 ul) was added and the reaction was stirred overnight at RT. The reaction was quenched with MeOH (10 ml) and NaOH (200 mg) and heating at reflux for 20 min. The mixture was extracted with EtOAc, washed with sat'd $NH_4Cl$, extracted with 10% HCl (20 ml). The acidic solution was treated with 5N NaOH (15 ml), extracted with EtOAc (30 ml) dried, filtered and evaporated to give the compound as a yellow solid. M+H 207.2, Calc'd 206.

The following compounds were prepared similarly to the procedure outlined above:
a) 4-Boc-2,2-dimethyl-6-nitro-3,4-dihydro-2H-benzo[1,4]oxazine.

Preparation LVII—2-Bromomethyl-4-nitro-1-pentafluoroethyl-benzene:

2-Methyl-4-nitro-1-pentafluoroethyl-benzene (2.55 g) was dissolved in $CCl_4$ (30 ml) and AIBN (164 mg) and NBS (1.96 g) were added. The reaction was heated to reflux and stirred for 24 h. The mix was diluted with $CH_2Cl_2$, washed with sat'd $NaHCO_3$, dried over $MgSO_4$ and concentrated to give the compound as an oil which was used without further purification.

Preparation LVIII—1-Methyl-4-(5-nitro-2-pentafluoroethyl-benzyl)-piperazine:

2-Bromomethyl-4-nitro-1-pentafluoroethyl-benzene (2.6 g) was added to N-methylpiperazine (5 ml) and stirred at RT for 3 h. The mixture was filtered and the filtrate was treated with 1-chlorobutane, extracted with 2N HCl (100 ml). The acidic solution was treated with 5N NaOH (6 ml) then extracted with EtOAc. The organic layer was removed, dried over $MgSO_4$ and concentrated to give the compound as an oil.

The following compounds were prepared similarly to the procedure outlined above:
a) 4-(5-Nitro-2-pentafluoroethyl-benzyl)-morpholine.

Preparation LIX—1-Boc-4-(5-nitro-2-pentafluoroethyl-benzyl)-piperazine.

2-Bromomethyl-4-nitro-1-pentafluoroethyl-benzene (2.5 g) was dissolved in $CH_2Cl_2$ and added to N-Boc-piperazine (2.5 g) and $NaHCO_3$ (1 g) and stirred at RT overnight. The mixture was diluted with $CH_2Cl_2$ (100 ml), washed with sat'd $NH_4Cl$, dried over $MgSO_4$, filtered and concentrated. The residue was purified by silica gel chromatography (hexane, $CH_2Cl_2$:hexane 2:8) to give the compound as a yellow solid.

Preparation LX—(4-Boc-piperazin-1-yl)-(3-nitro-5-trifluoromethyl-phenyl)-methanone:

A mixture of 3-nitro-5-trifluoromethyl-benzoic acid (4.13 g), 4-Boc-piperazine (2.97 g), EDC (3.88 g), HOBt (2.74 g), DIEA (3.33 ml) in $CH_2Cl_2$ (120 ml) was stirred at RT for 3 h. The mixture was diluted with $CH_2Cl_2$ (100 ml), washed with sat'd $NH_4Cl$, dried over $MgSO_4$, filtered and concentrated. The residue was purified by silica gel chromatography (hexane, $CH_2Cl_2$:hexane 1:2) to give the compound as a white solid.

Preparation LXI—1-Boc-4-(3-nitro-5-trifluoromethyl-benzyl)-piperazine:

(4-Boc-piperazin-1-yl)-(3-nitro-5-trifluoromethyl-phenyl)-methanone (403 mg) was dissolved in THF (6 ml) and $BH_3Me_2S$ (300 μl) was added and the reaction was stirred for 3 h at 60° C. and 2 h at RT. The reaction was quenched with MeOH (5 ml) and NaOH (100 mg) and stirred at RT for 1 h. The mixture was concentrated and dissolved in $CH_2Cl_2$, washed with sat'd $NH_4Cl/NaHCO_3$, dried (MgSO$_4$), filtered and evaporated to give the compound as an oil. M+H 390.3.

Preparation LXII—2-Ethyl-4-aminomethyl pyridine:

To a solution of 2-ethyl-4-thiopyridylamide (10 g) in MeOH (250 ml) was added Raney 2800 Nickel (5 g, Aldrich) in one portion. The mixture was stirred at RT for 2 days then at 60° C. for 16 h. The mixture was filtered, concentrated to provide the desired compound.

Preparation LXIII—N-Boc-[2-(4-morpholin-4-yl-butyl)-pyrimidin-4-ylmethyl]-amine:

N-Boc-(2-chloropyrimidine)-methylamine (663 mg) and 4-(aminopropyl)morpholine (786 mg) were dissolved in MeOH and concentrated in vacuo. The residue was heated at 100° C. for 15 min, forming a solid which was dissolved in CH$_2$Cl$_2$/MeOH then concentrated again and heated 15 min more. Concentrated in vacuo and dried under high vacuum. Triturated with a small amount of IpOH and allowed to settle over a weekend. Filtered, rinsing with a small amount of IpOH to provide the compound as a white solid.

The following compounds were prepared similarly to the procedure outlined above:

a) (4-Bocaminomethyl-pyrimidin-2-yl)-[2-(1-methyl-pyrrolidin-2-yl)-ethyl]-amine. M+H 336.5; Calc'd 335.45.

Preparation LXIV—2-fluoronicotinic acid:

In a flame dried 3-necked round bottom flask equipped with a dropping funnel and thermometer, under N$_2$, THF (250 ml) was added via cannula. LDA (2M in cyclohexane, 54 ml) was added via cannula as the flask was cooled to −78° C. At −78° C., 2-fluoropyridine (8.87 ml) was added dropwise over 10 min. The reaction was stirred for 3 h. Condensation was blown off (with N$_2$) a few cubes of solid CO$_2$ and they were added to the mixture. The mixture was warmed to RT once the solution turned yellow, and it was stirred overnight. The reaction was cooled to 0° C. and the pH was adjusted to ~2.5 with 5N HCl. The mixture was concentrated in vacuo and extracted with EtOAc. The EtOAc layer was washed with brine, dried over MgSO$_4$, filtered and concentrated to dryness. The resulting solid was slurried in EtOAc (100 ml), filtered, washed with cold EtOAc and dried at 50° C. for 1 h to afford 2-fluoronictinic acid. M+H 142.1; Calc'd 141.0.

Preparation LXV—4-cyano-2-methoxypyridine:

Under a stream of N$_2$ and with cooling, Na metal (2.7 g) was added to MeOH (36 ml) with a considerable exotherm. After the Na is dissolved, a solution of 2-chloro-4-cyanopyridine (15 g) in dioxane:MeOH (1:1, 110 ml) was added via dropping funnel over a 10 min period. The reaction was heated to reflux for 3.5 h then cooled at ~10° C. overnight. Solid was filtered off and the solid was washed with MeOH. The filtrate was concentrated to ~60 ml and H$_2$O (60 ml) was added to redissolve a precipitate. Upon further concentration, a precipitate formed which was washed with H$_2$O. Further concentration produced additional solids. The solids were combined and dried in vacuo overnight at 35° C. to provide 4-cyano-2-methoxypyridine which was used as is.

Preparation LXVI—(2-methoxypyridin-4-yl)methylamine:

4-Cyano-2-methoxypyridine (1.7 g) was dissolved in MeOH (50 ml) and conc. HCl (4.96 ml) was added. Pd/C (10%) was added and H$_2$ was added and let stand overnight. The solids were filtered through Celite® and the cake was washed with MeOH (~250 ml). Concentration in vacuo produced an oil which was dissolved in MeOH (~20 ml). Et$_2$O (200 ml) was added and stirred for 1 h. The resulting precipitate was filtered and washed with Et$_2$O to afford (2-methoxypyridin-4-yl)methylamine (HCl salt) as an off-white solid.

Preparation LXVII—2-(4-Amino-phenyl)-2-methyl-propionic acid methyl ester:

2-Methyl-2-(4-nitro-phenyl)-propionic acid methyl ester (2.1 g) was dissolved in THF (70 ml) and AcOH (5 ml) and Zn (10 g) were added. The mixture was stirred for 1 h and filtered through Celite®. The filtrate was rinsed with EtOAc and the organics were evaporated to a residue which was purified on silica gel chromatography (40% EtOAc/hexanes) to provide the desired compound as a yellow oil. M+H 194.

Preparation LXVIII—1-(2-tert-Butyl-phenyl)-4-methyl-piperazine:

2-tert-Butyl-phenylamine and bis-(2-chloro-ethyl)-methylamine were mixed together with K$_2$CO$_3$ (25 g), NaI (10 g) and diglyme (250 mL) and heated at 170° C. for 8 h. Cooled and filtered solid and evaporated solvent. Diluted with EtOAc, washed with NaHCO$_3$ solution, extracted twice more with EtOAc, washed with brine, dried over Na$_2$SO$_4$ and evaporated to give the compound as a dark solid.

The following compounds were prepared similarly to the procedure outlined above:

a) 1-Bromo-2-(2-methyl-allyloxy)-4-nitro-benzene was prepared from methallyl bromide.

Preparation LXIX—3-(1-Methyl-1,2,3,6-tetrahydro-pyridin-4-yl)-5-trifluoromethyl-phenylamine:

3-(5,5-Dimethyl-[1,3,2]dioxaborinan-2-yl)-5-trifluoromethyl-phenylamine (8.8 g, 0.032 mol) was added to trifluoro-methanesulfonic acid 1-methyl-1,2,3,6-tetrahydro-pyridin-4-yl ester (7.91 g, 0.032 mol) and 2N Na$_2$CO$_3$ aqueous solution (25 mL) was bubbled through N$_2$ for 5 min. Pd(PPh$_3$)$_4$ (3.7 g, 3.2 mmol) was added and the reaction was heated to 80° C. for 16 h. The reaction was cooled to RT and diluted with Et$_2$O (100 mL). The mixture was filtered through Celite® and the filtrate was washed with NaHCO$_3$ aqueous solution (25 ml) followed by brine (25 mL). The organic phase was dried over Na$_2$SO$_4$ and concentrated in vacuo. The desired compound was isolated by passing through silica gel column chromatography (EtOAc, then (2M NH$_3$) in MeOH/EtOAc) to provide a yellow oil.

Preparation LXX—3,3-Dimethyl-6-nitro-2,3-dihydro-benzo[d]isothiazole 1,1-dioxide:

3,3-Dimethyl-2,3-dihydro-benzo[d]isothiazole 1,1-dioxide was added to KNO$_3$ in H$_2$SO$_4$ cooled to 0° C. and stirred for 15 min. The reaction was warmed to RT and stirred overnight. The mix was poured into ice and extracted with EtOAc (3×), washed with H$_2$O and brine, dried and evaporated to give the compound which was used without further purification.

The following compounds were prepared similarly to the procedure outlined above:

a) 1,1,4,4-Tetramethyl-6-nitro-1,2,3,4-tetrahydro-naphthalene

Preparation LXXI—3-(1-Methyl-1,2,3,4-tetrahydro-pyridin-4-yl)-5-trifluoromethyl-phenylamine:

3-(5,5-Dimethyl-[1,3,2]dioxaborinan-2-yl)-5-trifluoromethyl-phenylamine (1.2 g) was added to trifluoro-methanesulfonic acid 1-methyl-1,2,3,6-tetrahydro-pyridin-4-yl ester (1.0 g), LiCl (500 mg, Aldrich), PPh$_3$ (300 mg, Aldrich) and 2M Na$_2$CO$_3$ aqueous solution (6 ml) and was bubbled with N$_2$ for 5 min. Pd(PPH$_3$)$_4$ (300 mg, Aldrich) was added and the reaction was heated to 80° C. for 16 h. The reaction was cooled to RT and diluted with Et$_2$O (100 mL). The mixture was filtered through Celite® and the filtrate was washed with NaHCO$_3$ aqueous solution (25 ml) followed by brine (25 mL). The organic phase was dried over Na$_2$SO$_4$ and concentrated in vacuo. The desired compound was isolated by silica gel column chromatography (EtOAc 10% (2M NH$_3$) in MeOH/EtOAc) to provide yellow oil. M+H 257.2; Calc'd 256.1.

Preparation LXXII—Trifluoromethylsulfonic acid 1-methyl-1,2,3,6-tetrahydro-pyridin-4-yl ester:

In a three-necked round bottom flask equipped with a thermometer and an additional funnel was placed anhydrous THF (200 mL) and 2M LDA (82.8 mL). The solution was cooled to −78° C. and a solution of 1-methyl-piperidin-4-one (20 mL) in anhydrous THF (70 mL) was added dropwise. The reaction was warmed to −10° C. over 30 min and cooled down again to −78° C. Tf$_2$NPh (54.32 g) in 200 mL of anhydrous THF was added through the additional funnel over 30 min and anhydrous THF (30 mL) was added to rinse the funnel. The reaction was warmed to RT and the reaction solution was concentrated in vacuo. The residue was dissolved in Et$_2$O purified on neutral Al$_2$O$_3$ column chromatography (Et$_2$O as elutant). The compound was obtained as orange oil. (20 g)

Preparation LXXIII—3-(5,5-Dimethyl-[1,3,2]dioxaborinan-2-yl)-5-trifluoromethyl-phenylamine:

N$_2$ was bubbled through a solution of 3-bromo-5-trifluoromethyl-phenylamine (2.38 g), 5,5,5',5'-tetramethyl-[2,2']bi[[1,3,2]dioxaborinanyl] (2.24 g, Frontier Scientific) and KOAc (2.92 g), dppf (165 mg, Aldrich) in anhydrous dioxane (50 ml) for 2 min. PdCl$_2$ (dppf) (243 mg, Aldrich) was added and the reaction was heated to 80° C. for 4 h. After cooling to RT, the mix was diluted with 50 mL of Et$_2$O, filtered through Celite®, and the filtrate was concentrated in vacuo. The residue was dissolved in Et$_2$O (100 mL), washed with sat. NaHCO$_3$ aqueous solution (50 mL) followed by brine (50 mL). The organic phase was dried over Na$_2$SO$_4$ and concentrated in vacuo. The residue was dissolved in 3:2 Et$_2$O/Hex (100 mL), filtered through Celite® and the filtrate was concentrated in vacuo to afford a dark brown semi-solid.

Preparation LXXIV—1-Boc-3-Hydroxymethyl-azetidine:

A solution of 1-Boc-azetidine-3-carboxylic acid (1.6 g) and Et$_3$N (2 ml) in anhydrous THF (60 ml) was cooled to 0° C. Isopropyl chloroformate (1.3 g) was added via a syringe slowly; forming a white precipitate almost immediately. The reaction was stirred for 1 h at 0° C. and the precipitate was filtered out. The filtrate was cooled to 0° C. again and aqueous NaBH$_4$ solution (900 mg, 5 ml) was added via pipette and stirred for 1 h. The reaction was quenched with NaHCO$_3$ solution (50 mL) and the compound was extracted with EtOAc (200 mL). The organic phase was washed with brine (50 mL), dried over Na$_2$SO$_4$ and concentrated in vacuo. The residue was dissolved in EtOAc and passed through a short silica gel pad. Concentrating the filtrate in vacuo provided the compound as a light yellow oil.

Preparation LXXV—1-Boc-3-(3-nitro-5-trifluoromethyl-phenoxymethyl)-azetidine:

A mixture of 1-Boc-3-methylsulfonyloxymethyl-azetidine (1.47 g), 3-nitro-5-trifluoromethyl-phenol (1.15 g) and K$_2$CO$_3$ (1.15 g) in DMF (20 ml) at 80° C. was stirred overnight. The reaction was cooled to RT and diluted with 25 mL of sat. NaHCO$_3$ and 50 mL of EtOAc. The organic phase was separated and washed with brine (25 mL), dried over Na$_2$SO$_4$ and concentrated in vacuo. The crude compound was purified by column chromatography (50% EtOAc/hex).

Preparation LXXVI—2,2-Dimethyl-6-nitro-3,4-dihydro-2H-benzo[1,4]oxazine:

2,2-Dimethyl-6-nitro-4H-benzo[1,4]oxazin-3-one was added to BH$_3$-THF complex (Aldrich) in THF with ice cooling. The mixture was heated to reflux for 2 h then carefully diluted with 12 mL of MeOH and heated to reflux for an additional 1 h. Concentrated HCl (12 mL) was added and heated to reflux for 1 h. The mixture was concentrated and the resulting solid was suspended in a dilute aqueous solution of NaOH (1 M) and extracted with EtOAc (100 mL×4). The organic layers were washed with H$_2$O and dried over MgSO$_4$. Evaporation of solvent gave a yellow solid.

Preparation LXXVII—2,2,4-Trimethyl-6-nitro-4H-benzo[1,4]oxazin-3-one:

2,2-Dimethyl-6-nitro-4H-benzo[1,4]oxazin-3-one (1.1 g) was mixed with MeI (850 mg, Aldrich), K$_2$CO$_3$ (1.38 g, Aldrich) and DMF (30 ml, Aldrich) at 40° C. for 48 h. The DMF was removed in vacuo and the residue was diluted with EtOAc (80 ml). The organic phase was washed with H$_2$O (50 ml), aqueous Na$_2$SO$_3$ (50 ml) and brine (50 ml). The resulting solution was dried (MgSO$_4$) and concentrated to provide the compound which was used as is.

Preparation LXXVIII—2-Bromo-N-(2-hydroxy-5-nitro-phenyl)-2-methyl-propionamide:

2-Amino-4-nitro-phenol (3.08 g, Aldrich) was stirred with THF (30 ml, Aldrich) in an ice bath. 2-Bromo-2-methyl-propionyl bromide (2.47 ml, Aldrich) and Et$_3$N (2.0 g, Aldrich) was slowly added via syringe. The mixture was stirred for 45 min then poured into ice. The aqueous phase was extracted by EtOAc (50 mL×4). The organic layer was dried and concentrated. The desired compound was crystallized from EtOAc. (Chem. Pharm. Bull 1996, 44(1) 103–114).

Preparation LXXIX—2,2-Dimethyl-6-nitro-4H-benzo[1,4]oxazin-3-one:

2-Bromo-N-(2-hydroxy-5-nitro-phenyl)-2-methyl-propionamide was mixed with K$_2$CO$_3$ in 20 mL of DMF and stirred overnight at 50° C. The reaction mixture was poured into ice H2O. The precipitate was collected by filtration and washed with H$_2$O. The crude compound was recrystallized from EtOH.

Preparation LXXX—4-[1-(2-Bromo-4-nitro-phenyl)-1-methyl-ethyl]-1-methyl-pyridinium iodide:

1-Methyl-4-[1-methyl-1-(4-nitro-phenyl)-ethyl]-pyridinium (8 g) was dissolved in glacial HOAc (10 ml) then diluted with H$_2$SO$_4$ (50 ml), then NBS (3.8 g) was added. After 1 h, additional NBS (1.2 g) was added, 30 min later another 0.5 g of NBS, then 15 min later 200 mg more NBS. After 1 h, the mixture was neutralized with NH$_4$OH (conc.) with ice bath cooling. The neutralized mixture was then concentrated and used as is.

Preparation LXXXI—4-[1-(2-Bromo-4-nitro-phenyl)-1-methyl-ethyl]-1-methyl-1,2,3,6-tetrahydro-pyridine:

4-[1-(2-Bromo-4-nitro-phenyl)-1-methyl-ethyl]-1-methyl-pyridiniumiodide was mixed with MeOH (400 ml) and CH$_2$Cl$_2$ (200 ml), then treated with NaBH$_4$ (2.5 g) in portions. After stirring at RT for 2 h, the mixture was extracted with CH$_2$Cl$_2$ (300 mL×3). The CH$_2$Cl$_2$ layer was washed with brine, dried over Na$_2$SO$_4$ and concentrated in vacuo, to provide the desired compound.

Preparation LXXXII—1-Methyl-4-[1-methyl-1-(4-nitro-phenyl)-ethyl]-pyridinium iodide:

4-(4-Nitro-benzyl)-pyridine (4.3 g) was mixed with MeI (4 ml, 9.12 g)/NaOH (5N, 30 ml), Bu$_4$NI (150 mg) and CH$_2$Cl$_2$ (50 ml) and stirred at RT overnight. Additional MeI (2 mL) was added along with 50 mL of NaOH (5N). 6 h later, more MeI (2 mL) was added. The mixture was stirred at RT over the weekend. The mixture was cooled on ice bath and the base was neutralized by conc. HCl (aq) addition dropwise to pH 7. The compound was used as is.

Preparation LXXXIII—1-Methyl-4-(4-nitro-benzyl)-1,2,3,6-tetrahydro-pyridine:

4-(4-Nitrobenzyl)pyridine (64 g) and TBAI (6 g) were dissolved in CH$_2$Cl$_2$ (500 mL) and the solution was suspended with NaOH (aq. 5N, 450 mL) in a 3L 3-necked round bottom flask. With vigorous stirring, CH$_3$I (213 g) was added and stirred vigorously at RT for 60 h (or until blue color disappears). The reaction was quenched with dimethylamine (100 mL) and MeOH (300 mL) and stirred for 2 h. NaBH$_4$ (19 g) was added to the mixture in small portions. The reaction mixture was stirred for 30 min at RT, then partitioned between CH$_2$Cl$_2$/H$_2$O (500 mL/500 mL) The organic layer was collected and the aqueous layer was washed with CH$_2$Cl$_2$ (300 mL×3). The combined organic layers was washed with brine then concentrated in vacuo. The residue was purified on a silica wash-column (7% TEA in EtOAc). The desired fractions were combined and concentrated under vacuum to give the desired compound as a dark gray solid. (MS: M+1=261).

Preparation LXXXIV—1-Boc-4-formylpiperidine:

4A Molecular sieves were heated to 100° C. and a vacuum was applied. They were cooled to RT and purged with N$_2$. CH$_2$Cl$_2$ (420 ml) and CH$_3$CN (40 ml), NMO (40 g) and 1-Boc-4-hydroxymethylpiperidine (50 g) were added and the mix was stirred for 5 min then cooled to 15° C. TPAP (4.1 g) is added and an exotherm was observed. The reaction was maintained at RT with external cooling. The reaction was stirred at RT for 3 h, filtered, concentrated, diluted with 50% EtOAc/hexanes and purified on a silica gel plug (50% EtOAc/hexanes). The eluant fractions were concentrated to afford a yellow oil.

Preparation LXXXV 2-Chloro-4-cyanopyridine:

2-Chloro-4-cyanopyridine was prepared similar to the method described by Daves et al., J. Het. Chem., 1, 130–32 (1964).

Preparation LXXXVI 4-(2-tert-Butyl-5-nitro-phenyl)-but-3-en-1-ol:

A mix of 1-(tert-butyl)-2-bromo-4-nitrobenzene (3.652 g), TEA (5.92 ml), 3-buten-1-ol (5.48 ml), Pd(OAc)$_2$ (32 mg), Pd(PPh$_3$)$_4$ (327 mg) and toluene (40 ml) was degassed with nitrogen and heated in a sealed vessel for 16 h at 120° C. The next day, the reaction mixture was cooled to RT, filtered, and concentrated in vacuo. The crude was eluted on a silica gel column with 15% to 22% EtOAc/hexanes gradient system to yield a yellow-brown oil.

Preparation LXXXVII 4-(2-tert-Butyl-5-nitro-phenyl)-but-3-enal:

4-(2-tert-Butyl-5-nitro-phenyl)-but-3-en-1-ol (1.024 g) was dissolved in 10 ml of CH$_2$Cl$_2$ and added dropwise over 5 min to a −78° C. mix of oxalyl chloride (0.645 ml), DMSO (0.583 ml), and 10 ml CH$_2$Cl$_2$. The reaction was stirred at −78° C. for 1 h, then treated with a solution of TEA (1.52 ml) in 7 ml CH$_2$Cl$_2$ and stirred at −78° C. for an additional 25 min, then warmed to −30° C. for 35 min. The reaction was treated with 50 ml of saturated aqueous NH$_4$Cl, diluted with H$_2$O and extracted with EtOAc. The organic layer was brine-washed, dried over Na$_2$SO$_4$, filtered, and concentrated in vacuo to yield a yellow oil which was used as is in Preparation LXXXVIII.

Preparation LXXXVIII 1-[4-(2-tert-Butyl-5-nitro-phenyl)-but-3-enyl]-pyrrolidine:

4-(2-tert-Butyl-5-nitro-phenyl)-but-3-enal (895 mg) was dissolved in 40 ml THF, and to the solution was added pyrrolidine (0.317 ml). To the deep orange solution was added NaBH(OAc)$_3$ (1.151 g) and glacial AcOH (0.207 ml). The reaction was stirred at RT overnight, then treated with saturated aqueous NaHCO$_3$ and diluted with Et$_2$O and some 1N NaOH. The layers were separated, and the organic layer was extracted with aqueous 2N HCl. The acidic aqueous layer was basified to pH>12 with 6 N NaOH, extracted with Et$_2$O, brine-washed, dried over Na$_2$SO$_4$, filtered, and concentrated in vacuo to provide 1-[4-(2-tert-butyl-5-nitrophenyl)-but-3-enyl]-pyrrolidine as a orange-brown oil.

Preparation LXXXVIX—N-Boc-(2-chloropyrimidin-4-yl)-methylamine:

To 2-chloropyrimidine-4-carbonitrile [2.5 g, prepared by the procedure of Daves et. al. [J. Het. Chem. 1964, 1, 130–132)] in EtOH (250 ml) under N$_2$ was added Boc$_2$O (7.3 g). After the mixture was briefly placed under high vacuum and flushed with N$_2$, 10% Pd/C (219 mg) was added. H$_2$ was bubbled though the mixture (using balloon pressure with a needle outlet) as it stirred 4.2 h at RT. After filtration through Celite®, addition of 1.0 g additional Boc$_2$O, and concentration, the residue was purified by silica gel chromatography (5:1→4:1 hexanes/EtOAc) to obtain N-Boc-(2-chloropyrimidin-4-yl)-methylamine.

Preparation XC—Methanesulfonic acid 1-Boc-azetidin-3-ylmethyl ester:

To a solution of (1-Boc-azetidin-3-yl)-methanol (1.06 g, 5.7 mmol), TEA (1.18 mL, 8.52mmol) in CH$_2$Cl$_2$ at 0° C. was added MeSO$_2$Cl (0.53 mL, 6.82 mmol) via a syringe. The reaction was warmed to RT over 2 h and stirring was continued at RT for 2 h. The white solid formed was removed by filtration and the filtrate was washed with 25 mL of H$_2$O. The organic phase was dried over Na$_2$SO$_4$, and concentrated in vacuo to afford yellow oil.

Preparation XCI—N-(2-bromo-5-nitrophenyl)acetamide:

2-Bromo-5-nitroaniline (10 g) was dissolved in 500 mL of CH$_2$Cl$_2$, DIEA (6.6 g) was added to the mixture, followed by DMAP (100 mg). The mixture was cooled to 0° C. in ice bath. Acetyl chloride (4 g in 50 mL CH$_2$Cl$_2$) was added dropwise to the reaction mixture. After the mixture was stirred at RT over 3 h, extracted once with saturated NaHCO$_3$ solution and once with brine, the resulting organic layer was dried over MgSO$_4$, filtered and concentrated in vacuo. The crude material was purified by flash chromatography on silica gel with 1:1 EtOAc:Hexane to 100% EtOAc to afford N-(2-bromo-5-nitrophenyl)acetamide as a white solid. MS: 258 (M−1). Calc'd. for C$_8$H$_7$BrN$_2$O$_3$—259.06.

Preparation XCII—N-(2-bromo-5-nitrophenyl)-N-(2-methylprop-2-enyl)acetamide:

A suspension of 2 g NaH (95% powder) in anhydrous DMF (100 mL) was cooled to −78° C., N-(2-bromo-5-nitrophenyl)acetamide (7 g) in dry DMF (50 mL) was added to the mixture under N$_2$ atmosphere. After the mixture was warmed to 0° C., 3-bromo-2-methylpropene (7.3 g in 20 dry DMF) was added to the mixture. The mixture was stirred at RT overnight. The mixture was poured into a container of ice and extracted between saturated NaHCO$_3$ solution and EtOAc. The resulting organic layer was dried over MgSO$_4$, filtered and concentrated in vacuo. The crude material was purified by flash chromatography on silica gel with 7:2 hexane:EtOAc to afford the title compound as a yellow gum. MS: 314 (M+1). Calc'd. for C$_{12}$H$_{13}$BrN$_2$O$_3$—313.15.

Preparation XCIII—1-(3,3-dimethyl-6-nitro-2,3-dihydroindol-1-yl)ethanone:

N-(2-Bromo-5-nitrophenyl)-N-(2-methylprop-2-enyl) acetamide (4.5 g) was dissolved in anhydrous DMF (50 mL), tetraethyl-ammonium chloride (2.5 g), sodium formate (1.2 g), NaOAc (3 g) were added, and the resulting mixture was bubbled with N$_2$ gas for 10 min. Pd(OAc)$_2$ (350 mg) was added and the mixture was heated at 80° C. under N$_2$ atmosphere overnight. After the mixture was concentrated in vacuo, it was partitioned between saturated NaHCO$_3$ solution and EtOAc, the resulting organic layer was dried over MgSO$_4$, filtered and concentrated in vacuo. The crude material was purified by flash chromatography on silica gel with 2:1 Hexane:EtOAc to afford the title compound as a yellow gum. MS: 235 (M+1). Calc'd. for C$_{12}$H$_{14}$N$_2$O$_3$—234.25.

Preparation XCIV—3,3-dimethyl-6-nitroindoline:

1-(3,3-Dimethyl-6-nitro-2,3-dihydro-indol-1-yl)ethanone (1.8 g) was dissolved in EtOH (50 mL), 12N HCl (50 mL) was added and the resulting mixture was heated at 70° C. overnight. After the mixture was concentrated in vacuo, it was partitioned between saturated NaHCO$_3$ solution and EtOAc, the resulting organic layer was dried over MgSO$_4$, filtered and concentrated in vacuo to afford a yellow solid. MS: 193 (M+1). Calc'd. for $C_{10}H_{12}N_2O_2$—192.21.

Preparation XCV—1-Acetyl-6-amino-3,3-dimethylindoline 1-(3,3-Dimethyl-6-nitro-2,3-dihydro-indol-1-yl)ethanone (250 mg) was dissolved in MeOH (20 mL), the mixture was bubbled with H$_2$ for 10 min. 10% Pd/C (50 mg) was added and the mixture was stirred under H$_2$ overnight. The mixture was filtered through Celite® and concentrated in vacuo. The crude material was purified by flash chromatography on silica gel with 1:1 EtOAc:CH$_2$Cl$_2$ to afford the title compound as a white crystalline material. MS: 205 (M+1). Calc'd. for $C_{12}H_{16}N_2O$—204.27.

Preparation XCVI—4-(1,1,2,2,3,3,4,4,4-nonafluorobutyl) phenylamine:

4-Nitro-(1,1,2,2,3,3,4,4,4-nonafluorobutyl)benzene was synthesized by a method analogous to that described by Gregory, W. A. et al. (J. Med. Chem, 1990, 33(9) 2569–2578). The mixture of the above nitro intermediate (1.0 mmol), iron powder (5.0 mmol) and NH$_4$Cl (0.7 mmol) in EtOH (3 mL) and H$_2$O (3 ml) was stirred for 4 h at 80° C. Filtration and concentration gave the crude title compound, which was used without further purification.

Preparation XCVII—2-bromo-1-tert-butyl-4-nitrobenzene:

NBS (125.0 g, 697.5 mmol, 1.5 eq) was slowly added to a solution of TFA:H$_2$SO$_4$ (5:1, 750 mL) and tert-butyl-4-nitrobenzene (100.0 g, 558.0 mmol) at RT. The solution was stirred for 24 h and poured over 5 kg of ice. The resulting suspension was filtered and washed with a 1:1 MeOH:H$_2$O solution (200 mL) and dried in a vacuum oven. MS (ES+): 258.1, 260.1 (M+H)$^+$. Calc'd for $C_{10}H_{12}BrNO_2$: 257.0.

Preparation XCVIII—4-(2-tert-butyl-5-nitrophenyl) pyridine:

To a solution of 2-bromo-1-tert-butyl-4-nitrobenzene (8.6 g, 33.3 mmol) and toluene (70 mL) in a 150 mL round bottom flask, 4-pyridylboronic acid (4.5 g, 36.6 mmol, 1.1 eq), Pd(PPh$_3$)$_4$ (3.8 g, 3.3 mmol, 0.1 eq) and K$_2$CO$_3$ (13.8 g, 99.9 mmol, 3 eq) were added. The solution was stirred for 24 h at 80° C. before cooling to RT. The solution was filtered through a pad of Celite® and purified by silica flash chromatography (30% EtOAc/Hexanes). This afforded the desired compound as a yellow solid. MS (ES+): 257.2 (M+H)$^+$; (ES−): 255.2 (M−H)$^−$. Calc'd for $C_{15}H_{16}N_2O_2$: 256.1.

Preparation XCIX—4-(2-tert-butyl-5-nitrophenyl)-1-methylpyridinium:

4-(2-tert-Butyl-5-nitrophenyl)pyridine (2.0 g, 7.8 mmol) was added to a round-bottom flask and dissolved in EtOH (10 mL). CH$_3$I (30 mL) was added to the flask which was placed in a 80° C. sand bath and heated to reflux. After 6 h, the solution was cooled to RT and the excess CH$_3$I and EtOH were stripped-off under reduced pressure resulting in the desired compound as a light brown solid. MS (ES+): 271.2 (M+H)$^+$; (ES−): 269.2 (M−H)$^−$. Calc'd for $C_{16}H_{19}N_2O_2^+$: 271.1.

Preparation C—4-tert-butyl-3-(1-methyl-1,2,3,6-tetrahydropyridin-4-yl)aniline:

4-(2-tert-Butyl-5-nitrophenyl)-1-methylpyridinium (2.1 g, 7.8 mmol, Step C) was added to a 100 mL round-bottom flask and dissolved in a 10% H$_2$O/EtOH mixture. To the flask iron dust (1.31 g, 23.4 mmol, 3 eq) and NH$_4$Cl (460 mg, 8.6 mmol, 1.1 eq) were added. The flask was placed in a 100° C. sand bath and heated to reflux. After 2 h, the solution was cooled to RT and filtered through a pad of Celite®. The resulting solution was stripped down to a yellow solid and redissolved in MeOH (20 mL, anhydrous). The solution was cooled to 0° C. by placing it in an ice bath and slowly adding NaBH$_4$ (450 mg, 11.7 mmol, 1.5 eq). After addition of the NaBH$_4$, the solution was cooled to RT and stirred for 30 min. The solvent was stripped-off under vacuum and the solid was redissolved in CH$_2$Cl$_2$ and filtered. The solution was concentrated in vacuo to afford an amorphous clear yellow solid. MS (ES+): 245.2 (M+H)$^+$. Calc'd for $C_{16}H_{24}N_2$: 244.2.

Preparation CI—[1-(4-amino-phenyl)-ethyl]carbamic acid tert-butyl ester:

A mixture of 1-(S)-1-(4-nitrophenyl)ethylamine hydrochloride (2 g), Boc$_2$O (2.6 g) and NaHCO$_3$ (3 g) in MeOH/H$_2$O (1:1, 200 ml) was stirred at RT overnight. The reaction was extracted with EtOAc twice then washed with H2O followed by brine. The organic layer was dried with Na$_2$SO$_4$ and evaporated under reduced pressure to give the protected nitrophenyl ethylamine. Boc-1-(S)-1-(4 nitrophenyl) ethylamine (1 g) was hydrogenated by H$_2$ atmosphere in the presence of Pd/C (200 mg) to give Boc protected aniline (0.8 g). The intermediate was deprotected with 4N HCl/dioxane to give the title compound as the HCl salt.

Preparation CII—1-[2-(tert-butyl)-5-aminophenyl]-4-methylpiperazine:

A mixture of 2-t-butylaniline (5.4 g) and methylchlorethylamine hydrochloride (7 g) and K$_2$CO$_3$ (5 g) in NaI (2 g) in diglyme (150 m) was heated at 170° C. for 8 h. The reaction was filtered and the filtrate was evaporated under high vacuum. The residue was mixed with EtOAc (200 ml) and H$_2$O (200 ml) and extracted with EtOAc twice. The combined organic layer was washed with brine and dried over Na$_2$SO$_4$ and evaporated to give crude 1-[2-(tert-butylphenyl]-4-methylpiperazine. The crude 1-[2-(tert-butylphenyl]-4-methylpiperazine (260 mg) was stirred with H$_2$SO$_4$ (3 ml) at 0° C. and HNO$_3$ (1.2 ml, 70%) was slowly added to the reaction. The reaction was warmed to RT, stirred for 30 min, poured on ice and basified with K$_2$CO$_3$ slowly. The solution was extracted with EtOAc three times, washed with H$_2$O, followed by brine, dried over Na$_2$SO$_4$ and evaporated under reduced pressure. The residue was purified by column chromatography to give 1-[2-(tert-butyl)-5-nitrophenyl]-4-methylpiperazine (260 mg), which was hydrogenated under H$_2$ atmosphere to give 1-[2-(tert-butyl)-5-aminophenyl]-4-methylpiperazine.

The following compounds were prepared similarly to the procedure outlined above:

a) 1-(5-aminophenyl)-4-methylpiperazine

Preparation CIII—4-(tert-butyl)-2-(4-methylpiperazinyl) phenylamine:

A mixture of 1-(tert-butyl)-2-bromo-4-nitrobenzene (3 g) and N-methylpiperazine (8 g) was heated neat at 130° C. for 4 h. The residue was purified by column chromatography to give 1-[4-bromo-5-(tert-butyl)-2-nitrophenyl]-4-methylpiperazine, which was hydrogenated to furnish 4-(tert-butyl)-2-(4-methylpiperazinyl)-phenylamine.

Preparation CIV—{2-[4-(tert-butyl)-2-aminophenoxy]ethyl}dimethylamine:

DEAD (2.6 ml) was added to a mixture of 2-nitro-4-tert-butylphenol (2 g) and N,N-dimethylethanolamine (1.3 g) and Ph$_3$P (4 g) in THF (50 ml). The reaction was stirred at RT for 1 h, diluted with EtOAc (50 ml) and washed with 1 N HCl twice. The aqueous layer was basified with NaHCO$_3$, extracted with EtOAc twice and washed with H$_2$O and brine.

The organic layer was dried over Na$_2$SO$_4$ and evaporated to give {2-[4-(tert-butyl)-2-nitrophenoxy]ethyl}-dimethylamine. It was hydrogenated under H$_2$ atmosphere to give {2-[4-(tert-butyl)-2-aminophenoxy]ethyl}-dimethylamine.

The following compounds were prepared similarly to the procedure outlined above:
a) [2-(2-aminophenoxy)ethyl]-dimethylamine.

Preparation CV—2-amino-5,6,7-trihydro-1,2,4-triazolo[3,4-a]isoquinoline:

7-Nitro-2,3,4-trihydroisoquinolin-1-one (500 mg) was heated in POCl$_3$ (10 ml) to reflux for 8 h. The mixture was evaporated, mixed with toluene and evaporated again. The residue was dissolved in THF, H$_2$NNH$_2$ (1 ml) was slowly added to the reaction and stirred for 2 h. The reaction was evaporated, heated with HC(OEt)$_3$ (15 ml) at 115° C. for 2 h, extracted with EtOAc and hydrogenated to give 2-amino-5,6,7-trihydro-1,2,4-triazolo[3,4-a]isoquinoline.

Preparation CVI—tert-butyl 4-[(6-nitro-3,3-dimethylindolinyl)methyl]piperidinecarboxylate:

3,3-Dimethyl-6-nitroindoline (450 mg) was dissolved in 20 mL of dichloroethane, N-boc-4-formylpiperidine (750 mg) was added to the mixture, followed by 2 g NaHB(OAc)$_3$ and 1 mL of glacial AcOH. The mixture was stirred at RT overnight. Saturated NaHCO$_3$ solution (20 mL) was added to the reaction mixture and stirred for 1 h. The resulting mixture was separated by separation funnel, the organic layer was extracted once with saturated NaHCO$_3$ solution and once with brine. The resulting organic layer was dried over MgSO$_4$, filtered and concentrated in vacuo. The crude material was purified by flash chromatography on silica gel with 9:1 Hexane:EtOAc to afford an orange oil. MS: 290 (M−99). Calc'd. for C$_{21}$H$_{31}$N$_3$O$_4$—389.5.

Preparation CVII—3,3-dimethyl-1-piperidin-4-ylmethyl-2,3-dihydro-1H-indol-6-ylamine:

tert-Butyl 4-[(6-nitro-3,3-dimethylindolinyl)-methyl]piperidinecarboxylate (900 mg) was dissolved in 10 mL MeOH, the mixture was bubbled with H$_2$ for 10 min. 10% Pd/C (30 mg) was added and the mixture was stirred under H$_2$ overnight. The mixture was filtered through Celite® and concentrated in vacuo. The crude material was purified by flash chromatography on silica gel with 1:1 Hexane:EtOAc to afford a colorless oil. MS: 360 (M+1). Calc'd. for C$_{21}$H$_{33}$N$_3$O$_2$— 359.5.

Preparation CVIII—(2-chloro-(3-pyridyl))-N-(4-phenoxyphenyl)carboxamide:

2-Chloronicotinoyl chloride (9.15 g, 0.052 mol) was added to a stirred solution of 4-phenoxyaniline (10 g, 0.054 mol) and DIEA (10 ml, 0.057 mol) in CH$_2$Cl$_2$ (100 ml) at RT. The mixture was stirred for 48 h before removal of solvent under reduced pressure The resulting residue was dissolved in EtOAc and washed several times with saturated NaHCO$_3$ aqueous solution and brine, respectively. The organic layer was dried over Na$_2$SO$_4$ and evaporated to leave a solid. This material was re-crystallized from EtOAc/Hexane mixture, followed by filtration and rinsing with Et$_2$O to give the desired compound as a white solid. MS m/z: 325 (M+1); 323 (M−1).

Preparation CIX—1-(1-methyl(4-piperidyl))-6-nitroindoline:

6-Nitroindoline (5 g) was dissolved in 200 mL of dichloroethane. N-Methyl-4-piperidone (5 g) was added to the mixture, followed by NaHB(OAc)$_3$ (12 g) and 1 mL of glacial AcOH. The mixture was stirred at RT overnight. A saturated NaHCO$_3$ (200 mL) solution was added to the reaction mixture and stirred for 1 h. The resulting mixture was separated by separation funnel. The organic layer was extracted once with saturated NaHCO$_3$ solution and once with brine. The resulting organic layer was dried over MgSO$_4$, filtered and concentrated in vacuo. The crude material was purified by flash chromatography on silica gel with 2:1 EtOAc:MeOH to afford orange oil. MS: 262 (M+1). Calc'd. for C$_{14}$H$_{19}$N$_3$O$_2$— 261.3.

Preparation CX—1-(1-methyl-4-piperidyl)indoline-6-ylamine:

1-(1-Methyl(4-piperidyl))-6-nitroindoline (3 g) was dissolved in 100 mL MeOH and the mixture was bubbled with H$_2$ for 10 min. 10% Pd/C (200 mg) was added and the mixture was stirred under H$_2$ overnight. The mixture was filtered through Celite® and concentrated in vacuo to afford light yellow oil. MS: 232 (M+1). Calc'd. for C$_{14}$H$_{21}$N$_3$— 231.3.

Preparation CXI—N-(2-bromo-5-nitrophenyl)acetamide:

2-Bromo-5-nitroaniline (10 g) was dissolved in CH$_2$Cl$_2$ (500 mL), DIEA (6.6 g) was added to the mixture, followed by 100 mg of DMAP. The mixture was cooled to 0° C. in ice bath. Acetyl chloride (4 g in 50 mL CH$_2$Cl$_2$) was added dropwise to the reaction mixture. After the mixture was stirred at RT over 3 h, and extracted once with saturated NaHCO$_3$ solution and once with brine. The resulting organic layer was dried over MgSO$_4$, filtered and concentrated in vacuo. The crude material was purified by flash chromatography on silica gel with 1:1 EtOAc:Hexane to 100% EtOAc to afford a white solid. MS: 258 (M−1). Calc'd. for C$_8$H$_7$BrN$_2$O$_3$—259.1.

Preparation CXII—N-(2-bromo-5-nitrophenyl)-N-(2-methylprop-2-enyl)acetamide:

A suspension of NaH (2 g) (95% powder) in 100 mL anhydrous DMF was cooled to −78° C., and N-(2-bromo-5-nitrophenyl)acetamide (7 g) in 50 mL dry DMF was added to the mixture under N$_2$. After the mixture was warmed to 0° C., 3-bromo-2-methylpropene (7.3 g in 20 dry DMF) was added to the mixture. The mixture was stirred at RT overnight. The mixture was poured into a container of ice and extracted between saturated NaHCO$_3$ solution and EtOAc. The resulting organic layer was dried over MgSO$_4$, filtered and concentrated in vacuo. The crude material was purified by flash chromatography on silica gel with 7:2 Hexane:EtOAc to afford a yellow gum. MS: 314 (M+1). Calc'd. for C$_{12}$H$_{13}$BrN$_2$O$_3$—313.1.

Preparation CXIII—1-(3,3-dimethyl-6-nitro-2,3-dihydro-indol-1-yl)ethanone:

N-(2-Bromo-5-nitrophenyl)-N-(2-methylprop-2-enyl)acetamide (4.5 g) was dissolved in 50 mL anhydrous DMF, 2.5 g tetraethyl-ammonium chloride, 1.2 g sodium formate, 3 g sodium acetate were added, the resulting mixture was bubbled with N$_2$ gas for 10 min. Pd(OAc)$_2$ (350 mg) was added and the mixture was heated at 80° C. under N$_2$ overnight. After the mixture was concentrated in vacuo, it was extracted between saturated NaHCO$_3$ solution and EtOAc, the resulting organic layer was dried over MgSO$_4$, filtered and concentrated in vacuo. The crude material was purified by flash chromatography on silica gel with 2:1 Hexane:EtOAc to afford a yellow gum. MS: 235 (M+1). Calc'd. for C$_{12}$H$_{14}$N$_2$O$_3$—234.2.

Preparation CXIV—3,3-dimethyl-6-nitroindoline:

1-(3,3-Dimethyl-6-nitro-2,3-dihydro-indol-1-yl)ethanone (1.8 g) was dissolved in 50 mL EtOH, 50 mL 12N HCl was added and the resulting mixture was heated at 70° C. overnight. After the mixture was concentrated in vacuo, it was extracted between saturated NaHCO$_3$ solution and EtOAc. The resulting organic layer was dried over MgSO$_4$, filtered and concentrated in vacuo to afford a yellow solid. MS: 193 (M+1). Calc'd. for C$_{10}$H$_{12}$N$_2$O$_2$—192.2.

Preparation CXV—3,3-dimethyl-1-(4-methyl-piperazin-1-yl)-6-nitro-2,3-dihydro-1H-indole:

3,3-Dimethyl-6-nitroindoline (0.8 g) was dissolved in 50 mL of dichloroethane, N-methyl-4-piperidone (1 g) was added to the mixture, followed by 2.5 g NaHB(OAc)$_3$ and 1 mL of glacial AcOH. The mixture was stirred at RT overnight. Saturated NaHCO$_3$ solution (50 mL) was added to the mixture and stirred for 1 h. The resulting mixture was separated by separation funnel, the organic layer was extracted once with saturated NaHCO$_3$ solution and once with brine, the resulting organic layer was dried over MgSO$_4$, filtered and concentrated in vacuo. The crude material was purified by flash chromatography on silica gel with 9:1 EtOAc:MeOH to afford an orange oil. MS: 290 (M+1). Calc'd. for $C_{16}H_{23}N_3O_2$—289.4

Preparation CXVI—3,3-dimethyl-1-(1-methyl(4-piperidyl))indoline-6-ylamine:

3,3-Dimethyl-1-(4-methyl-piperazin-1-yl)-6-nitro-2,3-dihydro-1H-indole (600 mg) was dissolved in 20 mL MeOH, the mixture was bubbled with H$_2$ for 10 min. 10% Pd/C (100 mg) was added and the mixture was stirred under H$_2$. The mixture was filtered through Celite® and concentrated in vacuo to afford an oil. MS: 260 (M+1). Calc'd. for $C_{16}H_{25}N_3$—259.4.

Preparation CXVII—3-(1-methyl-1,2,3,6-tetrahydro-pyridin-4-yl)-5-nitro-1H-indole:

5-Nitroindole (2.6 g) was dissolved in 100 mL anhydrous MeOH, followed by 5 g N-methyl-4-piperidone and NaOMe (5 g) powder. The mixture was heated to reflux under N$_2$ overnight. The mixture was concentrated in vacuo, and was extracted between saturated NaHCO$_3$ solution and EtOAc. The resulting organic layer was dried over MgSO$_4$, filtered and concentrated in vacuo to afford a yellow solid. This solid was washed with 5 mL EtOAc and 2 mL MeOH to afford a bright yellow solid. MS: 258 (M+1). Calc'd. for $C_{14}H_{15}N_3O_2$—257.29.

Preparation CXVIII—3-(1-methyl-4-piperidyl)indole-5-ylamine:

3-(1-Methyl-1,2,3,6-tetrahydro-pyridin-4-yl)-5-nitro-1H-indole (2.7 g) was dissolved in 50 mL MeOH, the mixture was bubbled with H$_2$ for 10 min. 10% Pd/C (150 mg) was added and the mixture and stirred under H$_2$ overnight. The mixture was filtered through Celite® and concentrated in vacuo to afford a yellow oil. MS: 230 (M+1). Calc'd. for $C_{14}H_{19}N_3$—229.3.

Preparation CXIX—{3-[3-amino-5-(trifluoromethyl)phenyl]propynyl}dimethylamine:

A mixture of 3-bromo-5-trifluoromethylaniline (1.4 g, 5.9 mmol), 1-dimethylamino-2-propyne (1.3 mL, 0.76 mmol), PdCl$_2$(PPh$_3$)$_2$ (0.26 g, 0.29 mmol) and CuI (114 mg, 0.60 mmol) in 10 mL of TEA was heated at 100° C. in a sealed tube for 3 h. The resulting mixture was filtered over Celite®. The filtrate was concentrated, and the residue was purified by prep-HPLC (reverse phase) to give the aniline. MS (ES+): 243 (M+H)$^+$; (ES−): 241 (M−H)$^-$. Calc'd $C_{12}H_{13}F_3N_2$—242.24.

Preparation CXX—{3-[3-amino-5-(trifluoromethyl)phenyl]propyl}dimethylamine:

A mixture of {3-[3-amino-5-(trifluoromethyl)-phenyl]propyl}dimethylamine (7 g, 29 mmol) and Pd(OH)$_2$ (0.5 g) in 250 mL of MeOH was stirred under 50 psi H$_2$. After 2 h, the resulting mixture was filtered over Celite®. The filtrate was concentrated, and the residue was diluted with aq. 1N HCl. The aq. layer was washed with Et$_2$O, made basic with aq. 5N NaOH, and extracted with CH$_2$Cl$_2$. The organic solution was dried over Na$_2$SO$_4$ and concentrated to give the titled compound. MS (ES+): 386 (M+H)$^+$; (ES−): 384 (M−H)$^-$. Calc'd $C_{18}H_{19}ClF_3N_3O$—385.8.

Preparation CXXI—4,4,5,5-tetramethyl-2-(1-methyl(4-1,2,5,6-tetrahydropyridyl))-1,3,2-dioxaborolane:

To a solution of LiHMDS (25 mL, 25 mmol, 1.0 M in THF) in 35 mL of THF was added 1-methyl-4-piperidinone (3.0 mL, 25 mmol) at −78° C. The resulting solution was stirred for 2 h, then Tf$_2$NPh (8.9 g, 25 mmol) was added. The resulting solution was warmed to RT and stirred for 2 h. The mixture was concentrated, and the residue was purified by alumina (neutral) chromatography to give 1-methyl-4-(1,2,5,6-tetrahydro)pyridyl-(trifluoromethyl) sulfonate. A mixture of above triflate (5.0 g, 20 mmol), bis(pinacolato)diboron (5.6 g, 22 mmol), potassium acetate (6.5 g, 66 mmol), PdCl$_2$dppf (0.44 g, 0.6 mmol), and (dppf)2 (0.33 g, 0.6 mmol) in 60 mL of dioxane was heated at 80° C. for 4 h. The resulting mixture was cooled to RT, diluted with Et$_2$O (150 mL). The ethereal solution was washed with H$_2$O followed by brine. The organic layer dried over Na$_2$SO$_4$, concentrated, and recrystallized in hexane-Et$_2$O to give the title intermediate.

Preparation CXXII—5-(1-methyl(4-1,2,5,6-tetrahydropyridyl))-3-(trifluoro-methyl)phenylamine:

To a mixture of 4,4,5,5-tetramethyl-2-(1-methyl(4-1,2,5,6-tetrahydropyridyl))-1,3,2-dioxaborolane (1.0 g, 4.4 mmol), PdCl$_2$pddf (0.16 g, 0.2 mmol) and K$_2$CO$_3$ (1.8 g, 13.2 mmol) and 3-amino-5-bromobenzotrifluoride (0.8 g, 3.3 mmol) in DMF (25 mL) was heated at 80° C. for 16 h. The resulting mixture was diluted with EtOAc, washed with H$_2$O, dried over Na$_2$SO$_4$, and concentrated. The residue was purified by SiO$_2$ chromatography to give the title intermediate. MS (ES+): 257 (M+H)$^+$. Calc'd $C_{13}H_{15}F_3N_2$—256.3.

Preparation CXXIII—4-phenylpiperidine:

4-Cyano-4-phenylpiperidine HCl (10.0 g, 45.0 mmol) was combined with KOH pellets and stirred vigorously under Ar at 160° C. for 4 h. The reaction mix was cooled to RT and dissolved into toluene (100 ml) and H$_2$O (100 ml). After separation of the layers, the aqueous layer was back-extracted two times with toluene. The combined organic layer was dried over Na$_2$SO$_4$, concentrated in vacuo, and dried under high vacuum, yielding a white solid.

Preparation CXXIV—1-methyl-4-phenylpiperidine:

To a stirring mixture at RT of 4-phenylpiperidine (5.24 g, 32.48 mmol) in CH$_3$CN (95 ml) was added a 37% solution of HCHO in H$_2$O (13 ml). To this mixture was added NaCNBH$_3$ (3.27 g, 51.97 mmol). AcOH was added dropwise every 10 min over the next h to maintain the reaction pH near 7. The reaction volume was then reduced in vacuo. The reaction mix was diluted with CH$_2$Cl$_2$ and washed with 2N NaOH and then brine. The crude was concentrated in vacuo and eluted through a silica gel column with 10% MeOH/CH$_2$Cl$_2$. The 1-methyl-4-phenylpiperidine was concentrated in vacuo, yielding a clear oil.

Preparation CXXV—4-(1-methyl-4-piperidyl)phenylamine:

To 1-methyl-4-phenylpiperidine (2.663 g, 15.19 mmol) was added carefully H$_2$SO$_4$ (15.2 ml). The reaction was cooled in an ice bath and a solution of H$_2$SO$_4$ (1.66 ml) and fuming HNO$_3$ (0.67 ml, 15.95 mmol) was added dropwise over 45 min. The mix was stirred at 0° C. for 3 h then at RT for 1.5 h before being poured over about 90 g ice and basified with 24 g solid NaOH. The mix was extracted with CH$_2$Cl$_2$. The organic layer was washed with H$_2$O, dried over Na$_2$SO$_4$, and concentrated in vacuo. The crude was eluted on a silica gel column with a MeOH/CH$_2$Cl$_2$ gradient to yield 1-methyl-4-(4-nitrophenyl)piperidine which was hydrogenated under H$_2$ to furnish the title compound.

Preparation CXXVI—1-piperidylprop-2-en-1-one:

To a 0° C. solution of acryloyl chloride (4.576 g, 50.558 mmol) in CH$_2$Cl$_2$ (50 ml) was added dropwise and very carefully piperidine (4.305 g, 50.558 mmol). The reaction flask was vented during the exothermic addition. After the addition was completed, the white slurry was stirred at 0° C. for 40 min and at RT for 1 h. The reaction was diluted with 70 ml $CH_2Cl_2$ and washed first with about 60 ml 2N HCl and then with about 60 ml of a mix of 2N NaOH and brine. The organic layer was dried over $Na_2SO_4$. The solution was evaporated by heating in a $H_2O$ bath at 60° C. without vacuum. Once most solvent had been evaporated off, dried the clear oil under high vacuum at RT for 30 min.

Preparation CXXVII—1-(tert-butyl)-2-bromo-4-nitrobenzene:

Bromine (17.4 ml) was added dropwise over 40 min to a stirred mixture of 4-tert-butylnitrobenzene (59.5 g, 332 mmol), silver(II)sulfate (56.5 g, 181 mmol), $H_2SO_4$ (300 ml), and $H_2O$ (33 ml) at RT. The mixture was stirred for a further 3 h and then poured into 0.1 M $Na_2S_2O_5/H_2O$ (1 L). The solid was filtered, washed with $H_2O$, $Et_2O$, and $CH_2Cl_2$. The filtrate layers were separated. The aqueous fraction was extracted with $Et_2O$. The combined organic layers were combined, dried over $Na_2SO_4$, and concentrated in vacuo. The yellow solid was triturated with hexanes to give a pale yellow crystalline solid.

Preparation CXXVIII—(2E)-3-[2-(tert-butyl)-5-nitrophenyl]-1-piperidylprop-2-en-1-one:

1-(tert-Butyl)-2-bromo-4-nitrobenzene (6.885 g, 26.674 mmol), 1-piperidylprop-2-en-1-one (4.827 g, 34.677 mmol), and TEA (7.44 ml, 53.35 mmol) were dissolved in toluene (70 ml). To this solution was added $Pd(OAc)_2$ (60 mg, 0.267 mmol) and $Pd(PPh_3)_4$ (617 mg, 0.5335 mmol). The mix was degassed with $N_2$ and heated in a sealed vessel at 120° C. for 15 h. The reaction mixture was cooled to RT, filtered, and concentrated in vacuo. The dark crude oil was eluted through a silica gel column with 15% to 22% EtOAc/hexanes gradient system to yield a thick amber oil as the title compound.

Preparation CXXIX—3-(5-amino-2-tert-butylphenyl)-1-piperidin-1-yl-propenone:

(2E)-3-[2-(tert-Butyl)-5-nitrophenyl]-1-piperidylprop-2-en-1-one (3.22 g, 10.177 mmol) was dissolved in dioxane (20 ml) and IpOH (40 ml). To the $N_2$-degassed solution was added Pd/C 10% by weight catalyst (2 g). The mix was placed in a Parr hydrogenator and stirred for 18 h under 60 psi $H_2$. The reaction was not complete the next day, so the reaction was continued for an additional 20 h with fresh catalyst. The mix was filtered through Celite® and concentrated in vacuo to give a foamy oil.

Preparation CXXX—4-(tert-butyl)-3-(3-piperidylpropyl)phenylamine:

3-(5-Amino-2-tert-butylphenyl)-1-piperidin-1-yl-propenone (2.312 g, 7.619 mmol) was dissolved in THF (100 ml) at RT. To this solution was added $LiAlH_4$ (434 mg, 11.43 mmol). After the reaction stopped exotherming, it was heated at reflux at about 80° C. for 4 h. The reaction mix was cooled to 0° C. and treated by dropwise addition of 0.458 ml $H_2O$, 0.730 ml 10% aqueous NaOH, and 1.19 ml $H_2O$, respectively. The mix was stirred at RT for 1 h. After 40 min about 3 g of $Na_2SO_4$ was added. The mix was filtered through Celite® and concentrated in vacuo. The crude was eluted through silica gel column with a gradient system of 95:5 to 90:10 $CH_2Cl_2$/MeOH, to yield an amber thick oil as the title compound.

The following compounds were prepared similarly to the procedure outlined above:
a) 3-((1E)-4-Pyrrolidinylbut-1-enyl)-4-(tert-butyl)phenylamine.
b) 4-(tert-Butyl)-3-(3-pyrrolidinylpropyl)phenylamine.
c) 4-(tert-Butyl)-3-(3-morpholin-4-ylpropyl)phenylamine.
d) 3-[3-(4-methylpiperazinyl)propyl]phenylamine.
e) 4-[3-(4-methylpiperazinyl)propyl]phenylamine.

Preparation CXXXI—3-(3-nitrophenyl)-1-(4-methylpiperazinyl)propan-1-one:

A slurry consisting of $CH_2Cl_2$ (15 ml), 3-nitrocinnamic acid (3.154 g, 16.329 mmol), 1-methylpiperazine (1.487 g, 14.845 mmol) and EDC (3.557 g, 18.556 mmol) were stirred at RT for 60 h. The reaction was diluted with $H_2O$ and EtOAc. The aqueous layer was back-extracted with EtOAc. The combined organic layers were washed with 2N NaOH and then brine, dried over $Na_2SO_4$, and concentrated in vacuo. The crude was eluted through a silica gel column with 5% MeOH/$CH_2Cl_2$, to yield an off-white solid, mostly trans-olefin compound.

Preparation CXXXII—3-(3-aminophenyl)-1-(4-methylpiperazinyl)propan-1-one:

To a nitrogen-degassed solution of 3-(3-nitrophenyl)-1-(4-methylpiperazinyl)propan-1-one (3.67 g, 13.330 mmol, Step A) in MeOH (50 ml) was added 10% by weight Pd/C (500 mg). The mix was stirred under $H_2$ atmosphere for 18 h then filtered through Celite® and concentrated in vacuo, yielding a thick amber oil which eventually solidified into a dark pink solid.

The following compounds were prepared similarly to the procedure outlined above:
a) 4-[3-(4-methylpiperazinyl)-3-oxopropyl]phenylamine.

Preparation CXXXIII—1-(2-morpholin-4-ylethyl)indol-6-ylamine:

$K_2CO_3$ (5.08 g, 36.726 mmol) was added to a slurry of 6-nitroindole (1.985 g, 12.242 mmol), 4-(2-chloroethyl)morpholine HCl (2.278 g, 12.242 mmol), and $CH_3CN$ (100 ml). The mix was heated to reflux for 18 h, then cooled to RT, filtered, and concentrated in vacuo. The crude was eluted through a silica gel column with a gradient of 3:97 to 5:95 and finally 8:92 MeOH/$CH_2Cl_2$, to yield upon drying the desired intermediate which was hydrogenated under conditions previously described.

Preparation CXXXIV—methyl 2-methyl-2-(4-nitrophenyl)propanoate:

To a stirred solution of 2-(4-nitrophenyl)propionic acid (9 g, 46 mmol, 1 eq) in MeOH (300 mL) was added HCl (4M in Dioxane, 11.5 mL, 46 mmol, 1 eq). The mixture was stirred at RT overnight and was quenched with aqueous $NaHCO_3$. The mixture was extracted with EtOAc. The organic layer was dried over $MgSO_4$ and evaporated under reduced pressure and the partial residue (4.34 g, 20.7 mmol, 1eq) at 0° C. in THF (100 mL) was added NaH (1.66 g, 41.5 mmol, 2 eq). Mixture was stirred at RT for 1h and $CH_3I$ (2.58 g, 41.5 mmol, 2 eq) was added. Reaction was stirred at RT overnight and was quenched with $H_2O$. Mixture was extracted with EtOAc. The organic layer was dried over $MgSO_4$ and evaporated under reduced pressure and used for the next step without further purification to give title compound.

Preparation CXXXV—3-methyl-3-(4-nitrophenyl)butan-1-one:

To a stirred solution of methyl 2-methyl-2-(4-nitrophenyl) propionate (5.32 g, 23.8 mmol) in THF (200 mL) at 0° C. was added a solution of 1M $BH_3$ in THF (25.8 mL, 45.8 mmol). The reaction was stirred at RT overnight and was quenched with MeOH. THF was evaporated under reduced pressure and the residue was diluted in EtOAc and aqueous HCl (1M) was added. The mixture was extracted with EtOAc, the organic layer was dried over $MgSO_4$ and evaporated under reduced pressure. Purification by flash chromatography using 40% EtOAc-hexane gave a yellow solid. To the yellow solid (2.08 g, 10.8 mmol) at 0° C. in $CH_2Cl_2$ was added NMO (1.9 g, 16.1 mmol), molecular sieves 4 Å and TPAP (76 mg, 0.2 mmol). The reaction was stirred for 1 h and filtered on a silica pad. Solvent was evaporated under reduced pressure, forming the crude aldehyde which was used as is. To a suspension of methoxymethyltriphenylphosphonium chloride (6.4 g, 18.6 mmol) in THF (150 mL) was added a solution of KHMDS 0.5 M in toluene (37 mL, 18.5 mmol). The mixture was stirred for 30 min and crude aldehyde was added. The reaction was stirred at RT for 1 h and quenched with $H_2O$. The mixture was extracted with EtOAc, dried and evaporated under reduced pressure. $Et_2O$ was added and a precipitate formed, which was filtered on a silica pad and rinsed with 40% EtOAc-hexane. The solvent was removed and crude material was dissolved in $CH_2Cl_2$. A solution of TFA-$H_2O$ (1:1, 10 mL) was added and the reaction was stirred for 2 h at RT. Aqueous $NaHCO_3$ was added until pH 7 and the mixture was extracted with $CH_2Cl_2$. The organic layer was dried, filtered and evaporated. Crude compound was purified by flash chromatography (40% EtOAc-hexane) to give the title compound as a yellow oil.

Preparation CXXXVI—4-(1,1-dimethyl-3-morpholin-4-ylpropyl)phenylamine:

To a stirred solution of 3-methyl-3-(4-nitrophenyl)butan-1-one (509 mg, 2.4 mmol) and morpholine (0.21 mL, 2.4 mmol) in THF (30 mL) was added $NaBH(OAc)_3$ (0.73 g, 3.4 mmol). The mixture was stirred at RT overnight and washed with HCl (1M). $CH_2Cl_2$ was added and the layers were separated. The aqueous layer was basified to pH 9 using NaOH 1M and extracted with $CH_2Cl_2$. The organic layer was dried and evaporated the nitro compound. To a solution of the nitro compound (0.50 g, 1.8 mmol) in THF (40 mL) was added AcOH (1.97 mmol, 34.5 mmol) followed by zinc (9.1 g, 137 mmol). The mixture was stirred for 1 h, filtered on Celite®, diluted with $H_2O$ and aqueous $NaHCO_3$, and the THF layer was evaporated. The residue was extracted with EtOAc, dried and evaporated to give the title compound.

Preparation CXXXVII—4-{2,2,2-trifluoro-1-[2-(2-methoxy)ethoxy]-1-(trifluoromethyl)ethyl}phenylamine:

Diethyl azodicarboxylate (366 mg, 2.1 mmol) was added drop-wise to a solution of 2-(4-aminophenyl)-1,1,1,3,3,3-hexafluoropropan-2-ol (520 mg, 2 mmol), 2-(2-methoxyethoxy)ethan-1-ol (240 mg, 2 mmol) and $PPh_3$ (550 mg, 2.1 mmol) in THF (10 mL). The mixture was stirred for 2 h, then partitioned between EtOAc and aqueous $NaHCO_3$ solution. The organic phase was washed with brine. After concentration in vacuo, the organic residue was purified by flash chromatography on silica to give the compound. MS: 362 (M+1). Calc'd. for $C_{14}H_{17}F_6NO_3$—361.29.

Preparation CXXXVIII—2-fluoropyridine-3-carbonyl chloride:

To a solution of 2-fluoropyridine (10 g, 100 mmol) in THF (150 mL) under −78° C. was added an LDA solution (2M in heptane/THF/ethylbenzene, 60 mL) dropwise. The mixture was stirred at −78° C. for 3 h, then was quenched with a stream of dry $CO_2$. After warming to RT, the mixture was partitioned between EtOAc (100 mL) and $H_2O$ (200 mL). The aqueous layer was acidified to pH between 3–4, and extracted with EtOAc. The organic solution was collected and washed with brine and dried over $Na_2SO_4$. After removing the solvent in vacuum, 2-fluoropyridine-3-carboxylic acid was obtained as a brown oil. MS: 140 (M−H). Calc'd. for $C_6H_4FNO_2$—141.10. 2-Fluoropyridine-3-carboxylic acid (7 g) was suspended in $SOCl_2$ (100 mL). After heating under reflux for 2 h, the mixture became homogeneous. Access $SOCl_2$ was removed in vacuo to afford a brown solid as desired compound.

Preparation CXXXIX—N-(3-Amino-5-chloro-phenyl)-2-dimethylamino-acetamide:

To a solution of 5-chloro-benzene-1,3-diamine (3 g, 21 mmol) and dimethylamino-acetic acid (2.2 g, 21 mmol) in $CH_2Cl_2$ (300 mL) was added EDC (5 g, 25 mmol), HOBt (2.9 g, 21 mmol), and DIEA (5 mL). The reaction mixture was stirred at RT for overnight. Solvent was removed in vacuum and the residue was purified through flash chromatography on silica gel (0–8% MeOH in EtOAc) to give the desired compound.

Preparation CXL—2-amino-4-nitro-benzamide:

To a solution of 2-amino-4-nitro-benzoic acid (9.1 g, 50 mmol) in $CH_2Cl_2$ (500 mL) was added EDC (12 gram, 60 mmol), HOBt (6.8 g, 50 mmol), DIEA (12 mL), and $NH_3$ in MeOH (2M, 40 mL). The reaction was stirred at RT for overnight, and a precipitation formed. The solid was isolated via vacuum filtration.

Preparation CXLI—6-nitro-3H-quinazolin-4-one: 2-Amino-4-nitro-benzamide was suspended in triethyl orthoformate (50 mL) and the mixture was heated to 140° C. for 5 h. Excess reagent was removed in vacuum. The residue was washed in hexanes to give the compound as a yellow solid.

Preparation CXLII—6-amino-3H-quinazolin-4-one: Hydrogenation of 6-nitro-3H-quinazolin-4-one (2 g) in EtOH (200 mL) was catalyzed by Pd/c (10%, 200 mg) under a H2 balloon for 1 h. MeOH (200 mL) was added to the mixture. The suspension was filtered through a layer of Celite® and the filtrate was concentrated in vacuum to give the desired compound.

Preparation CXLIII—(2,4-dinitro-phenyl)-acetic acid methyl ester:

To a solution of (2,4-dinitro-phenyl)-acetic acid (5 g) in MeOH (100 mL) was added concentrated $H_2SO_4$ (1 mL) and the resulting solution was heated at reflux for overnight. After removing solvent in vacuum, the residue was partitioned between EtOAc and aqueous $NaHCO_3$ (sat.). The organic solution was concentrated in vacuum to give the desired compound which was used without further purification.

Preparation CXLIV—6-amino-1,3-dihydro-indol-2-one:

An EtOH solution of (2,4-dinitro-phenyl)-acetic acid methyl ester was treated with H2 balloon and catalyzed with Pd/c (10%, 500 mg) at RT. The resulting mixture was filtered through a layer of Celite® and concentrated in vacuum to afford the desired compound.

Preparation CXLVI—3-Methyl-but-2-enoic acid (6-bromo-pyridin-2-yl)-amide:

To a solution of 2-amino-6-bromopyridine (3.015 g, 0.017 mol) and $Et_3N$ (2.40 mL, 0.017 mol) in $CH_2Cl_2$ (20.0 mL), was added 3,3-dimethylacryloylchloride (1.96 mL, 0.017 mol) under $N_2$ at 0° C. The mixture was slowly warmed to RT and stirred for 12 h. The reaction was quenched by the addition of $H_2O$ (20.0 mL), the organic layer was separated, dried over $Na_2SO_4$ and evaporated to dryness to yield crude compound which was used without purification.

Preparation CXLVI—3-Methyl-but-2-enoic acid (6-amino-pyridin-2-yl)-amide:

To a solution of 3-methyl-but-2-enoic acid (6-bromo-pyridin-2-yl)-amide (4.30 g, 0.017 mol) and copper (0.214 g, 3.372 mmol) in IpOH (20.0 mL), was added $NH_4OH$ (20.0 mL) in a sealed vessel under $N_2$. The reaction was sealed and heated to 90 ° C. for 12 h. The reaction mixture was cooled to RT and EtOAc (50.0 mL) was added. The organic layer was separated, and then the aq layer was washed with EtOAc (50.0 mL). Combined organic layers were evaporated to dryness, the resulting residue was dissolved in $CH_2Cl_2$ (50.0 mL) and washed with $H_2O$ (4×30 mL). The organic layer was dried over $Na_2SO_4$ and evaporated to dryness to yield crude aminopyridine which was used without purification.

Preparation CXLVII—7-Amino-4,4-dimethyl-3,4-dihydro-1H-[1,8]naphthyridin-2-one:

To a mixture of aminopyridine (1.12 g, 5.833 mmol) and $AlCl_3$ (3.11 g, 0.023 mol) was added chlorobenzene (10.0 mL) in a sealed vessel under Ar. The reaction was sealed and heated to 120° C. for 12 h. The reaction mixture was cooled to RT and the mixture was poured over ice/HCl mixture and extracted with EtOAc (3×50.0 mL). The aqueous layer was neutralized via addition of solid $NaHCO_3$ and extracted with EtOAc (5×50 mL). Combined organic layers were dried over $Na_2SO_4$ and evaporated to dryness to yield crude compound. Chromatography (Silica gel, $CH_2Cl_2$:MeOH, 99:1) yielded pure naphthyridin.

Preparation CXLVIII—2-[1-(3-Amino-phenyl)-2,2,2-trifluoro-1-trifluoromethyl-ethoxymethyl]-pyrrolidine-1-carboxylic acid tert-butyl ester:

To a mixture of 2-(3-amino-phenyl)-1,1,1,3,3,3-hexafluoro-propan-2-ol (1.30 g), 2-hydroxymethyl-pyrrolidine-1-carboxylic acid tert-butyl ester (1.04 g), $PPh_3$ (2.64 g) and molecular sieves 4 Å in THF (100 mL) was added diethyl diazocarboxylate (1.55 mL) slowly. The reaction was stirred at RT for 4 h and at reflux for overnight. After filtration to remove solids, the filtrate was concentrated and the residue was taken into $Et_2O$. The organic phase was washed with saturated $NaHCO_3$ and brine. The organic layer was dried over $MgSO_4$ and evaporated to give a crude compound as very viscous brown oil, which was purified by chromatography through silica gel (500 g, 30% to 50% EtOAc in hexanes) to afford 2-[1-(3-amino-phenyl)-2,2,2-trifluoro-1-trifluoromethyl-ethoxymethyl]-pyrrolidine-1-carboxylic acid tert-butyl ester as a light brown oil.

Preparation CXLIX—Pyrimidine-4-carbaldehyde oxime:

9.14 g (97.11 mmol) of 4-methylpyrimidine was slowly added to a 0° C. solution of 8.75 g HCl in 40 ml EtOH. To this white suspension was added, over 5 min, 61 ml of a 10–20% by weight solution of ethyl nitrite in EtOH. The reaction was stirred at 0° C. for 10 min and then at RT for 2.5 h. The white salt was filtered and dried under vacuum. The salt was dissolved into 20 ml $H_2O$ and very slowly treated with about 200 ml saturated aqueous $KHCO_3$. A white solid precipitated out of the purple solution. The solid was filtered and dried under vacuum to yield the titled compound.

Preparation CL—C-Pyrimidin-4-yl-methylamine dihydrogen chloride:

To a solution of 3.549 g (28.82 mmol) pyrimidine-4-carbaldehyde oxime in 200 ml MeOH was added after degassing with Ar, 800 mg of 10% by weight Pd/C. The mix was stirred under $H_2$ for 4 h, then filtered through a Celite® plug. The solution was concentrated under vacuum to a volume of about 50 ml and then treated carefully with 30 ml of 4N HCl in dioxane. The mix was concentrated and dried under vacuum to yield the titled compound as a pink solid.

Preparation CLI—2-(2,4-Dinitro-phenyl)-3,3,3-trifluoro-2-trifluoromethyl-propionic acid methyl ester:

A mixture of 7.08 g (38.07 mmol) 2,4-dinitrofluorobenzene, 2.43 g (41.88 mmol) KF, and 0.58 g (2.21 mmol) 18-crown-6-ether in 37 ml sulfolane was added 4.00 g (19.04 mmol) methyl 2-(trifluoromethyl)-3,3,3-trifluoropropionate dropwise over about 7 h via syringe pump. After the addition was complete, another 2.43 g KF, 0.58 g 18-Crown-6-ether were added and then 4.00 g Methyl 2-(trifluoromethyl)-3,3,3-trifluoropropionate were added dropwise over 12 h. The next day, repeated additions using same amounts and setting syringe pump addition over 14 h. The following day, the additions were again repeated, this time using half the amounts as above additions and setting syringe pump addition at 12 h. After addition was completed, the reaction mix was cooled to RT and diluted into $Et_2O$ and 0.5N aqueous HCl. The layers were separated, and the organic layer was washed with brine, dried over $Na_2SO_4$, filtered and concentrated under vacuum. The crude was eluted on a silica gel column with EtOAc/hexanes gradient, to yield the titled compound, as a yellow solid. [See Vlasov et al.; J.Org. Chemistry USSR (Engl. Trans.); 15; 1979; 1953–1964).]

Preparation CLII—6-Amino-1-hydroxy-3,3-bis-trifluoromethyl-1,3-dihydro-indol-2-one:

To an argon-degassed solution of 5.13 g (13.64 mmol) 2-(2,4-dinitro-phenyl)-3,3,3-trifluoro-2-trifluoromethyl-propionic acid methyl ester in 300 ml EtOH was added 0.5 g of 10% by weight Pd/C. The reaction was stirred under $H_2$ overnight and filtered through Celite®, concentrated down, and dried under vacuum, yielding the titled compound.

Preparation CLIII—6-Amino-3,3-bis-trifluoromethyl-1,3-dihydro-indol-2-one:

To a solution of 1.245 g (4.151 mmol) 6-amino-1-hydroxy-3,3-bis-trifluoromethyl-1,3-dihydro-indol-2-one in 80 ml THF was added 3.565 ml (62.27 mmol) glacial AcOH and 19 g (290.6 mmol) Zinc dust (100 mesh). The reaction was stirred 40 min at RT and then 5 h at reflux. The reaction was cooled to RT. The solvent was decanted and concentrated, then dissolved in EtOAc and filtered through Celite®. The EtOAc solution was then washed with saturated aqueous $NaHCO_3$ and brine, dried over $Na_2SO_4$, filtered, and concentrated and dried under vacuum, to yield the titled compound, as a yellow solid.

Preparation CLIV—N-[3-(2-Amino-ethoxy)-4-pentafluoroethyl-phenyl]-2-chloro-nicotinamide:

To a solution of 500 mg (0.98 mmol) Boc-N-[3-(2-Amino-ethoxy)-4-pentafluoroethyl-phenyl]-2-chloro-nicotinamide in 10 ml $CH_2Cl_2$ was added 10 ml TFA and stirred for 2 h. The reaction was concentrated down, treated with 6N aqueous NaOH, and extracted 3 times with $CH_2Cl_2$. The combined organic extracts were dried over $Na_2SO_4$, filtered, concentrated down, and dried under vacuum, yielding the titled compound.

Preparation CLV—2-Chloro-N-[3-(2-methanesulfonylamino-ethoxy)-4-pentafluoroethyl-phenyl]-nicotinamide:

To a solution of 381 mg (0.93 mmol) N-[3-(2-amino-ethoxy)-4-pentafluoroethyl-phenyl]-2-chloro-nicotinamide in 10 ml $CH_2Cl_2$ at 0° C. was added 0.389 ml $Et_3N$ and 0.072 ml (0.93 mmol) methanesulfonylchloride. After 5 min, the reaction was stirred at RT for 30 min. The reaction was diluted with $CH_2Cl_2$, washed with brine, dried over $Na_2SO_4$, filtered, concentrated, and dried under vacuum, yielding the titled compound as a white foamy solid.

Preparation CLVI—2-Methyl-2-(4-nitro-phenyl)-propionic acid:

To a solution of 2-(4-nitro-phenyl)-propionic acid (50 g, 0.26 mole) in 250 mL of MeOH was added 6 mL of concentrated HCl. The resulting solution was heated at reflux for 16 h. Then the resultant mixture was diluted with 200 mL of aq. $NaHCO_3$ and 500 mL of EtOAc. The organic layer was separated, dried over $Na_2SO_4$, and concentrated. The residue was diluted with 100 mL of THF and added to a suspension of NaH (11.2 g, 0.28 mole, 60% in mineral oil) in 600 mL of THF. To the resulting mixture was added $CH_3I$ (18.3 mL, 0.29 mole) in one portion. The resulting mixture was stirred for 48 h at 40° C., then was diluted with aq. NH$_4$Cl solution and EtOAc. The organic layer was separated, dried over Na$_2$SO4, and concentrated. The residue was used without further purification.

To a solution of the residue (54 g, 0.24 mole) in 500 ml of MeOH was added 5N aq. NaOH (144 mL, 0.72 mole). The mixture was stirred for 16 h at 40° C. The resulting mixture was concentrated, the residue was diluted with H$_2$O (500 mL), and acidified with 2N HCl to give a precipitate. The precipitate was filtered and dried to give the titled compound as a yellowish solid. MS: 210 (M+1), Calc'd for C$_{10}$H$_{12}$NO$_4$—210.20.

Preparation CLVII—2-Methyl-5-[1-methyl-1-(4-nitro-phenyl)-ethyl]-[1,3,4]oxadiazole:

A mixture of 2-methyl-2-(4-nitro-phenyl)-propionic acid (5 g, 24 mmol.) and a few drops of DMF in SOCl$_2$ was stirred at reflux for 16 h. The resulting solution was concentrated to give corresponding acid chloride as a brown solid. To a mixture of the acid chloride (2.33 g, 10.2 mmol), acetic acid hydrazide (0.91 g, 12.2 mmol.), Et$_3$N (2.86 mL, 20.2 mmol.) in CH$_2$Cl$_2$ (50 mL) was added 2 crystals of DMAP at RT. The mixture was stirred for 16 h and concentrated. A solution of the residue in 50 mL of phosphorous oxychloride was heated at 95° C. for 16 h. The mixture was concentrated and diluted with ice-water and EtOAc. The organic layer was washed with saturated aq. NaHCO$_3$ solution twice, dried over Na$_2$SO$_4$, and concentrated. The residue was purified by SiO$_2$ chromatography (hexane: EtOAc= 1:1) to give the titled compound as a pale yellow crystal. MS: 248 (M+1), Calc'd for C$_{12}$H$_{14}$N$_3$O$_3$—248.10.

Preparation CLVIII—2-Methyl-5-[1-methyl-1-(4-amino-phenyl)-ethyl]-[1,3,4]oxadiazole:

A mixture of 2-methyl-5-[1-methyl-1-(4-nitro-phenyl)-ethyl]-[1,3,4]oxadiazole (1.36 g, 5.5 mmol.) and Pd/C (68 mg) in EtOAc (50 mL), was stirred under 1 atm of H$_2$ for 16 h. The resultant was filtered over Celite®, and the filtrate was concentrated to give the titled compound as a pale yellow crystalline. MS: 218 (M+1) calc'd for C$_{12}$H$_{16}$N$_3$O—218.12.

Preparation CLIX—4-[1-Methyl-1-(4-nitro-phenyl)-ethyl]-pyrimidine:

To a mixture of 1-(4-nitro-phenyl)-propan-2-one (5.32 g, 29.7 mmol.), triethylbenzylammonium chloride (0.34 g, 1.5 mmol.), and 13 mL of aq. 5N KOH solution (65.3 mmol.) in CH$_2$Cl$_2$ was added CH$_3$I (4.06 mL, 65.3 mmol.). The resulting mixture was stirred at 40° C., and then diluted with EtOAc and H$_2$O. The organic layer was dried and concentrated. To the residue (1.0 g, 4.8 mmol.) in toluene (30 mL) was added dimethylformamide dimethylacetal (1.27 mL, 9.6 mmol.). The resulting mixture was heated at reflux for 6 h then concentrated to give 1-dimethylamino-4-methyl-4-(4-nitro-phenyl)-pent-1-en-3-one as a yellow solid (MS 263 (M+1) Calc'd for C$^{14}$H$_{19}$N$_2$O$_3$—263.13).

A mixture of 1-dimethylamino-4-methyl-4-(4-nitro-phenyl)-pent-1-en-3-one (0.5 g, 1.9 mmol.), formamidine HCl (0.305 g, 3.8 mmol.), and NaOEt (1.29 g, 4.0 mmol) was heated in Smith synthesizer under microwave for 10 min at 150° C. The resultant mixture was diluted with H$_2$O and EtOAc. The organic layer was dried, and the residue was used without further purification. MS: 244 (M+1) Calc'd for C$_{13}$H$_{14}$N$_3$O$_2$—244 .10.

Preparation CLX—5-[1-Methyl-1-(4-nitro-phenyl)-ethyl]-1H-pyrazole:

A mixture of 1-dimethylamino-4-methyl-4-(4-nitro-phenyl)-pent-1-en-3-one (0.36 g, 1.4 mmol.) and hydrazine hydrate (1.0 g, 6.25 mmol.) in EtOH was heated at 50° C. for 3 h. The mixture was concentrated, and the residue was diluted with H$_2$O and EtOAc. The organic layer was dried over Na$_2$SO$_4$ and concentrated to give the titled compound as a yellow solid. MS: 232 (M+1) Calc'd for C$_{12}$H$_{14}$N$_3$O$_2$—232.10.

Preparation CLXI—2-tert-Butyl-5-nitro-phenylamine:

Concentrated H$_2$SO$_4$ (1 L) was cooled to −10° C. with a dry ice IpOH bath in a 2 L 3-neck round bottom flask fitted with a mechanical stirrer and temperature probe. 2-t-Butylaniline (109 g, 730 mmol) was added, giving a clumpy solid. Once the temperature of the mixture was stabilized at −10° C., KNO$_3$ (101 g, 1001 mmol) was added portion-wise, as the solid, over 4 h, maintaining the temperature between −20 and −5° C. Once all of the KNO$_3$ was added, the reaction was stirred overnight with gradual warming to RT. The reaction was quenched by diluting with H$_2$O and extracting 3× with EtOAc. The EtOAc extracts were washed multiple times with saturated NaHCO$_3$ (aq), until gas evolution ceased, then with brine. The EtOAc extracts were combined, dried over anhydrous Na$_2$SO$_4$, filtered and concentrated under reduced pressure giving a black oil. The oil was eluted through a 36×7 cm column of silica gel with a 5%; 10%; 15%; 25%; and 50% EtOAc:Hexanes step gradient (2 L each step) giving 2-tert-butyl-5-nitro-phenylamine as a red solid.

Preparation CLXII—2-Bromo-N-(2-tert-butyl-5-nitro-phenyl)-acetamide:

2-tert-Butyl-5-nitro-phenylamine (70 g, 359 mmol) and a catalytic amount of DMAP were dissolved in THF (1.5 L) under N$_2$. TEA (109 g, 1077 mmol) was added and the solution was cooled to 0° C. Bromoacetyl bromide (207 g, 1023 mmol) was added and the reaction was gradually warmed to RT with stirring overnight. The reaction was partially concentrated under reduced pressure, treated with H$_2$O and extracted with EtOAc (3×). The EtOAc extracts were washed with brine, combined, dried over anhydrous Na$_2$SO$_4$, filtered and concentrated under reduced pressure giving a black oil. This oil was eluted through a 38×7 cm column of silica gel with 95:5:0.5 CH$_2$Cl$_2$:MeOH:NH$_4$OH$_{(aq)}$ eluant giving 2-bromo-N-(2-tert-butyl-5-nitro-phenyl)-acetamide as a brown solid.

Preparation CLXIII—N-(2-tert-Butyl-5-nitro-phenyl)-2-dimethylamino-acetamide:

2-Bromo-N-(2-tert-butyl-5-nitro-phenyl)-acetamide (80 g, 253 mmol) and K$_2$CO$_3$ (70 g, 506 mmol) were combined in a 3-L 3-neck round bottom flask fitted with a mechanical stirrer, N$_2$ inlet, and pressure equalizing addition funnel. THF (1.75 L) was added and the mixture was cooled to 0° C. under N$_2$. DMA (400 mL of a 2 M solution in THF, 800 mmol) was added to the mixture through the pressure equalizing addition funnel over 30 min. The mixture was gradually warmed to RT with stirring overnight. The reaction was quenched by filtering it under vacuum and then concentrating the filtrate under reduced pressure. The recovered material was eluted through a 36×7 cm column of silica gel with 50% EtOAc:Hexanes giving N-(2-tert-butyl-5-nitro-phenyl)-2-dimethylamino-acetamide as a brown solid.

The pyrolidino and morpholino analogs are prepared by substituting the dimethylamine with respectively pyrolidine or morpholine and using the same chemistry as described.

a) N-(2-tert-Butyl-5-nitro-phenyl)-2-pyrrolidin-1-yl-acetamide.

b) N-(2-tert-Butyl-5-nitro-phenyl)-2-morpholin-4-yl-acetamide.

Preparation CLXIV—N-(5-Amino-2-tert-butyl-phenyl)-2-dimethylamino-acetamide:

N-(2-tert-Butyl-5-nitro-phenyl)-2-dimethylamino-acetamide (25.8 g, 92 mmol) was dissolved in EtOH (1.4 L)

and 1,4-dioxane (200 mL). The solution was degassed under vacuum with stirring. 10% Pd/C (2.5 g) was added (as a slurry in EtOH). The mixture was degassed again, then the reaction vessel was charged with $H_2$ gas (balloon) and stirred overnight at RT. The reaction was filtered through Celite® with MeOH and the filtrate was concentrated under reduced pressure. The recovered material was eluted through a 36×7 cm column of silica gel with a 97.5:2.5:0.25 and 95:5:0.5 $CH_2Cl_2$:MeOH:$NH_4OH_{(aq)}$ step gradient giving N-(5-amino-2-tert-butyl-phenyl)-2-dimethylamino-acetamide as a brown solid.

Preparation CLXV—5-Chloro-1-methyl-1H-pyrazole-4-carboxylic acid (4-tert-butyl-phenyl)-amide:

5-Chloro-1-methyl-1H-pyrazole-4-carbonyl chloride (1.0 g, 5.6 mmol) was dissolved in $CH_2Cl_2$ (100 mL) under $N_2$ and cooled to 0° C. 4-t-Butylaniline was added and the reaction was stirred with gradual warming to RT overnight. The reaction was quenched with saturated $NaHCO_3$(aq) and extracted 3× with fresh $CH_2Cl_2$. The $CH_2Cl_2$ extracts were washed with brine, combined, dried over anhydrous $Na_2SO_4$, filtered and concentrated under reduced pressure giving 5-chloro-1-methyl-1H-pyrazole-4-carboxylic acid (4-tert-butyl-phenyl)-amide as a foamy pink solid.

Preparation CLXVI—1,2-dihydro-3-spiro-1'-cyclopropyl-1H-indole:

A solution of 3-(2-bromo-ethyl)-1H-indole (5 g) in anhydrous $CH_3CN$ (100 mL) was suspended with oven dried $K_2CO_3$ (20 g) and heated to reflux for 10 h. After cooling to RT, the mixture was filtered and the filter cake was washed with EtOH (50 mL). The combined filtrate was treated with $NaBH_4$ (300 mg) and stirred for 3 h at RT. Solvents were removed in vacuo and the residue was partitioned between $H_2O$ (160 mL) and EtOAc (60 mL). The organic layer was extracted with aqueous HCl (0.5N, 30 mL×2). The acid layer was basified with $NH_4OH$ (aq. Conc.) and extracted with EtOAc. The organic phase was washed with brine and dried over $Na_2SO_4$ and concentrated to give the desired compound as a colorless thin oil.

Preparation CLXVII—6-nitro-1,2-dihydro-3-spiro-1'-cyclopropyl-1H-indole: 1',2'-Dihydrospiro(cyclopropane-1,3'-[3H]indole)(1.8 g 12.4 mmol) was added in dropwise over a period of 20 min to a cooled (−5 to −10° C.) solution of $NaNO_3$ (1.3 g) in $H_2SO_4$ (conc., 30 mL). After the addition, the reaction was stirred for another 40 min., then the mixture was poured onto crushed ice (200 g) and the resulting mixture was basified with $NH_4OH$ (aq., conc.) with cooling. The basified mixture was extracted with EtOAc twice and the organic layer was washed with brine then dried over $Na_2SO_4$. After concentration in vacuo, the compound was isolated as a dark gray solid.

Preparation CLXVIII—Ethyl 6-nitro-1,2-dihydro-3-spiro-1'-cyclopropyl-1H-indole-1-carbamate:

A solution of 6-nitro-1,2-dihydro-3-spiro-1'-cyclopropyl-1H-indole (2.7 g) in $CH_2CL_2$ (100 mL) was suspended with $NaHCO_3$ (5 g), and ethyl chloroformate was added dropwise with vigorous stirring. After the addition, the reaction was stirred overnight. The mixture was washed with $H_2O$ (100 mL), then dried over $Na_2SO_4$ and concentrated in vacuo. The residue was recrystalized in MeOH to give the title compound as a dark gray crystalline.

Preparation CLXIX—Ethyl 6-amino-1,2-dihydro-3-spiro-1'-cyclopropyl-1H-indole-1-carbamate:

Ethyl 6-nitro-1,2-dihydro-3-spiro-1'-cyclopropyl-1H-indole-1-carbamate (2.1 g) was dissolved in EtOH (200 mL), suspended with Pd/C (10%, 560mg) and equipped with a balloon filled with $H_2$. The hydrogenation was finished in 3 h. The reaction mixture was filtered through a layer of Celite®. The filtrate was concentrated in vacuo to give the desired product as a white solid.

Preparation CLXX—4-[1-Methyl-1-(4-nitro-phenyl)-ethyl]-3,6-dihydro-2H-pyridine-1-carboxylic acid ethyl ester:

1-Methyl-4-[1-methyl-1-(4-nitro-phenyl)-ethyl]-1,2,3,6-tetrahydro-pyridine (5.2 g) was dissolved in toluene (100 mL) and ethyl chloroformate (2.4 g). The mixture was heated at reflux for overnight and cooled to RT. The toluene solution was washed with $NaHCO_3$ (aq., sat., 100 mL) then brine (100 mL) and dried over $Na_2SO_4$. The organic phase was concentrated in vacuo to give the desired compound which was used without purification.

Preparation CLXXI—4-[1-Methyl-1-(4-amino-phenyl)-ethyl]-3,6-dihydro-2H-pyridine-1-carboxylic acid ethyl ester:

4-[1-Methyl-1-(4-nitro-phenyl)-ethyl]-3,6-dihydro-2H-pyridine-1-carboxylic acid ethyl ester was dissolved in EtOH (150 mL) and suspended with Pd/C (10%, 1g). The reaction flask was equipped with a balloon filled with $H_2$. The hydrogenation was continued for 3 days. The mixture was filtered through a layer of Celite® and concentrated in vacuo to provide the desired compound as a light brown oil.

Preparation CLXXII: 3,3-dimethyl-6-nitroindoline 3-Methyl-but-2-enoic acid (3-acetylamino-phenyl)-amide:

3,3-Dimethylacryloyl chloride (3.3 ml, 29.3 mmol) was added to a mixture of 3'-aminoacetanilide (4.40 g, 29.3 mmol) and $Et_3N$ (4.5 ml, 32.2 mmol) in 50 ml of $CH_2Cl_2$ and 25 ml of THF at 0° C. under $N_2$. The mixture was stirred at RT overnight, diluted with 100 ml of $CH_2Cl_2$, washed with aqueous $Na_2CO_3$, then brine, condensed, and purified by flash column chromatography (15 to 30% of EtOAc in $CH_2Cl_2$). The titled compound was obtained as an off-white solid. MS (ES+): 233.1 $(M+H)^+$. Calc'd for $C_{13}H_{16}N_2O_2$—232.28.

The following compounds were prepared similarly to the procedure outlined above:

a) 3-Methyl-but-2-enoic acid phenylamide. MS(ES$^+$): 176.1 $(M+H)^+$. Calc'd for $C_{11}H_3NO$—175.23.

Preparation CLXXIII—N-(4,4-Dimethyl-2-oxo-1,2,3,4-tetrahydro-quinolin-7-yl)-acetamide:

The mixture of 3,3-dimethyl-6-nitroindoline 3-Methyl-but-2-enoic acid (3-acetylamino-phenyl)-amide (1.05 g, 4.52 mmol) and $AlCl_3$ (5.0 g, 37.5 mmol, Aldrich, 99.99%) in 50 ml of anhydrous chlorobenzene was stirred at 120° C. (oil bath temperature) under $N_2$ overnight, cooled to RT, poured into 10 ml of ice cold HCR, stirred for 30 min, and extracted with EtOAc. The organic portions were combined, washed with brine, dried with $Na_2SO_4$, filtered, condensed, and purified by flash column chromatography (1% of MeOH in $CH_2Cl_2$). The titled compound was obtained as an off-white solid. MS (ES$^+$): 233.2 $(M+H)^+$. Calc'd for $C_{13}H_{16}N_2O_2$—232.28.

The following compounds were prepared similarly to the procedure outlined above:

a) 4,4-Dimethyl-3,4-dihydro-1H-quinolin-2-one MS(ES$^+$): 175.6 $(M+H)^+$. Calc'd for $C_{11}H_{13}NO$—175.23.

Preparation CLXXIV: 7-Amino-4,4-dimethyl-3,4-dihydro-1H-quinolin-2-one:

N-(4,4-Dimethyl-2-oxo-1,2,3,4-tetrahydro-quinolin-7-yl)-acetamide (1.50 g, 6.46 mmol) in 10 ml of HCl (concentrated, 37%) and 30 ml of EtOH was stirred at 75° C. for 4 h. The solvents were removed under reduced pressure. The residue was dissolved in EtOAc/$H_2O$, neutralized with $NaHCO_3$, washed with brine, dried with $Na_2SO_4$, filtered, and condensed to give the titled compound as an off-white solid. MS (ES$^+$): 191.2 $(M+H)^+$. Calc'd for $C_{11}H_{14}N_2O$—190.24.

Preparation CLXXV—4,4-Dimethyl-1,2,3,4-tetrahydro-quinolin-7-ylamine:

The mixture of 7-amino-4,4-dimethyl-3,4-dihydro-1H-quinolin-2-one (1.07 g, 5.62 mmol) and borane dimethylsulfide complex (1.60 ml, 16.9 mmol) in 40 ml of anhydrous THF was heated at reflux under $N_2$ for 15 h. The solvents were removed under reduced pressure. The residue was heated at reflux in 20 ml of MeOH for 2 h, then 0.80 g of $NaHCO_3$ was added, and the mixture was heated at reflux for 2 h. The mixture was filtered, condensed, and the residue was purified by flash column chromatography (5 to 10% of EtOAc in $CH_2Cl_2$). The titled compound was obtained as a viscous oil. $MS(ES^+)$: 176.9 $(M+H)^+$. Calc'd for $C_{11}H_{16}N$—176.26.

The following compounds were prepared similarly to the procedure outlined above:
a) 4,4-Dimethyl-1,2,3,4-tetrahydroquinoline $MS(ES^+)$: 162.5 $(M+H)^+$. Calc'd for $C_{11}H_{15}N$—161.24.

Preparation CLXXVI—N-(4,4-Dimethyl-1,2,3,4-tetrahydro-quinolin-7-yl)-2-fluoronicotinamide:

The mixture of 4,4-dimethyl-1,2,3,4-tetrahydro-quinolin-7-ylamine (0.20 g, 1.13 mmol), 2-fluoronicotinic acid (0.16 g, 1.13 mmol), TBTU (0.36 g, 1.13 mmol), and DIEA (0.24 ml, 1.36 mmol) in 5 ml of DMF was stirred at RT for 3 h, then partitioned between EtOAc and $Na_2CO_3$ (aq). The organic layer was washed with $H_2O$, brine, dried with $MgSO_4$, filtered, condensed, and the residue was purified by flash column chromatography (20 to 30% of EtOAc in $CH_2Cl_2$). The titled compound was obtained as an off-white solid. MS $(ES^+)$: 300.1 $(M+H)^+$. Calc'd for $C_{17}H_{18}FN_3O$—299.34.

The following compounds were prepared similarly to the procedure outlined above:
a) N-(4,4-Dimethyl-2-oxo-1,2,3,4-tetrahydro-quinolin-7-yl)-2-fluoronicotinamide, as an off-white solid. $MS(ES^+)$: 314.2 $(M+H)^+$. Calc'd for $C_{17}H_{16}FN_3O_2$—313.33.
b) N-(1-Ethyl-4,4-dimethyl-1,2,3,4-tetrahydro-quinolin-7-yl)-2-fluoronicotinamide, $MS(ES^+)$: 328.3 $(M+H)^+$. Calc'd for $C_{19}H_{22}FN_3O$—327.40.

Preparation CLXXVII—4,4-Dimethyl-7-nitro-1,2,3,4-tetrahydro-quinoline:

To 13 ml of $H_2SO_4$ (96%) cooled in a salt ice bath was added dropwise 4,4-dimethyl-1,2,3,4-tetrahydro-quinoline (5.80 g, 36.0 mmol). The resulting slurry was stirred for 30 min upon when concomitant addition of $HNO_3$ (90%, 1.70 ml, 36.0 mmol) and $H_2SO_4$ (96%, 7 ml) was started, the addition was finished in 20 min, the mixture was stirred at 0° C. to 15° C. for 2 h, poured into ice, and extracted with EtOAc. The organic portion was washed with brine, condensed, and purified by flash column chromatography (0 to 10% of EtOAc in hexanes). The titled compound was obtained as a yellow oil. MS $(ES^+)$: 206.9 $(M+H)^+$. Calc'd for $C_{11}H_{14}N_2O_2$—206.24.

Preparation CLXXVIII—1-Ethyl-4,4-dimethyl-7-nitro-1,2,3,4-tetrahydroquinoline:

The mixture of 4,4-dimethyl-7-nitro-1,2,3,4-tetrahydro-quinoline (0.48 g, 2.33 mmol), iodoethane (0.21 ml, 2.56 mmol), and NaH (60%, 0.10 g, 2.5 mmol) in 10 ml of DMF was stirred at RT overnight, and partitioned between EtOAc and $H_2O$. The combined organic portions were washed with brine, dried with $MgSO_4$, filtered, and condensed. The crude compound was purified by flash column chromatography (5 to 10% of $CH_2Cl_2$ in hexanes). The titled compound was obtained as a yellow oil. MS $(ES^+)$: 235.3 $(M+H)^+$. Calc'd for $C_{13}H_{18}N_2O_2$—234.29.

Preparation CLXXIX: 1-Ethyl-4,4-dimethyl-1,2,3,4-tetrahydro-quinolin-7-ylamine:

The mixture of 1-ethyl-4,4-dimethyl-7-nitro-1,2,3,4-tetrahydro-quinoline (0.28 g) and Pd/C (0.060 g, 10% wt) in 10 ml of EtOAc was placed under $H_2$ which was provided by a balloon and stirred at RT overnight. Then the mixture was filtered through Celite®, condensed, and the residue was purified by flash column chromatography (2% of EtOAc in $CH_2Cl_2$). The titled compound was obtained as a pink oil. $MS(ES^+)$ 204.8 $(M+H)^+$. Calc'd for $C_{11}H_{16}N$—204.31.

Preparation CLXXX—1-(4-Nitro-phenyl)-cyclopropanecarbonitrile:

NaOH (5.0 N, 80ml) was added to a mixture of 4-nitrophenylacetonitrile (10.0 g, 61.7 mmol), 1,2-dibromoethane (8.0 ml, 92.5 mmol), and tetraethylammonium chloride hydrate (10.2 g, 61.7 mmol) in 200 ml of $CH_2Cl_2$ at RT. The resulting mixture was stirred at RT for 24 h, diluted with $CH_2Cl_2$, and acidified with HCl (10%, aq). The organic layer was separated, washed with brine, condensed, and the crude was purified by flash column chromatography. The titled compound was obtained as a light yellowish solid.

Preparation CLXXXI—C-[1-(4-Nitro-phenyl)-cyclopropyl]-methylamine:

The mixture of 1-(4-nitro-phenyl)-cyclopropanecarbonitrile (3.0 g, 15.9 mmol) and borane THF complex (1.0 M solution in THF, 32 ml, 32 mmol) in 50 ml of anhydrous THF was heated at reflux overnight. The mixture was cooled to RT, quenched with 2.5 ml of 50% AcOH aqueous solution, then partitioned between EtOAc and $NaHCO_3$ (aq). The combined organic portions were washed with brine, dried with $MgSO_4$, filtered, and condensed. The crude was purified by flash column chromatography (1 to 2% of MeOH in $CH_2Cl_2$). The titled compound was obtained as a light brownish solid. MS $(ES^+)$: 192.9. Calc'd for $C_{10}H_{12}N_2O_2$—192.2.

Preparation CLXXXII—2,2,2-Trifluoro-N-[1-(4-nitro-phenyl)-cyclopropylmethyl]-acetamide:

Trifluoroacetic anhydride (5.26 ml, 36.9 mmol) was added to a mixture of C-[1-(4-nitro-phenyl)-cyclopropyl]-methylamine (2.37 g, 12.3 mmol) and triethyl amine (8.6 ml, 61.5 mmol) in 50 ml of $CH_2Cl_2$ at RT. The resulting mixture was stirred for 2 h. The volatiles were removed under reduced pressure and the residue was partitioned between EtOAc and aqueous $NaHCO_3$. The organic layer was washed with brine, dired with $MgSO_4$, filtered, and condensed. The crude compound was purified by flash column chromatography (10 to 20% of EtOAc in hexanes), and the titled compound was obtained as an off-white solid.

Preparation CLXXXIII—1-(7-Nitro-4-spiro-1'-cyclopropane-3,4-dihydro-1H-isoquinolin-2-yl)-2,2,2-trifluoroethanone:

A mixture of 2,2,2-trifluoro-N-1-(4-nitro-phenyl)-cyclopropylmethyl]-acetamide (3.10 g, 10.7 mmol) and paraformaldehyde (0.54 g, 17.2 mmol) was added to a mixture of 12 ml of glacial AcOH and 20 ml of $H_2SO_4$ at RT. The resulting mixture was stirred at 40° C. for 12 h, poured into ice-water and extracted with EtOAc. The combined organic portion was washed with $NaHCO_3$ (aq), $H_2O$, brine, then dried with $MgSO_4$, and condensed. The crude compound was purified by flash column chromatography (10 to 20% of EtOAc in hexanes), and the titled compound was obtained as a white solid.

Preparation CLXXXIV—7-Nitro-4-spiro-1'-cyclopropane-1,2,3,4-tetrahydroisoquinoline:

A mixture of 1-(7-nitro-4-spiro-1'-cyclopropane-3,4-dihydro-1H-isoquinolin-2-yl)-2,2,2-trifluoroethanone (0.32 g, 1.07 mmol) and $K_2CO_3$ (1.50 g, 14.2 mmol) in 7 ml of MeOH and 2 ml of $H_2O$ was stirred at RT overnight. The mixture was filtered, and the filtrate was concentrated. The residue was dissolved in EtOAc, washed with $NH_4Cl$ (aq), brine, dried with $MgSO_4$, filtered, and condensed to give the titled compound as a light yellowish solid. MS ($ES^+$): 204.9 $(M+H)^+$. Calc'd for $C_{11}H_{12}N_2O_2$—204.23.

Preparation CLXXXV—tert-Butyl N-[7-nitro-4-spiro-1'-cyclopropane-3,4-dihydro-1H-isoquinoline-2-carbamate:

The mixture of 7-nitro-4-spiro-1'-cyclopropane-1,2,3,4-tetrahydroisoquinoline (0.20 g, 0.98 mmol), $BOC_2O$ (0.24 g, 1.08 mmol), DMAP(0.025 g, 0.20 mmol), DIEA (0.51 ml, 2.94 mmol) in 10 ml of $CH_2Cl_2$ was stirred at RT for 2 h. The solvent was removed, the residue was purified by flash column chromatography (5 to 10% of EtOAc in hexanes), and the titled compound was obtained as a white solid.

Preparation CLXXXVI: tert-Butyl N-[7-amino-4-spiro-1'-cyclopropane-3,4-dihydro-1H-isoquinoline]carbamate A mixture of tert-butyl N-[7-nitro-4-spiro-1'-cyclopropane-3,4-dihydro-2H-isoquinoline-2-carbamate (0.27 g, 0.89 mmol) and Pd/C (0.05 g, 10% wt) in 15 ml of MeOH was placed under $H_2$ which was provided by a balloon and stirred at RT for 1.5 h. The mixture was filtered through Celite®, and condensed to give the titled compound as a white solid. MS ($ES^+$): 274.8 $(M+H)^+$. Calc'd for $C_{16}H_{22}N_2O_2$—274.36.

Preparation CLXXXVII—4-methyl-6-[2-(1-methyl-pyrrolidin-2-yl)-ethyl]-pyrimidin-2-ylamine:

To a solution of (S)-(-)-1-methyl-2-pyrrolidine (320 mg, 2.78 mmol) in dry THF (10 mL) at 0° C. was added NaH (167 mg, 4.16 mmol). After stirred at RT for 1 h, 2-amino-4-chloro-6-methylpyrimidine (600 mg, 4.16 mmol) in dry THF (10 mL) was added dropwise via the addition funnel. The resulting mixture was heated to reflux under Ar gas for 20 h. The reaction was cooled to RT and quenched with sat. $NH_4Cl$. Solvent was removed. The residue was partitioned between $H_2O$ and $CHCl_3$. The organic layer was washed with $H_2O$, brine, dried over $MgSO_4$, and evaporated to dryness. This crude compound was purified in column eluted with $CH_2Cl_2$:MeOH=95%:5% to yield the title compound. MS m/z: 223.2 (M+H). Calc'd. for $C_{12}H_{20}N_4$—222.2.

Preparation CLXXXVIII—(6-bromo-pyridin-2-yl)3-Methyl-but-2-enoic-amide:

To a solution of 2-amino-6-bromopyridine (4, 3.015 g, 0.017 mol) and $Et_3N$ (2.40 mL, 0.017 mol) in $CH_2Cl_2$ (20.0 mL), was added 3,3-dimethylacryloylchloride (1.96 mL, 0.017 mol) under $N_2$ at 0° C. The reaction mixture was slowly warmed to RT and stirred for 12 h. The reaction was quenched by the addition of $H_2O$ (20.0 mL). The organic layer was separated, dried over $Na_2SO_4$ and evaporated to dryness to yield crude compound which was used without purification.

Preparation CLXXXIX—(6-amino-pyridin-2-yl) 3-Methyl-but-2-enoic-amide:

To a solution of 2-amino-6-bromopyridine (4.30 g, 0.017 mol) and copper (0.214 g, 3.372 mmol) in IPOH (20.0 mL), was added $NH_4OH$ (20.0 mL) in a sealed vessel under $N_2$. The reaction was sealed and heated to 90° C. for 12 h The mixture was cooled to RT and EtOAc (50.0 mL) was added. The organic layer was separated, and the aq layer was washed with EtOAc (50.0 mL). The combined organic layers were evaporated to dryness, the resulting residue was dissolved in $CH_2Cl_2$ (50.0 mL) and washed with $H_2O$ (4×30 mL). The organic layer was dried over $Na_2SO_4$ and evaporated to dryness to yield crude compound which was used without purification.

Preparation CXC—7-Amino-4,4-dimethyl-3,4-dihydro-1H-[1,8]naphthyridin-2-one:

To a mixture of aminopyridine 6 (1.12 g, 5.833 mmol) and $AlCl_3$ (3.11 g, 0.023 mol) was added chlorobenzene (10.0 mL) in a sealed vessel under Ar. The reaction was sealed and heated to 120° C. for 12 h. The reaction mixture was cooled to RT and the mixture was poured over ice/HCl mixture and extracted with EtOAc (3×50.0 mL). The Aq layer was neutralized with solid $NaHCO_3$ and extracted with EtOAc (5×50 mL). The combined organic layers were dried over $Na_2SO_4$ and evaporated to dryness to yield crude compound which was purified by chromatography (Silica gel, $CH_2Cl_2$:MeOH, 99:1) yielding the title compound.

Preparation CXCI—2-[1-(3-Amino-phenyl)-2,2,2-trifluoro-1-trifluoromethyl-ethoxymethyl]-pyrrolidine-1-carboxylic acid tert-butyl ester:

To a mixture of 2-(3-amino-phenyl)-1,1,1,3,3,3-hexafluoro-propan-2-ol (1.30 g), 2-hydroxymethyl-pyrrolidine-1-carboxylic acid tert-butyl ester (1.04 g), $PPh_3$ (2.64 g) and molecular sieves 4 Å in THF (100 mL) was added DEAD (1.55 mL) slowly. The reaction was stirred at RT for 4 h and at reflux overnight. After filtration to remove solids, the filtrate was concentrated and the residue was taken up into $Et_2O$. The organic phase was washed with saturated $NaHCO_3$ and brine. The organic layer was dried over $MgSO_4$ and evaporated to give a very viscous brown oil, which was purified by chromatography through silica gel (500 g, 30% to 50% EtOAc in hexanes) to afford 2-[1-(3-amino-phenyl)-2,2,2-trifluoro-1-trifluoromethyl-ethoxymethyl]-pyrrolidine-1-carboxylic acid tert-butyl ester as a light brown oil.

Preparation CXCII—N-(3-Amino-5-chloro-phenyl)-2-dimethylamino-acetamide:

To a solution of 5-chloro-benzene-1,3-diamine (3 g, 21 mmol) and dimethylamino-AcOH (2.2 g, 21 mmol) in $CH_2Cl_2$ (300 mL) was added EDC (5 g, 25 mmol), HOBt (2.9 g, 21 mmol), and DIEA (5 mL). The reaction mixture was stirred at RT overnight. Solvent was removed in vacuo and the residue was purified through flash chromatography on silica gel (0–8% MeOH in EtOAc) to give the desired compound.

General Procedure for the preparation of 2,6-diamonipyridines:

To a solution of 2-amino-6-bromopyridine (1.070 g, 6.061 mmol) in 2,4-dimethylphenol (2.0 mL) was added amine (6.667 mmol) and the reaction mixture was heated to 150° C. for 12 h. The mixture was cooled to RT and aq. HCl (2.0 M, 30 mL) was added. EtOAc (50 mL) was added and the organic layer was separated. The Aq layer was washed with EtOAc (2×40 mL) and the combined organic layers were washed with $H_2O$ (50 mL), dried over $Na_2SO_4$, concentrated under vacuo to yield crude compound which was used without purification.

The following compounds were prepared similarly to the procedure outlined above:
a) 3,4,5,6-Tetrahydro-2H-[1,2']bipyridinyl-6'-ylamine:
b) 6-(4-Methyl-piperazin-1-yl)-pyridin-2-ylamine:

Preparation CXCIII—2-Methyl-2-(4-nitrophenyl)propionic acid:

To a solution of 2-(4-nitrophenyl)propionic acid (50 g, 0.26 mol) in 250 mL of MeOH was added 6 mL of concentrated HCl. The resulting solution was heated at reflux for 16 h. The reaction was diluted with 200 mL of aq. $NaHCO_3$ and 500 mL of EtOAc. The organic layer was separated, dried over $Na_2SO_4$, and concentrated. The residue was diluted with 100 mL of THF and added to a suspension of NaH (11.2 g, 0.28 mol, 60% in mineral oil) in 600 mL of THF. To the resulting mixture was added CH$_3$I (18.3 mL, 0.29 mol) in one portion. The resulting mixture was stirred for 48 h at 40° C. and diluted with aq. NH$_4$Cl solution and EtOAc. The organic layer was separated, dried over Na$_2$SO4, and concentrated. The residue was used without further purification.

To a solution of the residue (54 g, 0.24 mol) in 500 mL of MeOH was added 5 N aq. NaOH solution (144 mL, 0.72 mol). The mixture was stirred for 16 h at 40° C., then, concentrated, and the residue was diluted with H$_2$O (500 mL) The aq. solution was acidified with 2N HCl to give a precipitate which was filtered and dried to give the titled compound as a yellowish solid. MS: (ES+) 210 (M+H). Calc'd for C$_{10}$H$_{12}$NO$_4$—210.20.

Preparation CXCIV—2-Methyl-5-[1-methyl-1-(4-nitro-phenyl)-ethyl]-[1,3,4]oxadiazole:

A mixture of 2-methyl-2-(4-nitro-phenyl)-propionic acid (5 g, 24 mmol) and a few drops DMF in SCOl$_2$ was stirred at reflux for 16 h The resulting solution was concentrated to give corresponding acid chloride as a brown solid.

To a mixture of the acid chloride (2.33 g, 10.2 mmol), acetic acid hydrazide (0.91 g, 12.2 mmol), Et$_3$N (2.86 mL, 20.2 mmol) in CH$_2$Cl$_2$ (50 mL) was added 2 crystals of DMAP at RT. The resulting mixture was stirred for 16 h and concentrated. A solution of the residue in 50 mL of POCl$_3$ was heated at 95° C. for 16 h. The resulting mixture was concentrated and diluted with ice-H$_2$O and EtOAc. The organic layer was washed with saturated aq. NaHCO$_3$ solution twice, dried over Na$_2$SO$_4$, and concentrated. The residue was purified by SiO$_2$ chromatography (hexane: EtOAc=1:1) to give the titled compound as a pale yellow crystalline solid. MS: (ES+) 248 (M+H). Calc'd for C$_{12}$H$_{14}$N$_3$O$_3$—248.10.

Preparation CXCV—2-Methyl-5-[1-methyl-1-(4-amino-phenyl)-ethyl]-[1,3,4]oxadiazole:

A mixture of 2-methyl-5-[1-methyl-1-(4-nitro-phenyl)-ethyl]-[1,3,4]oxadiazole (1.36 g, 5.5 mmol) and Pd/C (68 mg) in EtOAc (50 mL) was stirred under 1 atm of H$_2$ for 16 h. The resulting slurry was filtered over Celite®, and the filtrate was concentrated to give the titled compound as a pale yellow crystalline solid. MS: (ES+) 218 (M+H). Calc'd for C$_{12}$H$_{16}$N$_3$O—218.12.

Preparation CXCVI—4-[1-Methyl-1-(4-nitro-phenyl)-ethyl]-pyrimidine:

To a mixture of 1-(4-nitro-phenyl)-propan-2-one (5.32 g, 29.7 mmol), triethylbenzylammonium chloride (0.34 g, 1.5 mmol), and 13 mL of aq. 5N KOH solution (65.3 mmol) in CH$_2$Cl$_2$ was added CH$_3$I (4.06 mL, 65.3 mmol). The resulting mixture was stirred at 40° C. then diluted with EtOAc and H$_2$O. The organic layer was dried and concentrated.

To the residue (1.0 g, 4.8 mmol) in toluene (30 mL) was added dimethylformamide dimethylacetal (1.27 mL, 9.6 mmol). The resulting mixture was heated at reflux for 6 h, then concentrated to give 1-dimethylamino-4-methyl-4-(4-nitro-phenyl)-pent-1-en-3-one as a yellow solid. MS: (ES+) 263 (M+H). Calc'd for C$_{14}$H$_{19}$N$_2$O$_3$—263.13.

A mixture of 1-dimethylamino-4-methyl-4-(4-nitro-phenyl)-pent-1-en-3-one (0.5 g, 1.9 mmol), formamidine hydrochloride (0.305 g, 3.8 mmol), and NaOEt (1.29 g, 4.0 mmol) was heated in Smith synthesizer under microwave for 10 min at 150° C. The resultant was diluted with H$_2$O and EtOAc. The organic layer was dried, and the residue was used without further purification. MS: (ES+) 244 (M+H). Calc'd for C$_{13}$H$_{14}$N$_3$O$_2$—244.10.

Preparation CXCVII—5-[1-Methyl-1-(4-nitro-phenyl)-ethyl]-1H-pyrazole:

A mixture of 1-dimethylamino-4-methyl-4-(4-nitro-phenyl)-pent-1-en-3-one (0.36 g, 1.4 mmol) and hydrazine hydrate (1.0 g, 6.25 mmol) in EtOH was heated at 50° C. for 3 h. The mixture was concentrated, and the residue was diluted with H$_2$O and EtOAc. The organic layer was dried over Na$_2$SO$_4$ and concentrated to give the titled compound as a yellow solid. MS: (ES+) 232 (M+H.) Calc'd for C$_{12}$H$_{14}$N$_3$O$_2$—232.10.

Preparation CXCVIII—2-Methyl-2-(4-nitro-phenyl)-1-pyrrolidin-yl-propan-1-one:

To a round bottom flask charged with 2-methyl-2-(4-nitro-phenyl)-propionic acid, was added 6.5 ml of SOCl$_2$. The mixture was heated to 80° C., with stirring under inert atmosphere for 3.5 h. The mixture was cooled to RT, and then dried in-vacuo. The residue was placed under high vac. After completely dry, the residue was used without further purification.

To the residue was added 10 ml of CH$_2$Cl$_2$, along with Et$_3$N and the mixture was cooled to 0° C. on an ice/H$_2$O bath. Pyrrolidine 0.46 mL (1.25 eq.) was added into the mixture, then stirred to RT under inert atmosphere. After 3 h of stirring, the mixture was quenched with H$_2$O, diluted with CH$_2$Cl$_2$, and transferred to a separatory funnel. The organics were collected, combined, dried over Na$_2$SO$_4$ and filtered. The crude was concentrated in vacuo. After drying, the title compound was produced as an amorphous solid. MS: 263 (M+1); calc'd for C$_{14}$H$_{18}$N$_2$O$_3$—262

Preparation CXCIX—4-(1,1-Dimethyl-2-pyrrolidin-1-yl-ethyl-phenylamine:

To a 3-neck round bottom flask, charged with 2-Methyl-2-(4-nitro-phenyl)-1-pyrrolidin-yl-propan-1-one was added 66 ml of 1M BH$_3$/THF soln, while the mixture was maintained at 0° C. on an ice/H$_2$O bath. The mixture was stirred under inert atmosphere overnight. A couple drops of 5N NaOH was added slowly to the reaction mixture for quenching. After stirring an additional 5 min, 22 ml of 5N NaOH was added into the reaction mixture, then stirred vigorously for 3 h. The mixture was diluted with 50 ml of 1N NaOH and 100 ml of EtOAc, then transferred into a sep. funnel. The organics were collected and concentrated in vacuo. The residue was dissolved in CH$_2$CL$_2$, then NaHCO$_3$ soln. was added into the mixture the organic extracts were dried over Na$_2$SO$_4$, filtered, then concentrated in vacuo.

To a round bottom flask charged with Pd/C in MeOH under inert atmosphere, was added 1-[2-methyl-2-(4-nitro-phenyl)-propyl]-pyrrolidine in MeOH and H$_2$ was added while stirring vigorously overnight. The mixture was filtered through Celite® and concentrated in vacuo to yield a light yellow oil. MS: 219 (M+1); calc'd for C$_{14}$H$_{22}$N$_2$.

Preparation CC—1-methyl-1-(4-nitro-phenyl)-ethylamine:

To a round bottom flask charged with 2-methyl-2-(4-nitro-phenyl)-propionic acid (10 g; 0.0440 mole), was added SOCl$_2$ (32 ml ). The mixture was heated to reflux, until completion of the reaction. After heating, the residual SCOl$_2$ was removed by in vacuo, then placed the residue on high vac. The crude was used without further purification.

To the residue, was added 20 ml toluene and stirred. Then slowly NaN$_3$ (7.14 g; 0.1099 mole) was added into the mixture, and stirred vigorously under inert atmosphere for 1.5 h. The mixture was poured into 50 ml H$_2$O and transferred into a sep. funnel, with 50 ml EtOAc. The organics were collected, dried, filtered, and concentrated in-vacuo. The residue was dissolved in toluene and heated to 100° C. while stirring vigorously under inert atmosphere for 1 h. The solvent was removed in-vacuo, 20% HCl aq was added and the mixture stirred vigorously under reflux conditions at 100° C. for 9 h. The mixture was evaporated in-vacuo and to the residue was added 50 ml of 5N NaOH and 80 ml EtOAc, then transferred the mixture to a sep. funnel. The organic layer was collected, dried, filtered, and conc. in-vacuo. The residue was purified on silica-gel column in a solvent gradient of 80% EtOAc/Hexanes to 10% MeOH/ $CH_2CL_2$ yielding a brown solid resulted. MS: 181 (M+1); calc'd for $C_9H_{12}N_2O_2$—180.

Preparation CCI—[1-(4-Amino-phenyl)-1-methyl-ethyl]-(2-methylsulfanyl-pyrimidin-4-yl)-amine:

To a Personal Chemistry reaction tube, was added 1-methyl-1-(4-nitro-phenyl)-ethylamine, along with 4-chloro-2-methylsulfanyl-pyrimidine, DIEA (2.0 eq) and t-BuOH (0.6 ml). The tube was heated by microwave to 150° C. for 10 min. After heating, the crude was diluted with $CH_2CL_2$ and $H_2O$, then transferred into a sep. funnel. The organics were collected, dried over $Na_2SO_4$, then concentrated in vacuo. The crude was used without further purification.

To a round bottom flask charged with $PtO_2$ (12% wt.) in MeOH (5 ml), was added crude nitro-intermediate (0.170 g.; 0.0006 mole). The mixture was stirred vigorously under $H_2$ for 2.5 h. The mixture was filtered through Celite® and concentrated in-vacuo. The desired material was purified by silica-gel chromatography in a solvent gradient of 80% EtOAc/Hexanes to 5% MeOH/$CH_2CL_2$. After drying in high vac, the title compound resulted as a light yellow amorphous solid.

Preparation CCII—2-(2,2,2-Trifluoro-ethoxy)-isonicotinonitrile:

To the suspension of NaH (2.78 g, 0.11 mole) in THF 100 mL) 2,2,2-trifluoroethanol (10 g, 0.1 mol) was added slowly. The mixture was stirred at RT till it turned clear. A solution of 2-chloro-isonicotinonitrile (13.8 g, 0.1 mol) in THF (100 mL) was slowly added and stirred at reflux for 3 h. After filtration and concentration, the crude oily compound was purified through column chromatography providing pure compound as an oil.

Preparation CCIII—C-[2-(2,2,2-Trifluoro-ethoxy)-pyridin-4-yl]-methylamine hydrogen chloride:

A mixture of 2-(2,2,2-trifluoro-ethoxy)-isonicotinonitrile (3.90 g, 19.40 mmol), 12N HCl (8.0 mL) and 10% Pd/C (800 mg) in MeOH (100 ml) was stirred under a balloon of $H_2$ for 7 h. After filtration, the filtrate was concentrated to give compound as a white solid. MS (ES+): 206.9 (M+H)$^+$. Calc'd. for $C_8H_9F_3N_2O$—206.07.

Preparation CCIV—2-Bromomethyl-3-nitro-benzoic acid methyl ester:

The mixture of methyl 2-methyl-3-nitro benzoate (5.06 g, 25.9 mmol), NBS (5.54 g, 31.1 mmol), and AIBN (0.43 g, 2.59 mmol) in 100 ml of anhydrous $Cl_4$ was heated at reflux under $N_2$ for 22 h, cooled to RT, diluted with EtOAc, and washed with $Na_2CO_3$ (aq). The organic portion was separated, washed with brine, dried with $Na_2SO_4$, filtered, and condensed. The crude material was purified by flash column chromatography to yield pure product, which was used without further purification.

Preparation CCV—4-Nitro-2, 3-dihydro-isoindol-1-one:

$NH_3$ (2.0 M in MeOH, 50 ml) was slowly added to the solution of 2-bromomethyl-3-nitro-benzoic acid methyl ester (4.46 g, contaminated with a small amount of assumed starting material, 16.3 mmol) in 30 ml of MeOH at RT. The resulting mixture was stirred at RT overnight, to provide the title compound as a white solid. MS (ES$^+$): 179.2 (M+H)$^+$. Calc'd for $C_8H_6N_2O_3$—178.14.

Preparation CCVI—4-Amino-2, 3-dihydro-isoindol-1-one:

To the suspension of 4-nitro-2,3-dihydro-isoindol-1-one (2.40 g, 13.5 mmol) in 100 ml of MeOH was added Pd/C (10 wt %, 0.36 g). The mixture was then placed under $H_2$ from a balloon, stirred at RT for 24 h, filtered through Celite®, and condensed to give the titled compound as a light greenish solid. MS (ES$^+$): 149.1 (M+H)$^+$. Calc'd for $C_8H_8N_2O$—148.16.

Preparation CCVII—Pyridin-4-ylmethyl-carbamic acid tert-butyl ester:

Boc anhydride (23 g, 105 mmol) was carefully added to a solution of pyridin-4-yl-methylamine (11 g, 102 mmol) and DMAP (0.5 g, 4 mmole) in $CH_2CL_2$ (150 mL). The reaction was extended for 1 hr after the addition. The reaction mixture was concentrated in vacuo and the residue was recrystallized in EtOAc to afford an off white crystal as the desired compound.

Preparation CCVIII—(1-Oxy-pyridin-4-ylmethyl)-carbamic acid tert-butyl ester:

Pyridin-4-ylmethyl-carbamic acid tert-butyl ester (2.1 g, 10 mmol) was dissolved in a one to one mixture of aqueous MeOH (200 mL) with $NaHCO_3$ (5 g, 60 mmol) and Oxone® (12.3 g, 20 mmol). The mixture was stirred overnight then concentrated in vacuo to remove MeOH. The resulted aqueous mixture was diluted with $H_2O$ (150 mL) and filtered. The filter cake was washed with $H_2O$ and dried to afford a white solid as the desired compound.

Preparation CCIX—C-(1-Oxy-pyridin-4-yl)-methylamine:

Oxy-pyridin-4-ylmethyl)-carbamic acid tert-butyl ester (2.1 g, 9.4 mmol) was dissolved in a 4N HCl in dioxane solution (50 mL) and heated to 50 C for 2 h. After removing solvent in vacuo, a white solid was received as an HCl salt of the desired compound.

Preparation CCX—2-(4-Methoxy-benzylamino)-isonicotinonitrile:

To pyridine (500 mL) were added 2-chloroisonicotinonitrile (22.0 g, 159 mmole), para-methoxybenzylamine (25 g, 114% Meq.), and $NaHCO_3$ (30 g). The mixture was heated under reflux overnight. After cooling to RT, the mixture was filtered and the filter cake was rinsed with $CH_2Cl_2$. The combined filtrate was concentrated to dryness in vacuum to form a yellow solid. This solid is then recrystalized in EtOAc to give a light yellow crystalline compound and the mother liquor was concentrated and subjected to EtOAc again (repeating three times) to yield the desired compound.

Preparation CCXI—(4-Aminomethyl-pyridin-2-yl)-(4-methoxy-benzyl)-amine:

2-(4-Methoxy-benzylamino)-isonicotinonitrile (12 g, 50 mmole) was dissolved in a mixed solvent of EtOH (800 mL) $Et_3N$ (200 mL) and suspended with 2 g of Pd/C (10%). After removing air with vacuum, the flask was charged with $H_2$ with a balloon. The $H_2$ balloon was refilled every morning and evening. Pd/C was recharged twice (1.3 g each) on days 2 and 3. Reaction was completed on the 4$^{th}$ day and the reaction mixture was filtered through a pad of Celite®. The filter cake was rinsed with MeOH and the combined filtrate was concentrated in vacuo to give the desired compound as a light brown solid.

Preparation CCXII—4-Aminomethyl-pyridin-2-ylamine: (4-Aminomethyl-pyridin-2-yl)-(4-methoxy-benzyl)-amine (12 g, 50 mmole) was dissolved in TFA (150 mL) and heated to reflux for 1 h. After cooling, the reaction mixture was concentrated in vacuum and the residue was partitioned between HCl (1N, aq.) and EtOAc. The aqueous layer was washed with EtOAc then hexanes and concentrated to dryness in vacuum to give an off white solid as a dihydrochloric salt.

Preparation CCXIII—2-Methylamino-isonicotinonitrile:

To a solution of 2-chloroisonicotinonitrile (22.0 g, 159 mmole) in pyridine (500 mL) was added methylamine in THF (2N, 160 mL), and NaHCO$_3$ (54 g). The mixture was heated to 120° C. in a sealed vessel for 40 h. After cooled to RT, the mixture was filtered and the filter cake was washed with CH$_2$Cl$_2$. The combined filtrated was concentrated in vacuo to give a yellow solid (21 g) as the desired compound.

Preparation CCXIV—(4-Aminomethyl-pyridin-2-yl)-methyl-amine:

A suspension of 2-Methylamino-isonicotinonitrile (5.6 g) and Pd/C (10%, 4 g) in EtOH (150 mL) and TEA (40 mL) was placed in a 500 mL Parr Hydrogenation bottle and hydrogenated under 60 psi of H$_2$ over night. After filtering through a pad of Celite®, the reaction mixture was concentrated in vacuo to give a yellow oil as the desired compound.

Preparation CCXV—3-Fluoro-pyridine 1-oxide:

3-Chloroperoxybenzoic acid (70%, 35.0 g, 142 mmol) was added to the solution of 3-fluoropyridine (6.90 g, 71.1 mmol) in 200 ml of CH$_2$Cl$_2$, the mixture was stirred at RT overnight, washed with a small amount of saturated NaHCO$_3$ solution, dried with Na$_2$SO$_4$, filtered, condensed, the crude compound was purified by flash column chromatography (1 to 2% of MeOH in CH$_2$Cl$_2$), the titled compound was obtained as a light yellowish solid. MS (ES$^+$): 114.1 (M+H)$^+$. Calc'd for C$_5$H$_4$FNO—113.09.

Preparation CCXVI—3-Fluoro-pyridine-2-carbonitrile:

The mixture of 3-fluoro-pyridine 1-oxide (0.99 g, 8.75 mmol), trimethylsilyl cyanide (4.80 ml, 35.0 mmol), and triethyl amine (1.84 ml, 13.2 mmol) in 100 ml of CH$_3$CN was heated at reflux overnight. The solvents were removed, under reduced pressure and the residue was partitioned between EtOAc and saturated NaHCO$_3$. The organic portion was separated, dried with Na$_2$SO$_4$, filtered, condensed, the crude compound as purified by flash column chromatography (10 to 20% of EtOAc in hexanes). The titled compound was obtained as a light yellowish solid. MS (ES$^+$): 123.1 (M+H)$^+$. Calc'd for C$_6$H$_3$FN$_2$—122.10.

Preparation CCXVII—C-(3-Fluoro-pyridin-2-yl)-methylamine:

The mixture of 3-fluoro-pyridine-2-carbonitrile (0.81 g, 6.63 mmol) and Pd/C (0.20 g, 10% wt)in 10 ml of MeOH and 2.7 ml of concentrated HCl was placed under H$_2$ which was provided by a balloon and stirred at RT for 4 h, filtered through Celite®, condensed, the residue was purified by flash column chromatography, 0.13 g of the titled compound was obtained as a light yellowish oil. MS(ES$^+$): 127.1 (M+H)$^+$. Calc'd for C$_6$H$_7$FN$_2$—126.13.

Preparation CCXVIII: 5-Bromo-pyridine-2-carbonitrile:

The mixture of 2,5-dibromopyridine (4.74 g, 20.0 mmol), zinc cyanide (1.40 g, 12.0 mmol), zinc dust (0.059 g, 0.90 mmol), and Pd(dppf)Cl$_2$.CH$_2$Cl$_2$ (0.36 g, 0.44 mmol) in 25 ml of DMF was heated at reflux for 5 h, cooled to RT, diluted with H$_2$O, extracted with EtOAc, the organic portion was washed with brine, the solvents were removed, the crude compound was purified by flash column chromatography (5 to 15% of EtOAc in hexanes), the titled compound was obtained as an off-white solid.

Preparation CCXIX—5-Fluoro-pyridine-2-carbonitrile:

The mixture of 5-bromo-pyridine-2-carbonitrile (0.50 g, 2.73 mmol), and KF (0.48 g, 8.20 mmol) in 10 ml of 1-methyl-2-pyrrolidinone was stirred at 175° C. for 18 h, cooled to RT, diluted with H$_2$O, extracted with EtOAc, the combined organic portions were washed with H$_2$O, brine, dried with Na$_2$SO$_4$, filtered, condensed, the crude compound was purified by flash column chromatography (5 to 20% of EtOAc in hexanes). The titled compound was obtained as an off-white solid.

Preparation CCXX—C-(5-Fluoro-pyridin-2-yl)-methylamine:

The mixture of 5-fluoro-pyridine-2-carbonitrile (0.16 g, 1.27 mmol) and Pd/C (0.030 g, 10% wt) in 15 ml of MeOH and 0.50 ml of concentrated HCl was placed under H$_2$ which was provided by a balloon and stirred at RT for 4 h, filtered through Celite®, condensed, the residue was purified by flash column chromatography. The titled compound was obtained as a light yellowish solid. MS(ES$^+$): 127.2 (free base)(M+H)$^+$. Calc'd for C$_6$H$_7$FN$_2$ (free base)—126.13.

Preparation CCXXI—1H-Pyrrolo[2,3-b]pyridine 7-oxide:

To a suspension of 1H-pyrrolo[2,3-b]pyridine (10.0 g) and NaHCO$_3$ (45.2 g) in 1:1 MeOH/H$_2$O (1000 mL) was added Oxone® (106 g) in potions during 40 min period. The mixture was stirred at RT for 5 h. The sold was removed by filtration and the filtrate was concentrated to 200 mL in volume. This aqueous phase was extracted with CH$_2$Cl$_2$ (200 mL×7) to afford 1H-pyrrolo[2,3-b]pyridine 7-oxide.

Preparation CCXXII—4-chloro-1H-pyrrolo[2,3-b]pyridine:

To a cooled POCl$_3$ (50 mL) in a dried round bottom flask, 1H-pyrrolo[2,3-b]pyridine 7-oxide (5.73 g, step A) was added in potions. The mixture was heated to reflux for 5 h. After cooled down to RT, POCl$_3$ was evaporated under high vacuum under gentle heating (40–50° C.) to obtain black residue. 50 mL of H$_2$O was added slowly and pH was adjusted to 8–9 with Na$_2$CO$_3$ (first with solid, then saturated aqueous solution) The resulting priticipate was collected by filtration, washed with cold H$_2$O and dried in a vacuum oven (50° C.) to give 4-chloro-1H-pyrrolo[2,3-b]pyridine as tan powder.

Preparation CCXXIII—1-(4-iodo-pyrrolo[2,3-b]pyridin-1-yl)-ethanone:

To a suspension of 4-chloro-1H-pyrrolo[2,3-b]pyridine (3.80 g, step B) and NaI (19.15 g) in CH$_3$CN (40 mL) was added acetyl chloride (5.0 mL) slowly. The mixture was heated to reflux for overnight. After cooled to RT, 40 mL of 10% Na$_2$CO$_3$ and 40 mL of 10% NaHSO$_3$ were added. After stirring for 15 min, the mixture was extracted with EtOAc 4 times. The combined organic phases were washed with brine, dried over MgSO4 and concentrated to give a brown residue as the crude compound, which was purified by chromatography through silica gel (220 g, 5 to 15% EtOAc/hexanes to afford 1-(4-iodo-pyrrolo[2,3-b]pyridin-1-yl)-ethanone as white solid.

Preparation CCXXIV—1-acetyl-1H-pyrrolo[2,3-b]pyridine-4-carbonitrile:

A mixture of 1-(4-iodo-pyrrolo[2,3-b]pyridin-1-yl)-ethanone (4.30 g, step C), CuCN (6.841 g), Pd$_2$dba$_7$ (0.729 g), and dppf (1.636 g) in 85 mL of dioxane was heated to reflux for 2 h. Solid was removed by filtration through a pad of Celite®. The filtrate was concentrated to give a yellow solid as crude compound, which was purified by chromatography through silica gel (250 g, 5–30% EtOAc/hexanes, stepwise gradient) to afford 1-acetyl-1H-pyrrolo[2,3-b]pyridine-4-carbonitrile as a white fluffy solid.

Preparation CCXXV—1-(4-aminomethyl-pyrrolo[2,3-b]pyridin-1-yl)-ethanone:

A mixture of 1-acetyl-1H-pyrrolo[2,3-b]pyridine-4-carbonitrile (0.872 g, step D), 10% Pd/C (0.882 g), 20 mL of Et$_3$N, and 80 mL of EtOH was stirred at RT under balloon pressure of H$_2$ for overnight. Solid was removed by filtration through a pad of Celite® and the filtrate was concentrated to yield a cream color residue, which was purified by chromatography through silica gel (70 g, 2 to 5% MeOH/CHCl$_3$ with 1% NH$_4$OH) to afford 1-(4-aminomethyl-pyrrolo[2,3-b]pyridin-1-yl)-ethanone as a white solid.

Preparation CCXXVI—N-(1-acetyl-2,3-dihydro-1H-pyrrolo[2,3-b]pyridin-4-ylmethyl)-acetamide:

To a mixture of 1-acetyl-1H-pyrrolo[2,3-b]pyridine-4-carbonitrile (0.691 g, example 15, step D), 10% Pd/C (0.702 g), 5 mL of Et$_3$N, and 20 mL of EtOAc was added acetic anhydride (1.0 mL). The mixture was stirred at RT under balloon pressure of H$_2$ for overnight. Solid was removed by filtration through a pad of Celite® and the filtrate was concentrated to yield a white residue, which was purified by chromatography through silica gel (150 g, 1 to 5% MeOH/CHCl$_3$ with 1% NH$_4$OH, stepwise gradient) to afford N-(1-acetyl-2,3-dihydro-1H-pyrrolo[2,3-b]pyridin-4-ylmethyl)-acetamide (0.50 g) as white solid.

Preparation CCXXVII—C-(2,3-dihydro-1H-pyrrolo[2,3-b]pyridin-4-yl)-methylamine hydrogen chloride salt:

A mixture of N-(1-acetyl-2,3-dihydro-1H-pyrrolo[2,3-b]pyridin-4-ylmethyl)-acetamide (0.50 g, step A), HCl (conc., 3 mL) and EtOH (12 mL) was heated to 70° C. for overnight. Additional 3 mL of conc. HCl was added to the reaction and the heating was continued for 3 more days. Solvent was evaporated to give a white residue as crude C-(2,3-dihydro-1H-pyrrolo[2,3-b]pyridin-4-yl)-methylamine HCl salt, which was used without further purification.

General Procedure for the Preparation of 2-amino-4-methylaminopyridines

Preparation CCXXVIII—2-aminoisonicotinonitrile:

To a slurry of 2-chloro-4-cyanopyridine (10.00 g, 0.079 mol) and sodiumbicarbonate (19.92 g, 0.237 mol) in amine (0.174 mol) was added pyridine (35.0 mL) and the reaction was heated to 90° C. for 3 h. The reaction was then cooled to RT, diluted with the addition of CH$_2$Cl$_2$ (100 mL) and filtered. The solid was washed with EtOAc. Combined washes were concentrated in vacuo. A mixture of MeOH/hexanes was added and kept in the fridge for 12 h. The crystals that formed were filtered and washed with hexanes.

Preparation CCXXIX—2-amino-4-methylaminopyridine:

To a mixture of 2-aminoisonicotinonitrile (0.043 mol) and Pd/C (10%, 6.00 g) was added Et$_3$N (40.0 mL) and EtOH (160.0 mL)in a parr bottle and hydrogenated at 50 psi for 12 h. Crude mixture was filtered through Celite®, concentrated under vacuo and dried under high vacuum to yield compound.

Preparation CCXXX—(2-Pyrrolidin-1-yl-pyridin-4-yl)-methylamine:

Prepared according to the general procedure with pyrrolidine as the amine.

Preparation CCXXXI—(2-Morpholin-4-yl-pyridin-4-yl)-methylamine:

Prepared according to the general procedure with morpholine as the amine.

Preparation CCXXXII—3,9,9-Trimethyl-6-nitro-4,9-dihydro-3H-3-aza-fluorene:

4-[1-(2-Bromo-4-nitro-phenyl)-1-methyl-ethyl]-1-methyl-1,2,3,6-tetrahydro-pyridine (9 g), Pd(OAc)$_2$ (900 mg), and DIEA (15 mL) was dissolved in DMF (300 mL), and heated to 80° C. overnight. Solvents were removed in vacuo. The residue was partitioned between CH$_2$Cl$_2$/NaHCO$_3$(sat, aq.). The CH$_2$Cl$_2$ layer was washed with brine, dried over Na$_2$SO$_4$ and concentrated in vacuo. The residue was purified via flash chromatography on silica to give the desired compound. (MS: M+H=257)

Preparation CCXXXIII—3,9,9-Trimethyl-2,3,4,4a,9,9a-hexahydro-1H-3-aza-fluoren-6-ylamine(156):

3,9,9-Trimethyl-6-nitro-4,9-dihydro-3H-3-aza-fluorene (700 mg) was dissolved in EtOH (20 mL) with aqueous HCl (1N, 5 mL) and suspended with Pd/C (10%, 100 mg). The flask was capped with a balloon filled with H$_2$ The reaction was completed in 6 h at RT. The reaction mixture was filtered through a layer of Celite® with MeOH. The combined filtrate was concentrated to give desired compound. (MS: M+H=231).

Preparation CCXXXIV—2-Chloro-5-nitro-phenol:

A mixture of 2-chloro-4-nitroanisole (10 g, 53.3 mmol) and pyridinium chloride (50 g, 426 mmol) was heated at 200° C. for 3 h. After cooling to RT, the mixture was dissolved in 150 mL of aqueous 2N HCl and 150 mL of EtOAc. The organic phase was separated and was washed with aqueous 2N HCl (2×100 mL). The resulting organic phase was dried over MgSO$_4$ and concentrated in vacuo. The title compound was obtained via chromatography (silica gel, 10:1 hexane/EtOAc) as a yellow solid.

Preparation CCXXXV—3-(5-Amino-2-chloro-phenoxymethyl)-azetidine-1-carboxylic acid tert-butyl ester:

To a solution of 3-(2-chloro-5-nitro-phenoxymethyl)-azetidine-1-carboxylic acid tert-butyl ester (2.5 g, 7.29 mmol) in 60 mL of MeOH/H$_2$O (1:1) and 3 mL of acetic acid (J. T. Baker) was added Zn powder (2.3 g, 36.47 mmol, Aldrich) at 0° C. The reaction mixture was stirred at 0° C. for 2 h then stirred at 10° C. for 2 h The resulting mixture was filtered through a Celite® pad and the filtrate was concentrated in vacuo. The residue was treated with 60 mL of saturated aqueous NaHCO$_3$ and extracted with EtOAc (3×50 mL). The combined organic layers were washed with brine and dried with MgSO$_4$. The resulting solution was concentrated in vacuo and the title compound was obtained by column chromatography (silica gel, EtOAc) as a yellow solid.

Preparation CCXXXVI: 3-(Benzotriazol-1-yloxy)-6-chloro-pyridazine-4-carboxylic acid (4-tert-butyl-phenyl)-amide:

A mixture of 3,6-dichloropyridazine-4-carboxylic acid (1.00 g, 5.18 mmol), 4-tert-butylaniline (0.92 ml, 5.60 mmol), TBTU (1.75 g, 5.44 mmol), and DIEA (1.80 ml, 10.4 mmol) in 7.5 ml of anhydrous DMF was stirred at RT under N$_2$ overnight. The mixtrue was diluted with H$_2$O, extracted with EtOAc, and the combined organic portions were washed with brine, dried with Na$_2$SO$_4$, filtered, and condensed. The crude compound was purified by flash column chromatography (hexanes/EtOAc/CH$_2$Cl$_2$, 9:0:1 to 7:2:1), to provide the desired compound as a light yellowish solid. MS (ES$^+$): 423.0 (M+H)$^+$. Calc'd for C$_{21}$H$_{19}$ClN$_6$O$_2$—422.87.

Preparation CCXXXVII—3-Hydroxymethyl-azetidine-1-carboxylic acid benzyl ester:

To a mixture of azetidine-1,3-dicarboxylic acid monobenzyl ester (6.4 g) in THF (200 mL) was added BH$_3$. THF (6 eq, 163 mL, 1M solution) dropwise via an addition funnel at −40° C. under an N$_2$ atmosphere. The solution was warmed to RT and stirred overnight. To the reaction, 5N NaOH (50 mL) was added and then concentrated under vacuum. The resulting aqueous solution was extracted with Et$_2$O (3×100 mL). The organic layer was dried over Na$_2$SO$_4$ and evaporated to give the title compound which was used without further purification.

Preparation CCXXXVIII—3-Methanesulfonyloxymethyl-azetidine-1-carboxylic acid benzyl ester:

3-Hydroxymethyl-azetidine-1,3-dicarboxylic acid monobenzyl ester (6.6 g) was dissolved in CH$_2$Cl$_2$ (100 mL) and brought to −15 C. While stirring, TEA was added (3 eq, 9.43 g) followed by methanesulphonic chloride (2.0 eq, 7.69 g) and allowed to come to RT and stirred for 1 h. The resulting organic solution was extracted with water (3×100 mL). The organic layer was dried over Na$_2$SO$_4$ and evaporated to give the desired product as a clear oil which was used without further purification.

Preparation CCXXXIX—3-Nitro-5-trifluoromethyl-phenol:

A flask containing 1-Methoxy-3-nitro-5-trifluoromethyl-benzene (10 g) and hydrochloride pyridine (10 eq, 52.0 g) was heated to 210 C and stirred for 12 h. Once complete, the reaction was cooled and the residue was dissolved in $CH_2Cl_2$ and washed twice with water (100 mL). The organic layer was concentrated under vacuum and then set in the freezer overnight. The resulting crystalline product was filtered off and washed with ether and used as is.

Preparation CCXL—3-(3-Nitro-5-trifluoromethyl-phenoxymethyl)-azetidine-1-carboxylic acid benzyl ester:

A mixture of 3-nitro-5-trifluoromethyl-phenol (750 mg, Step C), $K_2CO_3$ (3 eq., 1.5 g) and 3-hydroxymethyl-azetidine-1-carboxylic acid benzyl ester (1.1 eq., 1.2 g) in DMF was heated to 80 C for 1 h. The solution was cooled to RT then filtered and concentraced under vacuum. The residue was dissolved in $CH_2Cl_2$ and washed with $H_2O$ twice, followed by brine. The organic layer was dried over $Na_2SO_4$ and evaporated under reduced pressure. The residue was purified by column chromatography using 5% MeOH/$CH_2Cl_2$ to provide the desired compound as a colorless solid.

Preparation CCXLI—3-(3-amino-5-trifluoromethyl-phenoxymethyl)-azetidine-1-carboxylic acid benzyl ester:

To a solution of 3-(3-nitro-5-trifluoromethyl-mg) and $NH_4Cl$ (1.1 eq., 80 mg) was added iron dust (3 eq., 220 mg) in a 10% water/EtOH solution. The solution was heated to reflux for 6 h. The solution was cooled, then filtered through a pad of Celite®. The resulting solution was concentrated under vacuum to provide the desired compound as a dark yellow solid and used as is.

Preparation CCXLII—3-nitro-5-(trifluoromethyl) phenylamine

To a solution of 3,5-dinitrobenzotrifluoride (10 g, 42 mmols, 1 eq.) in 150 mL of EtOH was added 17.6 mL (258.3 mmols, 6.15 eq.) of ammonium sulfide in water (50% by weight, Aldrich). The reaction was heated to reflux for 16 h during which time it became orange and a yellow precipitate formed. After cooling the volume was reduced to approximately 50 mL. The solid was removed by filtration and the filtrate evaporated to dryness in vacuo. The resulting orange solid was purified by column chromatography eluting with a step gradient of 20–30% EtOAc:hexane to provide the compound as a yellow/orange solid.

Preparation CCXLIII—N-(3-nitro-5-(trifluoromethyl) phenyl)methanesulfonamide

3-Nitro-5-(trifluoromethyl)phenylamine (2 g, 9.7 mmols, 1 eq) was dissolved in 100 mL of $CH_2Cl_2$. The yellow solution was cooled to 0° C. $Et_3N$ (2 mL, 14.55 mmols, 1.5 eq) was added followed by mesyl chloride (0.75 mL, 9.7 mmols, 1 eq). The reaction was stirred for 2 h at 0° C. and warmed to RT. Pyridine (0.785 mL, 9.7 mmols, 1 eq) and a catalytic amount of dimethylamine pyridine were added. The reaction was stirred at RT for 16 h. An additional equivalent of mesyl chloride was added and the reaction was heated to reflux for 24 h. After cooling, the solvent was removed in vacuo, and the residue redissolved in $CH_2Cl_2$. The solution was washed twice with 2 N HCl and once with brine. After drying over $Na_2SO_4$, the solution was filtered and the solvent removed. The resulting solid was triturated briefly with 10% EtOAc:hexane to provide a white solid that was a mixture of sulfonimide and sulfonimide.

The above mixture was dissolve in 20 mL of MeOH that had been saturated with $K_2CO_3$. After 30 min the reaction was stripped and the resulting solid portioned between 2 N HCl and $CH_2Cl_2$. The CH2Cl2 was dryed over $Na_2SO_4$ and stripped to provide and off-white solid.

Preparation CCXLIV—(3S)-tetrahydro-3-furanyl 3-nitro-5-(trifluoromethyl)phenylcarbamate 3-(S)-Hydroxytetrahydrofuran (4.8 mL, 60.7 mmols, 5 eq) was dissolved in 60 mL of toluene. The solution was cooled to 0° C. and $Et_3N$ (5.1 mL, 36.4 mmols, 3 eq) was added Trichloromethyl chloroformate (3.65 mL, 30.33 mmols, 2.5 eq) was added slowly. The solurion was stirred at 0° C. for 45 min. 3-Amino-5-ntrobenzotrifluoride (2.5 g, 12.13 mmols, 1 eq) was added dropwise in 20 mL of toluene. The reaction was stirred at 0° C. for 1 h. An additional 5 eq of 3-(S)-hydroxytetrahydrofuran was converted to the chloroformate as described above, and added to the reaction mixture. After an additional h at 0° C., the reaction was heated to 60° C. for 1 h. The reaction was cooled to RT and concentrated. The residue was dissolved in EtOAc, washed twice with saturated $NH_4Cl$ and once with brine. After being dried over $Na_2SO_4$ the solution was filtered and the solvent removed in vacuo. The crude product was purified using a Biotage chromatography system eluting with a gradient of 5% to 35% EtOAc:hexane to yield the desired compound.

Preparation CCXLV—N-(2-((3-nitro-5-(trifluoromethyl) phenyl)oxy)ethyl)-methanesulfonamide 2-((3-Nitro-5-(trifluoromethyl)phenyl)oxy)ethylamine (4.05 g, 16.2 mmols, 1 eq) was dissolved in 100 mL of $CH_2Cl_2$. The solution was cooled to 0° C. Pyridine (2.6 mL, 32.4 mmols, 2 eq) was added followed by mesyl chloride (1.25 mL, 16.2 mmols, 1 eq). The reaction was stirred for 18 h during which time it was warmed slowly to RT. The solvent was removed in vacuo, and the residue dissolved in EtOAc. The resulting solution was washed twice with 2 N HCl, once with water, and 3× with brine. After being dried over $Na_2SO_4$ the solution was filtered and concentrated. The crude was purified by silica gel chromatography eluting with 50% to 60% EtOAc:hexane to yield the desired compound.

Preparation CCXLVI—N-(2-((3-amino-5-(trifluoromethyl) phenyl)oxy)ethyl)methanesulfonamide N-(2-((3-Nitro-5-(trifluoromethyl)phenyl)oxy)ethyl)-methanesulfonamide (1.7 g, 5.2 mmols, 1 eq) was dissolved in 50 L of MeOH. 10% Pd/C (170 mg, 10 weight %) was added and the reaction sparged with $H_2$. The suspension was stirred for 5 h, then filtered trough Celite. The filtrate was stripped to yield the title compound.

The following compounds were prepared similarly to the procedure outlined above:

a) 3-((((2R)-1-acetyl-2-pyrrolidinyl)methyl)oxy)-5-(trifluoromethyl)phenylamine.

b) (3S)-tetrahydro-3-furanyl 3-amino-5-(trifluoromethyl) phenylcarbamate.

c) N-(3-amino-5-(trifluoromethyl)phenyl)-methanesulfonamide

Preparation CCXLVII—(2R)-1-acetyl-2-(((3-nitro-5-(trifluoromethyl)phenyl)oxy)methyl)pyrrolidine (2R)-2-(((3-nitro-5-(trifluoromethyl)phenyl)oxy)methyl) pyrrolidine (3.46 g, 11.9 mmols, 1 eq) was dissolved in 100 mL of $CH_2Cl_2$. $Et_3N$ (5 mL, 35.7 mmols, 3 eq) was added followed by $Ac_2O$ (1.2 mL, 13.1 mmols, 1.1 eq). The reaction was stirred at RT for 1.5 h. The solvent was removed in vacuo and the residue disolved in EtOAc. The solution was washed once each with saturated $NH_4Cl$, 1 N HCl, and twice with brine. The organic layer was dried over $Na_2SO_4$ filtered and concentrated in vacuo. The crude material was purified on a Biotage chromatography system eluting with a gradient of 10% to 75% EtOAc:hexane to yield the title compound.

Preparation CCXLVIII—3-(2-Chloro-5-nitro-phenoxymethyl)-azetidine-1-carboxylic acid tert-butyl ester:

To the mixture of 2-chloro-5-nitro-phenol (1.31 g, 7.54 mmol) and K$_2$CO$_3$ (1.57 g, 11.31 mmol) in 20 mL of DMF was added 3-methanesulfonyloxymethyl-azetidine-1-carboxylic acid tert-butyl ester (2.0 g, 7.54 mol). The reaction mixture was stirred at 50° C. for 1 h. After cooling to RT, the reaction mixture was diluted in 100 mL of EtOAc and quenched with 50 mL of water. The organic layer was separated and the aqueous layer was extracted with EtOAc (2×50 mL). The combined organic phases were washed with brine, dried over MgSO$_4$ and concentrated in vacuum. The title compound was obtained via column chromatography (silica gel, 1;1 hexane/EtOAc) as yellow oil with 93% yield.

EXAMPLE 1

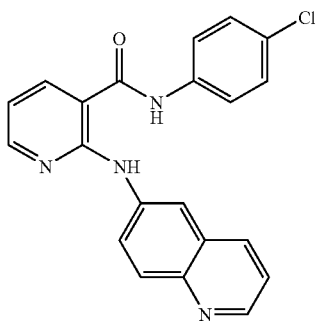

N-(4-Chlorophenyl)[2-(6-quinolylamino)(3-pyridyl)]carboxamide

Step A—Preparation of 2-(6-quinolylamino)pyridine-3-carboxylic acid

A mixture of 2-chloronicotinic acid (1.5 g) and 6-aminoquinoline (1.4 g) was heated at 140° C. neat for 2 h. The reaction was cooled to give a brown solid used in the next step without further purification. MS (ES+): 266 (M+H)$^+$; (ES−): 264 (M−H)$^−$.

Step B—Preparation of N-(4-chlorophenyl)[2-(6-quinolylamino)(3-pyridyl)]carboxamide To a mixture of 2-(6-quinolylamino)pyridine-3-carboxylic acid (250 mg, from Step A) and 4-chloroaniline (120 mg) and DIEA (220 ul) in DMF (15 ml) was added EDC (220 mg) and HOBt (130 mg). The reaction was stirred at 50° C. for 3 h. The solution was evaporated under reduced pressure and mixed with CH$_2$Cl$_2$ (50 ml). The resulting solution was washed with 1N HCl, saturated NaHCO$_3$, H$_2$O and brine. The organic layer was dried over Na$_2$SO$_4$, evaporated under reduced pressure and triturated with CH$_2$Cl$_2$. The precipitate was filtered and washed with EtOH to give the titled compound. MS (ES+): 375 (M+H)$^+$; (ES−): 373 (M−H)$^−$. Calc'd for C$_{21}$H$_{15}$ClN$_4$O—374.8.

EXAMPLE 2

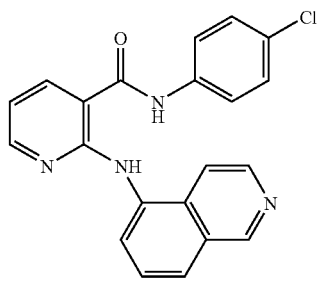

N-(4-Chlorophenyl)[2-(5-isoquinolylamino)(3-pyridyl)]carboxamide

The title compound was analogously synthesized by the method described in Example 1. MS (ES+): 375 (M+H)$^+$. Calc'd for C$_{21}$H$_{15}$ClN$_4$O—374.8.

EXAMPLE 3

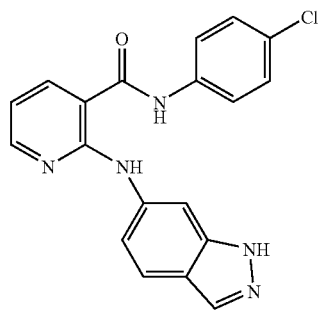

N-(4-Chlorophenyl)[2-(1H-indazol-6-ylamino)(3-pyridyl)]carboxamide

Step A—Preparation of (2-chloro(3-pyridyl))-N-(4-chlorophenyl)carboxamide

To a mixture of 2-chloronicotinic acid (4 g) and 4-chloroanaline (3.2 g) and DIEA (6 ml) in CH$_2$Cl$_2$ (200 ml) was added EDC (6 g) and HOBt (3.3 g). The reaction was stirred at RT overnight and washed with 2 N NaOH (100 ml), H$_2$O (150 ml) and brine (100 ml). The organic layer was dried over Na$_2$SO$_4$ and evaporated to give (2-chloro(3-pyridyl))-N-(4-chlorophenyl)carboxamide.

Step B—Preparation of N-(4-chlorophenyl)[2-(1H-indazol-5-ylamino)(3-pyridyl)]carboxamide A mixture of (2-chloro(3-pyridyl))-N-(4-chlorophenyl)carboxamide (200 mg, from Step A) and 6-aminoindazole (150 mg) was heated at 150° C. neat for 2 h. The reaction was cooled and washed with MeOH. The resulting solid was filtered to give the titled product. MS (ES$^+$),: 364 (M+H)$^+$; (ES−): 362 (M−H). Calc'd for C$_{19}$H$_{14}$ClN$_5$O—363.8.

EXAMPLE 4

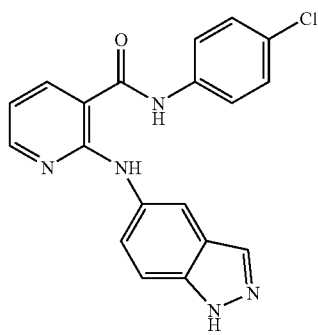

N-(4-Chlorophenyl)[2-(1H-indazol-5-ylamino)(3-pyridyl)]carboxamide

The title compound was analogously synthesized by the method described in Example 3. MS (ES+): 364 (M+H)$^+$; (ES−): 362 (M−H)$^-$. Calc'd for $C_{19}H_{14}ClN_5O$—363.8.

EXAMPLE 5

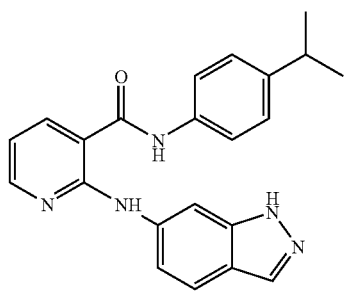

2-(1H-Indazol-6-ylamino)-N-(4-isopropyl-phenyl) nicotinamide

Step A: Preparation of (2-chloro(3-pyridyl))-N-(4-isopropylphenyl)carboxamide

To a mixture of 2-chloronicotinic acid (6.3 g) and 4-isopropylaniline (5.26 ml) and DIEA (10 ml) in $CH_2Cl_2$ (200 ml) was added EDC (10 g) and HOBt (5.4 g). The reaction was stirred at RT overnight and washed with 2N NaOH (100 ml), $H_2O$ (250 ml) and brine (100 ml). The organic layer was dried over $Na_2SO_4$ and evaporated to give (2-chloro(3-pyridyl))-N-(4-isopropylphenyl)carboxamide.

Step B: Preparation of [2-(1H-indazol-6-ylamino)(3-pyridyl)]-N-[4-(methylethyl)phenyl]carboxamide hydrochloride A mixture of (2-chloro(3-pyridyl))-N-(4-isopropylphenyl)carboxamide (1.5 g, Step A) and 6-aminoindazole (880 mg) was heated at 160° C. in NMP for 3 h. The reaction was cooled and diluted with $CH_2Cl_2$ and washed with water twice, followed by brine. The organic layer was dried with $Na_2SO_4$ and evaporated under reduced pressure. The residue was purified by column chromatography with 35% EtOAc/Hexane and further mixed with MeOH and 1 N $HCl/Et_2O$ (3 ml). The solution was evaporated to furnish the titled compound. MS (ES+): 372 (M+H)$^+$; (ES−): 371 (M−H). Calc'd for $C_{22}H_{21}N_5O$—371.2.

The following compounds (Examples 6–23) were analogously synthesized by the method described in Example 5. Detailed intermediate preparations are described.

EXAMPLE 6

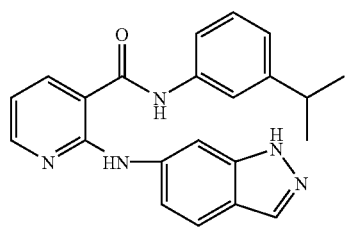

[2-(1H-Indazol-6-ylamino)(3-pyridyl)]-N-[3-(methylethyl)phenyl]carboxamide

MS (ES+):372 (M+H)$^+$. Calc'd. for $C_{22}H_{21}N_5O$—371.2.

EXAMPLE 7

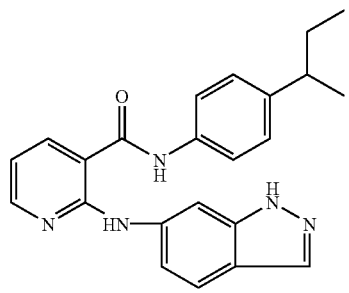

[2-(1H-Indazol-6-ylamino)(3-pyridyl)]-N-[4-(methylpropyl)phenyl]carboxamide

MS (ES+) :386 (M+H)$^+$; (ES−): 384 (M−H). Calc'd. for $C_{23}H_{23}N_5O$—385.2.

EXAMPLE 8

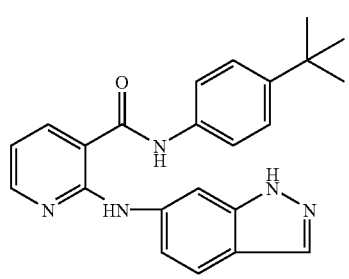

N-[4-(tert-Butyl)phenyl][2-(1H-indazol-6-ylamino)(3-pyridyl)]carboxamide

MS (ES+) :386 (M+H)$^+$; (ES−): 384 (M−H). Calc'd. for $C_{23}H_{23}N_5O$—385.2.

EXAMPLE 9

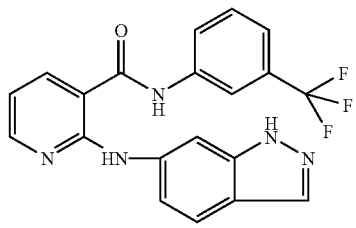

[2-(1H-Indazol-6-ylamino)(3-pyridyl)]-N-[3-(trifluoromethyl)phenyl]carboxamide

MS (ES+): 398(M+H)$^+$; (ES−) :396 (M−H). Calc'd. for C$_{20}$H$_{14}$F$_3$N$_5$O—397.1.

EXAMPLE 10

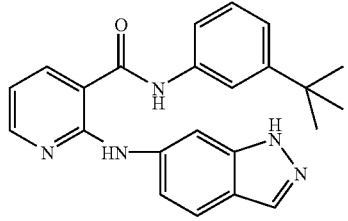

N-[3-(tert-Butyl)phenyl][2-(1H-indazol-6-ylamino)(3-pyridyl)]carboxamide

MS (ES+) :386 (M+H)$^+$; (ES−): 384 (M−H). Calc'd. for C$_{23}$H$_{23}$N$_5$O—385.2.

EXAMPLE 11

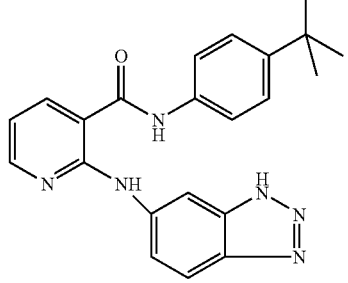

[2-(Benzotriazol-6-ylamino)(3-pyridyl)]-N-[4-(tert-butyl)phenyl]carboxamide

MS (ES+) :387 (M+H)$^+$; (ES−): 385 (M−H). Calc'd. for C$_{22}$H$_{22}$N$_6$O—386.2.

EXAMPLE 12

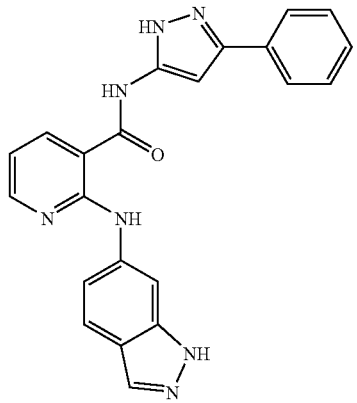

[2-(1H-Indazol-6-ylamino)(3-pyridyl)]-N-(3-phenylpyrazol-5-yl)carboxamide

MS: 396 (M+1). Calc'd. for C$_{22}$H$_{17}$N$_7$O—395.4.

EXAMPLE 13

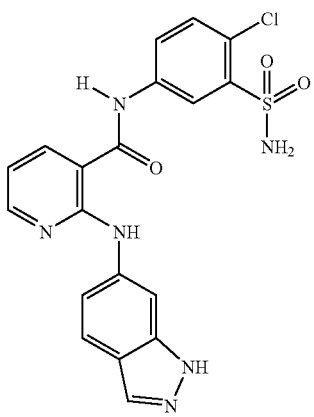

N-3-aminosulfonyl(4-chloro-phenyl)[2-(1H-indazol-6-ylamino)(3-pyridyl)]carboxamide MS (ES+): 443 (M+H); (ES−): 441 (M−H). Calc'd. for C$_{19}$H$_{15}$ClN$_6$O$_3$S—442.1.

EXAMPLE 14

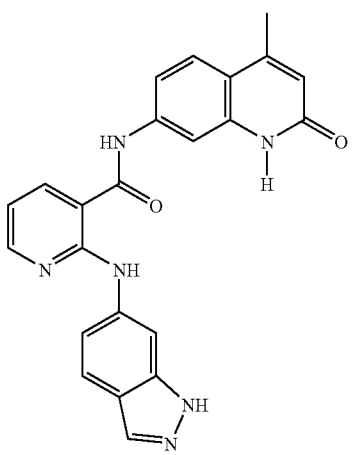

[2-(1H-Indazol-6-ylamino)(3-pyridyl)]-N-(4-methyl-2-oxo-1,2-dihydroquinol-7-yl)carboxamide MS (ES+): 411 (M+H); (ES−): 409 (M−H). Calc'd. for C$_{23}$H$_{18}$N$_6$O$_2$—410.1.

EXAMPLE 15

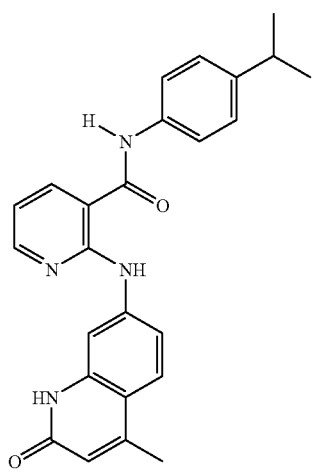

N-[4-(Methylethyl)phenyl]{2-[(4-methyl-2-oxo(7-hydroquinolyl))amino](3-pyridyl)}carboxamide MS (ES+): 413 (M+H); (ES−): 411 (M−H). Calc'd. for $C_{25}H_{24}N_4O_2$—412.2.

EXAMPLE 16

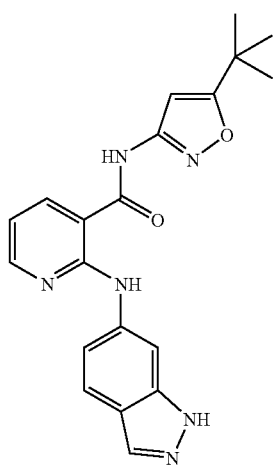

N-[5-(tert-Butyl)isoxazol-3-yl][2-(1H-indazol-6-ylamino)(3-pyridyl)]carboxamide

MS (ES+): 377 (M+H); (ES−): 375 (M−H). Calc'd. for $C_{20}H_{20}N_6O_2$—412.2.

EXAMPLE 17

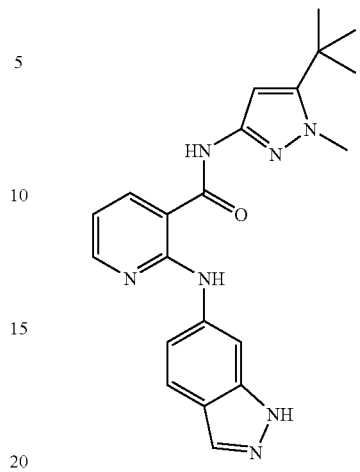

N-[5-(tert-Butyl)-1-methylpyrazol-3-yl][2-(1H-indazol-6-ylamino)(3-pyridyl)]carboxamide MS (ES+): 390 (M+H); (ES−): 388 (M−H). Calc'd. for $C_{21}H_{23}N_7O$—389.2.

EXAMPLE 18

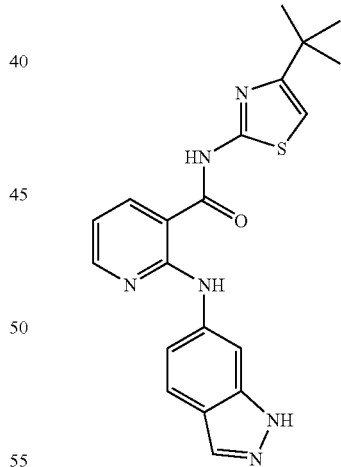

N-[4-(tert-Butyl)(1,3-thiazol-2-yl)][2-(1H-indazol-6-ylamino)(3-pyridyl)]carboxamide MS (ES+): 393 (M+H); (ES−): 391 (M−H). Calc'd. for $C_{20}H_{20}N_6OS$—392.5.

EXAMPLE 19

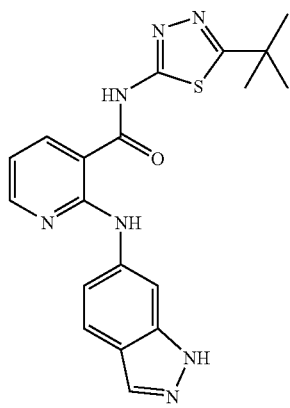

N-[5-(tert-Butyl)(1,3,4-thiadiazol-2-yl)][2-(1H-indazol-6-ylamino)(3-pyridyl)]carboxamide MS (ES+): 394 (M+H); (ES−): 392 (M−H). Calc'd. for C₁₉H₁₉N₇OS—393.5.

EXAMPLE 20

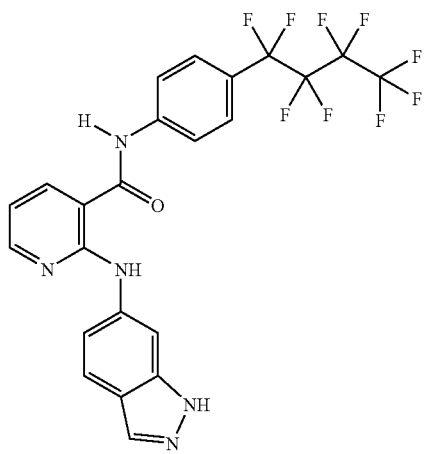

[2-(1H-Indazol-6-ylamino)(3-pyridyl)]-N-[4-(1,1,2,2,3,3,4,4,4-nonafluorobutyl)phenyl]carboxamide The title compound was prepared from 4-(1,1,2,2,3,3,4,4,4-nonafluorobutyl)phenylamine similar to the method described in Example 5. MS (ES+): 548 (M+H); (ES−): 546 (M−H). Calc'd. for C₂₂H₁₅F₉N₄O—522.4.

EXAMPLE 21

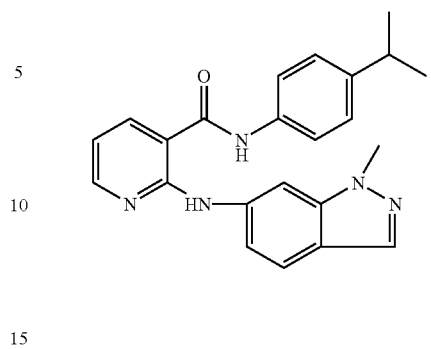

{2-[(1-Methyl(1H-indazol-6-yl))amino](3-pyridyl)}-N-[4-(methylethyl)phenyl]carboxamide Step A: Preparation of 1-methyl-6-amino-1H-indazole To a solution of 6-nitroindazole (8 g) in THF (200 ml) was added NaH (2.5 g) at 0° C. The reaction was stirred for 30 min and MeI (3.7 ml) was added and stirred at RT overnight. The reaction was quenched with water and extracted with EtOAc twice, then was further purified by column chromatography to give 1-methyl-6-nitro-1H-indazole which was hydrogenated with an H₂ atmosphere in the presence of Pd/C (400 mg) to give 1-methyl-6-amino-1H-indazole.

Step B Preparation of {2-[(1-methyl(1H-indazol-6-yl))amino](3-pyridyl)}-N-[4-(methylethyl)phenyl]-carboxamide The title compound was prepared from 1-methyl-6-amino-1H-indazole (Step A) similar to the method described in Example 5. MS (ES+):386 (M+H)⁺; (ES−): 384 (M−H). Calc'd. for C₂₃H₂₃N₅O—385.2.

EXAMPLE 22

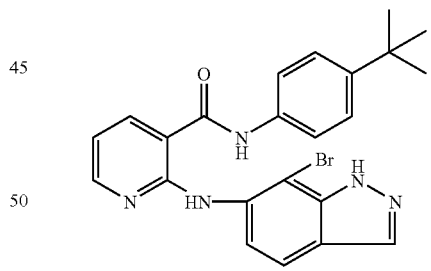

N-[4-(tert-Butyl)phenyl]{2-[(7-bromo(1H-indazol-6-yl))amino](3-pyridyl)}carboxamide A mixture of N-[4-(tert-butyl)phenyl][2-(1H-indazol-6-ylamino)(3-pyridyl)]carboxamide (620 mg) (Example 8) and NBS (330 mg) in benzene (50 ml) was heated at 80° C. for 3 h. The solvent was evaporated under reduced pressure and the residue was purified by column chromatography to give the title compound. MS (ES+):464 (M+H)⁺; (ES−): 462 (M−H) Calc'd. for C₂₃H₂₂BrN₅O—463.1.

EXAMPLE 23

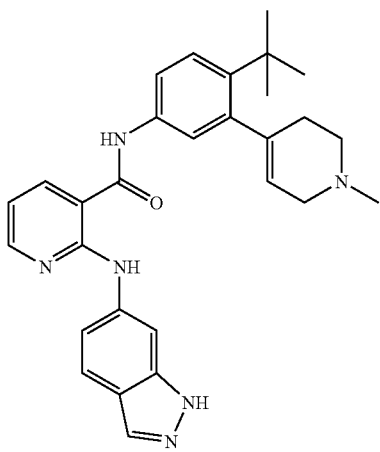

2-(1H-Indazol-6-ylamino)-N-[4-tert-butyl-3-(1,2,3,6-tetrahydropyridin-4-yl)phenyl]nicotinamide The title compound was prepared from 4-tert-butyl-3-(1-methyl-1,2,3,6-tetrahydropyridin-4-yl)aniline similar to the method described in Example 5. MS: (ES+) 480.3 (M+H). Calc'd for $C_{29}H_{32}N_6O$—480.6.

EXAMPLE 24

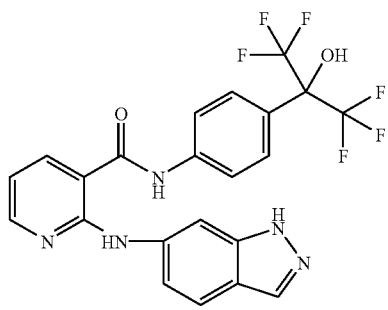

[2-(1H-Indazol-6-ylamino)(3-pyridyl)]-N-({4-[2,2,2-trifluoro-1-hydroxy-1-(trifluoromethyl)ethyl]phenyl}carboxamide Step A: Preparation of 2-(1H-indazol-6-ylamino)pyridine-3-carboxylic acid A mixture of 6-aminoindazole (6.7 g) and 2-chloronicotinic acid (8 g) was heated neat at 150° C. for 2 h. The reaction was cooled and washed with acetone to give 2-(1H-indazol-6-ylamino)pyridine-3-carboxylic acid.

Step B: Preparation of [2-(1H-indazol-6-ylamino)(3-pyridyl)]-N-{4-[2,2,2-trifluoro-1-hydroxy-1-(trifluoromethyl)ethyl]phenyl}carboxamide 2-(1H-Indazol-6-ylamino)pyridine-3-carboxylic acid (500 mg, Step A) was reacted with 4-[2,2,2-trifluoro-1-hydroxy-1-(trifluoromethyl)ethyl]phenylamine (340 mg) and EDC (500 mg) and HOBt (270 mg) in DMF at RT overnight. The reaction was diluted with $CH_2Cl_2$ and washed with $H_2O$ followed by brine. The organic layer was dried with $Na_2SO_4$ and evaporated under reduced pressure. The residue was purified by column chromatography to give the title compound. MS (ES+):496(M+H)$^+$; (ES-):394(M-H). Calc'd. for $C_{22}H_{15}F_6N_5O_2$— 495.1.

The following compounds (Examples 25–42) were synthesized similar to the method described in Example 24. Detailed intermediate preparations are described.

EXAMPLE 25

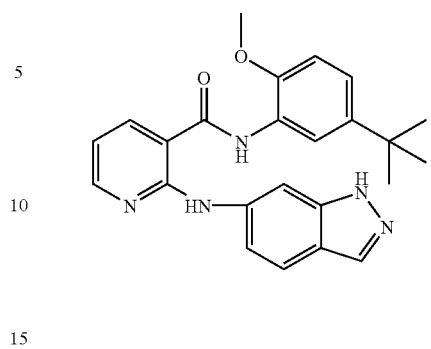

N-[5-(tert-Butyl)-2-methoxyphenyl][2-(1H-indazol-6-ylamino)(3-pyridyl)]carboxamide MS (ES+):416(M+H)$^+$; (ES-):414(M-H). Calc'd. for $C_{24}H_{25}N_5O_2$—415.2.

EXAMPLE 26

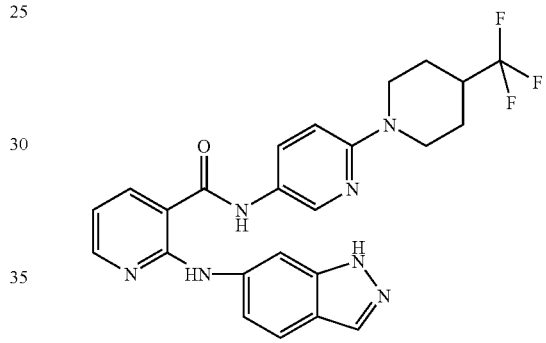

[2-(1H-Indazol-6-ylamino)(3-pyridyl)]-N-{6-[4-(trifluoromethyl)piperidyl](3-pyridyl)}carboxamide MS (ES+):482(M+H)$^+$; (ES-):480(M-H). Calc'd. for $C_{24}H_{22}F_3N_7O$—481.2.

EXAMPLE 27

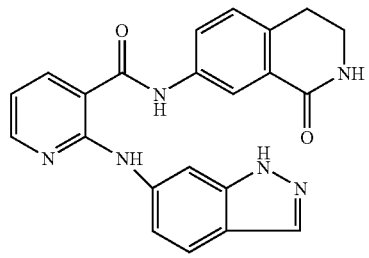

2-(1H-Indazol-6-ylamino)-N-(1-oxo-1,2,3,4-tetrahydro-isoquinolin-7-yl)-nicotinamide MS (ES+):399(M+H)$^+$; (ES-):397(M-H). Calc'd. $C_{22}H_{18}N_6O_2$— 398.1.

EXAMPLE 28

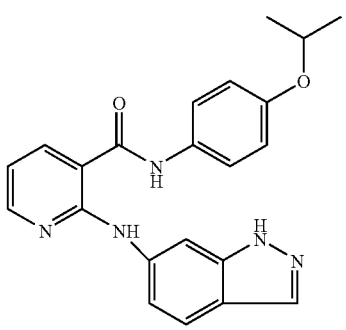

[2-(1H-Indazol-6-ylamino)(3-pyridyl)]-N-[4-(methylethoxy)phenyl]carboxamide

MS (ES+):388(M+H)$^+$; (ES−):386(M−H). Calc'd. for $C_{22}H_{21}N_5O_2$—387.2.

EXAMPLE 29

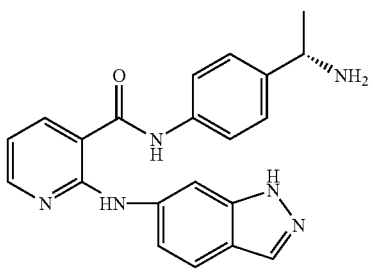

[2-(1H-Indazol-6-ylamino)(3-pyridyl)]-N-{4-[2,2,2-trifluoro-1-hydroxy-1-(trifluoromethyl)ethyl]phenyl}carboxamide The title compound was prepared from [1-(4-aminophenyl)ethyl]carbamic acid tert-butyl ester similar to the method described in Example 24. MS (ES$^+$): 373(M+H)$^+$; (ES$^-$) :371(M−H). Calc'd. for $C_{21}H_{20}N_6O$—372.2.

EXAMPLE 30

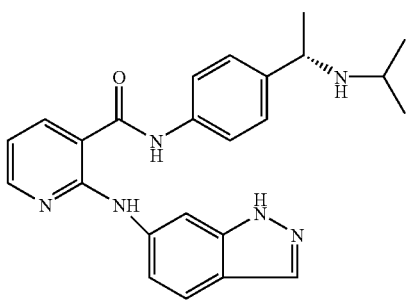

N-(4-{(1S)-1-[(Methylethyl)amino]ethyl}phenyl)[2-(1H-indazol-6-ylamino)(3-pyridyl)]carboxamide A mixture of [2-(1H-indazol-6-ylamino)(3-pyridyl)]-N-{4-[2,2,2-trifluoro-1-hydroxy-1-(trifluoromethyl)-ethyl]phenyl}carboxamide (100 mg, Example 29), NaBH(OAc)$_3$ (2 eq), acetone (5 ml) and AcOH (0.2 ml) in CH$_2$Cl$_2$ was stirred at RT for 4 h. The solvent was evaporated and the residue was purified by prep-HPLC to give the title compound as TFA salt. MS (ES+):415(M+H)$^+$; (ES−):413(M−H). Calc'd. for $C_{24}H_{26}N_6O$—414.2.

EXAMPLE 31

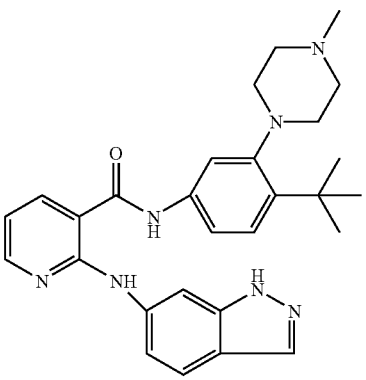

N-[4-(tert-Butyl)-3-(4-methylpiperazinyl)phenyl][2-(1H-indazol-6-ylamino)(3-pyridyl)]carboxamide The title compound was prepared from 1-[2-(tert-butyl)-5-aminophenyl]-4-methylpiperazine similar to the method described in Example 24. MS (ES+): 484(M+H)$^+$; (ES−) :482(M−H). Calc'd. $C_{28}H_{33}N_7O$—483.3.

EXAMPLE 32

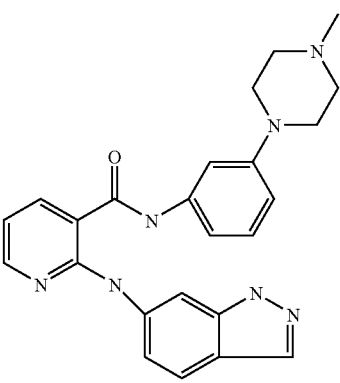

[2-(1H-Indazol-6-ylamino)(3-pyridyl)]-N-[3-(4-methylpiperazinyl)phenyl]carboxamide The title compound was prepared from 1-(5-aminophenyl)-4-methylpiperazine similar to the method described in Example 24. MS (ES+): 428(M+H)$^+$; (ES−):426(M−H). Calc'd. $C_{24}H_{25}N_7O$—427.2.

EXAMPLE 33

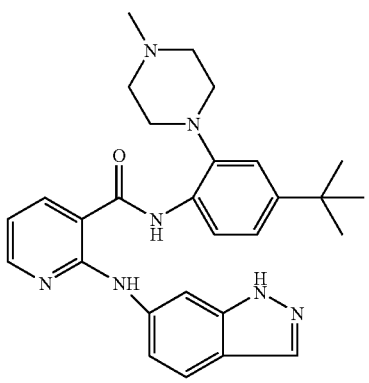

N-[4-(tert-Butyl)-2-(4-methylpiperazinyl)phenyl][2-(1H-indazol-6-ylamino)(3-pyridyl)]carboxamide The title compound was prepared from 4-(tert-butyl)-2-(4-methylpiperazinyl)phenylamine similar to the method described in Example 24. MS (ES+): 484(M+H)$^+$; (ES−): 482(M−H). Calc'd. $C_{28}H_{33}N_7O$—483.3.

EXAMPLE 34

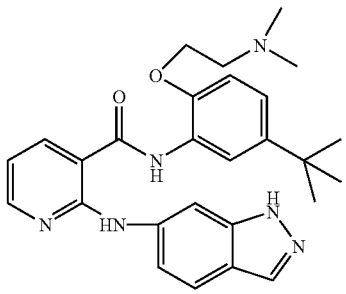

N-{2-[2-(Dimethylamino)ethoxy]-5-(tert-butyl)phenyl}[2-(1H-indazol-6-ylamino)(3-pyridyl)]carboxamide The title compound was prepared from {2-[4-(tert-butyl)-2-aminophenoxy]ethyl}dimethylamine similar to the method described in Example 24. MS (ES+): 473(M+H)$^+$; (ES−) :471(M−H). Calc'd. for $C_{27}H_{32}N_6O_2$—472.3.

EXAMPLE 35

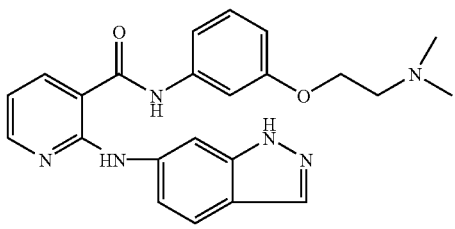

N-{3-[2-(Dimethylamino)ethoxy]phenyl}[2-(1H-indazol-6-ylamino)(3-pyridyl)]carboxamide The title compound was prepared from [2-(2-aminophenoxy)ethyl]dimethylamine similar to the method described in Example 24. MS (ES+): 417(M+H)$^+$; (ES−):. 415(M−H). Calc'd. for $C_{23}H_{24}N_6O_2$—416.2.

EXAMPLE 36

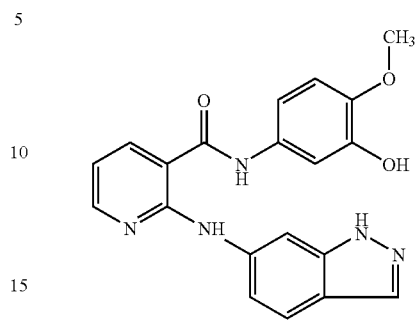

N-(3-Hydroxy-4-methoxyphenyl)[2-(1H-indazol-6-ylamino)(3-pyridyl)]carboxamide

MS (ES+):376(M+H)$^+$; (ES−):374(M−H). Calc'd. for $C_{20}H_{17}N_5O_3$—375.1.

EXAMPLE 37

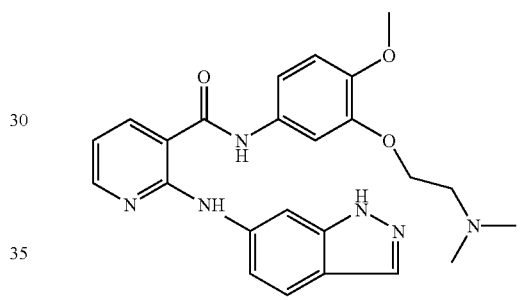

N-{3-[2-(Dimethylamino)ethoxy]-4-methoxyphenyl)[2-(1H-indazol-6-ylamino)(3-pyridyl)]carboxamide The title compound was prepared from N-(3-hydroxy-4-methoxyphenyl)[2-(1H-indazol-6-ylamino)(3-pyridyl)]carboxamide (Example 36) by a method similar to that described in Example 34. MS (ES$^+$):447 (M+H)$^+$; (ES−): 445 (M−H). Calc'd. for $C_{24}H_{26}N_6O_3$—446.2.

EXAMPLE 38

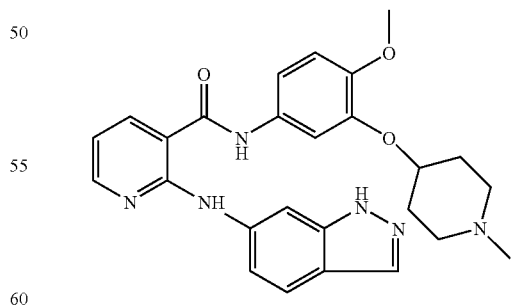

[2-(1H-Indazol-6-ylamino)(3-pyridyl)]-N-[4-methoxy-3-(1-methyl(4-piperidyl)oxy)phenyl]carboxamide The title compound was prepared from N-(3-hydroxy-4-methoxyphenyl)[2-(1H-indazol-6-ylamino)(3-pyridyl)]- carboxamide (Example 36) by a method similar to that described in Example 34 using 4-hydroxy-N-methylpiperidine. MS (ES+): 473 (M+H) +; (ES−):471 (M−H). Calc'd. for $C_{26}H_{28}N_6O_3$— 472.2.

EXAMPLE 39

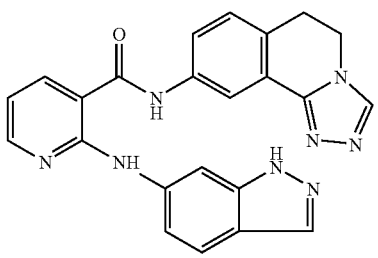

[2-(1H-Indazol-6-ylamino)(3-pyridyl)]-N-(5,6,7-trihydro-1,2,4-triazolo[3,4-a]isoquinolin-2-yl)carboxamide The title compound was prepared from 2-amino-5,6,7-trihydro-1,2,4-triazolo[3,4-a]isoquinoline similar to the method described in Example 24. MS (ES+): 473(M+H)+; (ES−) :471(M−H). Calc'd. for $C_{23}H_{18}N_8O$—422.2.

EXAMPLE 40

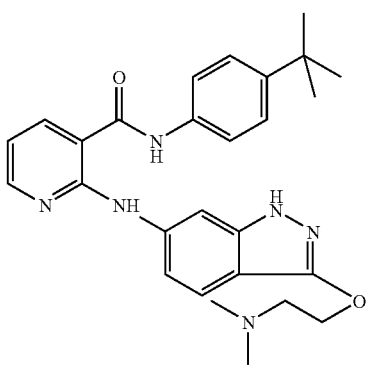

[2-({3-[2-(Dimethylamino)ethoxy](1H-indazol-6-yl)}amino)(3-pyridyl)]-N-[4-(tert-butyl)phenyl]carboxamide Step A: Preparation of 6-nitro-1-Boc-2-hydroindazol-3-one A mixture of 6-nitro-1H-2-hydroindazol-3-one (1.8 g) and Boc$_2$O (3 g) and DMAP (300 mg) in CH$_2$Cl$_2$ (30 ml) was stirred at RT overnight. The reaction was washed with water followed by brine. The organic layer was dried with Na$_2$SO$_4$ and evaporated under reduced pressure to give Boc-protected indazole.

Step B: Preparation of [2-((3-[2-(dimethylamino)ethoxy] (1H-indazol-6-yl)}amino)(3-pyridyl)]-N-[4-(tert-butyl)phenyl]carboxamide To a mixture of 6-nitro-1-Boc-2-hydroindazol-3-one (800 mg, Step A) and N,N-dimethylethanolamine (400 mg) and PPh$_3$ (1.1 g) in THF (20 ml) was added DEAD (0.75 ml). The reaction was stirred at RT for 2 h, diluted with EtOAc (50 ml) and washed with H$_2$O and brine. The organic layer was dried over Na$_2$SO$_4$, evaporated and the residue was purified by column chromatography to give dimethyl[2-(6-nitro(1-Boc-indazol-3-yloxy))ethyl]amine. It was hydrogenated in an H$_2$ atmosphere in the presence of Pd/C (100 mg)

to give dimethyl[2-(6-amino-(1-Boc-indazol-3-yloxy))ethyl]amine. This compound (40 mg) and 2-chloronicotinic acid were heated at 130° C. in pentanol overnight and coupled and deprotected simultaneously. The solvent was evaporated and the residue was used for coupling to give the title compound. MS (ES+): 473(M+H)+; (ES−):471(M−H). Calc'd. for $C_{27}H_{32}N_6O_2$—472 .3.

EXAMPLE 41

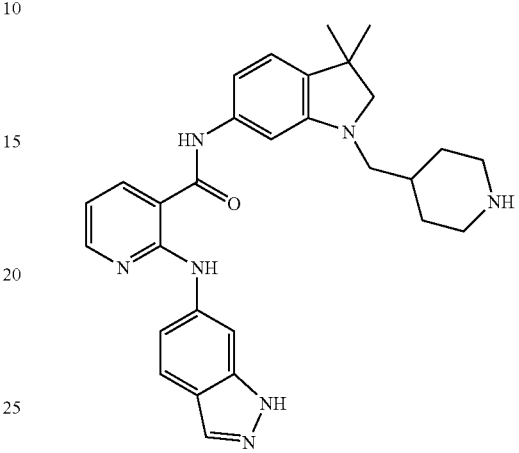

N-[3,3-Dimethyl-1-(4-piperidylmethyl)indolin-6-yl][2-(1H-indazol-6-ylamino)(3-pyridyl)]carboxamide The title compound was prepared from 3,3-dimethyl-1-piperidin-4-ylmethyl-2,3-dihydro-1H-indol-6-ylamine similar to the method described in Example 24. MS: 496 (M+1). Calc'd. for $C_{29}H_{33}N_7O$—495.6.

EXAMPLE 42

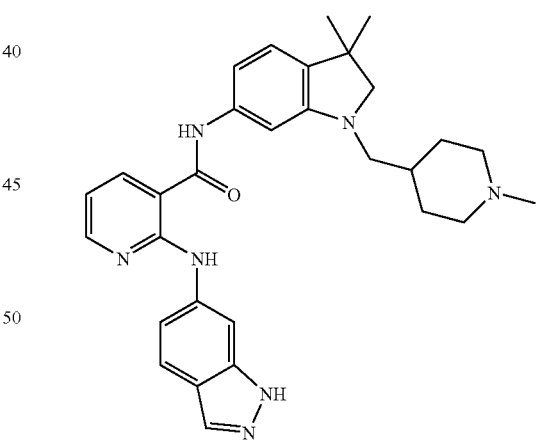

N-[3,3-Dimethyl-1-(1-methyl-piperidin-4-ylmethyl)-2,3-dihydro-1H-indol-6-yl]-2-(1H-indazol-6-ylamino)-nicotinamide N-[3,3-Dimethyl-1-(4-piperidylmethyl)indolin-6-yl][2-(1H-indazol-6-ylamino)(3-pyridyl)]carboxamide (140 mg, Example 41) was dissolved in 10 mL EtOH. Formaldehyde (10 mL, 37%) was added, followed by 100 mg of NaCNBH$_3$. The mixture was stirred at RT overnight, and concentrated in vacuo. The crude was extracted between saturated NaHCO$_3$ solution and EtOAc, the resulting organic layer was dried over MgSO₄, filtered and concentrated in vacuo to afford a yellow solid. This material was further purified by preparative HPLC to yield a white solid. MS: 510 (M+1). Calc'd. for $C_{30}H_{35}N_7O$—509.6.

EXAMPLE 43

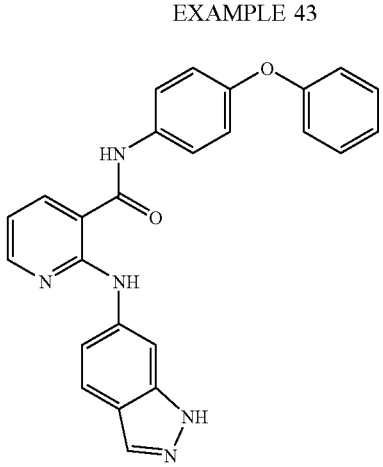

2-(1H-Indazol-6-ylamino)-N-(4-phenoxy-phenyl)-nicotinamide

The title compound was analogously synthesized by the method described in Example 5 from (2-chloro-(3-pyridyl))-N-(4-phenoxyphenyl)carboxamide. MS: (ES+) 422 (M+1)⁺; (ES−) : 420 (M−1)⁻. Calc'd. for $C_{25}H_{19}N_5O_2$—421.1.

The following compounds (Examples 44–63) were analogously synthesized by the method described in Example 43. Detailed intermediate preparations are described.

EXAMPLE 44

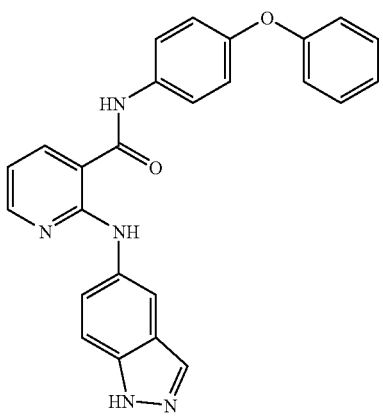

[2-(1H-Indazol-5-ylamino)(3-pyridyl)]-N-(4-phenoxyphenyl)carboxamide

MS: (ES+) 422 (M+1)⁺; (ES−): 420 (M−1)⁻. Calc'd. for $C_{25}H_{19}N_5O_2$—421.1.

EXAMPLE 45

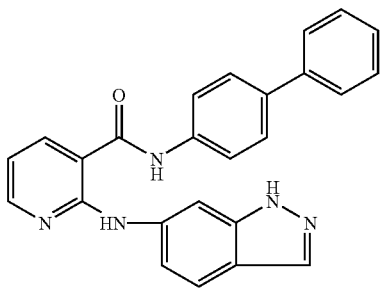

[2-(1H-Indazol-6-ylamino)(3-pyridyl)]-N-(4-phenylphenyl)carboxamide

MS: (ES+) 406 (M+1)⁺; (ES−): 404 (M−1)⁻. Calc'd. for $C_{25}H_{19}N_5O$—405.2.

EXAMPLE 46

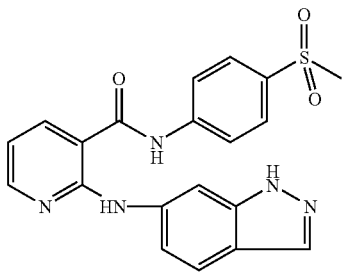

[2-(1H-Indazol-6-ylamino)(3-pyridyl)]-N-[4-(methylsulfonyl)phenyl]carboxamide

MS: (ES+) 408 (M+1)⁺; (ES−): 406 (M−1)⁻. Calc'd. for $C_{20}H_{17}N_5O_3S$—407.1.

EXAMPLE 47

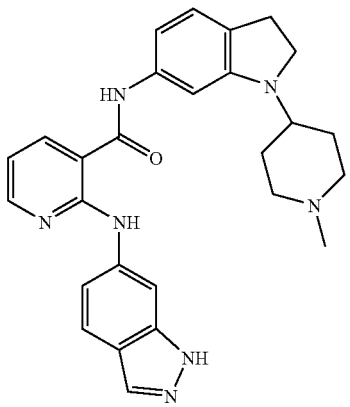

[2-(1H-Indazol-6-ylamino)(3-pyridyl)]-N-[1-(1-methyl(4-piperidyl))indolin-6-yl]carboxamide MS: 468 (M+1). Calc'd. for $C_{27}H_{29}N_7O$—467.6.

EXAMPLE 48

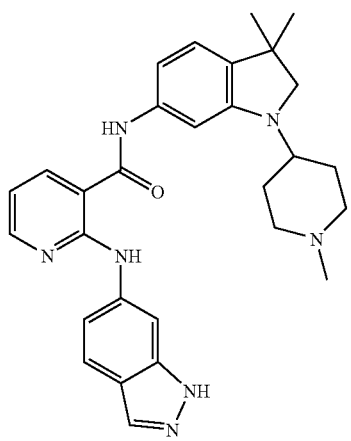

N-[3,3-Dimethyl-1-(1-methyl(4-piperidyl))indolin-6-yl][2-(1H-indazol-6-ylamino)(3-pyridyl)]carboxamide The title compound was analogously synthesized by the method described in Example 43 from 3,3-dimethyl-1-(1methyl(4-piperidyl))indoline-6-ylamine. MS: 496 (M+1). Calc'd. for $C_{29}H_{33}N_7O$—495.6.

EXAMPLE 49

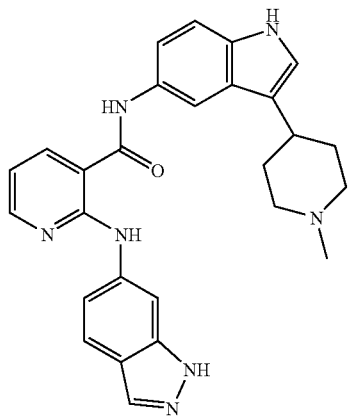

[2-(1H-Indazol-6-ylamino)(3-pyridyl)]-N-[3-(1-methyl(4-piperidyl))indol-5-yl]carboxamide The title compound was analogously synthesized by the method described in Example 43 from 3-(1-methyl-4-piperidyl)indole-5-ylamine. MS: 466 (M+1). Calc'd. for $C_{27}H_{27}N_7O$—465.6.

EXAMPLE 50

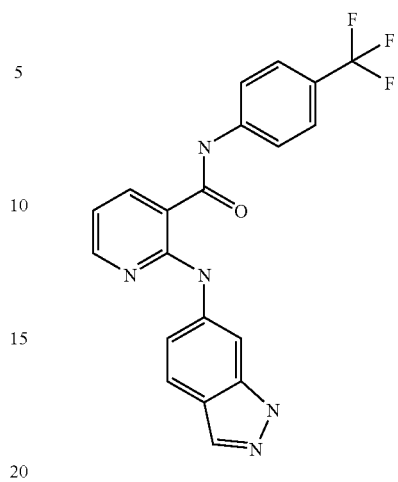

[2-(1H-Indazol-6-ylamino)(3-pyridyl)]-N-[4-(trifluoromethyl)phenyl]carboxamide

MS (ES+): 513 (M+H)$^+$; (ES−): 511. Calc'd $C_{20}H_{14}F_3N_5O$—397.4.

EXAMPLE 51

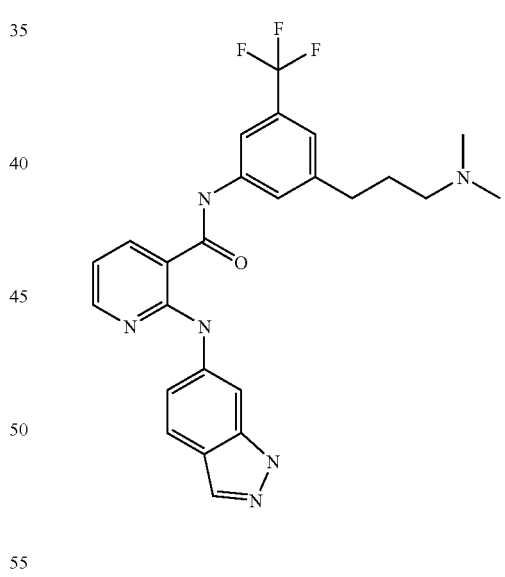

N-{3-[3-(Dimethylamino)propyl]-5-(trifluoromethyl)phenyl}[2-(1H-indazol-6-ylamino)(3-pyridyl)]carboxamide The title compound was analogously synthesized by the method described in Example 43 from {3-[3-amino-5-(trifluoromethyl)phenyl]propyl}dimethylamine. MS (ES+): 483 (M+H)$^+$; (ES−): 481 (M−H)$^-$. Calc'd $C_{25}H_{25}F_3N_6O$—482.5.

EXAMPLE 52

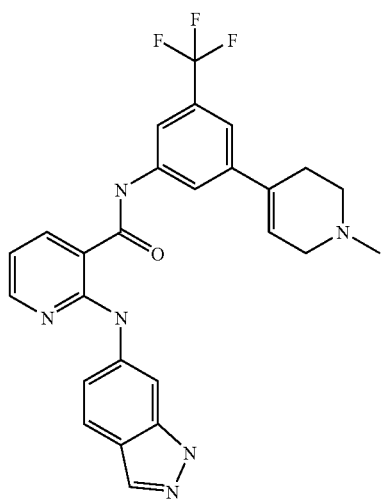

[2-(1H-Indazol-6-ylamino)(3-pyridyl)]-N-[5-(1-methyl(4-1,2,5,6-tetrahydropyridyl))-3-(trifluoromethyl)phenyl]carboxamide The title compound was analogously synthesized by the method described in Example 43 from 5-(1-methyl(4-1,2,5,6-tetrahydropyridyl))-3-(trifluoro-methyl)phenylamine. MS (ES+): 493 (M+H)+; (ES−): 491. Calc'd $C_{26}H_{23}F_3N_6O$—492.5.

EXAMPLE 53

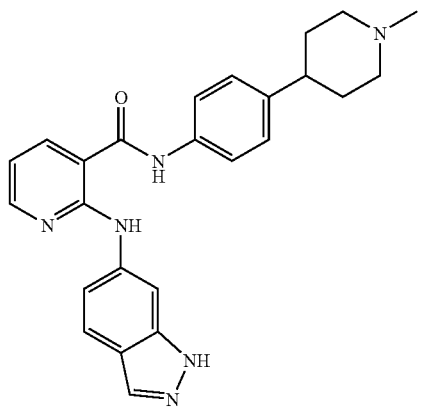

[2-(1H-Indazol-6-ylamino)(3-pyridyl)]-N-[4-(1-methyl(4-piperidyl))phenyl]carboxamide The title compound was analogously synthesized by the method described in Example 43 from 4-(1-methyl-4-piperidyl)phenylamine. MS: 427.0 (M+1). Calc'd for $C_{25}H_{26}N_6O$—426.5.

EXAMPLE 54

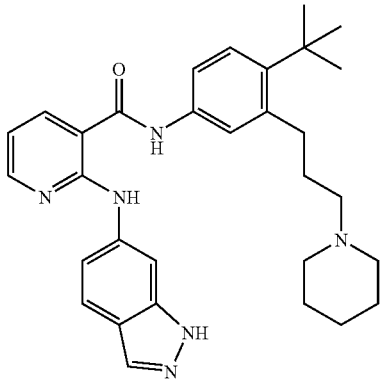

N-[4-(tert-Butyl)-3-(3-piperidylpropyl)phenyl][2-(1H-indazol-6-ylamino)(3-pyridyl)]carboxamide The title compound was analogously synthesized by the method described in Example 43 from 4-(tert-butyl)-3-(3-piperidylpropyl)phenylamine. MS: 511.4 (M+1). Calc'd. for $C_{31}H_{38}N_6O$—510.7.

EXAMPLE 55

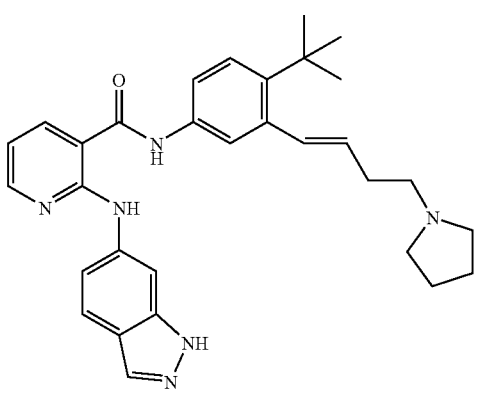

N-[3-((1E)-4-Pyrrolidinylbut-1-enyl)-4-(tert-butyl)phenyl][2-(1H-indazol-6-ylamino)(3-pyridyl)]carboxamide MS: 509.4 (M+1). Calc'd. for $C_{31}H_{36}N_6O$—508.7.

EXAMPLE 56

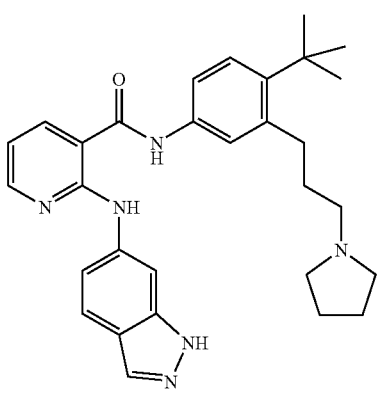

N-[4-(tert-Butyl)-3-(3-pyrrolidinylpropyl)phenyl][2-(1H-indazol-6-ylamino)(3-pyridyl)]carboxamide MS: 497.2 (M+1). Calc'd. for $C_{30}H_{36}N_6O$—496.7.

EXAMPLE 57

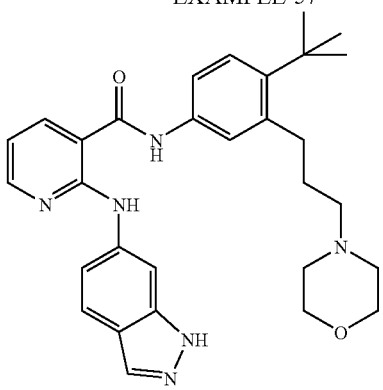

N-[4-(tert-Butyl)-3-(3-morpholin-4-ylpropyl)phenyl]
[2-(1H-indazol-6-ylamino)(3-pyridyl)]carboxamide MS: 513.5 (M+1). Calc'd. for $C_{30}H_{36}N_6O_2$—512.7.

EXAMPLE 58

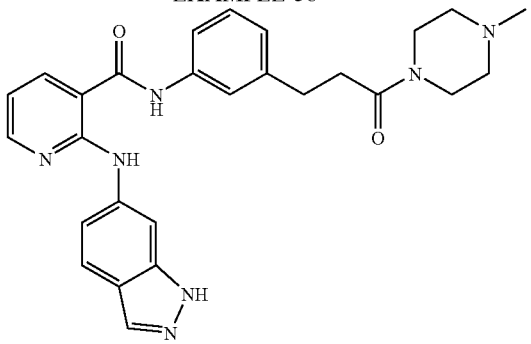

[2-(1H-Indazol-6-ylamino)(3-pyridyl)]-N-{3-[3-(4-methylpiperazinyl)-3-oxopropyl]phenyl}carboxamide The title compound was analogously synthesized by the method described in Example 54 from 3-(3-aminophenyl)-1-(4-methylpiperazinyl)propan-1-one. MS: 484.4 (M+1). Calc'd. for $C_{27}H_{29}N_7O_2$—483.6.

EXAMPLE 59

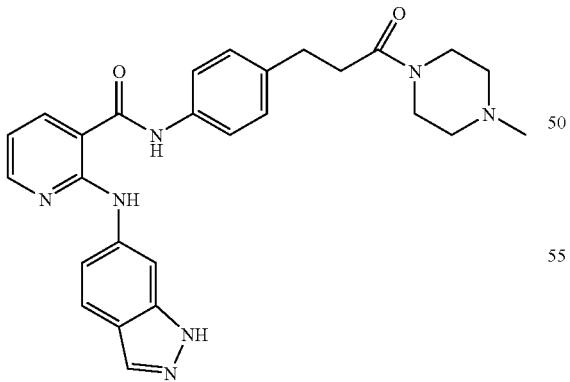

[2-(1H-Indazol-6-ylamino)(3-pyridyl)]-N-{4-[3-(4-methylpiperazinyl)-3-oxopropyl]phenyl}carboxamide The title compound was analogously synthesized by the method described in Example 58. MS: 484.4 (M+1). Calc'd. for $C_{27}H_{29}N_7O_2$—483.6.

EXAMPLE 60

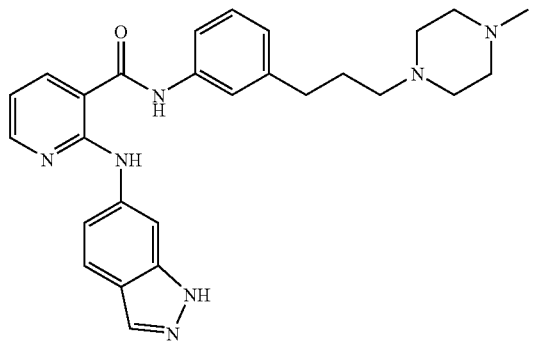

[2-(1H-Indazol-6-ylamino)(3-pyridyl)]-N-{3-[3-(4-methylpiperazinyl)propyl]phenyl}carboxamide The title compound was analogously synthesized by the method described in Example 58. MS: 470 (M+1). Calc'd. for $C_{27}H_{31}N_7O$—469.6.

EXAMPLE 61

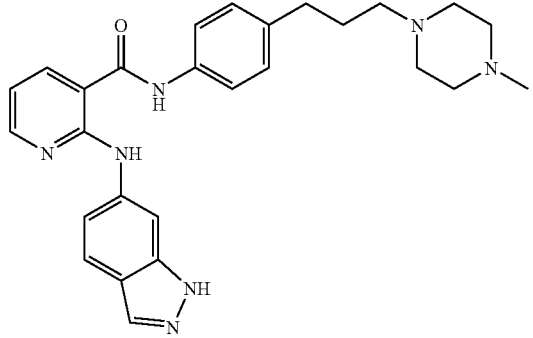

[2-(1H-Indazol-6-ylamino)(3-pyridyl)]-N-{4-[3-(4-methylpiperazinyl)propyl]phenyl}carboxamide The title compound was analogously synthesized by the method described in Example 58. MS: 470 (M+1). Calc'd. for $C_{27}H_{31}N_7O$—469.6.

EXAMPLE 62

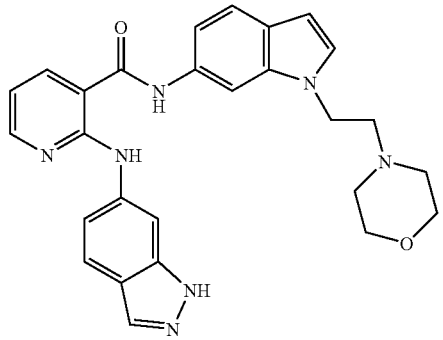

[2-(1H-Indazol-6-ylamino)(3-pyridyl)]-N-[1-(2-morpholin-4-ylethyl)indol-6-yl]carboxamide The title compound was analogously synthesized by the method described in Example 54 from 1-(2-morpholin-4-

EXAMPLE 63

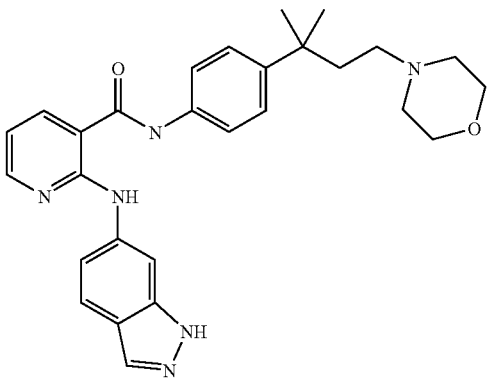

N-[4-(1,1-Dimethyl-3-morpholin-4-ylpropyl)phenyl][2-(1H-indazol-6-ylamino)(3-pyridyl)]carboxamide The title compound was analogously synthesized by the method described in Example 54 from 4-(1,1-dimethyl-3-morpholin-4-ylpropyl)phenylamine. MS: 485.5 (M+1). Calc'd. for $C_{28}H_{32}N_6O_2$—484.6.

EXAMPLE 64

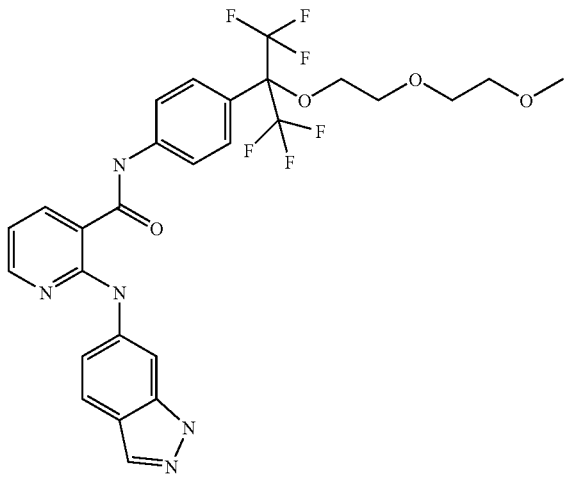

2-(1H-indazol-6-ylamino)-N-(4-{2,2,2-trifluoro-1-[2-(2-methoxy-ethoxy)-ethoxy]-1-trifluoromethyl-ethyl})-phenyl)-nicotinamide To a suspension of 2-fluoropyridine-3-carbonyl chloride (180 mg, 0.5 mmol) and $NaHCO_3$ (300 mg) in $CH_2Cl_2$ (5 ml), a solution of 4-{2,2,2-trifluoro-1-[2-(2-methoxy)ethoxy]-1-(trifluoromethyl)ethyl }phenylamine (95 mg) was added dropwise, and the suspension was stirred at RT for 1.5 h. Solid inorganic salts were removed via filtration. The filtrate was concentrated to afford (2-fluoro(3-pyridyl))-N-(4-{2,2,2-trifluoro-1-[2-(2-methoxyethoxy)ethoxy]-1-(trifluoromethyl)ethyl }phenyl)-carboxamide as a brown solid. (2-Fluoro(3-pyridyl))-N-(4-{2,2,2-trifluoro-1-[2-(2-methoxyethoxy)ethoxy]-1-(trifluoromethyl)ethyl}-phenyl)carboxamide (240 mg, 0.5 mmol) and 6-amino-indazole (133 mg, 1 mmol) were dissolved in DMS0 (2 mL). The solution was heated to 120° C. for 8 h, then partitioned between $CH_2Cl_2$ and aqueous $NaHCO_3$ (sat.). The organic layer was washed with brine, dried over $Na_2SO_4$, and concentrated in vacuo. The residue was purified via preparative HPLC to give a yellow powder as a TFA salt of the title compound. MS: 598 (M+1). Calc'd. for $C_{27}H_{25}F_6N_5O_4$—597.5.

The following compounds (Examples 65–68) were analogously synthesized by the method described in Example 64. Detailed intermediate preparations were described.

EXAMPLE 65

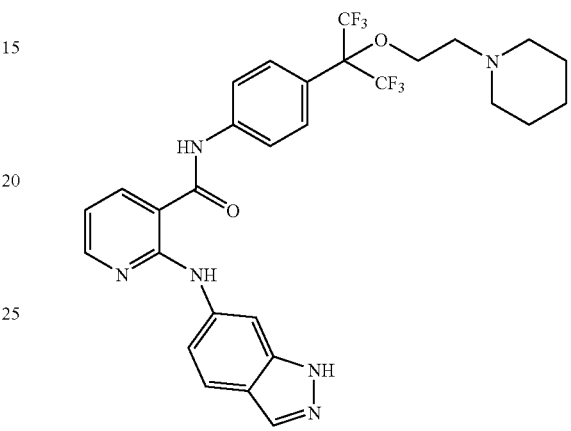

[2-(1H-Indazol-6-ylamino)(3-pyridyl)]-N-{4-[2,2,2-trifluoro-1-(2-piperidylethoxy)-1-(trifluoromethyl)ethyl]phenyl}carboxamide MS: 607 (M+1). Calc'd. for $C_{29}H_{28}F_6N_6O_2$—606.6.

EXAMPLE 66

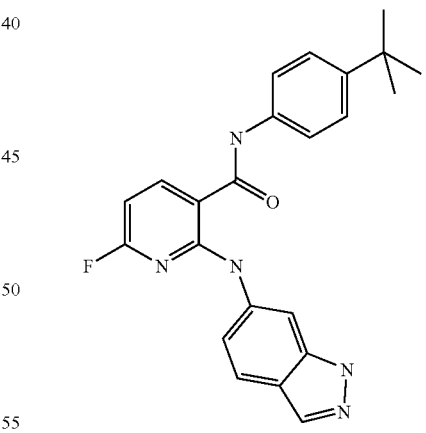

N-[4-(tert-Butyl)phenyl][6-fluoro-2-(1H-indazol-6-ylamino)(3-pyridyl)]carboxamide Step A: Preparation of (2,6-difluoro(3-pyridyl))-N-[4-(tert-butyl)phenyl]-carboxamide A solution of 2,6-difluoropyridine-3-carboxylic acid (prepared similar to that described for 2-fluoropyridine-3-carboxylic acid, Example 64) (3.2 g, 20 mmol), t-butylaniline 11 (3.0 g, 20 mmol), HOBt (2.6 g, 20 mmol), EDAC (8 g, 40 mmole), and DIEA (8 mL) in $CH_2Cl_2$ (80 mL) was stirred at RT for 1 h. The mixture was washed with aq. NaHCO₃ and brine. The organic solution was dried over Na₂SO₄ and concentrated in vacuo. The residue was purified via flash chromatography on silica (Hex:EtOAc=4:1) to give a light yellow flaky crystal as the desired product.

Step B: Preparation of N-[4-(tert-butyl)phenyl][6-fluoro-2-(1H-indazol-6-ylamino)(3-pyridyl)]carboxamide The title compound was analogously synthesized by the method described in Example 64 from (2,6-difluoro(3-pyridyl))-N-[4-(tert-butyl)phenyl]-carboxamide (Step A). MS: 404 (M+1). Calc'd. for C₂₃H₂₂FN₅O—403.5.

EXAMPLE 67

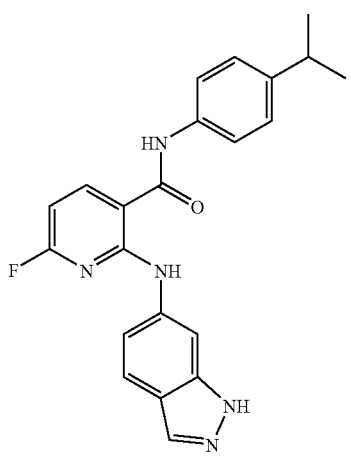

[6-Fluoro-2-(1H-indazol-6-ylamino)(3-pyridyl)]-N-[4-(methylethyl)phenyl]carboxamide MS: 390 (M+1). Calc'd. for C₂₂H₂₀FN₅O—389.4.

EXAMPLE 68

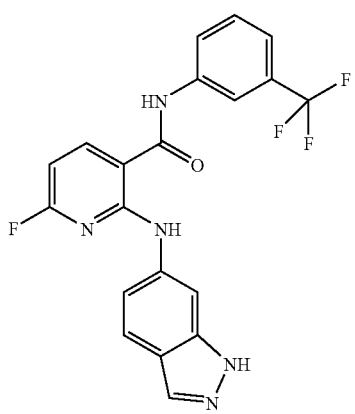

[6-Fluoro-2-(1H-indazol-6-ylamino)(3-pyridyl)]-N-[3-(trifluoromethyl)phenyl]carboxamide MS: 416 (M+1). Calc'd. for C₂₀H₁₃F₄N₅O—415.3.

EXAMPLE 69

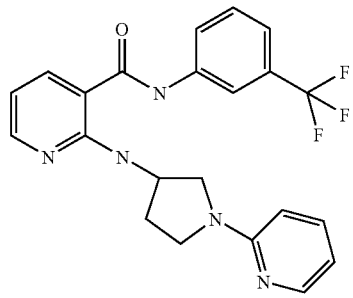

{2-[(1-(2-Pyridyl)pyrrolidin-3-yl)amino](3-pyridyl)}-N-[3-(trifluoromethyl)phenyl]carboxamide Step A: Preparation of 1-(2-pyridyl)pyrrolidine-3-ylamine 2-Fluoropyridine (2 g, 0.02 mol) and Boc-aminopyrrolidine (3.6 g, 0.02 mol) were heated neat at 120° C. for 2 h. The reaction was cooled, 4N HCl/Dioxane (100 mg) was added and the reaction was stirred at RT for 4 h. The solvent was evaporated and 2 N NaOMe/MeOH was added to adjust to basic pH. The precipitate was filtered and the filtrate was evaporated. The residue was dissolved in CH₂Cl₂, the solution was filtered and the filtrate was evaporated to give the crude material, was used in next step without further purification.

Step B: Preparation of {2-[(1-(2-pyridyl)pyrrolidin-3-yl)amino](3-pyridyl)}-N-[3-(trifluoromethyl)phenyl]-carboxamide A mixture of (2-chloro(3-pyridyl))-N-(3-trifluoromethylphenyl)carboxamide and 1-(2-pyridyl)pyrrolidine-3-ylamine (Step A) was heated at 130° C. neat for 3 h. The reaction was cooled and diluted with CH₂Cl₂ and washed with H₂O twice followed by brine. The organic layer was dried with Na₂SO₄ and evaporated under reduced pressure. The residue was purified by column chromatography with EtOAc and further mixed with MeOH and 1 N HCl/Et₂O (2 ml). The solution was evaporated to furnish the titled compound. MS (ES+): 428 (M+H); (ES−): 426 (M−H). Calc'd. for C₂₂H₂₀F₃N₅O—427.2.

EXAMPLE 70

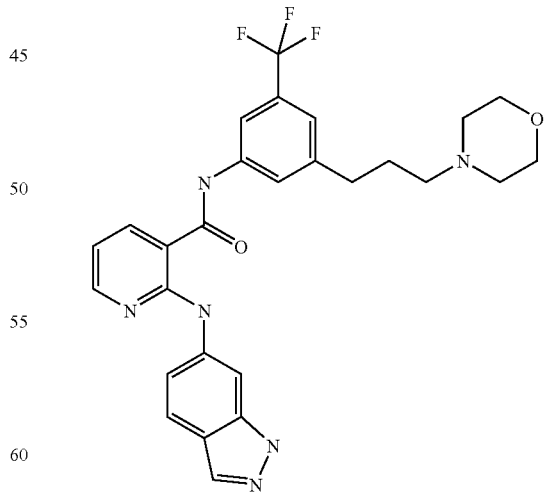

2-(1H-Indazol-6-ylamino)-N-[3-(3-morpholin-4-yl-propyl)-5-trifluoromethyl-phenyl]-nicotinamide 2-Chloro-N-[3-(3-morpholin-4-yl-propyl)-5-trifluoromethyl-phenyl]-nicotinamide (2.95 g) was dissolved in a small volume of IpOH. 6-amino indazole (2.75 g) and 0.53 mL of TFA were added. The reaction mixture was heated to 155° C. in an open flask for 3.5 h. After cooling to RT the residue was dissolved in 2 N HCl. The aqueous solution was extracted 2 times with $CH_2Cl_2$, basified to pH 12 by the addition of $Na_2CO_3$ and 1 N NaOH. The solution was extracted 6 times with $CH_2Cl_2$ to isolate the product. The combined 5 extractions were dried over $Na_2SO_4$, filtered and stripped. The crude product was purified by silica gel chromatography eluting with a step gradient of 3–5% $MeOH:CH_2Cl_2$ to yield the titled compound. MS: 525 (M+1) Calc'd for $C_{27}H_{27}F_3N_6O_2$—524.5.

The following compounds (Examples 71–95) were synthesized by the method described in Example 70 unless specifically described.

EXAMPLE 71

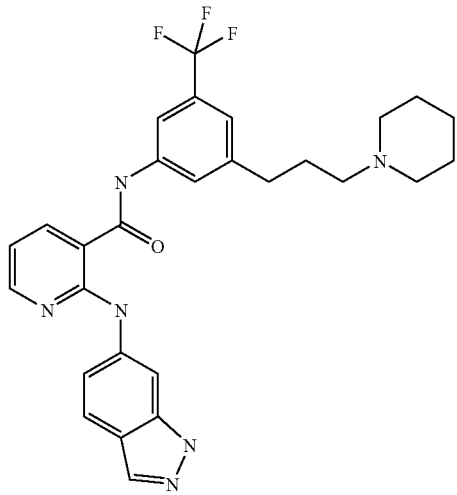

2-(1H-Indazol-6-ylamino)-N-[3-(3-piperidin-1-yl-propyl)-5-trifluoromethyl-phenyl]-nicotinamide MS: 523.5 (M+1). Calc'd. for $C_{28}H_{29}F_3N_6O$—522.6.

EXAMPLE 72

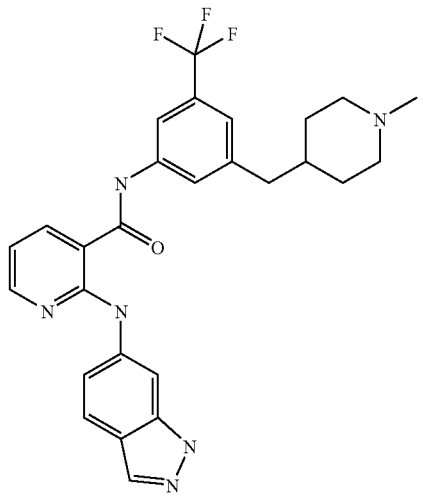

2-(1H-Indazol-6-ylamino)-N-[3-(1-methyl-piperidin-4-ylmethyl)-5-trifluoromethyl-phenyl]-nicotinamide MS: 509 (M+1). Calc'd. for $C_{27}H_{27}F_3N_6O$—508.5.

EXAMPLE 73

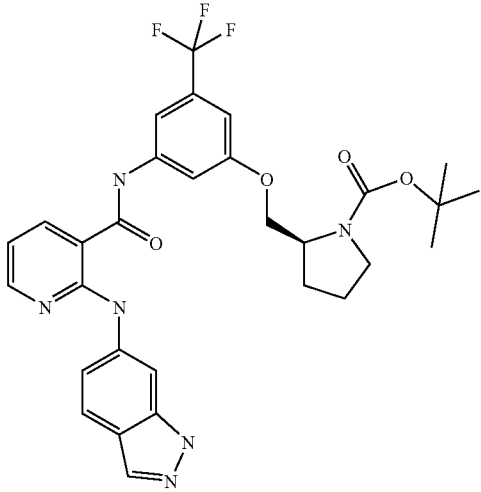

2-(1H-Indazol-6-ylamino)-N-[3-(1-methyl-pyrrolidin-2-ylmethoxy)-5-trifluoromethyl-phenyl]-nicotinamide

EXAMPLE 74

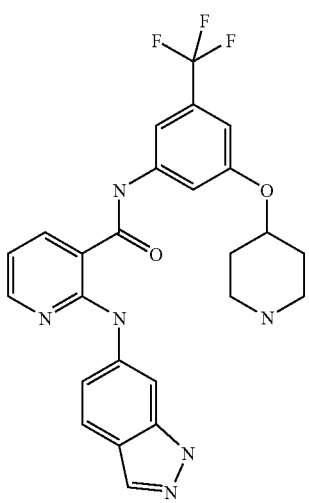

2-(1H-Indazol-6-ylamino)-N-[3-(piperidin-4-yloxy)-5-trifluoromethyl-phenyl]-nicotinamide MS: 497 (M+1). Calc'd. for $C_{25}H_{23}F_3N_6O$—496.5.

EXAMPLE 75

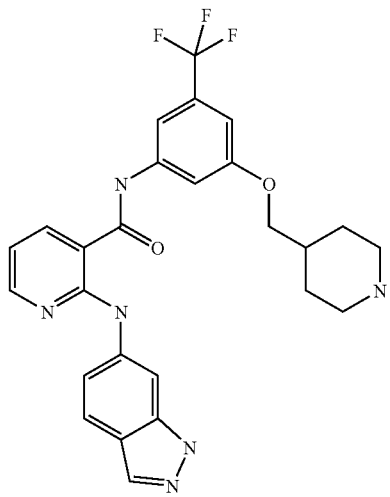

2-(1H-Indazol-6-ylamino)-N-[3-(piperidin-4-ylmethoxy)-5-trifluoromethyl-phenyl]-nicotinamide MS (ES+): 511 (M+H), Calc'd for $C_{26}H_{25}F_3N_6O_2$—510.52.

EXAMPLE 76

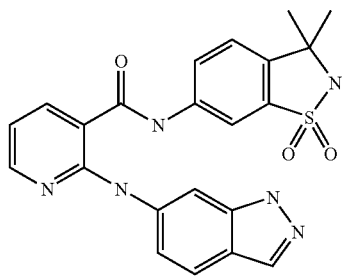

N-(3,3-Dimethyl-1,1-dioxo-2,3-dihydro-1H-116-benzo[d]isothiazol-6-yl)-2-(1H-indazol-6-ylamino)-nicotinamide MS (ES+): 449 (M+H)+; (ES−): 447 (M−H). Calc'd for $C_{22}H_{20}N_6O_3S$—448.

EXAMPLE 77

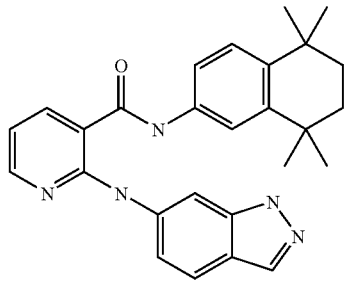

2-(1H-Indazol-6-ylamino)-N-(5,5,8,8-tetramethyl-5,6,7,8-tetrahydro-naphthalen-2-yl)-nicotinamide MS (ES+): 440 (M+H)+; (ES−): 438 (M−H). Calc'd for $C_{27}H_{29}N_5O$—439.

EXAMPLE 78

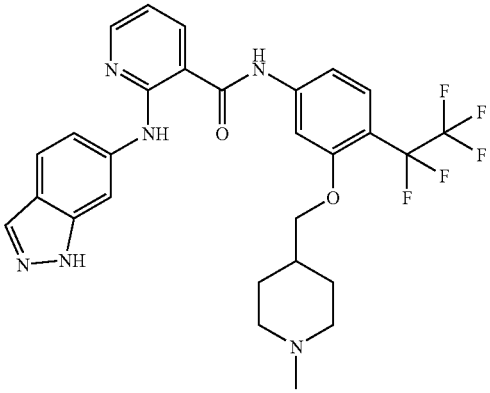

2-(1H-Indazol-6-ylamino)-N-[3-(1-methyl-piperidin-4-ylmethoxy)-4-pentafluoroethyl-phenyl]-nicotinamide M+H 575; Calc'd. for $C_{28}H_{27}F_5N_6O_2$—574.

EXAMPLE 79

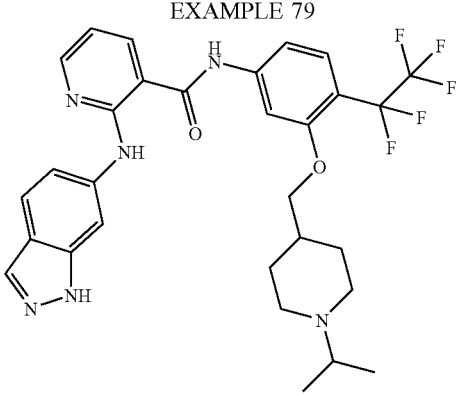

2-(1H-Indazol-6-ylamino)-N-[3-(1-isopropyl-piperidin-4-ylmethoxy)-4-pentafluoroethyl-phenyl]-nicotinamide M+H 603; Calc'd. for $C_{30}H_{31}F_5N_6O_2$—602.

EXAMPLE 80

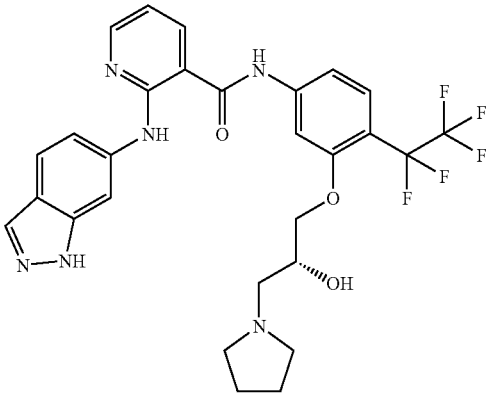

N-[3-(2-Hydroxy-3-pyrrolidin-1-yl-propoxy)-4-pentafluoroethyl-phenyl]-2-(1H-indazol-6-ylamino)-nicotinamide M+H 591; Calc'd. for $C_{28}H_{27}F_5N_6O_3$—590.

EXAMPLE 81

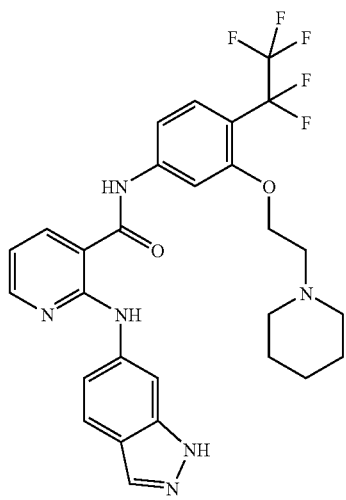

2-(1H-Indazol-6-ylamino)-N-[4-pentafluoroethyl-3-(2-piperidin-1-yl-ethoxy)-phenyl]-nicotinamide M+H 575; Calc'd. for $C_{28}H_{27}F_5N_6O_2$—574.

EXAMPLE 82

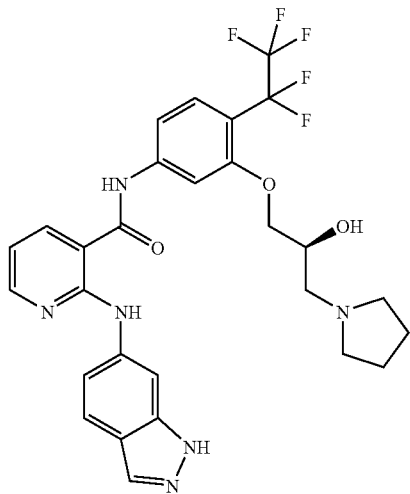

N-[3-(2-Hydroxy-3-pyrrolidin-1-yl-propoxy)-4-pentafluoroethyl-phenyl]-2-(1H-indazol-6-ylamino)-nicotinamide M+H 591; Calc'd. for $C_{28}H_{27}F_5N_6O_3$—590.

EXAMPLE 83

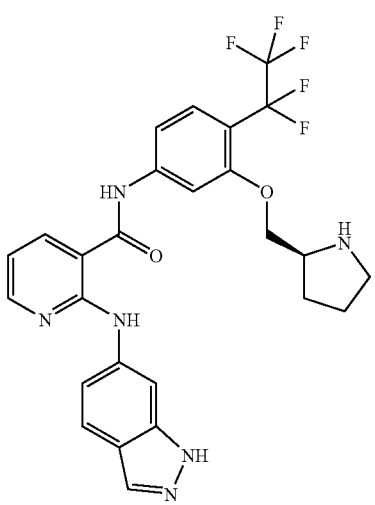

2-(1H-Indazol-6-ylamino)-N-[4-pentafluoroethyl-3-(2S-pyrrolidin-2-ylmethoxy)-phenyl]-nicotinamide M+H 547; Calc'd. for $C_{26}H_{23}F_5N_6O_2$—546.

EXAMPLE 84

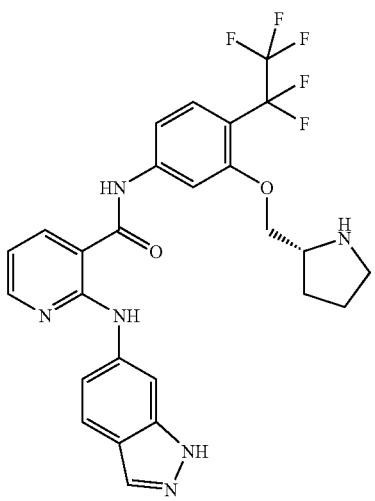

2-(1H-Indazol-6-ylamino)-N-[4-pentafluoroethyl-3-(2R-pyrrolidin-2-ylmethoxy)-phenyl]-nicotinamide M+H 547; Calc'd. for $C_{26}H_{23}F_5N_6O_2$—546.

EXAMPLE 85

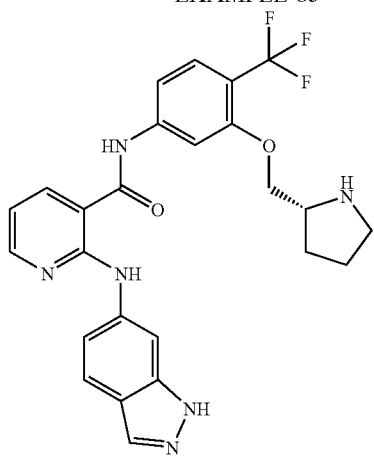

2-(1H-Indazol-6-ylamino)-N-[3-(pyrrolidin-2-ylmethoxy)-4-trifluoromethyl-phenyl]-nicotinamide M+H 497; Calc'd. for $C_{25}H_{23}F_3N_6O_2$—496.

EXAMPLE 86

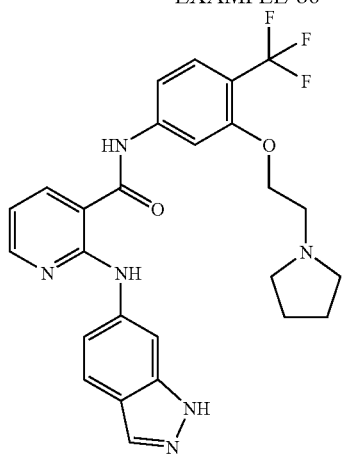

2-(1H-Indazol-6-ylamino)-N-[3-(2-pyrrolidin-1-yl-ethoxy)-4-trifluoromethyl-phenyl]-nicotinamide M+H 511; Calc'd. for $C_{26}H_{25}F_3N_6O_2$—510.

EXAMPLE 87

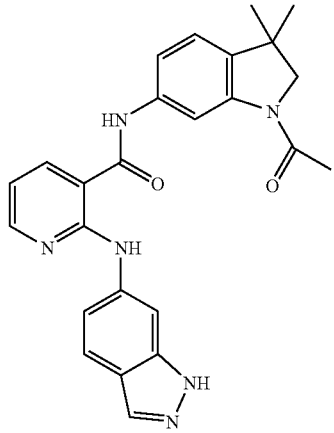

N-(1-Acetyl-3,3-dimethyl-2,3-dihydro-1H-indol-6-yl)-2-(1H-indazol-6-ylamino)-nicotinamide M+H 441.3; Calc'd for $C_{25}H_{24}N_6O_2$: 440.2.

EXAMPLE 88

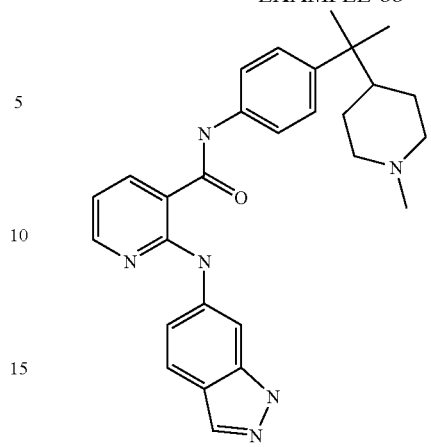

2-(1H-Indazol-6-ylamino)-N-{4-[1-methyl-1-(1-methyl-piperidin-4-yl)-ethyl]-phenyl}-nicotinamide MS (ES+): 469 (M+1)+, Calc'd for $C_{28}H_{32}N_6O$—468.26

EXAMPLE 89

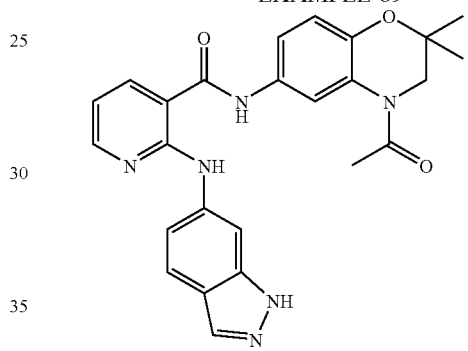

N-(4-Acetyl-2,2-dimethyl-3,4-dihydro-2H-benzo[1,4]oxazin-6-yl)-2-(1H-indazol-6-ylamino)-nicotinamide MS (ES+): 457.5 (M+H)+; (ES−) 455.5 (M−H). Calc'd for $C_{25}H_{24}N_6O_3$—456.5

EXAMPLE 90

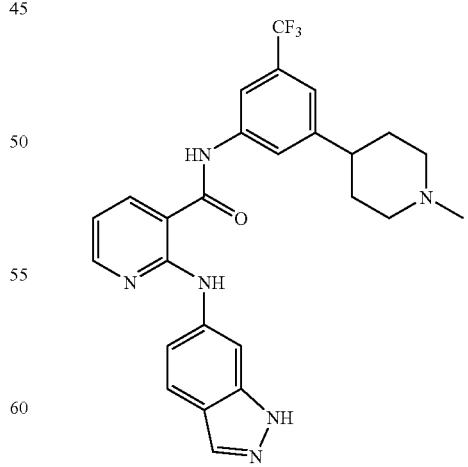

2-(1H-Indazol-6-ylamino)-N-[3-(1-methyl-piperidin-4-yl)-5-trifluoromethyl-phenyl]-nicotinamide MS (ES+): 495.1 (M+H)+; (ES−) 493.2 (M−H). Calc'd for $C_{26}H_{25}F_3N_6O$: 494.20.

EXAMPLE 91

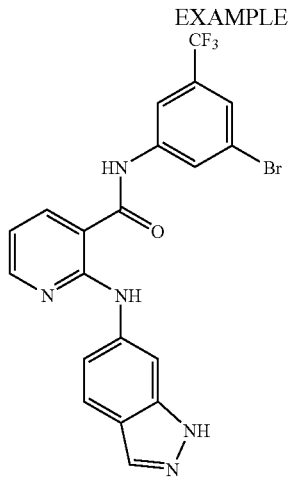

N-(3-Bromo-5-trifluoromethyl-phenyl)-2-(1H-indazol-6-ylamino)-nicotinamide
MS (ES+): 475.9 (M+H)+; (ES−) 474.0 (M−H). Calc'd for $C_{20}H_{13}BrF_3N_5O$: 475.30.

EXAMPLE 92

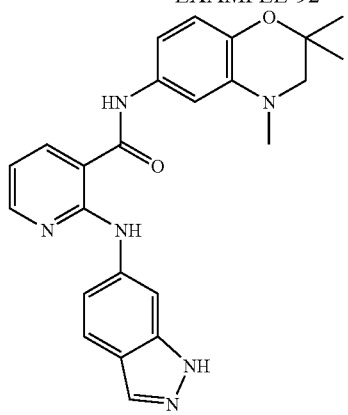

2-(1H-Indazol-6-ylamino)-N-(2,2,4-trimethyl-3,4-dihydro-2H-benzo[1,4]oxazin-6-yl)-nicotinamide
MS (ES+): 429.2 (M+H)+; (ES−) 427.4 (M−H). Calc'd for $C_{24}H_{24}N_6O_2$: 428.2.

EXAMPLE 93

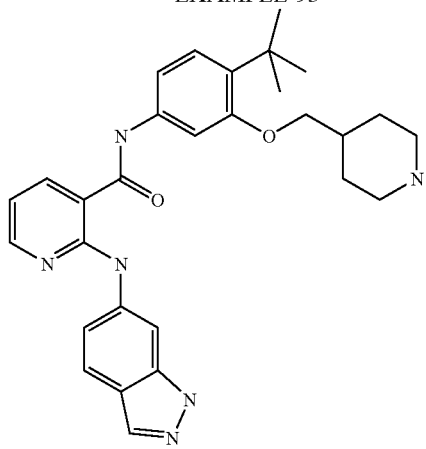

N-[4-tert-Butyl-3-(piperidin-4-ylmethoxy)-phenyl]-2-(1H-indazol-6-ylamino)-nicotinamide
M+H 499: Calc'd for $C_{29}H_{34}N_6O_2$: 498.

EXAMPLE 94

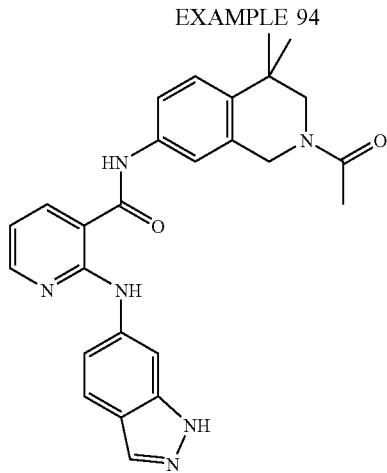

N-(2-Acetyl-4,4-dimethyl-1,2,3,4-tetrahydro-isoquinolin-7-yl)-2-(1H-indazol-6-ylamino)-nicotinamide
M+H 455.3. Calc'd for $C_{26}H_{26}N_6O_2$: 454.2.

EXAMPLE 95

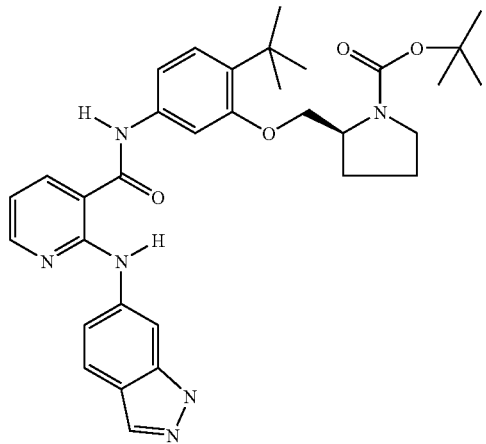

1-Boc-2-(2-tert-Butyl-5-{[2-(1H-indazol-6-ylamino)-pyridine-3-carbonyl]-amino}-phenoxymethyl)-pyrrolidine
M+H 585; Calc'd for $C_{33}H_{40}N_6O_4$: 584.

EXAMPLE 96

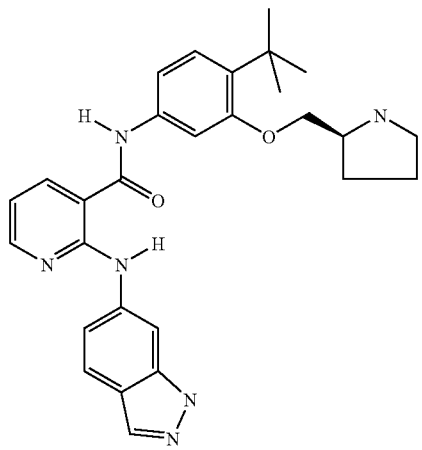

N-[4-tert-Butyl-3-(pyrrolidin-2-ylmethoxy)-phenyl]-2-(1H-indazol-6-ylamino)-nicotinamide
The title compound was deprotected by a method analogous to that described in Example 69, step a. M+H 485; Calc'd for $C_{28}H_{32}N_6O_2$: 484.

EXAMPLE 97

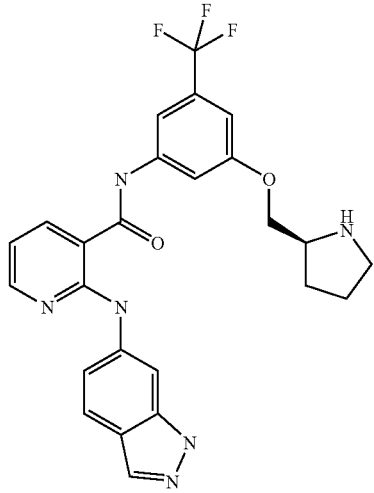

2-(1H-Indazol-6-ylamino)-N-[3-(2S-pyrrolidin-2-ylmethoxy)-5-trifluoromethyl-phenyl]-nicotinamide The title compound was deprotected by a method analogous to that described in Example 69, step a. MS: 497 (M+1). Calc'd. for $C_{25}H_{23}F_3N_6O_2$—496.5.

EXAMPLE 98

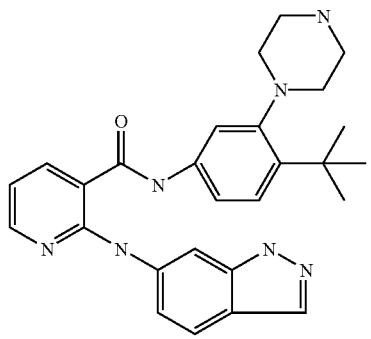

N-(4-tert-Butyl-3-piperazin-1-yl-phenyl)-2-(1H-indazol-6-ylamino)-nicotinamide

The title compound was deprotected by a method analogous to that described in Example 69, step a. MS (ES+): 470 (M+H)+; (ES−): 468 (M−H). Calc'd. for $C_{27}H_{31}N_7O$—469.

EXAMPLE 99

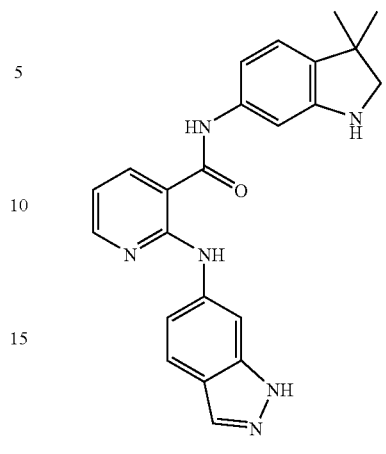

N-(3,3dimethyl-2,3-dihydro-1H-indol-6-yl)-2-(1H-indazol-6-ylamino)-nicotinamide

N-(1-Acetyl-3,3-dimethyl-2,3-dihydro-1H-indol-6-yl)-2-(1H-indazol-6-ylamino)-nicotinamide (500 mg) was deprotected heating with 12 N HCl (3 ml) and EtOH (3 ML) at reflux for 1 h. Dried under vacuum and purified via HPLC. M+H 399.3; Calc'd for $C_{23}H_{22}N_6O$: 398.2.

EXAMPLE 100

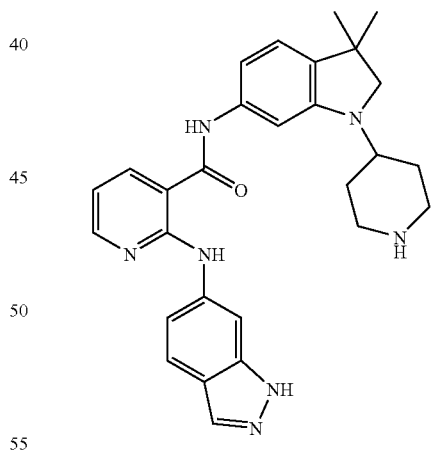

N-(3,3-Dimethyl-1-piperidin-4-yl-2,3-dihydro-1H-indol-6-yl)-2-(1H-indazol-6-ylamino)-nicotinamide The title compound was deprotected by a method analogous to that described in Example 99. MS (M+H)=482.4; Calc'd for $C_{28}H_{31}N_7O$: 481.2.

EXAMPLE 101

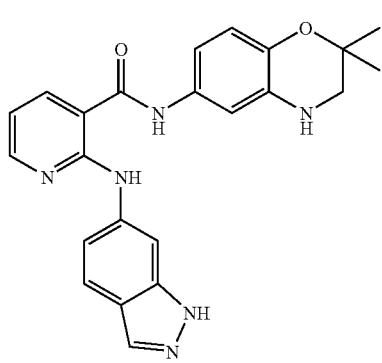

N-(2,2-Dimethyl-3,4-dihydro-2H-benzo[1,4]oxazin-6-yl)-2-(1H-indazol-6-ylamino)-nicotinamide The title compound was deprotected by a method analogous to that described in Example 99. MS (ES+): 415.3 (M+H)+; (ES−) 413.2 (M−H). Calc'd for $C_{23}H_{22}N_6O_2$—414.5.

EXAMPLE 102

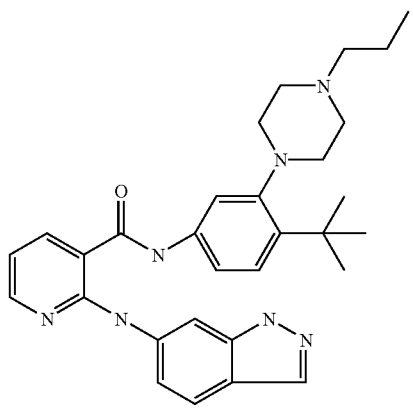

N-[4-tert-Butyl-3-(4-propyl-piperazin-1-yl)-phenyl]-2-(1H-indazol-6-ylamino)-nicotinamide N-[4-tert-Butyl-3-(4-propyl-piperazin-1-yl)-phenyl]-2-(1H-indazol-6-ylamino)-nicotinamide was alkylated by a method analogous to that described in Example 63, step c. MS (ES+): 512 (M+H)+; (ES−): 510 (M−H). Calc'd. for $C_{30}H_{37}N_7O$—511.

EXAMPLE 103

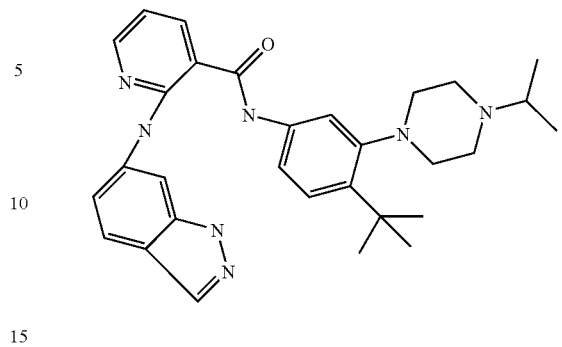

N-[4-tert-Butyl-3-(4-isopropyl-piperazin-1-yl)-phenyl]-2-(1H-indazol-6-ylamino)-nicotinamide N-[4-tert-Butyl-3-(4-propyl-piperazin-1-yl)-phenyl]-2-(1H-indazol-6-ylamino)-nicotinamide was alkylated by a method analogous to that described in Example 63, step c. MS (ES+): 512 (M+H)+; (ES−): 510 (M−H). Calc'd. for $C_{30}H_{37}N_7O$—511.

EXAMPLE 104

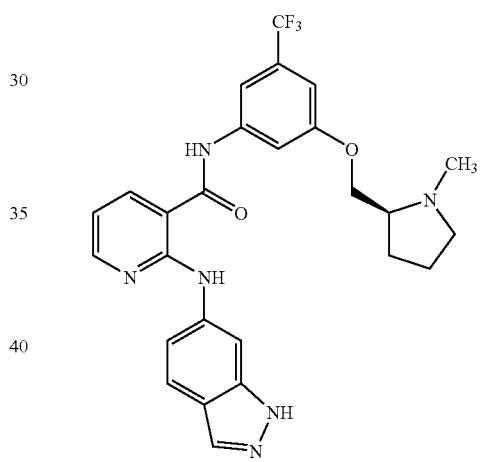

2-(1H-Indazol-6-ylamino)-N-[3-(1-methylpyrrolidin-2-ylmethoxy)-5-trifluoromethyl-phenyl]-nicotinamide The title compound was prepared by a method analogous to that described in Example 70. M+H 511.4. Calc'd for $C_{26}H_{25}F_3N_6O_2$: 510.5.

EXAMPLE 105

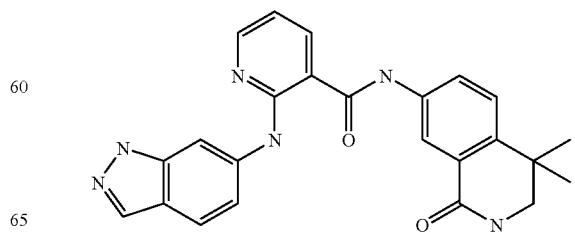

N-(4,4-Dimethyl-1-oxo-1,2,3,4-tetrahydro-isoquinolin-7-yl)-2-(1H-indazol-6-ylamino)-nicotinamide The title compound was prepared by a method analogous to that described in Example 70. (M+H) 427, Calc. for $C_{24}H_{22}N_6O_2$: 426.2.

EXAMPLE 106

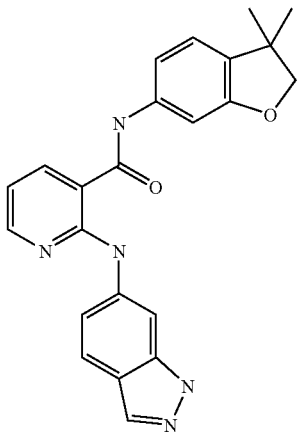

N-(3,3-Dimethyl-2,3-dihydro-benzofuran-6-yl)-2-(1H-indazol-6-ylamino)-nicotinamide The title compound was prepared by a method analogous to that described in Example 70. MS: 400 (M+1). Calc'd. for $C_{23}H_{21}N_5O_2$—399.4.

EXAMPLE 107

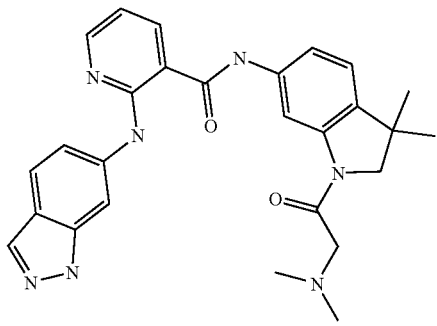

N-[1-(2-Dimethylamino-acetyl)-3,3-dimethyl-2,3-dihydro-1H-indol-6-yl]-2-(1H-indazol-6-ylamino)-nicotinamide The title compound was prepared by a method analogous to that described in Example 70. M+H 484.3; Calc'd for $C_{27}H_{29}N_7O_2$: 483.2.

EXAMPLE 108

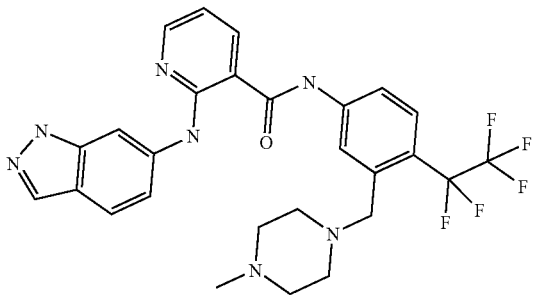

2-(1H-Indazol-6-ylamino)-N-[3-(4-methyl-piperazin-1-ylmethyl)-4-pentafluoroethyl-phenyl]-nicotinamide The title compound was prepared by a method analogous to that described in Example 70. M+H 560.4. Calc'd for $C_{27}H_{26}F_5N_7O$: 559.2.

EXAMPLE 109

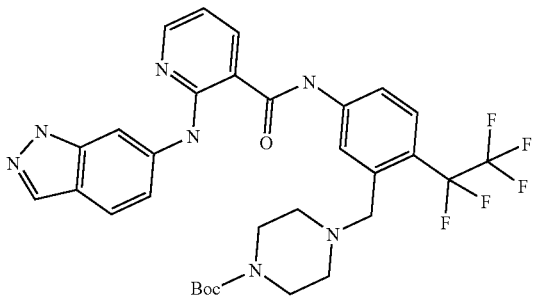

2-(1H-Indazol-6-ylamino)-N-[3-(4-Boc-piperazin-1-ylmethyl)-4-pentafluoroethyl-phenyl]-nicotinamide The title compound was prepared by a method analogous to that described in Example 70. M+H 646.4. Calc'd for $C_{31}H_{32}F_5N_7O_3$: 645.2.

EXAMPLE 110

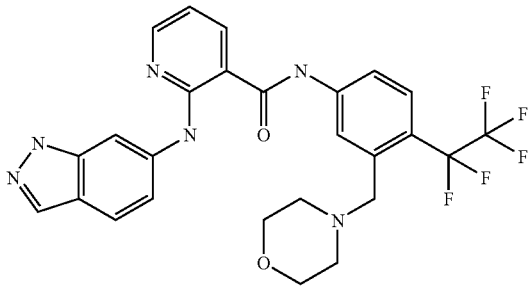

2-(1H-Indazol-6-ylamino)-N-(3-morpholin-4-ylmethyl-4-pentafluoroethyl-phenyl)-nicotinamide The title compound was prepared by a method analogous to that described in Example 70. M+H 547.1. Calc'd for $C_{26}H_{23}F_5N_6O_2$: 546.2.

EXAMPLE 111

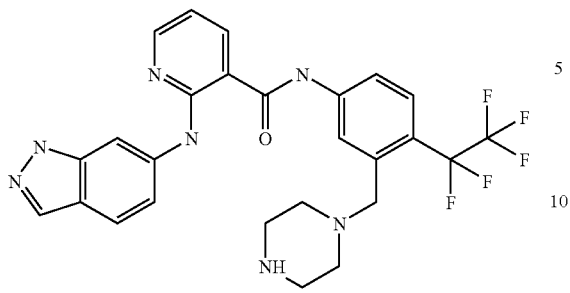

2-(1H-Indazol-6-ylamino)-N-(4-pentafluoroethyl-3-piperazin-1-ylmethyl-phenyl)-nicotinamide The title compound was prepared by a method analogous to that described in Example 69, step a. M+H 546.4. Calc'd for $C_{26}H_{24}F_5N_7O$: 545.2.

EXAMPLE 112

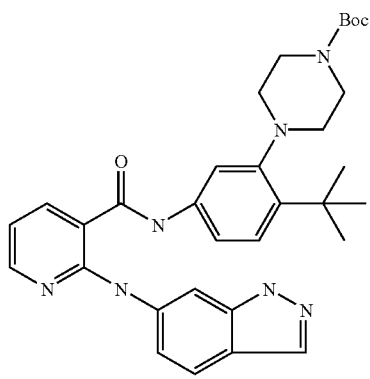

N-[4-tert-Butyl-3-(4-Boc-piperazin-1-yl)-phenyl]-2-(1H-indazol-6-ylamino)-nicotinamide The title compound was prepared by a method analogous to that described in Example 1, Step B. (ES+) 570 (M+1)$^+$; (ES−): 568 (M−1)$^−$. Calc'd. $C_{32}H_{39}N_7O_3$—569.7.

EXAMPLE 113

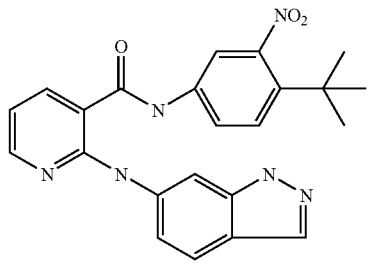

N-(4-tert-Butyl-3-nitro-phenyl)-2-(1H-indazol-6-ylamino)-nicotinamide

The title compound was prepared from N-(4-tert-butyl-3-nitro-phenyl)-2-chloro-nicotinamide by a method analogous to that described in Example 70, step E. MS (ES+): 401 (M+H), Calc'd for $C_{23}H_{24}N_6O$—400.5.

EXAMPLE 114

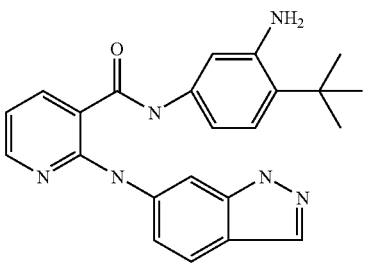

N-(3-Amino-4-tert-butyl-phenyl)-2-(1H-indazol-6-ylamino)-nicotinamide

The title compound was prepared from N-(4-tert-butyl-3-nitro-phenyl)-2-(1H-indazol-6-ylamino)-nicotinamide by dissolving in EtOH (20 ml) and adding Sn(II)Cl$_2$ (12.58 g) and stirred at RT for 5 h and at 0° C. overnight. The mix was warmed to RT and quenched by pouring onto ice, neutralized with NaHCO$_3$ and basified with 6N NAOH. An emulsion formed upon addition of EtOAc which was filtered through Celite and the aqueous layer was extracted with EtOAc. The combined organic layers were washed with H$_2$O, brine and dried over MgSO$_4$ then purified by flash chromatography (3–5% MeOH to afford the product as a orange-yellow solid.

EXAMPLE 115

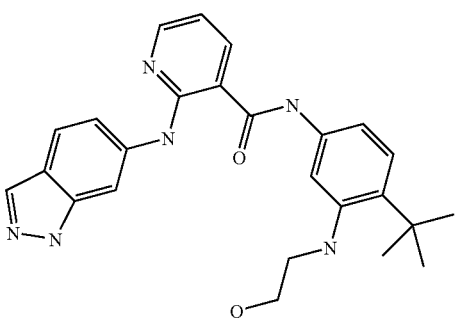

N-[4-tert-Butyl-3-(2-hydroxy-ethylamino)-phenyl]-2-(1H-indazol-6-ylamino)-nicotinamide The title compound was prepared from N-(3-amino-4-tert-butyl-phenyl)-2-(1H-indazol-6-ylamino)-nicotinamide by a method analogous to that described in Example 42. MS (ES+): 445 (M+H), Calc'd for $C_{25}H_{28}N_6O_2$—444.5.

EXAMPLE 116

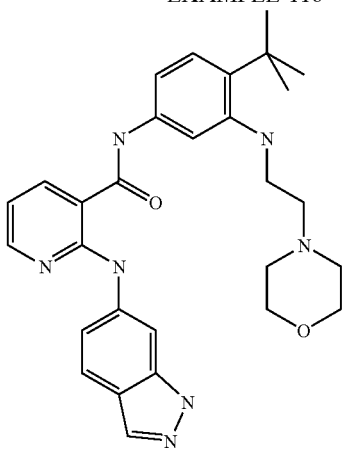

N-[4-tert-Butyl-3-(2-morpholin-4-yl-ethylamino)-phenyl]-2-(1H-indazol-6-ylamino)-nicotinamide Step A—N-[3-(2-Bromo-ethylamino)-4-tert-butyl-phenyl]-2-(1H-indazol-6-ylamino)-nicotinamide The title compound was prepared from N-[4-tert-butyl-3-(2-hydroxy-ethylamino)-phenyl]-2-(1H-indazol-6-ylamino)-nicotinamide by dissolving in $CH_2Cl_2$ (5 ml) and adding $CBr_4$ (215 mg) and bis(diphenylphosphino)-propane (270 mg). The reaction was stirred at RT for 3 h then worked up with partitioning between $H_2O$ and $CH_2Cl_2$. The aqueous layer was extracted with $CH_2Cl_2$ (3×) and the combined organic fractions were washed with $H_2O$, brine and dried ($MgSO_4$). The crude material was purified by flash chromatography to yield a yellow foamed solid. M+H 508.

Step B—N-[4-tert-Butyl-3-(2-morpholin-4-yl-ethylamino)-phenyl]-2-(1H-indazol-6-ylamino)-nicotinamide N-[3-(2-Bromo-ethylamino)-4-tert-butyl-phenyl]-2-(1H-indazol-6-ylamino)-nicotinamide was dissolved in DMF (2 ml) morpholine (0.09 ml) was added and stirred overnight at RT. The mixture was partitioned between sat'd NaHCO3 and EtOAc. The aqueous layer was extracted with EtOAc and the organic layers were washed with $H_2O$, brine and dried ($MgSO_4$). The crude material was purified by flash chromatography (5% $MeOH/CH_2Cl_2$) to yield a yellow foamed solid. MS (ES+): 514 (M+H), Calc'd for $C_{29}H_{35}N_7O_2$—513.6.

EXAMPLE 117

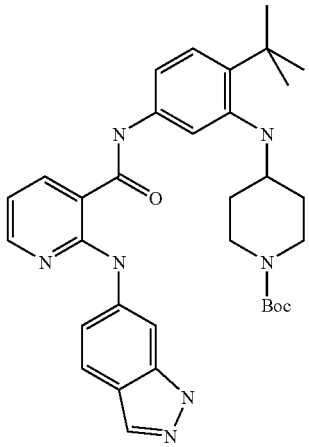

N-[4-tert-Butyl-3-(1-Boc-piperidin-4-ylamino)-phenyl]-2-(1H-indazol-6-ylamino)-nicotinamide The title compound was prepared from N-(3-amino-4-tert-butyl-phenyl)-2-(1H-indazol-6-ylamino)-nicotinamide and Boc-piperidin-4-one by a method analogous to that described in Example 42. MS (ES+): 584 (M+H), Calc'd for $C_{33}H_{41}N_7O_3$—583.7.

EXAMPLE 118

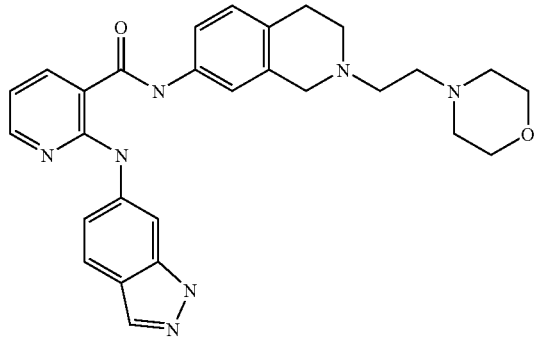

2-(1H-Indazol-6-ylamino)-N-[2-(2-morpholin-4-yl-ethyl)-1,2,3,4-tetrahydro-isoquinolin-7-yl]-nicotinamide 498 (M+1); 497 (M−1). Calc'd. for $C_{28}H_{31}N_7O_2$—497.6.

EXAMPLE 119

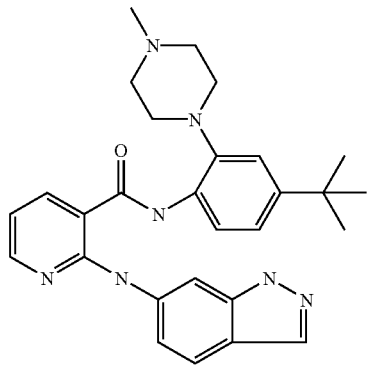

N-[4-tert-Butyl-2-(4-methyl-piperazin-1-yl)-phenyl]-2-(1H-indazol-6-ylamino)-nicotinamide MS (ES+): 484(M+H)$^+$; (ES−):482 (M−H). Calc'd. for $C_{28}H_{33}N_7O$—483.3.

EXAMPLE 120

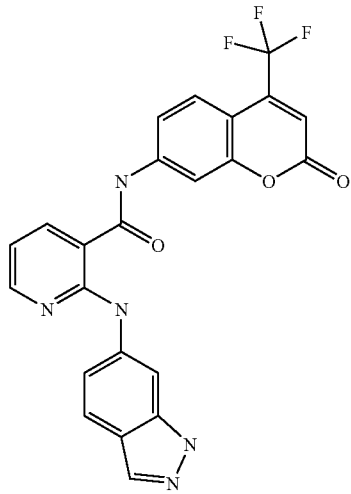

2-(1H-Indazol-6-ylamino)-N-(2-oxo-4-trifluoromethyl-2H-chromen-7-yl)-nicotinamide M+H 466. Calc'd for $C_{23}H_{14}F_3N_5O_3$: 465.1.

EXAMPLE 121

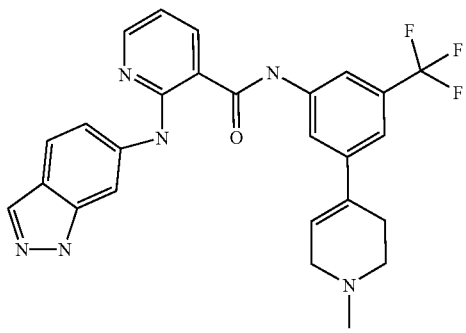

2-(1H-Indazol-6-ylamino)-N-[3-(1-methyl-1,2,3,6-tetrahydro-pyridin-4-yl)-5-trifluoromethyl-phenyl]-nicotinamide M+H, 493; M−H, 491; Calc'd for $C_{26}H_{23}F_3N_6O$: 492.

EXAMPLE 122

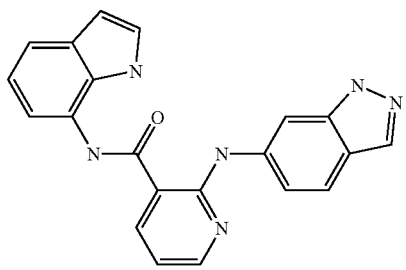

2-(1H-Indazol-6-ylamino)-N-(1H-indol-7-yl)-nicotinamide

MS: 369 (M+1). Calc'd. for $C_{21}H_{16}N_6O$—368.4.

EXAMPLE 123

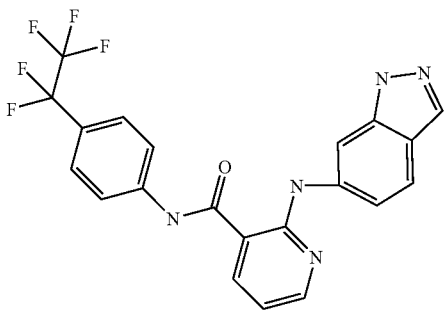

2-(1H-Indazol-6-ylamino)-N-(4-pentafluoroethyl-phenyl)-nicotinamide

M+H 448. Calc'd for $C_{21}H_{14}F_5N_5O$: 447.

EXAMPLE 124

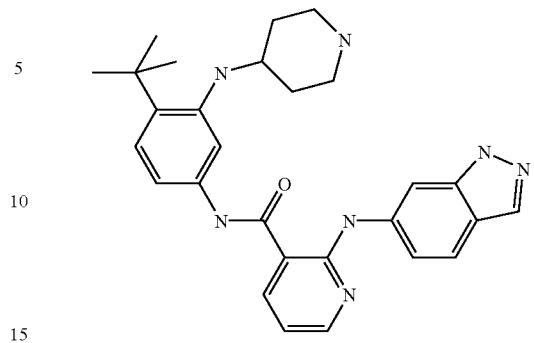

N-[4-tert-Butyl-3-(piperidin-4-ylamino)-phenyl]-2-(1H-indazol-6-ylamino)-nicotinamide MS (ES+): 484 (M+H), Calc'd for $C_{28}H_{33}N_7O$—483.6.

EXAMPLE 125

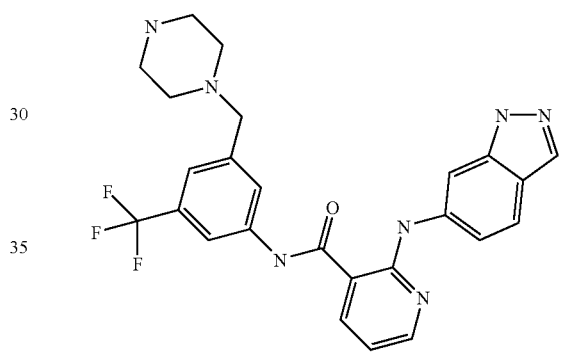

2-(1H-Indazol-6-ylamino)-N-(3-piperazin-1-ylmethyl-5-trifluoromethyl-phenyl)-nicotinamide M+H 496.3; Calc'd for $C_{25}H_{24}F_3N_7O$: 495.2.

EXAMPLE 126

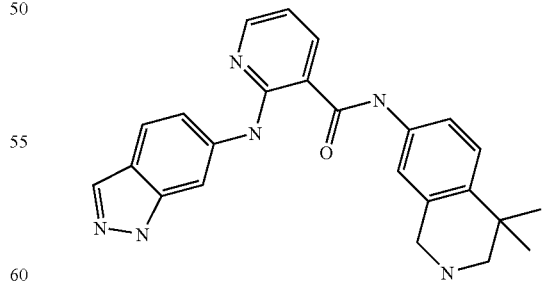

N-(4,4-Dimethyl-1,2,3,4-tetrahydro-isoquinolin-7-yl)-2-(1H-indazol-6-ylamino)-nicotinamide M+H 413.4. Calc'd for $C_{24}H_{24}N_6O$: 412.2.

EXAMPLE 127

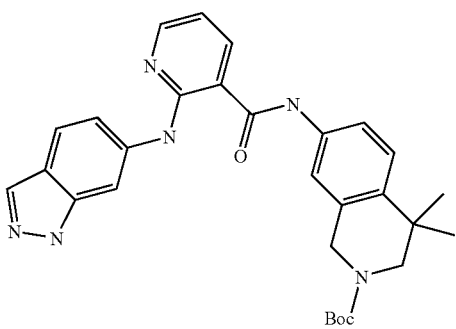

N-(1-Boc-4,4-Dimethyl-1,2,3,4-tetrahydro-isoquinolin-7-yl)-2-(1H-indazol-6-ylamino)-nicotinamide M+H 513. Calc'd for $C_{29}H_{32}N_6O_3$: 512.2.

EXAMPLE 128

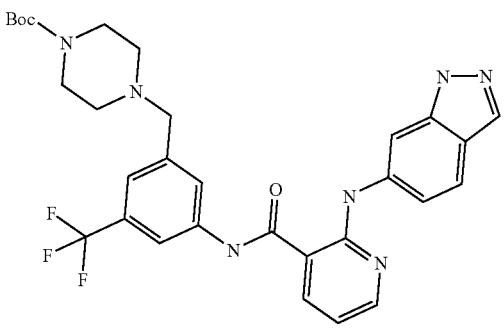

2-(1H-Indazol-6-ylamino)-N-[3-(4-Boc-piperazin-1-ylmethyl)-5-trifluoromethyl-phenyl]-nicotinamide M+H 596.4; Calc'd for $C_{30}H_{32}F_3N_7O_3$: 595.2.

EXAMPLE 129

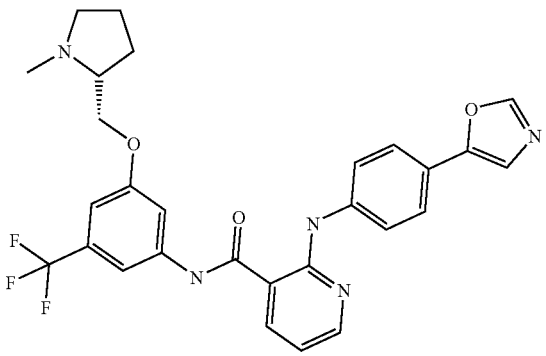

N-[3-(1-Methyl-pyrrolidin-2-ylmethoxy)-5-trifluoromethyl-phenyl]-2-(4-oxazol-5-yl-phenylamino)-nicotinamide M+H 538.2. Calc'd for $C_{28}H_{26}F_3N_5O_3$: 537.2.

Other compounds included in this invention are set forth in Tables 1–5 below.

TABLE 1

| # | R¹ | R² |
|---|---|---|
| 130. | 2-chlorophenyl | H |
| 131. | 4-benzimidazolyl | H |
| 132. | 5-benzimidazolyl | H |
| 133. | 7-benzimidazolyl | H |
| 134. | 2-chlorophenyl | 5-F |
| 135. | 3-isoquinolinyl | 5-F |
| 136. | 2-quinolinyl | 5-F |
| 137. | 2-benzthiazolyl | 5-F |
| 138. | 2-benzimidazolyl | 5-F |
| 139. | 4-benzimidazolyl | 5-F |
| 140. | 5-benzimidazolyl | 5-F |
| 141. | 6-benzimidazolyl | 5-F |
| 142. | 7-benzimidazolyl | 5-F |
| 143. | 4-chlorophenyl | 3-pyridyl |
| 144. | 4-pyridyl | H |
| 145. | 4-pyridyl | 6-CH₃ |
| 146. | 4-chlorophenyl- | 5-Cl |
| 147. | 3,4-dichlorophenyl- | 5-F |
| 148. | 4-fluorophenyl | 6-CH₃ |
| 149. | 3-chlorophenyl | 6-F |
| 150. | 3-fluorophenyl | 6-F |
| 151. | 3-fluoro-4-methoxyphenyl | 6-CH₃ |
| 152. | 3-fluoro-4-methylphenyl | 6-Cl |
| 153. | 4-phenoxyphenyl | H |
| 154. | 3-phenoxyphenyl | H |
| 155. | 4-biphenyl | H |
| 156. | 4-cyclohexylphenyl | H |
| 157. | 2-quinolyl | H |
| 158. | 3-isoquinolyl | H |
| 159. | 3-quinolyl | H |
| 160. | 1-isoquinolyl | H |
| 161. | 5-quinolyl | H |
| 162. | 5-isoquinolyl | H |
| 163. | 6-quinolyl | H |
| 164. | 6-isoquinolyl | H |
| 165. | 7-quinolyl | H |
| 166. | 7-isoquinolyl | H |
| 167. | 4-quinolyl | H |
| 168. | 4-isoquinolyl | H |
| 169. | 4-pyridyl | H |
| 170. | 4-pyrimidinyl | H |
| 171. | 2-pyrimidinyl | H |
| 172. | 6-pyrimidinyl | H |
| 173. | 4-pyridazinyl | H |
| 174. | 5-pyridazinyl | H |
| 175. | 4-indolyl | H |
| 176. | 5-isoindolyl | H |
| 177. | 5-naphthyridinyl | H |
| 178. | 6-quinozalinyl | H |
| 179. | 6-isoquinolyl | H |
| 180. | 4-naphthyridinyl | H |
| 181. | 5-quinozalinyl | H |
| 182. | 4-naphthyridinyl | H |
| 183. | 7-tetrahydroquinolinyl | H |
| 184. | 6-indazolyl | H |
| 185. | 6-isoindolyl | H |
| 186. | 5-indazolyl | H |
| 187. | 5-isoindolyl | H |
| 188. | 6-benzothienyl | H |
| 189. | 6-benzofuryl | H |
| 190. | 5-benzothienyl | H |
| 191. | 5-benzofuryl | H |

TABLE 1-continued

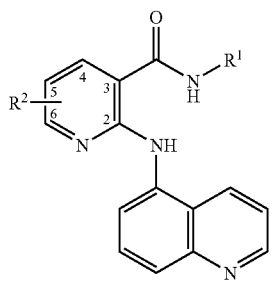

| # | R¹ | R² |
|---|---|---|
| 192. | 2-benzimidazolyl | H |
| 193. | 2-benzoxazolyl | H |
| 194. | 2-benzthiazolyl | H |
| 195. | 6-benzimidazolyl | H |
| 196. | 6-benzoxazolyl | H |
| 197. | 6-benzthiazolyl | H |
| 198. | 2-quinazolinyl | H |
| 199. | 3-(phenoxy)-6-pyridyl | H |
| 200. | 4-(phenylcarbonyl)phenyl | H |
| 201. | 4-(phenylamino)phenyl | H |
| 202. | 4-cyclohexyloxyphenyl | H |
| 203. | 4-(3-thienyl)phenyl | H |
| 204. | 4-(pyrazol-3-yl)phenyl | H |
| 205. | 4-chlorophenyl | 6-Cl |
| 206. | 4-pyridyl | 6-Cl |
| 207. | 3-methoxyphenyl | 6-Cl |
| 208. | 4-hydroxyphenyl | 6-Cl |
| 209. | 3-hydroxyphenyl | H |
| 210. | 2-hydroxyphenyl | H |
| 211. | 4-chlorophenyl | 6-phenyl |
| 212. | 4-phenoxyphenyl | 6-F |
| 213. | 4-biphenyl | 6-phenyl |
| 214. | 4-hydroxyphenyl | 6-phenyl |
| 215. | 4-cyclohexylphenyl | 6-F |
| 216. | 3-isoquinolyl | 6-phenyl |
| 217. | 4-piperidinylmethylphenyl | H |
| 218. | 4-morpholinylmethylphenyl | H |

TABLE 2a

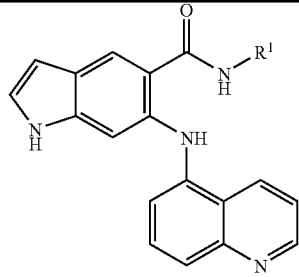

| # | R¹ |
|---|---|
| 219. | 4-chlorophenyl |
| 220. | 3,4-dichlorophenyl |
| 221. | 4-phenoxyphenyl |
| 222. | 4-biphenyl |

TABLE 2a-continued

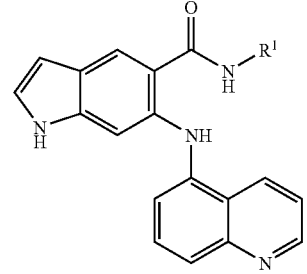

| # | R¹ |
|---|---|
| 223. | 4-cyclohexylphenyl |
| 224. | 3-isoquinolyl |

TABLE 2b

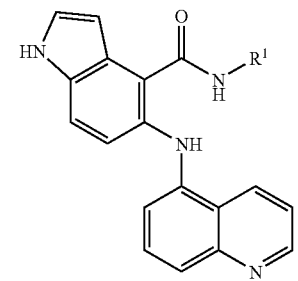

| # | R¹ |
|---|---|
| 225. | 4-chlorophenyl |
| 226. | 3,4-dichlorophenyl |
| 227. | 4-phenoxyphenyl |
| 228. | 4-biphenyl |
| 229. | 4-cyclohexylphenyl |
| 230. | 3-isoquinolyl |

TABLE 2c

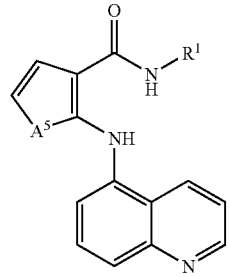

| # | R¹ | A⁵ |
|---|---|---|
| 231. | 4-chlorophenyl | NH |
| 232. | 3,4-dichlorophenyl | NH |
| 233. | 4-phenoxyphenyl | NH |
| 234. | 4-biphenyl | NH |
| 235. | 4-cyclohexylphenyl | NH |
| 236. | 3-isoquinolyl | NH |
| 237. | 4-chlorophenyl | O |
| 238. | 3,4-dichlorophenyl | O |
| 239. | 4-phenoxyphenyl | O |
| 240. | 4-biphenyl | O |
| 241. | 4-cyclohexylphenyl | O |
| 242. | 3-isoquinolyl | O |
| 243. | 3,4-dichlorophenyl | S |
| 244. | 4-phenoxyphenyl | S |
| 245. | 4-biphenyl | S |
| 246. | 4-cyclohexylphenyl | S |
| 247. | 3-isoquinolyl | S |

TABLE 2d

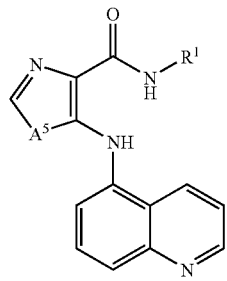

| # | R¹ | A⁵ |
|---|---|---|
| 248. | 4-chlorophenyl | NH |
| 249. | 3,4-dichlorophenyl | NH |
| 250. | 4-phenoxyphenyl | NH |
| 251. | 4-biphenyl | NH |
| 252. | 4-cyclohexylphenyl | NH |
| 253. | 3-isoquinolyl | NH |
| 254. | 4-chlorophenyl | O |
| 255. | 3,4-dichlorophenyl | O |
| 256. | 4-phenoxyphenyl | O |
| 257. | 4-biphenyl | O |
| 258. | 4-cyclohexylphenyl | O |
| 259. | 3-isoquinolyl | O |
| 260. | 3,4-dichlorophenyl | S |
| 261. | 4-phenoxyphenyl | S |
| 262. | 4-biphenyl | S |
| 263. | 4-cyclohexylphenyl | S |
| 264. | 3-isoquinolyl | S |

TABLE 2e

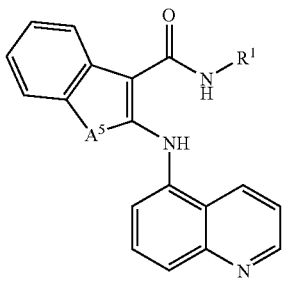

| # | R¹ | A⁵ |
|---|---|---|
| 265. | 4-chlorophenyl | NH |
| 266. | 3,4-dichlorophenyl | NH |
| 267. | 4-phenoxyphenyl | NH |
| 268. | 4-biphenyl | NH |
| 269. | 4-cyclohexylphenyl | NH |
| 270. | 3-isoquinolyl | NH |
| 271. | 4-chlorophenyl | O |
| 272. | 3,4-dichlorophenyl | O |
| 273. | 4-phenoxyphenyl | O |
| 274. | 4-biphenyl | O |
| 275. | 4-cyclohexylphenyl | O |
| 276. | 3-isoquinolyl | O |
| 277. | 3,4-dichlorophenyl | S |
| 278. | 4-phenoxyphenyl | S |
| 279. | 4-biphenyl | S |
| 280. | 4-cyclohexylphenyl | S |
| 281. | 3-isoquinolyl | S |

TABLE 2f

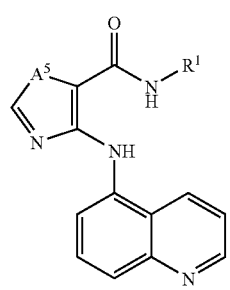

| # | R¹ | A⁵ |
|---|---|---|
| 282. | 4-chlorophenyl | NH |
| 283. | 3,4-dichlorophenyl | NH |
| 284. | 4-phenoxyphenyl | NH |
| 285. | 4-biphenyl | NH |
| 286. | 4-cyclohexylphenyl | NH |
| 287. | 3-isoquinolyl | NH |
| 288. | 4-chlorophenyl | O |
| 289. | 3,4-dichlorophenyl | O |
| 290. | 4-phenoxyphenyl | O |
| 291. | 4-biphenyl | O |
| 292. | 4-cyclohexylphenyl | O |
| 293. | 3-isoquinolyl | O |
| 294. | 3,4-dichlorophenyl | S |
| 295. | 4-phenoxyphenyl | S |
| 296. | 4-biphenyl | S |
| 297. | 4-cyclohexylphenyl | S |
| 298. | 3-isoquinolyl | S |

TABLE 2g

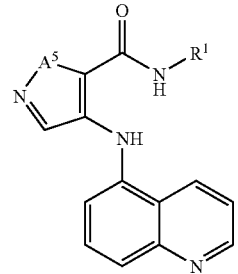

| # | R¹ | A⁵ |
|---|---|---|
| 299. | 4-chlorophenyl | NH |
| 300. | 3,4-dichlorophenyl | NH |
| 301. | 4-phenoxyphenyl | NH |
| 302. | 4-biphenyl | NH |
| 303. | 4-cyclohexylphenyl | NH |
| 304. | 3-isoquinolyl | NH |
| 305. | 4-chlorophenyl | O |
| 306. | 3,4-dichlorophenyl | O |
| 307. | 4-phenoxyphenyl | O |
| 308. | 4-biphenyl | O |
| 309. | 4-cyclohexylphenyl | O |
| 310. | 3-isoquinolyl | O |

TABLE 2h

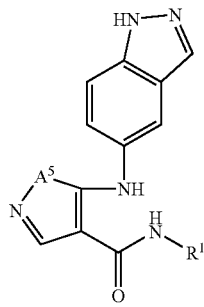

| # | R¹ | A⁵ |
|---|---|---|
| 311. | 4-chlorophenyl | NCH₃ |
| 312. | 3,4-dichlorophenyl | NCH₃ |
| 313. | 4-phenoxyphenyl | NH |
| 314. | 4-biphenyl | NH |
| 315. | 4-cyclohexylphenyl | NH |
| 316. | 4-tertbutylphenyl | NCH₃ |
| 317. | 4-chlorophenyl | O |
| 318. | 3,4-dichlorophenyl | O |
| 319. | 4-phenoxyphenyl | O |
| 320. | 4-biphenyl | O |
| 321. | 4-cyclohexylphenyl | O |
| 322. | 3-isoquinolyl | O |

TABLE 3

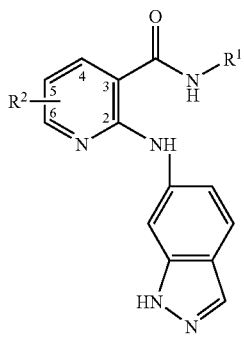

| # | R¹ | R² |
|---|---|---|
| 323. | 4-chlorophenyl | 5-Br |
| 324. | 3-chlorophenyl | H |
| 325. | 3-chlorophenyl | 5-Br |
| 326. | 3-isoquinolyl | H |
| 327. | 3-isoquinolyl | 5-Br |
| 328. | 4-phenoxyphenyl | 5-Br |
| 329. | (3-tert-butyl-5-methylisoxazolyl) | 5-Br |
| 330. | (5-tert-butyl-3-methylpyrazolyl) | H |
| 331. | (4-tert-butylphenyl) | 5-Br |

TABLE 3-continued

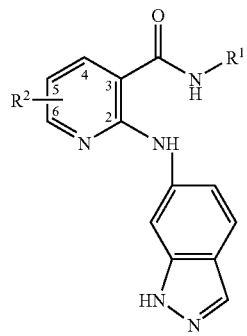

| # | R¹ | R² |
|---|---|---|
| 332. | (3,3-dimethyl-6-methylindolinyl) | 5-Br |
| 333. | 4-chlorophenyl | 6-Cl |
| 334. | 3,4-dichlorophenyl | H |
| 335. | 4-fluorophenyl | H |
| 336. | 3-fluorophenyl | H |
| 337. | 3-fluoro-4-methoxyphenyl | H |
| 338. | 3-fluoro-4-methylphenyl | H |
| 339. | 3-phenoxyphenyl | H |
| 340. | 4-cyclohexylphenyl | H |
| 341. | 2-quinolyl | H |
| 342. | 3-quinolyl | H |
| 343. | 1-isoquinolyl | H |
| 344. | 5-quinolyl | H |
| 345. | 5-isoquinolyl | H |
| 346. | 6-quinolyl | H |
| 347. | 6-isoquinolyl | H |
| 348. | 7-quinolyl | H |
| 349. | 7-isoquinolyl | H |
| 350. | 4-quinolyl | H |
| 351. | 4-isoquinolyl | H |
| 352. | 4-pyridyl | H |
| 353. | 4-pyrimidinyl | H |
| 354. | 2-pyrimidinyl | H |
| 355. | 6-pyrimidinyl | H |
| 356. | 4-pyridazinyl | H |
| 357. | 5-pyridazinyl | H |
| 358. | 4-indolyl | H |
| 359. | 5-isoindolyl | H |
| 360. | 5-naphthyridinyl | H |
| 361. | 6-quinozalinyl | H |
| 362. | 6-isoquinolyl | H |
| 363. | 4-naphthyridinyl | H |
| 364. | 5-quinozalinyl | H |
| 365. | 4-naphthyridinyl | H |
| 366. | tetrahydroquinolinyl | H |
| 367. | 6-indazolyl | H |
| 368. | 6-isoindolyl | H |
| 369. | 5-indazolyl | H |
| 370. | 5-isoindolyl | H |
| 371. | 6-benzothienyl | H |
| 372. | 6-benzofuryl | H |
| 373. | 5-benzothienyl | H |
| 374. | 5-benzofuryl | H |
| 375. | 6-benzthiazolyl | H |
| 376. | 2-quinazolinyl | H |
| 377. | 3-(phenoxy)-6-pyridyl | H |
| 378. | 4-(phenylcarbonyl)phenyl | H |
| 379. | 4-(phenylamino)phenyl | H |
| 380. | cyclohexyloxyphenyl | H |
| 381. | 4-(3-thienyl)phenyl | H |
| 382. | 4-(pyrazol-3-yl)phenyl | 6-CH₃ |
| 383. | 2-benzimidazolyl | H |

TABLE 3-continued
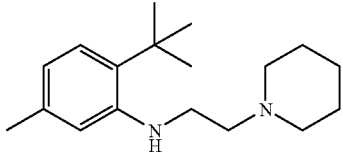
| # | R¹ | R² |
|---|---|---|
| 384. | 2-benzoxazolyl | H |
| 385. | 2-benzthiazolyl | H |
| 386. | 6-benzimidazolyl | H |
| 387. | 6-benzoxazolyl | H |
| 388. | 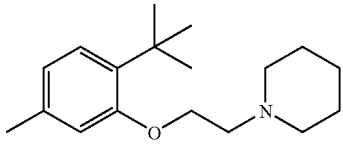 | H |
| 389. | 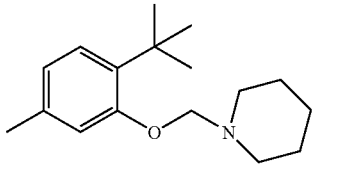 | H |
| 390. | 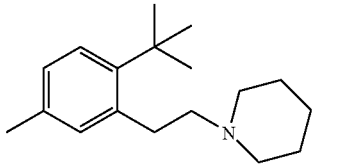 | H |
| 391. | 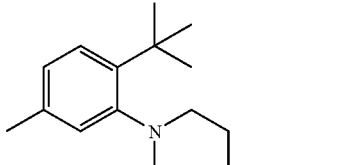 | H |
| 392. | 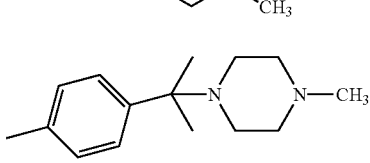 | 5-Br |
| 393. | 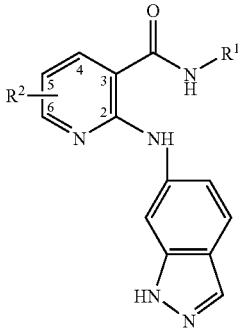 | H |
TABLE 3-continued
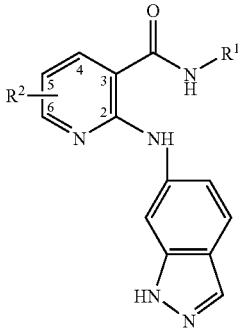
| # | R¹ | R² |
|---|---|---|
| 394. | 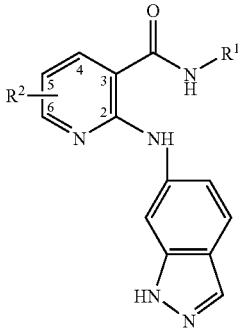 | H |
| 395. | 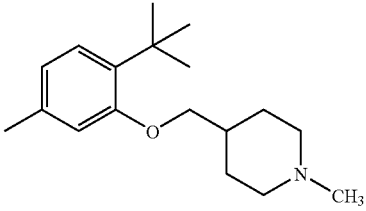 | H |
| 396. | 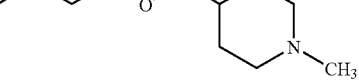 | H |
| 397. | 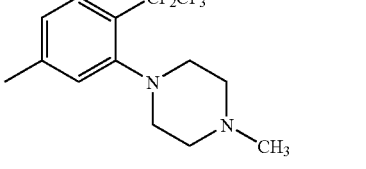 | H |
| 398. | 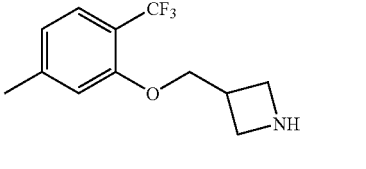 | H |
| 399. |  | 5-Br |
| 400. | 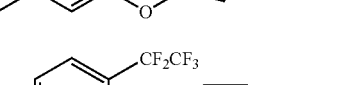 | H |

TABLE 3-continued

| # | R¹ | R² |
|---|---|---|
| 401. | 3-CF₃, 5-methyl-phenyl-N-(4-methylpiperazin-1-yl) | H |
| 402. | 3,3,6-trimethyl-1-(piperidin-4-ylmethyl)indoline | 5-Br |
| 403. | 3,3,6-trimethyl-1-((1-methylpiperidin-4-yl)methyl)indoline | 5-Br |
| 404. | 3,3,6-trimethyl-1-(1-methylpiperidin-4-yl)indoline | 5-Br |
| 405. | (3-CF₃, 5-methyl-phenyl)(4-methylpiperazin-1-yl)methanone | H |
| 406. | 3,3,6-trimethyl-1-(pyrrolidin-2-ylmethyl)indoline | H |
| 407. | 2-tert-butyl-5-methyl-phenyl-C≡C-CH₂-N(CH₃)₂ | H |
| 408. | 4-bromo-2-fluoro-1-methyl-phenyl | H |
| 409. | 6-methyl-2-(2-morpholinoethyl)-1,2,3,4-tetrahydroisoquinoline | H |
| 410. | 3-CF₃, 5-(2-(dimethylamino)ethoxy)-phenyl-CN | H |
| 411. | 3-CF₃, 5-(2-(pyrrolidin-1-yl)ethoxy)-phenyl-CN | H |

TABLE 3-continued

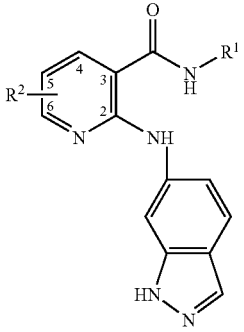

| # | R¹ | R² |
|---|---|---|
| 412. | 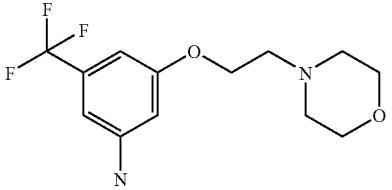 | H |
| 413. | 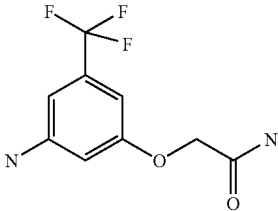 | H |
| 414. | 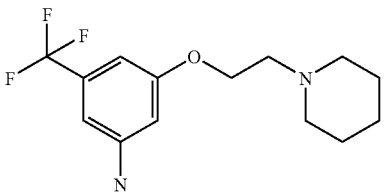 | H |
| 415. | 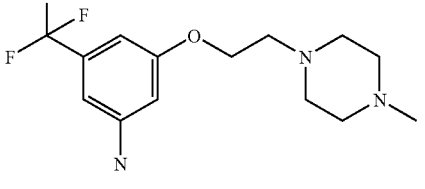 | H |
| 416. | 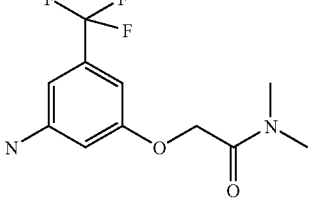 | H |

TABLE 3-continued

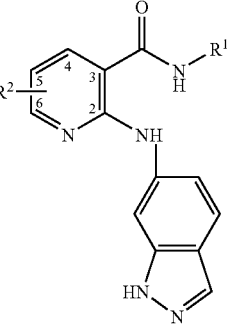

| # | R¹ | R² |
|---|---|---|
| 417. | 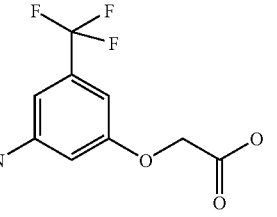 | H |

TABLE 4

| # | R¹ | R² |
|---|---|---|
| 418. | 4-chlorophenyl | 6-Cl |
| 419. | 3,4-dichlorophenyl | 5-Cl |
| 420. | 4-fluorophenyl | H |
| 421. | 3-chlorophenyl | H |
| 422. | 3-fluorophenyl | H |
| 423. | 3-fluoro-4-methoxyphenyl | H |
| 424. | 3-fluoro-4-methylphenyl | H |
| 425. | 4-phenoxyphenyl | H |
| 426. | 3-phenoxyphenyl | H |
| 427. | 4-biphenyl | H |
| 428. | 4-cyclohexylphenyl | H |
| 429. | 2-quinolyl | H |
| 430. | 3-isoquinolyl | H |
| 431. | 3-quinolyl | H |
| 432. | 1-isoquinolyl | H |
| 433. | 5-quinolyl | H |
| 434. | 5-isoquinolyl | H |
| 435. | 6-quinolyl | H |
| 436. | 6-isoquinolyl | H |
| 437. | 7-quinolyl | H |
| 438. | 7-isoquinolyl | H |
| 439. | 4-quinolyl | H |

TABLE 4-continued

| # | R¹ | R² |
|---|---|---|
| 440. | 4-isoquinolyl | H |
| 441. | 4-pyridyl | H |
| 442. | 4-pyrimidinyl | H |
| 443. | 2-pyrimidinyl | H |
| 444. | 6-pyrimidinyl | H |
| 445. | 4-pyridazinyl | H |
| 446. | 5-pyridazinyl | H |
| 447. | 4-indolyl | H |
| 448. | 5-isoindolyl | H |
| 449. | 5-naphthyridinyl | H |
| 450. | 6-quinozalinyl | H |
| 451. | 6-isoquinolyl | H |
| 452. | 4-naphthyridinyl | H |
| 453. | 5-quinozalinyl | H |
| 454. | 4-naphthyridinyl | H |
| 455. | tetrahydroquinolinyl | H |
| 456. | 6-indazolyl | H |
| 457. | 6-isoindolyl | H |
| 458. | 5-indazolyl | H |
| 459. | 5-isoindolyl | H |
| 460. | 6-benzothienyl | H |
| 461. | 6-benzofuryl | H |
| 462. | 5-benzothienyl | H |
| 463. | 5-benzofuryl | H |
| 464. | 2-benzimidazolyl | H |
| 465. | 2-benzoxazolyl | H |
| 466. | 2-benzthiazolyl | H |
| 467. | 6-benzimidazolyl | H |
| 468. | 6-benzoxazolyl | H |
| 469. | 6-benzthiazolyl6-benzoxazolyl | H |
| 470. | 2-quinazolinyl6-benzoxazolyl | H |
| 471. | 3-(phenoxy)-6-pyridyl | H |
| 472. | 4-(phenylcarbonyl)phenyl | H |
| 473. | 4-(phenylamino)phenyl | H |
| 474. | cyclohexyloxyphenyl | H |
| 475. | 4-(3-thienyl)phenyl | H |
| 476. | 4-(pyrazol-3-yl)phenyl | H |
| 477. | 4-chlorophenyl | EtO₂CCH=CH— |
| 478. | 4-chlorophenyl | 5-Br |

TABLE 5

| # | R¹ |
|---|---|
| 479. | 4-chlorophenyl |
| 480. | 3-chlorophenyl |
| 481. | 3-chlorophenyl |
| 482. | 3-isoquinolyl |
| 483. | 3-isoquinolyl |
| 484. | 4-phenoxyphenyl |
| 485. | (3-tert-butyl-5-methylisoxazolyl structure) |
| 486. | (3-tert-butyl-5-methylpyrazolyl structure) |
| 487. | 4-chlorophenyl |
| 488. | 3,4-dichlorophenyl |
| 489. | 4-fluorophenyl |
| 490. | 3-fluorophenyl |
| 491. | 3-fluoro-4-methoxyphenyl |
| 492. | 3-fluoro-4-methylphenyl |
| 493. | 3-phenoxyphenyl |
| 494. | 4-cyclohexylphenyl |
| 495. | 2-quinolyl |
| 496. | 3-quinolyl |
| 497. | 1-isoquinolyl |
| 498. | 5-quinolyl |
| 499. | 5-isoquinolyl |
| 500. | 6-quinolyl |
| 501. | 6-isoquinolyl |
| 502. | 7-quinolyl |
| 503. | 7-isoquinolyl |
| 504. | 4-quinolyl |
| 505. | 4-isoquinolyl |
| 506. | 4-pyridyl |
| 507. | 4-pyrimidinyl |
| 508. | 2-pyrimidinyl |
| 509. | 6-pyrimidinyl |
| 510. | 4-pyridazinyl |
| 511. | 5-pyridazinyl |
| 512. | 4-indolyl |
| 513. | 5-isoindolyl |
| 514. | 5-naphthyridinyl |
| 515. | 6-quinozalinyl |
| 516. | 6-isoquinolyl |
| 517. | 4-naphthyridinyl |
| 518. | 5-quinozalinyl |
| 519. | 4-naphthyridinyl |
| 520. | tetrahydroquinolinyl |
| 521. | 6-indazolyl |
| 522. | 6-isoindolyl |
| 523. | 5-indazolyl |
| 524. | 5-isoindolyl |

TABLE 5-continued

| # | R¹ |
|---|-----|
| 525. | 6-benzothienyl |
| 526. | 6-benzofuryl |
| 527. | 5-benzothienyl |
| 528. | 5-benzofuryl |
| 529. | 6-benzthiazolyl |
| 530. | 2-quinazolinyl |
| 531. | 3-(phenoxy)-6-pyridyl |
| 532. | 4-(phenylcarbonyl)phenyl |
| 533. | 4-(phenylamino)phenyl |
| 534. | cyclohexyloxyphenyl |
| 535. | 4-(3-thienyl)phenyl |
| 536. | 4-(pyrazol-3-yl)phenyl |
| 537. | 2-benzimidazolyl |
| 538. | 2-benzoxazolyl |
| 539. | 2-benzthiazolyl |
| 540. | 6-benzimidazolyl |
| 541. | 6-benzoxazolyl |
| 542. | |
| 543. | |
| 544. | |
| 545. | |
| 546. | |
| 547. | |
| 548. | |
| 549. | |
| 550. | |
| 551. | |
| 552. | |

TABLE 5-continued
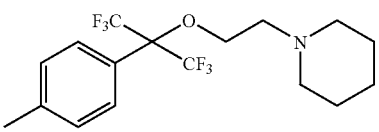
| # | R¹ |
|---|---|
| 553. | 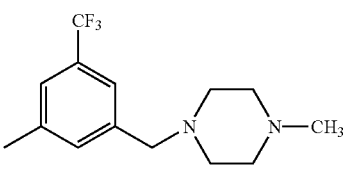 |
| 554. | 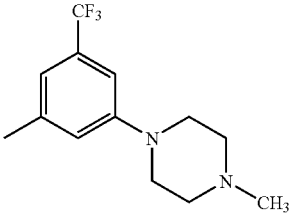 |
| 555. | 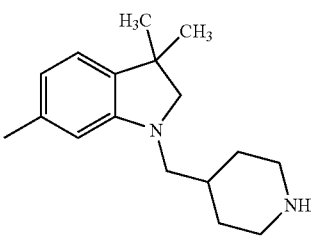 |
| 556. | 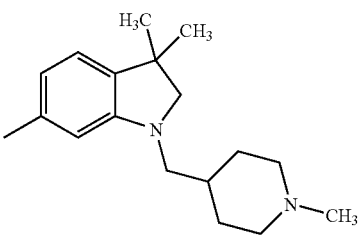 |
| 557. | 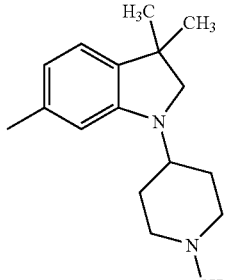 |
TABLE 5-continued
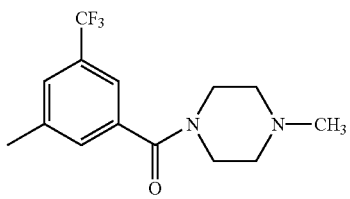
| # | R¹ |
|---|---|
| 558. | 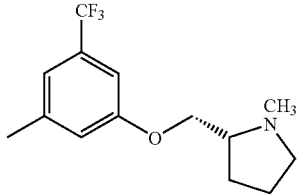 |
| 559. | 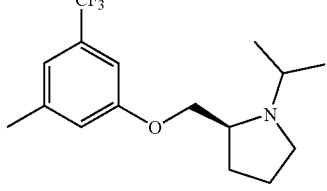 |
| 560. | 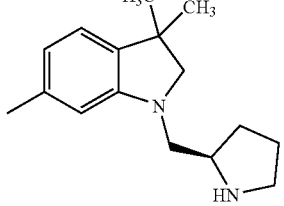 |
| 561. |  |
| 562. |  |

TABLE 5-continued

| # | R¹ |
|---|---|
| 563. | 2-tert-butyl-5-methylphenyl with 3-(dimethylamino)prop-1-ynyl substituent |
| 564. | 5-bromo-2-methyl-3-fluorophenyl |
| 565. | 6-methyl-2-(2-morpholinoethyl)-1,2,3,4-tetrahydroisoquinolin-yl |
| 566. | 3-(trifluoromethyl)-5-[2-(dimethylamino)ethoxy]phenyl with N |
| 567. | 3-(trifluoromethyl)-5-[2-(pyrrolidin-1-yl)ethoxy]phenyl with N |
| 568. | 3-(trifluoromethyl)-5-[2-morpholinoethoxy]phenyl with N |
| 569. | 3-(trifluoromethyl)-5-[(carbamoylmethyl)oxy]phenyl with N |
| 570. | 3-(trifluoromethyl)-5-[2-(piperidin-1-yl)ethoxy]phenyl with N |
| 571. | 3-(trifluoromethyl)-5-[2-(4-methylpiperazin-1-yl)ethoxy]phenyl with N |
| 572. | 3-(trifluoromethyl)-5-[(N,N-dimethylcarbamoylmethyl)oxy]phenyl with N |
| 573. | 3-(trifluoromethyl)-5-(carboxymethoxy)phenyl with N |

EXAMPLE 574

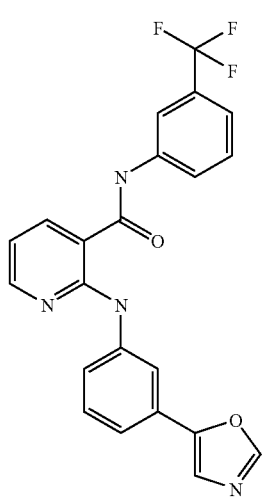

2-(3-Oxazol-5-yl-phenylamino)-N-(3-trifluoromethyl-phenyl)-nicotinamide

MS: 447.4 [M+Na]$^+$, 424.9 [M+H]$^+$. Calc'd for C$_{22}$H$_{15}$F$_3$N$_4$O$_2$ 424.4.

EXAMPLE 575

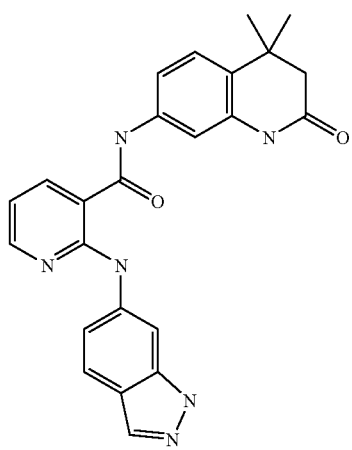

N-(4,4-Dimethyl-2-oxo-1,2,3,4-tetrahydro-quinolin-7-yl)-2-(1H-indazol-6-ylamino)-nicotinamide MS: [M+H]$^+$—427.1. Calc'd for C$_{24}$H$_{22}$N$_6$O$_2$: 426.2.

EXAMPLE 576

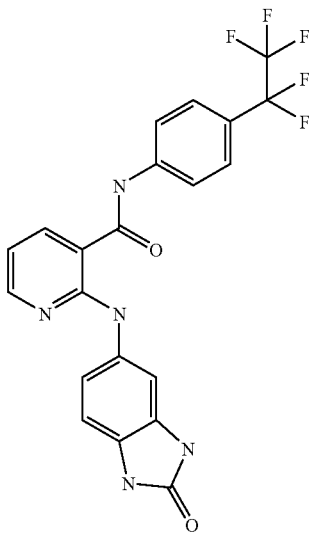

2-(2-Oxo-2,3-dihydro-1H-benzoimidazol-5-ylamino)-N-(4-pentafluoroethyl-phenyl)-nicotinamide MS: M+H 464. Calc'd for C$_{21}$H$_{14}$F$_5$N$_5$O$_2$: 463.1.

EXAMPLE 577

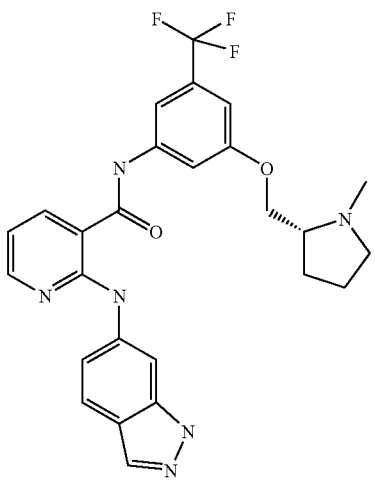

2-(1H-Indazol-6-ylamino)-N-(3-((((2R)-1-methyl-2-pyrrolidinyl)methyl)oxy)-5-(trifluoromethyl)phenyl)-3-pyridinecarboxamide MS: Calc'd for C$_{26}$H$_{25}$F$_3$N$_6$O$_2$—510.517; M+H 511.

EXAMPLE 578

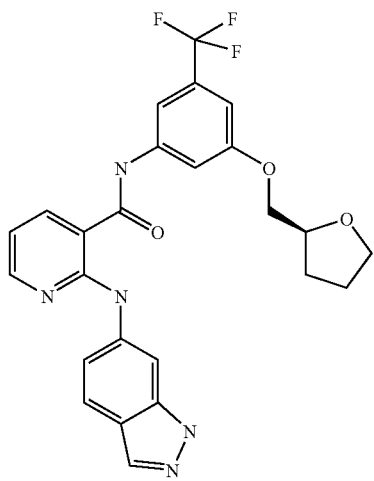

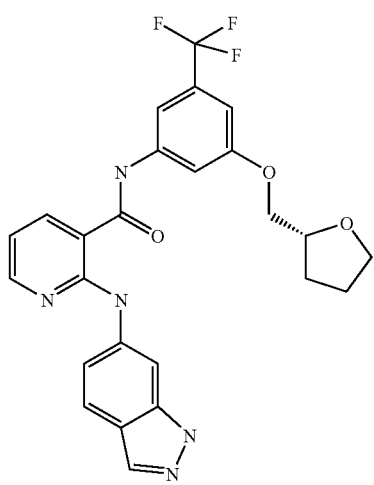

2-(1H-Indazol-6-ylamino)-N-(3-(((2S)-tetrahydro-2-furanylmethyl)oxy)-5-(trifluoromethyl)phenyl)-3-pyridinecsarboxamide 2-(1H-Indazol-6-ylamino)-N-(3-(((2R)-tetrahydro-2-furanylmethyl)oxy)-5-(trifluoromethyl)phenyl)-3-pyridinecsarboxamide MS: $C_{25}H_{22}F_3N_5O_3$—497.475; M+H 498, M+Na 520.

EXAMPLE 579

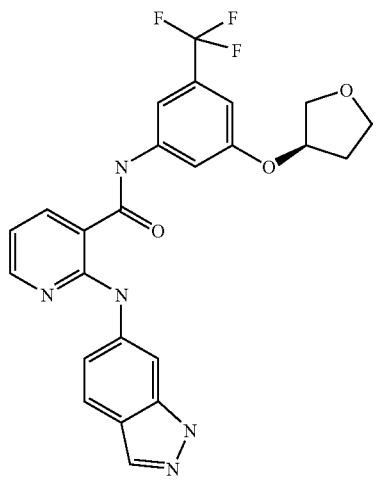

2-(1H-Indazol-6-ylamino)-N-(3-(((3R)-tetrahydro-3-furanyloxy)-5-(trifluoromethyl)phenyl)-3-pyridinecarboxamide

MS: $C_{24}H_{20}F_3N_5O_3$—483.448; M+H 484.

EXAMPLE 580

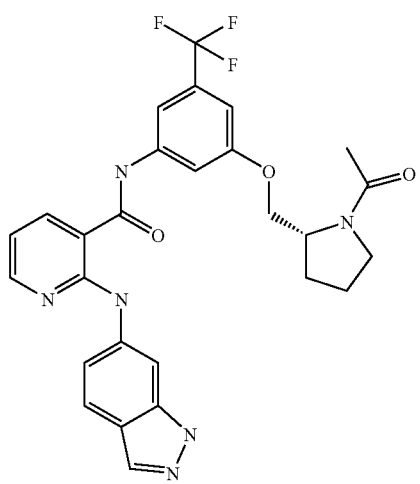

N-(3-((((2R)-1-Acetyl-2-pyrrolidinyl)methyl)oxy)-5-(trifluoromethyl)phenyl)-2-(1H-indazol-6-ylamino)-3-pyridinecarboxamide

MS: $C_{27}H_{25}F_3N_6O_3$—538.528; M+H 539.

EXAMPLE 581

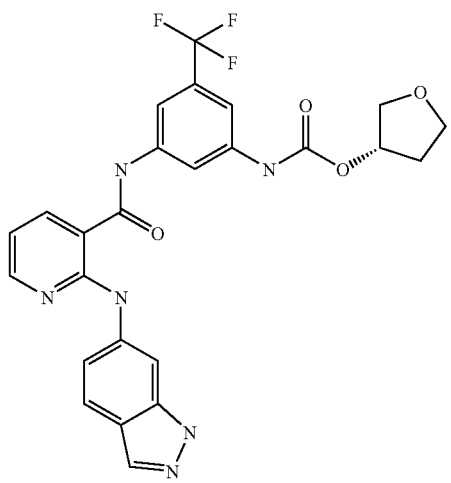

(3S)-Tetrahydro-3-furanyl 3-(((2-(1H-indazol-6-ylamino)-3-pyridinyl)carbonyl)amino)-5-(trifluoromethyl)phenylcarbamate

MS: $C_{25}H_{21}F_3N_6O_4$—526.473; M+H 527.

EXAMPLE 582

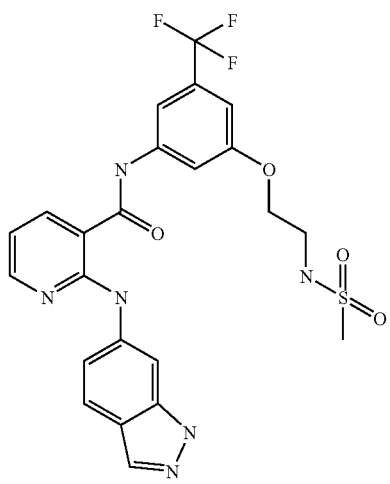

2-(1H-Indazol-6-ylamino)-N-(3-((2-((methylsulfonyl)amino)ethyl)oxy)-5-(trifluoromethyl)phenyl)-3-pyridinecarboxamide MS: $C_{23}H_{21}F_3N_6O_4S$—534.517; M+H 535, M+Na 557.

EXAMPLE 583

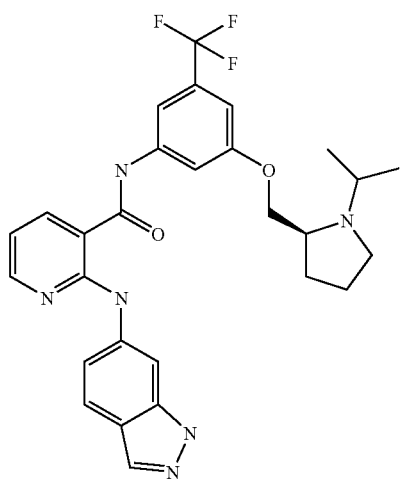

2-(1H-Indazol-6-ylamino)-N-(3-(((((2S)-1-(1-methylethyl)-2-pyrrolidinyl)methyl)oxy)-5-(trifluoromethyl)phenyl)-3-pyridinecarboxamide

MS: $C_{28}H_{29}F_3N_6O_2$—538.571; M+H 539.

EXAMPLE 584

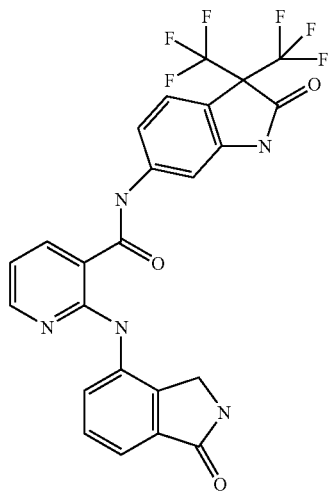

N-(2-Oxo-3,3-bis(trifluoromethyl)-2,3-dihydro-1H-indol-6-yl)-2-((1-oxo-2,3-dihydro-1H-isoindol-4-yl)amino)-3-pyridinecarboxamide MS: M+H 536; Calc'd for $C_{24}H_{15}F_6N_5O_3$—535.403.

EXAMPLE 585

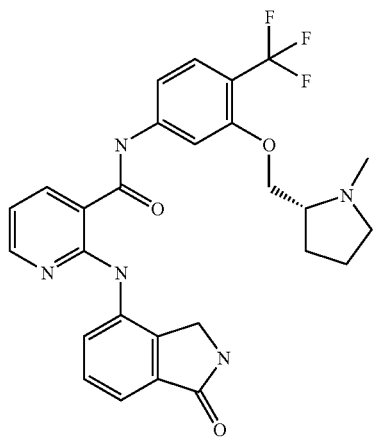

N-(3-((((2R)-1-Methyl-2-pyrrolidinyl)methyl)oxy)-4-(trifluoromethyl)phenyl)-2-((1-oxo-2,3-dihydro-1H-isoindol-4-yl)amino)-3-pyridinecarboxamide MS: M+H 526.1; Calc'd for $C_{27}H_{26}F_3N_5O_3$—525.528.

EXAMPLE 586

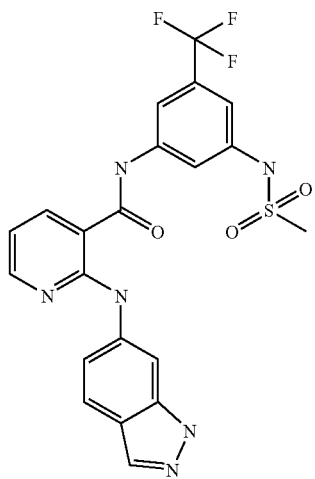

2-(1H-Indazol-6-ylamino)-N-(3-((methylsulfonyl)amino)-5-(trifluoromethyl)phenyl)-3-pyridinecarboxamide

MS: $C_{21}H_{17}F_3N_6O_3S$—490.464; M+H 491.

EXAMPLE 587

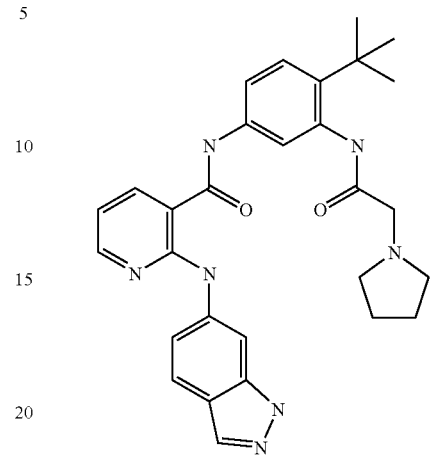

N-(4-(1,1-Dimethylethyl)-3-((1-pyrrolidinylacetyl)amino)phenyl)-2-(1H-indazol-6-ylamino)-3-pyridinecarboxamide MS: Calc'd for $C_{29}H_{33}N_7O_2$—511.627; M+H 512.

EXAMPLE 588

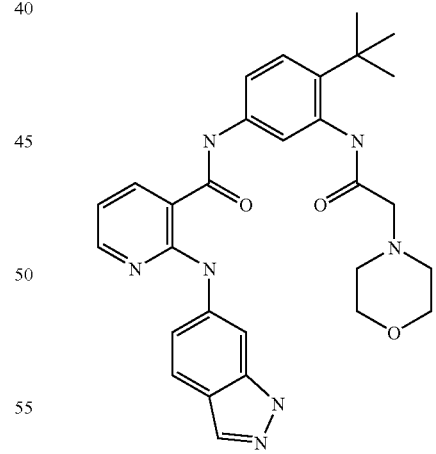

N-(4-(1,1-Dimethyl)-3-((4-morpholinylacetyl)amino)phenyl)-2-(1H-indazol-6-ylamino)-3-pyridinecarboxamide MS: Calc'd for $C_{29}H_{33}N_7O_3$—527.626; M+H 528.

EXAMPLE 589

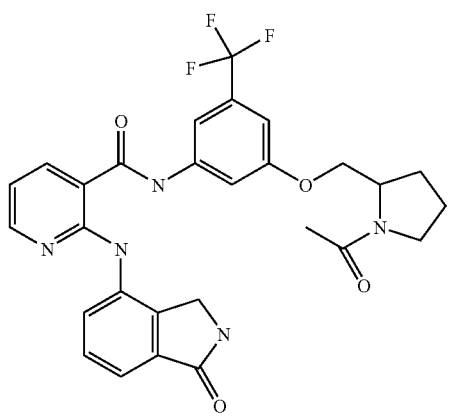

4-((3-((3-(2-(1-Acetyl-2-pyrrolidinyl)ethyl)-5-(trifluoromethyl)phenyl)acetyl)-2-pyridinyl)amino)-2,3-dihydro-1H-isoindol-1-one

EXAMPLE 590

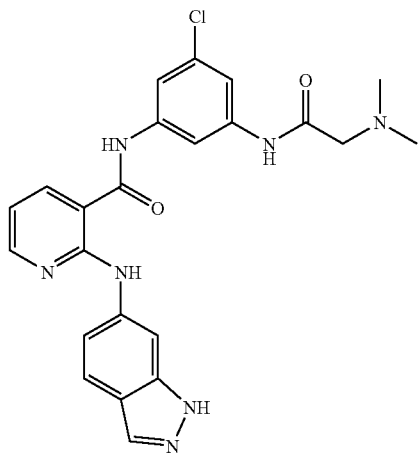

N-[3-Chloro-5-(2-dimethylamino-acetylamino)-phenyl]-2-(1H-indazol-6-ylamino)-nicotinamide MS: (ES+) 464 (M+H). Calc'd. for $C_{23}H_{22}ClN_7O_2$—463.93.

EXAMPLE 591

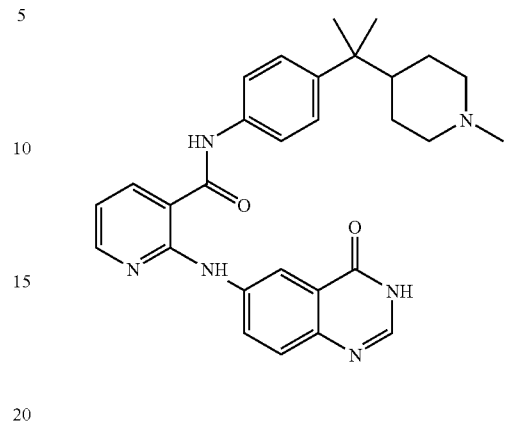

N-{4-[1-Methyl-1-(1-methyl-piperidin-4-yl)-ethyl]-phenyl}-2-(4-oxo-3,4-dihydro-quinazolin-6-ylamino)-nicotinamide MS: (ES+) 497 (M+H). Calc'd. for $C_{29}H_{32}N_6O_2$—496.61.

EXAMPLE 592

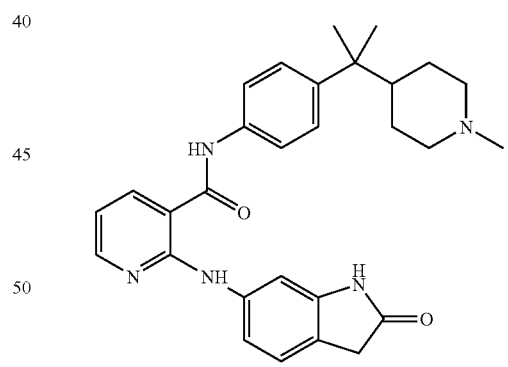

N-{4-[1-Methyl-1-(1-methyl-piperidin-4-yl)-ethyl]-phenyl}-2-(2-oxo-2,3-dihydro-1H-indol-6-ylamino)-nicotinamide MS: (ES+) 484 (M+H). Calc'd. for $C_{29}H_{33}N_5O_2$—483.61.

EXAMPLE 593

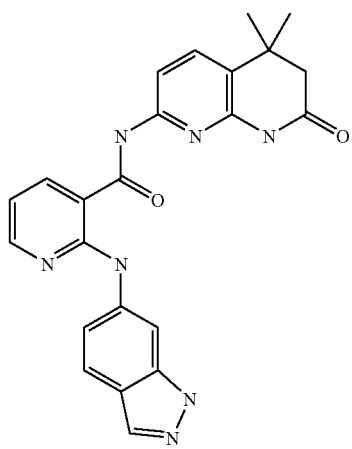

N-(5,5-Dimethyl-7-oxo-5,6,7,8-tetrahydro-[1,8]naphthyridin-2-yl)-2-(1H-indazol-6-ylamino)-nicotinamide MS: (ES+) 428.2 (M+H). Calc'd. for $C_{23}H_{21}N_7O_2$—427.47.

EXAMPLE 594

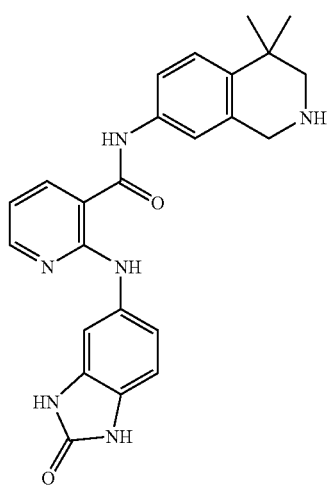

N-(4,4-Dimethyl-1,2,3,4-tetrahydro-isoquinolin-7-yl)-2-(2-oxo-2,3-dihydro-1H-benzoimidazol-5-ylamino)-nicotinamide MS (ES+): 429 (M+H)$^+$. Calc'd. for $C_{24}H_{24}N_6O_2$—428.20

EXAMPLE 595

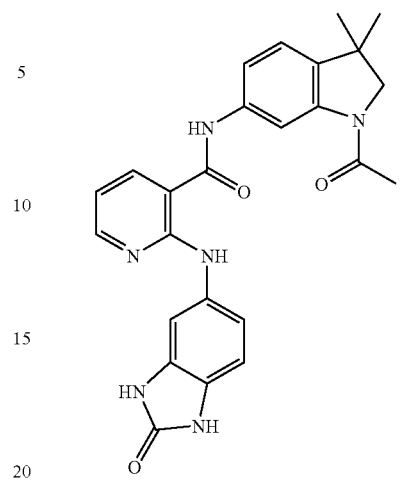

N-(1-Acetyl-3,3-dimethyl-2,3-dihydro-1H-indol-6-yl)-2-(2-oxo-2,3-dihydro-1H-benzoimidazol-5-ylamino)-nicotinamide MS (ES+): 457 (M+H)$^+$. Calc'd. for $C_{25}H_{24}N_6O_3$—456.19.

EXAMPLE 596

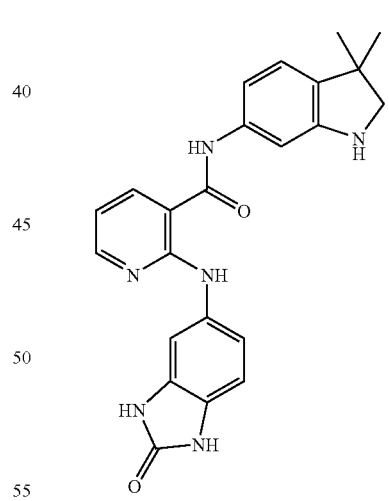

N-(3,3-Dimethyl-2,3-dihydro-1H-indol-6-yl)-2-(2-oxo-2,3-dihydro-1H-benzoimidazol-5-ylamino)-nicotinamide MS (ES+): 415 (M+H)$^+$. Calc'd. for $C_{23}H_{22}N_6O_2$—414.18.

EXAMPLE 597

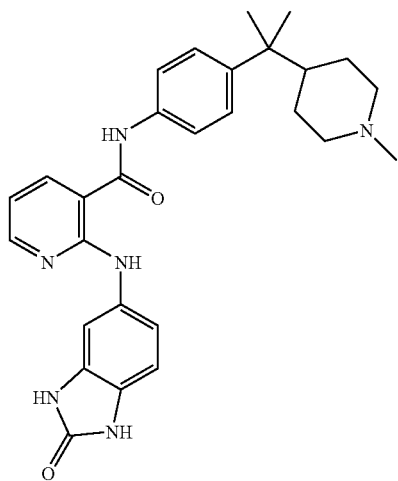

N-{4-[1-Methyl-1-(1-methyl-piperidin-4-yl)-ethyl]-phenyl}-2-(2-oxo-2,3-dihydro-1H-benzoimidazol-5-ylamino)-nicotinamide MS (ES+): 485 (M+H)$^+$. Calc'd. for $C_{28}H_{32}N_6O_2$—484.26.

EXAMPLE 598

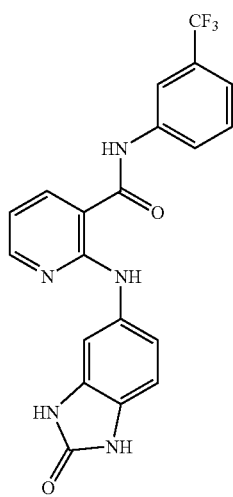

2-(2-Oxo-2,3-dihydro-1H-benzoimidazol-5-ylamino)-N-(3-trifluoromethyl-phenyl)-nicotinamide MS (ES+): 414 (M+H)$^+$. Calc'd. for $C_{20}H_{14}F_3N_5O_2$—413.11.

EXAMPLE 599

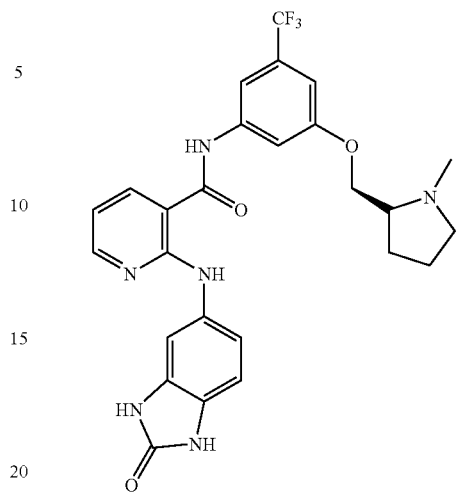

N-[3-(1-Methyl-pyrrolidin-2-ylmethoxy)-5-trifluoromethyl-phenyl]-2-(2-oxo-2,3-dihydro-1H-benzoimidazol-5-ylamino)-nicotinamide MS (ES+): 527 (M+H)$^+$. Calc'd. for $C_{26}H_{25}F_3N_6O_3$—526.19.

EXAMPLE 600

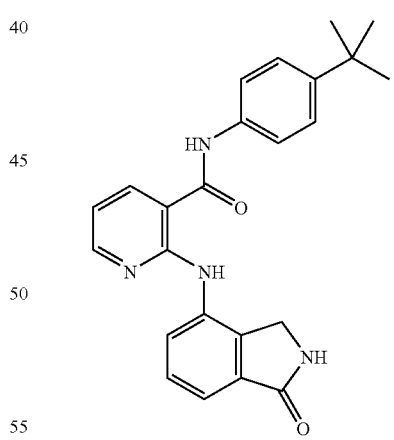

N-(4-tert-Butyl-phenyl)-2-(1-oxo-2,3-dihydro-1H-isoindol-4-ylamino)-nicotinamide MS (ES+): 401 (M+H)$^+$. Calc'd. for $C_{24}H_{24}N_4O_2$—400.19.

EXAMPLE 601

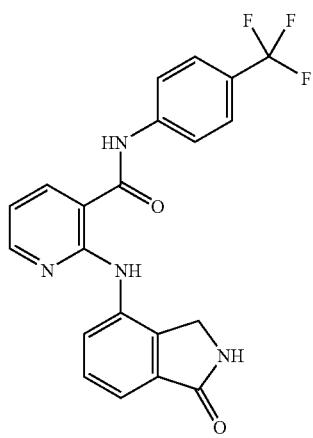

2-(1-Oxo-2,3-dihydro-1H-isoindol-4-ylamino)-N-(4-trifluoromethyl-phenyl)-nicotinamide MS (ES+): 413 (M+H)$^+$. Calc'd. for $C_{21}H_{15}F_3N_4O_2$—412.11.

EXAMPLE 602

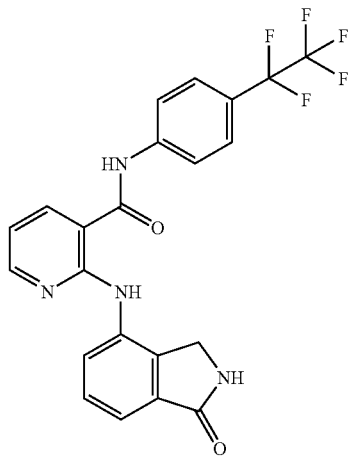

2-(1-Oxo-2,3-dihydro-1H-isoindol-4-ylamino)-N-(4-pentafluoroethyl-phenyl)-nicotinamide MS (ES+): 463 (M+H)$^+$. Calc'd. for $C_{22}H_{15}F_5N_4O_2$—462.37.

EXAMPLE 603

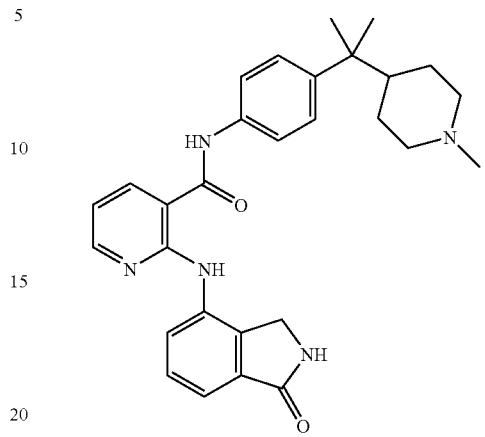

N-{4-[1-Methyl-1-(1-methyl-piperidin-4-yl)-ethyl]-phenyl}-2-(1-oxo-2,3-dihydro-1H-isoindol-4-ylamino)-nicotinamide MS (ES+): 484 (M+H)$^+$. Calc'd. for $C_{29}H_{33}N_5O_2$—483.26.

EXAMPLE 604

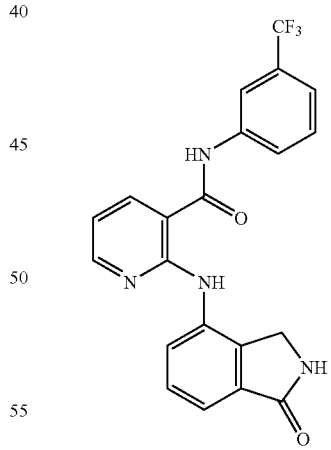

2-(1-Oxo-2,3-dihydro-1H-isoindol-4-ylamino)-N-(3-trifluoromethyl-phenyl)-nicotinamide MS (ES+): 413 (M+H)$^+$. Calc'd. for $C_{21}H_{15}F_3N_4O_2$—412.11.

EXAMPLE 605

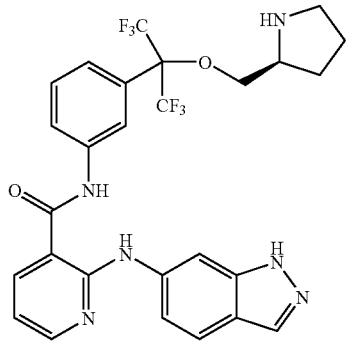

2-(1H-Indazol-6-ylamino)-N-{3-[2,2,2-trifluoro-1-(pyrrolidin-2-ylmethoxy)-1-trifluoromethyl-ethyl]-phenyl}-nicotinamide MS: (ES+) 579 (M+H). Calc'd. for $C_{27}H_{24}F_6N_6O_2$—578.51.

EXAMPLE 606

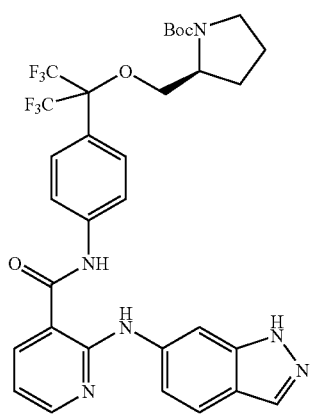

2-[2,2,2-Trifluoro-1-(4-{[2-(1H-indazol-6-ylamino)-pyridine-3-carbonyl]-amino}-phenyl)-1-trifluoromethyl-ethoxymethyl]-pyrrolidine-1-carboxylic acid tert-butyl ester MS: (ES+) 679 (M+H). Calc'd. for $C_{32}H_{32}F_6N_6O_4$—678.62.

EXAMPLE 607

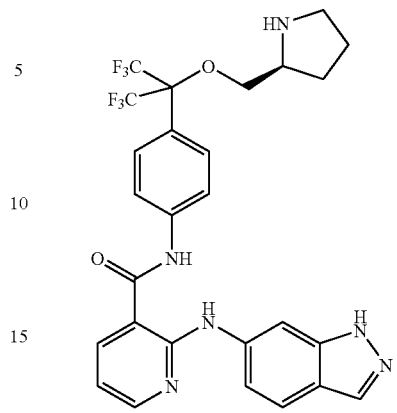

2-(1H-Indazol-6-ylamino)-N-{4-[2,2,2-trifluoro-1-(pyrrolidin-2-ylmethoxy)-1-trifluoromethyl-ethyl]-phenyl}-nicotinamide The title compound was prepared via the standard acidic de-protection conditions from Example 606 for Boc protected amines. MS: (ES+) 579 (M+H). Calc'd. for $C_{27}H_{24}F_6N_6O_2$—578.51.

EXAMPLE 608

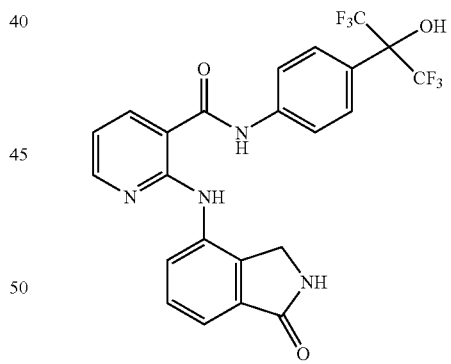

2-(1-Oxo-2,3-dihydro-1H-isoindol-4-ylamino)-N-[4-(2,2,2-trifluoro-1-hydroxy-1-trifluoromethyl-ethyl)-phenyl]-nicotinamide MS (ES+): 511 (M+H)$^+$. Calc'd. for $C_{23}H_{16}F_6N_4O_3$—510.11.

EXAMPLE 609

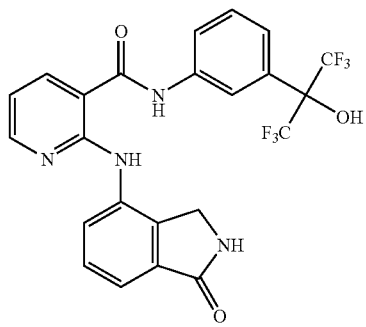

2-(1-Oxo-2,3-dihydro-1H-isoindol-4-ylamino)-N-[3-(2,2,2-trifluoro-1-hydroxy-1-trifluoromethyl-ethyl)-phenyl]-nicotinamide MS (ES+): 511 (M+H)$^+$. Calc'd. for $C_{23}H_{16}F_6N_4O_3$—510.11.

EXAMPLE 610

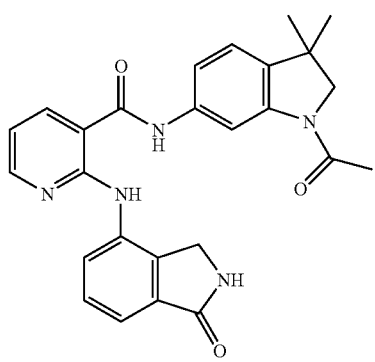

N-(1-Acetyl-3,3-dimethyl-2,3-dihydro-1H-indol-6-yl)-2-(1-oxo-2,3-dihydro-1H-isoindol-4-ylamino)-nicotinamide Same procedure was used as Example 608. MS (ES+): 456 (M+H)$^+$. Calc'd. for $C_{26}H_{25}N_5O_3$—455.20.

EXAMPLE 611

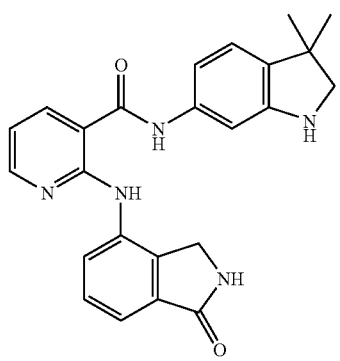

N-(3,3-Dimethyl-2,3-dihydro-1H-indol-6-yl)-2-(1-oxo-2,3-dihydro-1H-isoindol-4-ylamino)-nicotinamide MS (ES+): 414(M+H)$^+$. Calc'd. for $C_{24}H_{23}N_5O_2$—413.19.

EXAMPLE 612

2-(1-Oxo-2,3-dihydro-1H-isoindol-4-ylamino)-N-[3-(tetrahydro-furan-3-yloxy)-5-trifluoromethyl-phenyl]-nicotinamide MS (ES+): 499 (M+H)$^+$. Calc'd. for $C_{25}H_{21}F_3N_4O_4$—498.15.

EXAMPLE 613

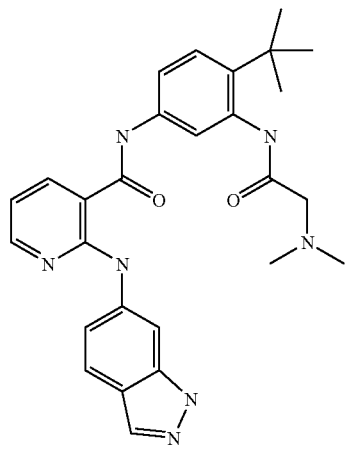

N-(4-(1,1-Dimethylethyl)-3-((N,N-dimethylglycyl)amino)phenyl)-2-(1H-indazol-6-ylamino)-3-pyridinecarboxamide MS: Calc'd for $C_{27}H_{31}N_7O_2$—485.589; M+H 486.

EXAMPLE 614

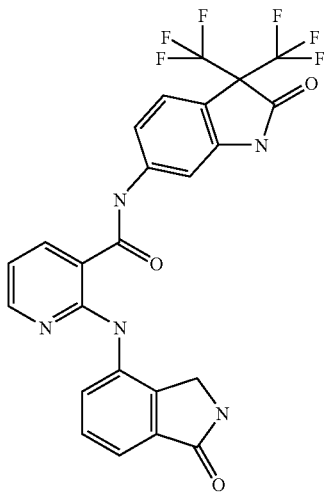

N-(2-Oxo-3,3-bis(trifluoromethyl)-2,3-dihydro-1H-indol-6-yl)-2-((1-oxo-2,3-dihydro-1H-isoindol-4-yl)amino)-3-pyridinecarboxamide

MS: $C_{24}H_{15}F_6N_5O_3$ 535.403; M+H 536.

EXAMPLE 615

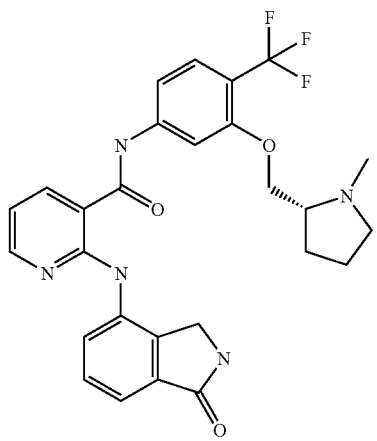

N-(3-((((2R)-1-Methyl-2-pyrrolidinyl)methyl)oxy)-4-(trifluoromethyl)phenyl)-2-((1-oxo-2,3-dihydro-1H-isoindol-4-yl)amino)-3-pyridinecarboxamide (R) 2-Fluoro-N-[3-(1-methyl-pyrrolidin-2-ylmethoxy)-4-trifluoromethyl-phenyl]-nicotinamide (402 mg, 1.0116 mmol) was dissolved in tert-butanol (1 mL). To this mix was added TFA (115 mg, 1.0116 mmol) and 4-amino-2,3-dihydro-isoindol-1-one (450 mg, 3.035 mmol). The mix was heated for 6 h at 150° C., allowing the solvent to boil off. The reaction was cooled to RT, dissolved into 1N aqueous HCl, basified to pH 10 with solid NaOH, extracted twice with EtOAc, and dried over $Na_2SO_4$. The product precipitated out of solution along with a minor by-product. The EtOAc was filtered off. The crude product was dissolved in MeOH and filtered. The MeOH solution was concentrated down and eluted on silica gel column to yield the titled compound as a light yellow solid. MS: $C_{27}H_{26}F_3N_5O_3$—525.528; M+H 526.1

EXAMPLE 616

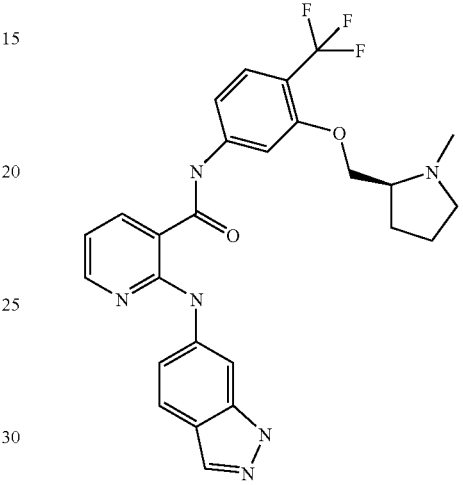

2-(1H-indazol-6-ylamino)-N-(3-((((2S)-1-methyl-2-pyrrolidinyl)methyl)oxy)-4-(trifluoromethyl)phenyl)-3-pyridinecarboxamide

MS: $C_{26}H_{25}F_3N_6O_2$ 510.517 M+H 511.4.

EXAMPLE 617

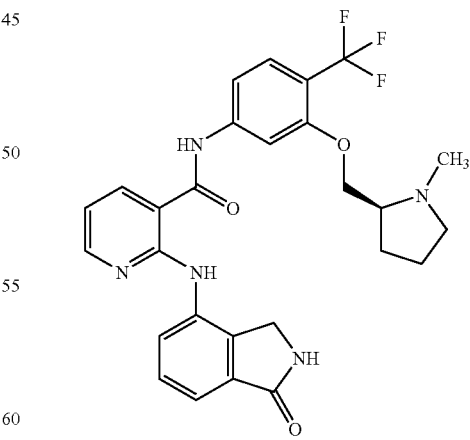

N-[3-(1-Methyl-pyrrolidin-2-ylmethoxy)-4-pentafluoroethyl-phenyl]-2-(1-oxo-2,3-dihydro-1H-isoindol-4-ylamino)-nicotinamide

EXAMPLE 618

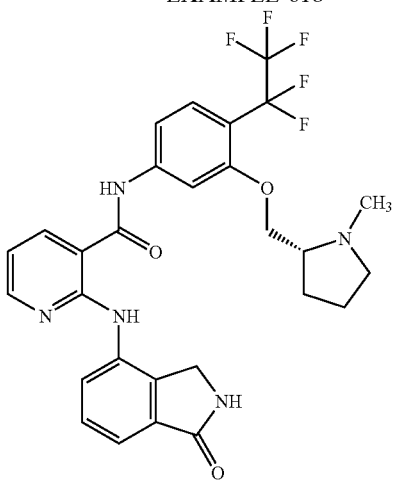

N-[3-(1-Methyl-pyrrolidin-2-ylmethoxy)-4-
trifluoromethyl-phenyl]-2-(1-oxo-2,3-dihydro-1H-
isoindol-4-ylamino)-nicotinamide

EXAMPLE 619

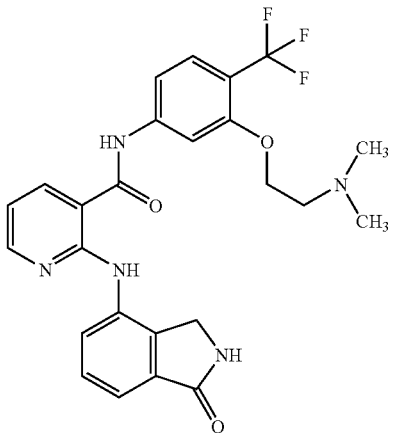

N-[3-(2-Dimethylamino-ethoxy)-4-trifluoromethyl-
phenyl]-2-(1-oxo-2,3-dihydro-1H-isoindol-4-
ylamino)-nicotinamide

EXAMPLE 620

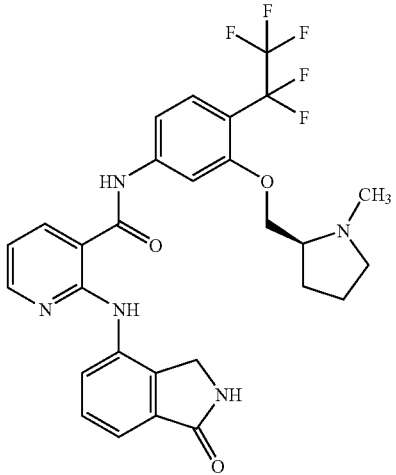

N-[3-(1-Methyl-pyrrolidin-2-ylmethoxy)-4-
pentafluoroethyl-phenyl]-2-(1-oxo-2,3-dihydro-1H-
isoindol-4-ylamino)-nicotinamide

EXAMPLE 621

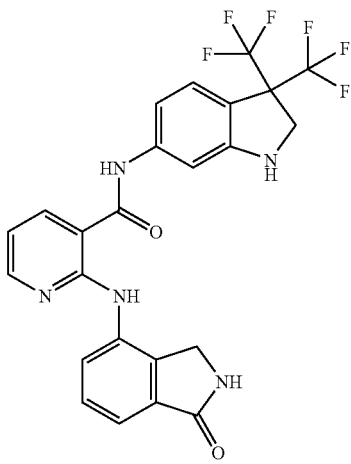

N-(3,3-Bis-trifluoromethyl-2,3-dihydro-1H-indol-6-
yl)-2-(1-oxo-2,3-dihydro-1H-isoindol-4-ylamino)-
nicotinamide

EXAMPLE 622

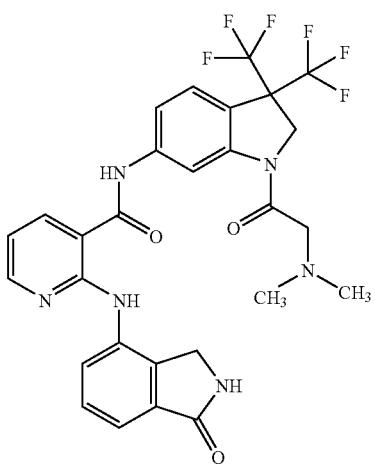

N-[1-(2-Dimethylamino-acetyl)-3,3-bis-
trifluoromethyl-2,3-dihydro-1H-indol-6-yl]-2-(1-
oxo-2,3-dihydro-1H-isoindol-4-ylamino)-
nicotinamide

EXAMPLE 623

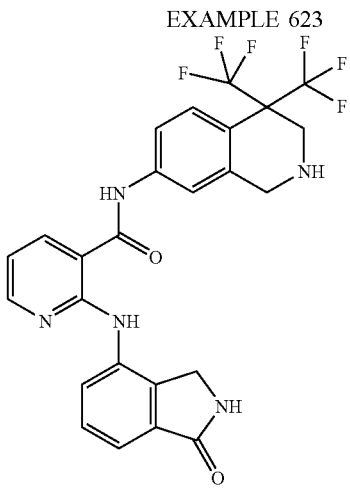

N-(4,4-Bis-trifluoromethyl-1,2,3,4-tetrahydro-isoquinolin-7-yl)-2-(1-oxo-2,3-dihydro-1H-isoindol-4-ylamino)-nicotinamide

EXAMPLE 624

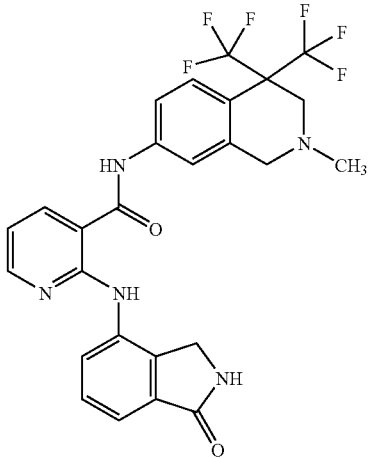

N-(2-Methyl-4,4-bis-trifluoromethyl-1,2,3,4-tetrahydro-isoquinolin-7-yl)-2-(1-oxo-2,3-dihydro-1H-isoindol-4-ylamino)-nicotinamide

EXAMPLE 625

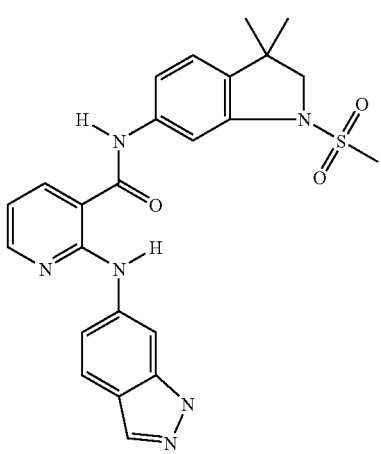

N-(3,3-dimethyl-1-(methylsulfonyl)-2,3-dihydro-1H-indol-6-yl)-2-(1H-indazol-6-ylamino)-3-pyridinecarboxamide MS: Calc'd for C24 H24 N6 O3 S—476.559; M+H 477.1.

EXAMPLE 626

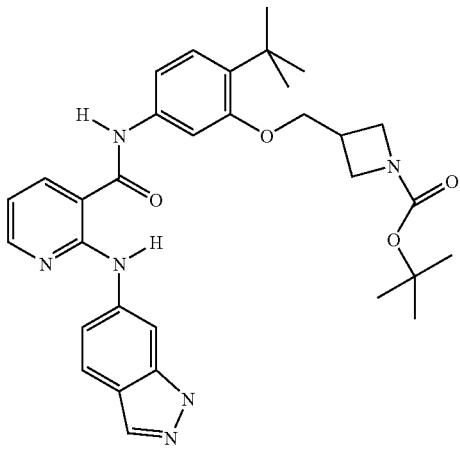

1,1-Dimethylethyl 3-(((2-(1,1-dimethylethyl)-5-(((2-(1H-indazol-6-ylamino)-3-pyridinyl)carbonyl)amino)phenyl)oxy)methyl)-1-azetidinecarboxylate MS: Calc'd for $C_{32}H_{38}N_6O_4$—570.69; M-BOC 471.3.

EXAMPLE 627

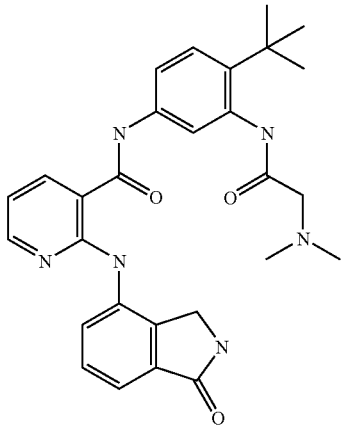

N-[4-tert-Butyl-3-(2-dimethylamino-acetylamino)-phenyl]-2-(1-oxo-2,3-dihydro-1H-isoindol-4-ylamino)-nicotinamide

EXAMPLE 628

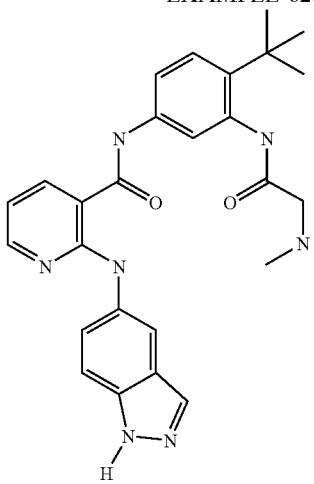

N-[4-tert-Butyl-3-(2-methylamino-acetylamino)-phenyl]-2-(3H-indazol-5-ylamino)-nicotinamide

EXAMPLE 629

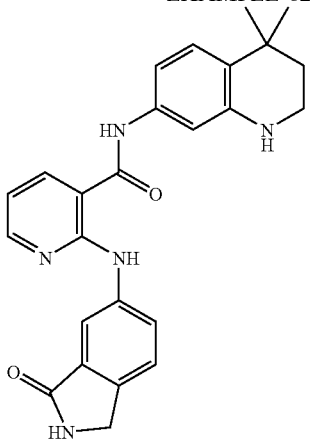

N-(4,4-Dimethyl-1,2,3,4-tetrahydro-isoguinolin-7-yl)-2-(1-oxo-2,3-dihydro-1H-isoindol-4-ylamino)-nicotinamide

EXAMPLE 630

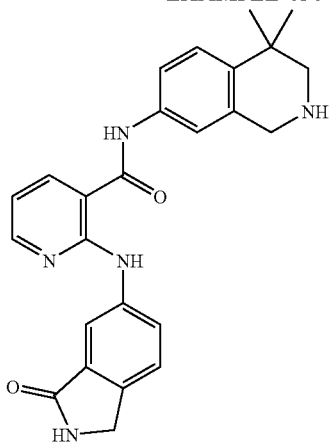

N-(4,4-Dimethyl-1,2,3,4-tetrahydro-isoquinolin-7-yl)-2-(1-oxo-2,3-dihydro-1H-isoindol-4-ylamino)-nicotinamide

EXAMPLE 631

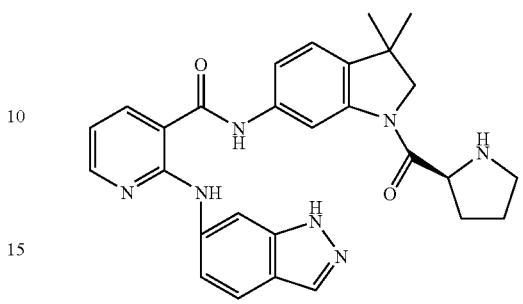

N-[3,3-Dimethyl-1-(pyrrolidine-2-carbonyl)-2,3-dihydro-1H-indol-6-yl]-2-(1H-indazol-6-ylamino)-nicotinamide Although the pharmacological properties of the compounds of Formula I–XI vary with structural change, in general, activity possessed by compounds of Formula I–XI may be demonstrated in vivo. The pharmacological properties of the compounds of this invention may be confirmed by a number of pharmacological in vitro assays. The exemplified pharmacological assays which follow have been carried out with the compounds according to the invention and their salts. Compounds of the present invention showed inhibition of KDR at doses less than 50 μm.

Biological Evaluation

HUVEC Proliferation Assay

Human Umbilical Vein Endothelial cells are purchased from Clonetics, Inc., as cryopreserved cells harvested from a pool of donors. These cells, at passage 1, are thawed and expanded in EBM-2 complete medium, until passage 2 or 3. The cells are trypsinized, washed in DMEM+10% FBS+antibiotics, and spun at 1000 rpm for 10 min. Prior to centrifugation of the cells, a small amount is collected for a cell count. After centrifugation, the medium is discarded, and the cells are resuspended in the appropriate volume of DMEM+10% FBS+antibiotics to achieve a concentration of $3 \times 10^5$ cells/mL. Another cell count is performed to confirm the cell concentration. The cells are diluted to $3 \times 10^4$ cells/mL in DMEM+10% FBS+antibiotics, and 100 μL of cells are added to a 96-well plate. The cells are incubated at 37° C. for 22 h.

Prior to the completion of the incubation period, compound dilutions are prepared. Five-point, five-fold serial dilutions are prepared in DMSO, at concentrations 400-fold greater than the final concentrations desired. 2.5 μL of each compound dilution are diluted further in a total of 1 mL DMEM+10% FBS+antibiotics (400× dilution). Medium containing 0.25% DMSO is also prepared for the 0 μM compound sample. At the 22-hour timepoint, the medium is removed from the cells, and 100 μL of each compound dilution is added. The cells are incubated at 37° C. for 2–3 h.

During the compound pre-incubation period, the growth factors are diluted to the appropriate concentrations. Solutions of DMEM+10% FBS+antibiotics, containing either VEGF or bFGF at the following concentrations: 50, 10, 2, 0.4, 0.08, and 0 ng/mL are prepared. For the compound-treated cells, solutions of VEGF at 550 ng/mL or bFGF at 220 ng/mL for 50 ng/mL or 20 ng/mL final concentrations, respectively, are prepared since 10 μL of each will be added to the cells (110 μL final volume). At the appropriate time after adding the compounds, the growth factors are added. VEGF is added to one set of plates, while bFGF is added to another set of plates. For the growth factor control curves, the media on wells B4-G6 of plates 1 and 2 are replaced with media containing VEGF or bFGF at the varying concentrations (50–0 ng/mL). The cells are incubated at 37° C. for an additional 72 h.

At the completion of the 72 h incubation period, the medium is removed, and the cells are washed twice with PBS. After the second wash with PBS, the plates are tapped gently to remove excess PBS, and the cells are placed at −70° C. for at least 30 min. The cells are thawed and analyzed using the CyQuant fluorescent dye (Molecular Probes C-7026), following the manufacturer's recommendations. The plates are read on a Victor/Wallac 1420 workstation at 485 nm/530 nm (excitation/emission). Raw data are collected and analyzed using a 4-parameter fit equation in XLFit. $IC_{50}$ values are then determined.

The compounds of examples 3, 5–10, 13–14, 20, 22–25, 27–28, 31, 36–39, 40–43, 45–46, 48, 50–51, 54–57, 61–68, 70–83, 84–90, 92–108, 110–111, 115–116, 118, 120–121, 123–126, 406–409, 575, 577, 580–581, 583, 586–588, 593–594, 600, 602–603, 607–609, 613, 616, 625 and 629–631 inhibited VEGF-stimulated HUVEC proliferation at a level below 50 nm.

Angiogenesis Model

To determine the effects of the present compounds on angiogenesis in vivo, selective compounds are tested in the rat corneal neovascularization micropocket model or the angiogenesis assay of Passaniti, Lab. Invest., 67, 519–28 (1992).

Rat Corneal Neovascularization Micropocket Model

In Life Aspects: Female Sprague Dawley rats weighing approximately 250 g were randomized into one of five treatment groups. Pretreatment with the vehicle or compound was administered orally, 24 h prior to surgery and continued once a day for seven additional days. On the day of surgery, the rats were temporarily anesthetized in an Isofluorane gas chamber (delivering 2.5 liters/min oxygen+ 5% Isofluorane). An othoscope was then placed inside the mouth of the animal to visualize the vocal cords. A tip-blunted wire was advanced in between the vocal cords and used as a guide for the placement of an endotracheal Teflon tube (Small Parts Inc. TFE-standard Wall R-SWTT-18). A volume-controlled ventilator (Harvard Apparatus, Inc. Model 683) was connected to the endotracheal tube to deliver a mixture of oxygen and 3% Isofluorane. Upon achieving deep anesthesia, the whiskers were cut short and the eye areas and eyes gently washed with Betadine soap and rinsed with sterile saline. The corneas were irrigated with one to two drops of Proparacaine HCl ophthalmic topical anesthetic solution (0.5%) (Bausch and Lomb Pharmaceuticals, Tampa Fla.). The rat was then positioned under the dissecting microscope and the corneal surface brought into focus. A vertical incision was made on the midline of the cornea using a diamond blade knife. A pocket was created by using fine scissors to separate the connective tissue layers of the stroma, tunneling towards the limbus of the eye. The distance between the apex of the pocket and the limbus was approximately 1.5 mm. After the pocket had been made, the soaked nitrocellulose disk filter (Gelman Sciences, Ann Arbor Mich.) was inserted under the lip of the pocket. This surgical procedure was performed on both eyes. rHu-bFGF soaked disks were placed into the right eye, and the rHu-VEGF soaked disks were placed into the left eye. Vehicle soaked disks were placed in both eyes. The disk was pushed into position at the desired distance from the limbal vessels. Ophthalmic antibiotic ointment was applied to the eye to prevent drying and infection. After seven days, the rats were euthanized by $CO_2$ asphyxiation, and the eyes enucleated. The retinal hemisphere of the eye was windowed to facilitate fixation, and the eye placed into formalin overnight.

Post Mortem Aspects: After twenty-four hours in fixative, the corneal region of interest was dissected out from the eye, using fine forceps and a razorblade. The retinal hemisphere was trimmed off and the lens extracted and discarded. The corneal dome was bisected and the superfluous cornea trimmed off. The iris, conjunctiva and associated limbal glands were then carefully teased away. Final cuts were made to generate a square 3×3 mm containing the disk, the limbus, and the entire zone of neovascularization.

Gross Image Recording: The corneal specimens were digitally photographed using a Sony CatsEye DKC5000 camera (A.G. Heinz, Irvine Calif.) mounted on a Nikon SMZ-U stereo microscope (A.G. Heinz). The corneas were submerged in distilled water and photographed via trans-illumination at approximately 5.0 diameters magnification.

Image analysis: Numerical endpoints were generated using digital micrographs collected from the whole mount corneas after trimming and were used for image analysis on the Metamorph image analysis system (Universal Imaging Corporation, West Chester Pa.). Three measurements were taken: Disk placement distance from the limbus, number of vessels intersecting a 2.0 mm perpendicular line at the midpoint of the disk placement distance, and percent blood vessel area of the diffusion determined by thresholding.

General Formulations:
0.1% BSA in PBS vehicle: 0.025 g of BSA was added to 25.0 ml of sterile 1× phosphate buffered saline, gently shaken until fully dissolved, and filtered at 0.2 μm. Individual 1.0 ml samples were aliquoted into 25 single use vials, and stored at −20° C. until use. For the rHu-bFGF disks, a vial of this 0.1% BSA solution was allowed to thaw at room temperature. Once thawed, 10 μl of a 100 mM stock solution of DTT was added to the 1 ml BSA vial to yield a final concentration of 1 mM DTT in 0.1% BSA.
rHu-VEGF Dilutions:
Prior to the disk implant surgery, 23.8 μl of the 0.1% BSA vehicle above was added to a 10 μg rHu-VEGF lyophilized vial yielding a final concentration of 10 μM.
rHu-bFGF: Stock concentration of 180 ng/μl:
R&D rHu-bFGF: Added 139 μl of the appropriate vehicle above to the 25 μg vial lyophilized vial. 13.3 μl of the [180 ng/μl] stock vial and added 26.6 μl of vehicle to yield a final concentration of 3.75 μM concentration.
Nitro-cellulose disk preparation: The tip of a 20-gauge needle was cut off square and beveled with emery paper to create a punch. This tip was then used to cut out ≅0.5 mm diameter disks from a nitrocellulose filter paper sheet (Gelman Sciences). Prepared disks were then placed into Eppendorf microfuge tubes containing solutions of either 0.1% BSA in PBS vehicle, 10 μM rHu-VEGF (R&D Systems, Minneapolis, Minn.), or 3.75 μM rHu-bFGF (R&D Systems, Minneapolis, Minn.) and allowed to soak for 45–60 min before use. Each nitrocellulose filter disk absorbs approximately 0.1 µl of solution.

In the rat micropocket assay, compounds of the present invention will inhibit angiogenesis at a dose of less than 50 mg/kg/day.

Tumor Model

A431 cells (ATCC) are expanded in culture, harvested and injected subcutaneously into 5–8 week old female nude mice (CD1 nu/nu, Charles River Labs) (n=5–15). Subsequent administration of compound by oral gavage (10–200 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control. Compounds of the present invention are active at doses less than 150 mpk.

Rat Adjuvant Arthritis Model

The rat adjuvant arthritis model (Pearson, Proc. Soc. Exp. Biol. 91, 95–101 (1956)) is used to test the anti-arthritic activity of compounds of the formula 1, or salts thereof. Adjuvant Arthritis can be treated using two different dosing schedules: either (i) starting time of immunization with adjuvant (prophylactic dosing); or from day 15 when the arthritic response is already established (therapeutic dosing). Preferably a therapeutic dosing schedule is used.

Rat Carrageenan-induced Analgesia Test

The rat carrageenan analgesia test was performed with materials, reagents and procedures essentially as described by Hargreaves, et al., (Pain, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined.

Formulations

Also embraced within this invention is a class of pharmaceutical compositions comprising the active compounds of Formula I–X in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg or 5 to 1000 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.1 and about 50 mg/kg, and more preferably about 0.1 and about 20 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:

1. A compound of formula XI

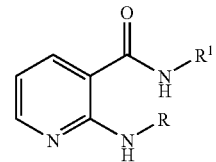

wherein R is selected from unsubstituted or substituted 9- or 10-membered fused nitrogen-containing heteroaryl selected from 6-indazolyl, 1-oxo-2,3-dihydro-1H-isoindol-4-yl, 2-oxo-2,3-dihydro-1H-benzoimidazol-5-yl, and 4-oxo-3,4-dihydro-quinazolin-6-yl;

wherein R¹ is selected from unsubstituted or substituted
aryl,
cycloalkyl,
5–6 membered heteroaryl and
9–10 membered bicyclic and 11–14 membered tricyclic heterocyclyl,
wherein substituted R¹ is substituted with one or more substituents selected from halo, C$_{1-6}$-alkyl, optionally substituted C$_{3-6}$-cycloalkyl, optionally substituted phenyl, optionally substituted phenyl-C$_1$-C$_4$-alkylenyl, C$_{1-2}$-haloalkoxy, optionally substituted phenyloxy, optionally substituted 4–6 membered heterocyclyl-C$_1$-C$_6$-alkyl, optionally substituted 4–6 membered heterocyclyl-C$_2$-C$_4$-alkenyl, optionally substituted 4–6 membered heterocyclyl, optionally substituted 4–6 membered heterocyclyloxy, optionally substituted 4–6 membered heterocyclyl-C$_{1-4}$-alkoxy, optionally substituted 4–6 membered heterocyclylsulfonyl, optionally substituted 4–6 membered heterocyclylamino, optionally substituted 4–6 membered heterocyclylcarbonyl, optionally substituted 4–6 membered heterocyclyl-C$_{1-4}$-alkylcarbonyl, optionally substituted 4–6 membered heterocyclylcarbonyl-C$_{1-4}$-alkyl, optionally substituted 4–6 membered heterocyclyl-C$_{1-4}$-alkylcarbonylamino, optionally substituted 4–6 membered heterocyclyl-oxycarbonylamino, C$_{1-2}$-haloalkyl, C$_{1-4}$-aminoalkyl, nitro, amino, C$_{1-3}$-alkylsulfonylamino, hydroxy, cyano, aminosulfonyl, C$_{1-2}$-alkylsulfonyl, halosulfonyl, C$_{1-4}$-alkylcarbonyl, amino-C$_{1-4}$-alkylcarbonyl, C$_{1-3}$-alkylamino-C$_{1-4}$-alkylcarbonyl, C$_{1-3}$-alkylamino-C$_{1-4}$-alkylcarbonylamino, C$_{1-4}$-alkoxycarbonyl-C$_{1-4}$-alkyl, C$_{1-3}$-alkylamino-C$_{1-3}$-alkyl, C$_{1-3}$-alkylamino-C$_{1-3}$-alkoxy, C$_{1-3}$-alkylamino-C$_{1-3}$-alkoxy-C$_{1-3}$-alkoxy, C$_{1-4}$-alkoxycarbonyl, C$_{1-4}$-alkoxycarbonylamino-C$_{1-4}$-alkyl, C$_{1-3}$-alkylsulfonylamino-C$_{1-3}$-alkoxy, C$_{1-4}$-hydroxyalkyl,

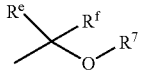

and C$_{1-4}$-alkoxy; and
wherein R$^e$ and R$^f$ are independently selected from H and C$_{1-2}$-haloalkyl; and
wherein R$^7$ is selected from H, C$_{1-3}$-alkyl, optionally substituted phenyl, optionally substituted phenyl-C$_{1-3}$-alkyl, 4–6 membered heterocyclyl, optionally substituted 4–6 membered heterocyclyl-C$_1$-C$_3$-alkyl, C$_{1-3}$-alkoxy-C$_{1-2}$-alkyl and C$_{1-3}$-alkoxy-C$_{1-3}$-alkoxy-C$_{1-3}$-alkyl;
and pharmaceutically acceptable derivatives thereof.

2. Compound of claim 1 wherein R is 6-indazolyl.

3. Compound of claim 1 wherein R is 1-oxo-2,3-dihydro-1H-isoindol-4-yl.

4. Compound of claim 1 wherein R is 2-oxo-2,3-dihydro-1H-benzoimidazol-5-yl.

5. Compound of claim 1 wherein R is 4-oxo-3,4-dihydroquinazolin-6-yl.

6. Compound of claim 1 wherein R¹ is selected from phenyl, tetrahydronaphthyl, indanyl, indenyl, naphthyl, cyclohexyl, isoxazolyl, pyrazolyl, thiazolyl, thiadiazolyl, thienyl, pyridyl, pyrimidinyl, pyridazinyl, 1,2-dihydroquinolyl, 1,2,3,4-tetrahydroisoquinolyl, 1',2'-dihydro-spiro[cyclopropane-1,3'-[3H]indol]-6'-yl, isoquinolyl, quinolyl, indolyl, isoindolyl, 2,3-dihydro-1H-indolyl, naphthyridinyl, 3,4-dihydro-[1,8]naphthyridinyl, 1,2,3,4-tetrahydro-[1,8]naphthyridinyl, quinozalinyl, benzo[d]isothiazolyl, 3,4-dihydro-quinazolinyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, 2,1,3-benzothiadiazolyl, benzodioxanyl, benzothienyl, benzofuryl, benzimidazolyl, dihydro-benzimidazolyl, benzoxazolyl and benzthiazolyl, where R¹ is unsubstituted or substituted with one or more substituents selected from bromo, chloro, fluoro, iodo, nitro, amino, cyano, Boc-aminoethyl, hydroxy, oxo, fluorosulfonyl, methylsulfonyl, aminosulfonyl, 4-methylpiperazinylsulfonyl, cyclohexyl, phenyl, phenylmethyl, 4-pyridylmethyl, 4-morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, 2-methyl-2-(4-pyrimidinyl)ethyl, 2-methyl-2-(5-methyloxadiazol-2-yl)ethyl, 2-methyl-2-(pyrazol-5-yl)ethyl, 2-methyl-2-(1-ethoxycarbonyl-1,2,3,6-tetrahydropyridin-4-yl)ethyl, morpholinylethyl, 1-(4-morpholinyl)-2,2-dimethylpropyl, 1-(4-morpholinyl)-2,2-dimethylethyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, 1-(pyrrolidin-1-yl)-2-methylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, methylcarbonyl, Boc, piperidin-1-ylmethylcarbonyl, pyrrolidin-1-ylcarbonyl, 4-pyridylcarbonyl, 4-methylpiperazin-1-ylcarbonylethyl, CH$_3$O—C(=O)—CH$_2$—, methoxycarbonyl, aminomethylcarbonyl, dimethylaminomethylcarbonyl, methylsulfonylamino, dimethylaminomethylcarbonylamino, 1-pyrrolidinyl-CH$_2$—C(=O)—NH—, 4-morpholinyl-CH$_2$—C(=O)—NH—, 3-tetrahydrofuryl-O—C(=O)—NH—, cyclohexyl-N(CH$_3$)—, (4-pyrimidinyl)amino, (2-methylthio-4-pyrimidinyl)amino, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(pyrrolidin-2-ylmethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, 3-tetrahydrofuryloxy, dimethylaminoethoxy, 4-chlorophenoxy, phenyloxy, azetidin-3-ylmethoxy, 1-Boc-azetidin-3-ylmethoxy, 3-tetrahydrofurylmethoxy, pyrrolidin-2-ylmethoxy, 1-methylcarbonyl-pyrrolidin-2-ylmethoxy, 1-Boc-pyrrolidin-2-ylmethoxy, pyrrolidin-1-ylmethoxy, 1-methyl-pyrrolidin-2-ylmethoxy, 1-isopropyl-pyrrolidin-2-ylmethoxy, 1-Boc-piperdin-4-ylmethoxy, (1-pyrrolidinyl)ethoxy, piperdin-4-ylmethoxy, piperdin-3-ylmethoxy, 1-methylpiperdin-4-yloxy, methylsulfonylaminoethoxy, isopropoxy, methoxy and ethoxy; and pharmaceutically acceptable derivatives thereof.

7. Compound of claim 6 wherein R¹ is selected from phenyl, 1,2,3,4-tetrahydroisoquinolyl, 2,3-dihydro-1H-indolyl, 1,2,3,4-tetrahydro-[1,8]naphthyridinyl, 1',2'- dihydro-spiro[cyclopropane-1,3'-[3H]indol]-6'-yl, and tetrahydroquinolinyl, where $R^1$ is unsubstituted or substituted with one or more substituents selected from chloro, oxo, methylsulfonyl, 2-methyl-2-(1-methylpiperidin-4-yl) ethyl, pyrrolidin-1-yl-carbonyl, methylsulfonylamino, dimethylaminomethylcarbonylamino, 1-pyrrolidinyl-$CH_2$—C(=O)—NH—, 4-morpholinyl-$CH_2$—C(=O)—NH—, 3-tetrahydrofuryl-O—C(=O)—NH—, methyl, tert-butyl, trifluoromethyl, pentafluoroethyl, 1,1-di(trifluoromethyl)-1-hydroxymethyl, 1,1-di(trifluoromethyl)-1-(pyrrolidin-2-ylmethoxy)methyl, 3-tetrahydrofuryloxy, 1-methylcarbonyl-pyrrolidin-2-ylmethoxy, 1-methyl-pyrrolidin-2-ylmethoxy, and methylsulfonylaminoethoxy; and pharmaceutically acceptable derivatives thereof.

8. Compound of claim 6 wherein $R^1$ is substituted with one or more substituents selected from 2-methyl-2-(1-ethoxycarbonyl-1,2,3,6-tetrahydropyridin-4-yl)ethyl, 1-(4-morpholinyl)-2,2-dimethylethyl, pyrrolidin-1-yl-carbonyl, $CH_3O$—C(=O)—$CH_2$—, methylsulfonylamino, dimethylaminomethylcarbonylamino, 1-pyrrolidinyl-$CH_2$—C(=O)—NH—, 4-morpholinyl-$CH_2$—C(=O)—NH—, 3-tetrahydrofuryl-O—C(=O)—NH—, 1,1-di(trifluoromethyl)-1-(pyrrolidin-2-ylmethoxy)methyl, 3-tetrahydrofuryloxy, 1-methylcarbonyl-pyrrolidin-2-ylmethoxy, and methylsulfonylaminoethoxy; and pharmaceutically acceptable derivatives thereof.

9. Compound of claim 6 wherein $R^1$ is phenyl substituted with one or more substituents selected from chloro, 2-methyl-2-(1-methylpiperidin-4-yl)ethyl, methylsulfonylamino, dimethylaminomethylcarbonylamino, 1-pyrrolidinyl-$CH_2$—C(=O)—NH—, 4-morpholinyl-$CH_2$—C(=O)—NH—, 3-tetrahydrofuryl-O—C(=O)—NH—, tert-butyl, trifluoromethyl, pentafluoroethyl, 1,1-di(trifluoromethyl)-1-hydroxymethyl, 1,1-di(trifluoromethyl)-1-(pyrrolidin-2-ylmethoxy)methyl, 3-tetrahydrofuryloxy, 1-methylcarbonyl-pyrrolidin-2-ylmethoxy, 1-methyl-pyrrolindin-2-ylmethoxy, and methylsulfonylaminoethoxy; and pharmaceutically acceptable derivatives thereof.

10. Compound of claim 6 wherein $R^1$ is 4,4-dimethyl-3,4-dihydro-2-oxo-1H-quinolinyl; and pharmaceutically acceptable derivatives thereof.

11. Compound of claim 6 wherein $R^1$ is 4,4-dimethyl-1,2,3,4-tetrahydro-1H-quinolinyl; and pharmaceutically acceptable derivatives thereof.

12. Compound of claim 6 wherein $R^1$ is 4,4-dimethyl-3,4-dihydro-2-oxo-1H-[1,8]naphthyridinyl; and pharmaceutically acceptable derivatives thereof.

13. Compound of claim 6 wherein $R^1$ is 3,3-dimethyl-2,3-dihydro-1H-indolyl optionally substituted with a substituent selected from pyrrolidin-1-yl-carbonyl, methylcarbonyl, and methylsulfonyl; and pharmaceutically acceptable derivatives thereof.

14. Compound of claim 6 wherein $R^1$ is 4,4-dimethyl-1,2,3,4-tetrahydro-1H-isoquinolinyl.

15. Compound of claim 1 and pharmaceutically acceptable salts thereof selected from
N-(4,4-Dimethyl-2-oxo-1,2,3,4-tetrahydro-quinolin-7-yl)-2-(1H-indazol-6-ylamino)-nicotinamide;
2-(1H-Indazol-6-ylamino)-N-(3-(((((2R)-1-methyl-2-pyrrolidinyl)methyl)oxy)-5-(trifluoromethyl)phenyl)-3-pyridinecarboxamide;
N-(3-((((2R)-1-Acetyl-2-pyrrolidinyl)methyl)oxy)-5-(trifluoromethyl)phenyl)-2-(1H-indazol-6-ylamino)-3-pyridinecarboxamide;
(3S)-Tetrahydro-3-furanyl 3-(((2-(1H-indazol-6-ylamino)-3-pyridinyl)carbonyl)amino)-5-(trifluoromethyl)phenylcarbamate;
2-(1H-Indazol-6-ylamino)-N-(3-(((((2S)-1-(1-methylethyl)-2-pyrrolidinyl)methyl)oxy)-5-(trifluoromethyl)phenyl)-3-pyridinecarboxamide;
2-(1H-Indazol-6-ylamino)-N-(3-((methylsulfonyl)amino)-5-(trifluoromethyl)phenyl)-3-pyridinecarboxamide;
N-(4-(1,1-Dimethylethyl)-3-((1-pyrrolidinylacetyl)amino) phenyl)-2-(1H-indazol-6-ylamino)-3-pyridinecarboxamide;
N-(4-(1,1-Dimethylethyl)-3-((4-morpholinylacetyl)amino) phenyl)-2-(1H-indazol-6-ylamino)-3-pyridinecarboxamide;
N-(5,5-Dimethyl-7-oxo-5,6,7,8-tetrahydro-[1,8] naphthyridin-2-yl)-2-(1H-indazol-6-ylamino)-nicotinamide;
N-(4,4-Dimethyl-1,2,3,4-tetrahydro-isoquinolin-7-yl)-2-(2-oxo-2,3-dihydro-1H-benzoimidazol-5-ylamino)-nicotinamide;
N-(4-tert-Butyl-phenyl)-2-(1-oxo-2,3-dihydro-1H-isoindol-4-ylamino)-nicotinamide;
2-(1-Oxo-2,3-dihydro-1H-isoindol-4-ylamino)-N-(4-pentafluoroethyl-phenyl)-nicotinamide;
N-{4-[1-Methyl-1-(1-methyl-piperidin-4-yl)-ethyl]-phenyl}-2-(1-oxo-2,3-dihydro-1H-isoindol-4-ylamino)-nicotinamide;
2-(1H-Indazol-6-ylamino)-N-{4-[2,2,2-trifluoro-1-(pyrrolidin-2-ylmethoxy)-1-trifluoromethyl-ethyl]-phenyl}-nicotinamide;
2-(1-Oxo-2,3-dihydro-1H-isoindol-4-ylamino)-N-[4-(2,2,2-trifluoro-1-hydroxy-1-trifluoromethyl-ethyl)-phenyl]-nicotinamide;
2-(1-Oxo-2,3-dihydro-1H-isoindol-4-ylamino)-N-[3-(2,2,2-trifluoro-1-hydroxy-1-trifluoromethyl-ethyl)-phenyl]-nicotinamide;
N-(4-(1,1-Dimethylethyl)-3-((N,N-dimethylglycyl)amino) phenyl)-2-(1H-indazol-6-ylamino)-3-pyridinecarboxamide;
2-(1H-indazol-6-ylamino)-N-(3-(((((2S)-1-methyl-2-pyrrolidinyl)methyl)oxy)-4-(trifluoromethyl)phenyl)-3-pyridinecarboxamide;
N-(3,3-dimethyl-1-(methylsulfonyl)-2,3-dihydro-1H-indol-6-yl)-2-(1H-indazol-6-ylamino)-3-pyridinecarboxamide;
N-(4,4-Dimethyl-1,2,3,4-tetrahydro-isoquinolin-7-yl)-2-(1-oxo-2,3-dihydro-1H-isoindol-4-ylamino)-nicotinamide;
N-(4,4-Dimethyl-1,2,3,4-tetrahydro-isoquinolin-7-yl)-2-(1-oxo-2,3-dihydro-1H-isoindol-4-ylamino)-nicotinamide; and
N-[3,3-Dimethyl-1-(pyrrolidine-2-carbonyl)-2,3-dihydro-1H-indol-6-yl]-2-(1H-indazol-6-ylamino)-nicotinamide.

16. A compound and pharmaceutically acceptable salts thereof selected from
2-(1H-Indazol-6-ylamino)-N-(3-(((((2R)-1-methyl-2-pyrrolidinyl)methyl)oxy)-5-(trifluoromethyl)phenyl)-3-pyridinecarboxamide;
2-(1H-Indazol-6-ylamino)-N-(3-((((2S)-tetrahydro-2-furanylmethyl)oxy)-5-(trifluoromethyl)phenyl)-3-pyridinecsarboxamide;
2-(1H-Indazol-6-ylamino)-N-(3-((((2R)-tetrahydro-2-furanylmethyl)oxy)-5-(trifluoromethyl)phenyl)-3-pyridinecsarboxamide;
2-(1H-Indazol-6-ylamino)-N-(3-(((3R)-tetrahydro-3-furanyloxy)-5-(trifluoromethyl)phenyl)-3-pyridinecarboxamide;
N-(3-((((2R)-1-Acetyl-2-pyrrolidinyl)methyl)oxy)-5-(trifluoromethyl)phenyl)-2-(1H-indazol-6-ylamino)-3-pyridinecarboxamide;
(3S)-Tetrahydro-3-furanyl 3-(((2-(1H-indazol-6-ylamino)-3-pyridinyl)carbonyl)amino)-5-(trifluoromethyl) phenylcarbamate;

2-(1H-Indazol-6-ylamino)-N-(3-((2-((methylsulfonyl)amino)ethyl)oxy)-5-(trifluoromethyl)phenyl)-3-pyridinecarboxamide;

2-(1H-Indazol-6-ylamino)-N-(3-(((((2S)-1-(1-methylethyl)-2-pyrrolidinyl)methyl)oxy)-5-(trifluoromethyl)phenyl)-3-pyridinecarboxamide;

N-(2-Oxo-3,3-bis(trifluoromethyl)-2,3-dihydro-1H-indol-6-yl)-2-((1-oxo-2,3-dihydro-1H-isoindol-4-yl)amino)-3-pyridinecarboxamide;

N-(3-(((((2R)-1-Methyl-2-pyrrolidinyl)methyl)oxy)-4-(trifluoromethyl)phenyl)-2-((1-oxo-2,3-dihydro-1H-isoindol-4-yl)amino)-3-pyridinecarboxamide;

2-(1H-Indazol-6-ylamino)-N-(3-((methylsulfonyl)amino)-5-(trifluoromethyl)phenyl)-3-pyridinecarboxamide;

N-(4-(1,1-Dimethylethyl)-3-((1-pyrrolidinylacetyl)amino)phenyl)-2-(1H-indazol-6-ylamino)-3-pyridinecarboxamide;

N-(4-(1,1-Dimethylethyl)-3-((4-morpholinylacetyl)amino)phenyl)-2-(1H-indazol-6-ylamino)-3-pyridinecarboxamide;

4-((3-((3-(2-(1-Acetyl-2-pyrrolidinyl)ethyl)-5-(trifluoromethyl)phenyl)acetyl)-2-pyridinyl)amino)-2,3-dihydro-1H-isoindol-1-one;

N-[3-Chloro-5-(2-dimethylamino-acetylamino)-phenyl]-2-(1H-indazol-6-ylamino)-nicotinamide;

N-{4-[1-Methyl-1-(1-methyl-piperidin-4-yl)-ethyl]-phenyl}-2-(4-oxo-3,4-dihydro-quinazolin-6-ylamino)-nicotinamide;

N-{4-[1-Methyl-1-(1-methyl-piperidin-4-yl)-ethyl]-phenyl}-2-(2-oxo-2,3-dihydro-1H-indol-6-ylamino)-nicotinamide;

N-(5,5-Dimethyl-7-oxo-5,6,7,8-tetrahydro-[1,8]naphthyridin-2-yl)-2-(1H-indazol-6-ylamino)-nicotinamide;

N-(4,4-Dimethyl-1,2,3,4-tetrahydro-isoquinolin-7-yl)-2-(2-oxo-2,3-dihydro-1H-benzoimidazol-5-ylamino)-nicotinamide;

N-(1-Acetyl-3,3-dimethyl-2,3-dihydro-1H-indol-6-yl)-2-(2-oxo-2,3-dihydro-1H-benzoimidazol-5-ylamino)-nicotinamide;

N-(3,3-Dimethyl-2,3-dihydro-1H-indol-6-yl)-2-(2-oxo-2,3-dihydro-1H-benzoimidazol-5-ylamino)-nicotinamide;

N-{4-[1-Methyl-1-(1-methyl-piperidin-4-yl)-ethyl]-phenyl}-2-(2-oxo-2,3-dihydro-1H-benzoimidazol-5-ylamino)-nicotinamide;

2-(2-Oxo-2,3-dihydro-1H-benzoimidazol-5-ylamino)-N-(3-trifluoromethyl-phenyl)-nicotinamide;

N-[3-(1-Methyl-pyrrolidin-2-ylmethoxy)-5-trifluoromethyl-phenyl]-2-(2-oxo-2,3-dihydro-1H-benzoimidazol-5-ylamino)-nicotinamide;

N-(4-tert-Butyl-phenyl)-2-(1-oxo-2,3-dihydro-1H-isoindol-4-ylamino)-nicotinamide;

2-(1-Oxo-2,3-dihydro-1H-isoindol-4-ylamino)-N-(4-trifluoromethyl-phenyl)-nicotinamide;

2-(1-Oxo-2,3-dihydro-1H-isoindol-4-ylamino)-N-(4-pentafluoroethyl-phenyl)-nicotinamide;

N-{4-[1-Methyl-1-(1-methyl-piperidin-4-yl)-ethyl]-phenyl}-2-(1-oxo-2,3-dihydro-1H-isoindol-4-ylamino)-nicotinamide;

2-(1-Oxo-2,3-dihydro-1H-isoindol-4-ylamino)-N-(3-trifluoromethyl-phenyl)-nicotinamide;

2-(1H-Indazol-6-ylamino)-N-{3-[2,2,2-trifluoro-1-(pyrrolidin-2-ylmethoxy)-1-trifluoromethyl-ethyl]-phenyl}-nicotinamide;

2-[2,2,2-Trifluoro-1-(4-{[2-(1H-indazol-6-ylamino)-pyridine-3-carbonyl]-amino}-phenyl)-1-trifluoromethyl-ethoxymethyl]-pyrrolidine-1-carboxylic acid tert-butyl ester;

2-(1H-Indazol-6-ylamino)-N-{4-[2,2,2-trifluoro-1-(pyrrolidin-2-ylmethoxy)-1-trifluoromethyl-ethyl]-phenyl}-nicotinamide;

2-(1-Oxo-2,3-dihydro-1H-isoindol-4-ylamino)-N-[4-(2,2,2-trifluoro-1-hydroxy-1-trifluoromethyl-ethyl)-phenyl]-nicotinamide;

2-(1-Oxo-2,3-dihydro-1H-isoindol-4-ylamino)-N-[3-(2,2,2-trifluoro-1-hydroxy-1-trifluoromethyl-ethyl)-phenyl]-nicotinamide;

N-(1-Acetyl-3,3-dimethyl-2,3-dihydro-1H-indol-6-yl)-2-(1-oxo-2,3-dihydro-1H-isoindol-4-ylamino)-nicotinamide;

N-(3,3-Dimethyl-2,3-dihydro-1H-indol-6-yl)-2-(1-oxo-2,3-dihydro-1H-isoindol-4-ylamino)-nicotinamide;

2-(1-Oxo-2,3-dihydro-1H-isoindol-4-ylamino)-N-[3-(tetrahydro-furan-3-yloxy)-5-trifluoromethyl-phenyl]-nicotinamide;

N-(4-(1,1-Dimethylethyl)-3-((N,N-dimethylglycyl)amino)phenyl)-2-(1H-indazol-6-ylamino)-3-pyridinecarboxamide;

N-(2-Oxo-3,3-bis(trifluoromethyl)-2,3-dihydro-1H-indol-6-yl)-2-((1-oxo-2,3-dihydro-1H-isoindol-4-yl)amino)-3-pyridinecarboxamide;

N-(3-(((((2R)-1-Methyl-2-pyrrolidinyl)methyl)oxy)-4-(trifluoromethyl)phenyl)-2-((1-oxo-2,3-dihydro-1H-isoindol-4-yl)amino)-3-pyridinecarboxamide;

2-(1H-indazol-6-ylamino)-N-(3-(((((2S)-1-methyl-2-pyrrolidinyl)methyl)oxy)-4-(trifluoromethyl)phenyl)-3-pyridinecarboxamide;

N-[3-(1-Methyl-pyrrolidin-2-ylmethoxy)-4-pentafluoroethyl-phenyl]-2-(1-oxo-2,3-dihydro-1H-isoindol-4-ylamino)-nicotinamide;

N-[3-(1-Methyl-pyrrolidin-2-ylmethoxy)-4-trifluoromethyl-phenyl]-2-(1-oxo-2,3-dihydro-1H-isoindol-4-ylamino)-nicotinamide;

N-[3-(2-Dimethylamino-ethoxy)-4-trifluoromethyl-phenyl]-2-(1-oxo-2,3-dihydro-1H-isoindol-4-ylamino)-nicotinamide;

N-[3-(1-Methyl-pyrrolidin-2-ylmethoxy)-4-pentafluoroethyl-phenyl]-2-(1-oxo-2,3-dihydro-1H-isoindol-4-ylamino)-nicotinamide;

N-(3,3-Bis-trifluoromethyl-2,3-dihydro-1H-indol-6-yl)-2-(1-oxo-2,3-dihydro-1H-isoindol-4-ylamino)-nicotinamide;

N-[1-(2-Dimethylamino-acetyl)-3,3-bis-trifluoromethyl-2,3-dihydro-1H-indol-6-yl]-2-(1-oxo-2,3-dihydro-1H-isoindol-4-ylamino)-nicotinamide;

N-(4,4-Bis-trifluoromethyl-1,2,3,4-tetrahydro-isoquinolin-7-yl)-2-(1-oxo-2,3-dihydro-1H-isoindol-4-ylamino)-nicotinamide;

N-(2-Methyl-4,4-bis-trifluoromethyl-1,2,3,4-tetrahydro-isoquinolin-7-yl)-2-(1-oxo-2,3-dihydro-1H-isoindol-4-ylamino)-nicotinamide;

N-(3,3-dimethyl-1-(methylsulfonyl)-2,3-dihydro-1H-indol-6-yl)-2-(1H-indazol-6-ylamino)-3-pyridinecarboxamide;

1,1-Dimethylethyl 3-(((2-(1,1-dimethylethyl)-5-(((2-(1H-indazol-6-ylamino)-3-pyridinyl)carbonyl) amino)phenyl) oxy)methyl)-1-azetidinecarboxylate;

N-[4-tert-Butyl-3-(2-dimethylamino-acetylamino)-phenyl]-2-(1-oxo-2,3-dihydro-1H-isoindol-4-ylamino)-nicotinamide;

N-[4-tert-Butyl-3-(2-methylamino-acetylamino)-phenyl]-2-(3H-indazol-5-ylamino)-nicotinamide;

N-(4,4-Dimethyl-1,2,3,4-tetrahydro-isoquinolin-7-yl)-2-(1-oxo-2,3-dihydro-1H-isoindol-4-ylamino)-nicotinamide;

N-(4,4-Dimethyl-1,2,3,4-tetrahydro-isoquinolin-7-yl)-2-(1-oxo-2,3-dihydro-1H-isoindol-4-ylamino)-nicotinamide; and N-[3,3-Dimethyl-1-(pyrrolidine-2-carbonyl)-2,3-dihydro-1H-indol-6-yl]-2-(1H-indazol-6-ylamino)-nicotinamide.

17. A pharmaceutical composition comprising a pharmaceutically-acceptable carrier and a compound as in any of claims 1–16.

18. A method of treating angiogenesis in a subject, said method comprising administering an effective amount of a compound as in any of claims 1–16.

19. A method of treating KDR-related disorders in a niammnal, said method comprising administering an effective amount of a compound of claims 1–16.

20. A method of treating diabetic retinopathy in a subject, said method comprising administering an effective amount of a compound as in any of claims 1–16.

* * * * *